United States Patent [19]
Ohno et al.

[11] Patent Number: 4,564,620
[45] Date of Patent: Jan. 14, 1986

[54] 5,6,7,-TRINOR-4,8-INTER-M-PHENYLENE PGI₂ DERIVATIVES AND ANTI-ULCER, ANTI-THROMBOTIC AND ANTI-HYPERTENSIVE PHARMACEUTICAL COMPOSITIONS CONTAINING THEM

[75] Inventors: Kiyotaka Ohno, Fujisawa; Hiroshi Nagase; Mamoru Ishikawa, both of Kamakura; Kazuhisa Matsumoto, Fujisawa; Shintaro Nishio, Ebina, all of Japan

[73] Assignee: Toray Industries, Inc., Tokyo, Japan

[21] Appl. No.: 567,755

[22] Filed: Jan. 3, 1984

Related U.S. Application Data

[63] Continuation of Ser. No. 353,875, Mar. 2, 1982, abandoned.

[30] Foreign Application Priority Data

Mar. 3, 1981 [JP] Japan ................................. 56-29357

[51] Int. Cl.⁴ ..................... A61K 31/34; C07D 307/93
[52] U.S. Cl. .................................... 514/337; 514/444; 514/460; 514/468; 546/269; 549/60; 549/414; 549/415; 549/458

[58] Field of Search ................ 549/60, 458, 415, 414; 546/269; 414/263, 285, 283, 275; 514/337, 468, 460, 444

[56] References Cited

U.S. PATENT DOCUMENTS 4,301,164  11/1981  Ohno et al. ......................... 549/458

Primary Examiner—Henry R. Jiles
Assistant Examiner—Bernard I. Dentz
Attorney, Agent, or Firm—Austin R. Miller

[57] ABSTRACT

Pharmaceutically useful compounds are 5,6,7-trinor-4,8-inter-m-phenylene PGI₂ derivatives such as 5,6,7-trinor-4,8-inter-m-phenylene-13,14-didehydro PGI₂, 5,6,7-trinor-4,8-inter-m-phenylene-16,16-dimethyl PGI₂, 5,6,7-trinor-4,8-inter-m-phenylene-17-α-methyl-20-homo PGI₂, 5,6,7-trinor-4,8-inter-m-phenylene-17,18,19,20-tetranor-16-phenoxy PGI₂, 5,6,7-trinor-4,8-inter-m-phenylene-20-isopropylidene PGI₂, 5,6,7-trinor-4,8-inter-(5-methyl-1,3-phenylene) PGI₂, and 5,6,7-trinor-4,8-inter-m-phenylene-2,3-didehydro-16,17,18,19,20-pentanor-15-phenyl PGI₂. They are useful in treatment of ulcers, thrombii and hypertension for example.

36 Claims, No Drawings

5,6,7,-TRINOR-4,8-INTER-M-PHENYLENE PGI$_2$ DERIVATIVES AND ANTI-ULCER, ANTI-THROMBOTIC AND ANTI-HYPERTENSIVE PHARMACEUTICAL COMPOSITIONS CONTAINING THEM

BACKGROUND OF THE INVENTION

This is a continuation of application Ser. No. 353,875, filed Mar. 2, 1982 now abandoned.

Prostaglandin I$_2$ (PGI$_2$, prostacyclin) is a compound discovered by J. R. Vane et al in 1976, biosynthesized from arachidonic acid via endo peroxide (PGH$_2$ or PGG$_2$) in the arterial wall, attracting attention as a substance having a strong platelet aggregation inhibiting activity and vasodilating activity.

[Refer to C & EN, Dec. 20, 1976, p 17 and S. Moncada, R. Gryglewski, S. Bunting, J. R. Vane, "Nature," 263,633 (1976)]

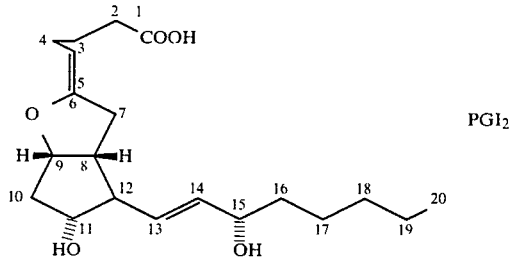

PGI$_2$

Because of the unstable exoenol ether structure, PGI$_2$ is very unstable even in a neutral aqueous solution, changing into 6-oxo PGF$_{1\alpha}$ having hardly any physiological activity. The instability of PGI$_2$ becomes a serious drawback when it is used as a medicinal compound. Further, PGI$_2$ is unstable inside an organism, having another drawback in that its physiological action has no continuity.

It is an object of this invention to overcome these disadvantages of PGI$_2$.

SUMMARY OF THE INVENTION

The above-mentioned object of the invention is achieved by a compound of the formula

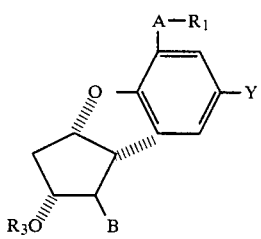

(I)

wherein

R$_1$ denotes a carboxyl group or a functional derivative thereof,

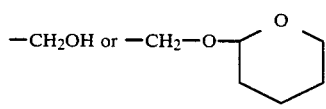

A denotes (i) —(CH$_2$)$_n$—,
(ii) —CH=CH—CH$_2$—,
(iii) —CH$_2$CH=CH— or
(iv) —CH$_2$—O—CH$_2$—, wherein n is an integer of 1-3, Y denotes hydrogen, alkyl having 1-4 carbon atoms, chlorine, fluorine, bromine, formyl, methoxy or nitro, B denotes to all A and Y (i)

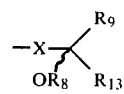

or (ii)

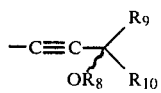

further, when A is (ii) —CH=CH—CH$_2$—, (iii) —CH$_2$CH=CH—, (iv) —CH$_2$—O—CH$_2$— or when Y is an alkyl group having 1-4 carbon atoms, chlorine, fluorine, bromine, formyl, methoxy or nitro, B further denotes (iii)

(i)

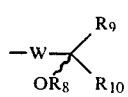

wherein R$_9$ denotes hydrogen or an alkyl group having 1-4 carbon atoms, R$_8$ denotes hydrogen, acyl having 1-12 carbon atoms, aroyl having 6-15 carbon atoms, tetrahydropyranyl, tetrahydrofuranyl, 1-ethoxy ethyl or t-butyl, X denotes
(i) —CH$_2$CH$_2$—,
(ii) —CH=CH— (trans) or
(iii) —C≡C—

R$_{10}$ denotes
(i) straight chain alkyl having 4-10 carbon atoms, or
(ii)

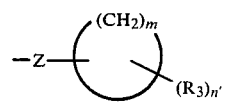

wherein Z denotes valence bond, or straight chain or branched alkylene which may be represented by C$_t$H$_{2t}$, wherein t denotes an integer of 1-5, further, m denotes an integer of 5-12, R$_3$ denotes hydrogen or alkyl having 1-5 carbon atoms, and n' denotes an integer of 1-3, or (iii) —Z—Ar$_2$, wherein Z is the same as defined above, and Ar$_2$ denotes phenyl, α-naphthyl, β-naphthyl or at least one chlorine, bromine, fluorine, trifluoromethyl, alkyl having 1-4 carbon atoms, nitro, methoxy, phenyl or phenoxy-substituted phenyl, R$_{13}$ denotes
(i) branched alkyl having 5-10 carbon atoms, or (ii) —$C_lH_{2l}OR_{14}$, wherein $C_lH_{2l}$ is the same as defined above, and $R_{14}$ denotes straight chain or branched alkyl having 1-5 carbon atoms,

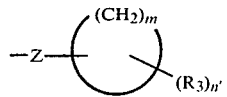

or —$Z$—$Ar_2$, wherein Z, m, $R_3$, n' and $Ar_2$ are the same as defined above, or (iii)

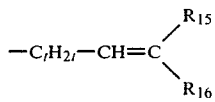

(wherein $C_lH_{2l}$ is the same as defined above, $R_{15}$ and $R_{16}$ denote hydrogen, methyl, ethyl, propyl or butyl group, W denotes
(i) —$CH_2CH_2$— or
(ii) —CH=CH— (trans) and the general formula denotes d form, l form or dl form.)

DETAILED DESCRIPTION OF THE INVENTION

Hereinafter preferable $R_1$, A, B, $R_8$ and Y, and preferable combination thereof are shown.

(a) The following groups (A), (B) and (C) are preferable $R_1$. In these groups (A) (i) and —$COOCH_3$ are the most preferable.

(A) $COOR_2$, wherein $R_2$ denotes (i) hydrogen or a pharmacologically acceptable cation, (ii) straight chain alkyl having 1-12 carbon atoms or branched alkyl having 3-12 carbon atoms, (iii)

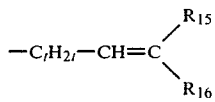

wherein Z, m, $R_3$ and n' are the same as defined above, (iv) —$(CH_2CH_2O)_l$ $CH_3$, wherein l is an integer of 1-5, (v) —Z—$Ar_1$, wherein Z is the same as defined above, $Ar_1$ denotes phenyl, α-naphthyl, β-naphthyl, 2-pyridyl, 3-pyridyl, 4-pyridyl, α-furyl, β-furyl, α-thienyl, β-thienyl or substituted phenyl (wherein the substituent is at least one chlorine, bromine, fluorine, trifluoromethyl, alkyl having 1-4 carbon atoms, nitro, methoxy, phenyl, phenoxy,

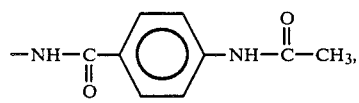

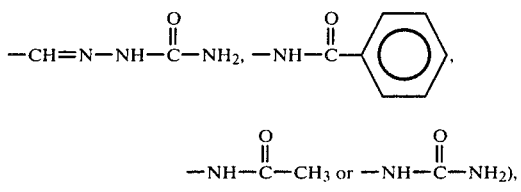

(vi) —$C_lH_{2l}COOR_3$ (vii) —$CH_2C_lH_{2l}N(R_3)_2$ (wherein l and $R_3$ are the same as defined above), (viii)

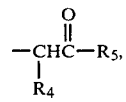

wherein $R_4$ denotes hydrogen or benzoyl and $R_5$ denotes phenyl, p-bromophenyl, p-biphenyl, p-benzamidophenyl or 2-naphthyl, (ix) —$C_pH_{2p}$—B', wherein B' is

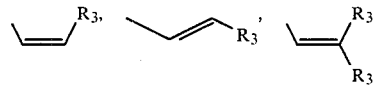

or —C≡C—$R_6$, wherein $R_3$ is the same as defined above, $R_6$ denotes straight chain or branched alkyl having 1-30 carbon atoms, and p is an integer of 1-5, or (x)

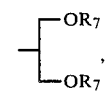

wherein $R_7$ denotes alkyl or acyl having 1-30 carbon atoms, (B) —$CH_2OH$, and (C)

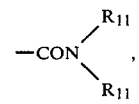

wherein $R_{11}$ denotes hydrogen, alkyl having 1-10 carbon atoms, cycloalkyl having 3-12 carbon atoms, phenyl, substituted phenyl, aralkyl having 7-12 carbon atoms or —$SO_2R_{12}$, wherein $R_{12}$ denotes alkyl having 1-12 carbon atoms, cycloalkyl having 3-12 carbon atoms, phenyl, substituted phenyl or aralkyl having 7-12 carbon atoms, two $R_{11}$ may be the same or different, however, when one denotes —$SO_2R_{12}$, the other is not —$SO_2R_{12}$.

(b) Preferable A is (i) —$(CH_2)_n$— or (iii) —$CH_2CH=CH$—, wherein n is an integer of 1-3.

In these groups, —$(CH_2)_3$— is the most preferable.

(c) When A is (i) —$(CH_2)_n$— or (iii) —$CH_2CH=CH$—, preferable B is (i)

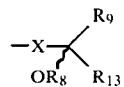

or (ii)

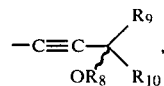

wherein n, X, $R_8$, $R_9$, $R_{10}$, and $R_{13}$ are the same as defined above. In this case, the following is more preferable:

n is 3, $R_8$ and $R_9$ are both hydrogen.

(d) When A is (i) —$(CH_2)_n$— or (iii) —$CH_2CH=CH$— and B is (i)

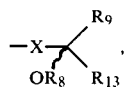

preferable X and $R_{13}$ are as follows:

X is (ii) —CH=CH— (trans) or (iii) —C≡C—, $R_{13}$ is (i) branched alkyl having 5–10 carbon atoms, or (iii)

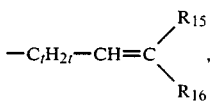

wherein n, t, $R_9$, $R_{15}$ and $R_{16}$ are the same as defined above. Preferably t is 3 or 4, $R_{15}$ is hydrogen or methyl and $R_{16}$ is methyl or ethyl.

In this case, preferable $R_8$ and Y are both hydrogen, and preferable n is 3.

(e) When A is (i) —$(CH_2)_n$— or (iii) —$CH_2CH=CH$— and B is (ii)

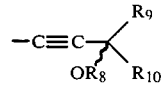

preferable $R_{10}$ is as follows:

$R_{10}$ is (i) straight chain alkyl having 4–10 carbon atoms, or (ii)

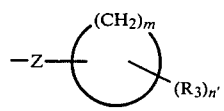

wherein n, n', m, $R_3$, $R_8$, $R_9$ and Z are the same as defined above.

Preferably n is 3, n' is 1 or 2, m is 5 or 6, $R_3$ is hydrogen, methyl or ethyl, and $R_8$ and $R_9$ are both hydrogen.

In this case, preferable Y is hydrogen.

(f) When A is (iii) —$CH_2CH=CH$—, the following group is also preferable as group B:

(iii)

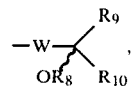

wherein $R_8$, $R_9$, $R_{10}$ and W are the same as defined above.

(g) Whe A is (iii) —$CH_2CH=CH$— and B is (iii)

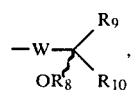

Preferable W and $R_{10}$ are as follows:

W is (ii) —CH=CH— (trans), $R_{10}$ is (i) straight chain alkyl having 4–10 carbon atoms, or (ii)

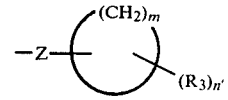

wherein m, n', $R_3$, $R_8$, $R_9$ and Z are the same as defined above. Preferably $R_8$ is hydrogen or acetyl (hydrogen is more preferable), Y is hydrogen, n' is 1 or 2, m is 5 or 6, $R_3$ is hydrogen, methyl, ethyl or propyl and $R_9$ is hydrogen.

(h) In the case of the above (b)–(g), it is more preferable to select $R_1$ as is shown in (a).

More specifically, when $R_2$ is a pharmacologically acceptable cation, such cation includes a metal cation, ammonium cation, amine cation or quaternary ammonium cation, and especially preferable metal cations are derived from alkaline metals, for example, lithium, sodium and potassium and alkaline earth metals, for example, magnesium and calcium.

It is needless to say that cations of metals, for examle, aluminium, zinc and iron are included in the present invention.

Pharmacologically acceptable protonated amines are derived from primary, secondary or tertiary amine. Examples of suitable amines include methyl amine, dimethyl amine, triethyl amine, ethyl amine, dibutyl amine, triisopropyl amine, N-methylhexyl amine, decyl amine, dodecyl amine, allyl amine, crotyl amine, cyclopentyl amine, dicyclohexyl amine, benzyl amine, dibenzyl amine, α-phenylethyl amine, β-phenylethyl amine, ethylene diamine, diethylene triamine and similar aliphatic, alicyclic and heterocyclic amines each containing up to about 18 carbon atoms, for example, 1-methyl piperidine, 4-ethyl morpholine, 1-isopropyl pyrrolidine, 2-methyl pyrrolidine, 4-dimethyl piperazine and 2-methyl piperidine, further, amines having water-soluble or hydrophilic groups, for example, mono- di- and tri-ethanol amines, ethyl diethyl amine, N-butyl ethanol amine, 2-amino-1-butanol, 2-amino-2-ethyl-1,3-propane diol, tris(hydroxymethyl)amino methane, N-phenyl ethanol amine, N-(p-tert-amyl phenyl)diethanol amine, galactamine, N-methyl glutamine, N-methyl glucosamine, ephedrine, phenyl ephrine, epinephrine and procaine, further, basic amino acid, especially, lysine and agrinine. As examples of $R_2$ which is a straight chain alkyl group having 1–12 carbon atoms, there may be cited methyl, ethyl, propyl, butyl, pentyl, hexyl, heptyl, octyl and dodecyl. Furthermore, as examples of $R_2$ which is a branched alkyl group having 3–12 carbon atoms, there may be cited isopropyl, sec-butyl, t-butyl, 2-methyl pentyl and 6-methyl heptyl.

And as examples of $R_2$ and $R_{10}$, either one or both of which may be represented by

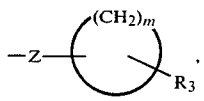

there may be cited, for example, cyclopentyl, cyclohexyl, cycloheptyl, cyclooctyl, cyclododecyl, cyclopentylmethyl, cyclohexylmethyl, cycloheptylmethyl, cyclododecylmethyl, cyclopentylethyl, cyclohexylethyl, cycloheptylethyl, cyclopentylpropyl, cyclohexylpropyl, cyclopentylbutyl, cyclohexylbutyl, cyclohexylpentyl, 2-methylcyclopentyl, 3-methylcyclopentyl, 2-methylcyclohexyl, 3-methylcyclohexyl, 4-methylcyclohexyl, 2-methylcycloheptyl, 3-methylcycloheptyl, 4-methylcycloheptyl, 4-methylcyclooctyl, 2-ethylcyclopentyl, 3-ethylcyclopentyl, 2-ethylcyclohexyl, 3-ethylcyclohexyl, 4-ethylcyclohexyl, 2-ethylcycloheptyl, 2-ethylcyclooctyl, 3-ethylcyclooctyl, 2-methylcyclopentylmethyl, 3-methylcyclopentylmethyl, 2-methylcyclohexylmethyl, 3-methylcyclohexylmethyl, 4-methylcyclohexylmethyl, 2-methylcycloheptylmethyl, 3-methylcycloheptylmethyl, 2-methylcyclooctylmethyl, 2-(2-methylcyclopentyl)ethyl, 2-(3-methylcyclopentyl)ethyl, 2-(2-methylcyclohexyl)ethyl, 2-(3-methylcyclohexyl)ethyl, 2-(4-methylcyclohexyl)ethyl, 2-(2-methylcycloheptyl)ethyl, 2-(2-methylcyclooctyl)ethyl, 3-(2-methylcyclopentyl)propyl, 3-(3-methylcyclopentyl)propyl, 3-(2-methylcyclohexyl)propyl, 3-(3-methylcyclohexyl)propyl, 3-(4-methylcyclohexyl)propyl, 5-(2-methylcyclopentyl)pentyl, 2-ethylcyclopentylmethyl, 3-ethylcyclopentylmethyl, 2-ethylcyclohexylmethyl, 3-ethylcyclohexylmethyl, 4-ethylcyclohexylmethyl, 2-ethylcycloheptylmethyl, 3-methylcycloheptylmethyl, 2-ethylcyclooctylmethyl, 2-(2-ethylcyclopentyl)ethyl, 2-(3-ethylcyclopentyl)ethyl, 2-(4-ethylcyclohexyl)ethyl, 2-(2-ethylcycloheptyl)ethyl, 2-(2-ethylcyclooctyl)ethyl, 3-(2-ethycyclopentyl)propyl, 3-(3-ethylcyclopentyl)propyl, 3-(2-ethylcyclohexyl)propyl, 3-(3-ethylcyclohexyl)propyl, 3-(4-ethylcyclohexyl)propyl, 5-(2-ethylcyclopentyl)pentyl and 5-(2-ethylcyclopentyl)pentyl.

When $R_2$ is —$(CH_2CH_2O)_lCH_3$, examples include 2-methoxyethyl, 2-(2-methoxyethoxy)ethyl and 2-[2-(methoxyethoxy)ethoxy]ethyl.

When $R_2$ is —$C_lH_{2l}COOR_3$, examples include carbomethoxymethyl group (—$CH_2COOCH_3$), (1-carbomethoxy)ethyl

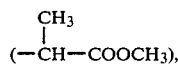

carboethoxymethyl(—$CH_2COOC_2H_5$), carbopropoxymethyl(—$CH_2COOC_3H_7$), carbobutoxymethyl(—$CH_2COOC_4H_9$), 3-carbomethoxypropyl(—$(CH_2)_3COOCH_3$), carboethoxypropyl(—$(CH_2)_3COOC_2H_5$), —$(CH_2)_3COOC_3H_7$ and —$(CH_2)_3COOC_4H_9$. $R_3$ is methyl, ethyl, propyl, butyl and pentyl groups.

When $R_2$ is

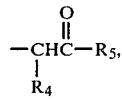

there may be cited, for example, phenacyl

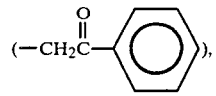

p-bromophenacyl

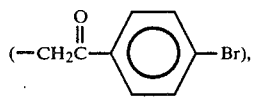

p-phenylphenacyl

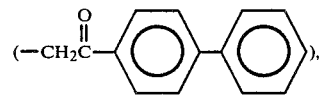

p-nitrophenacyl

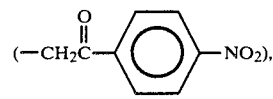

p-benzoylamino phenacyl

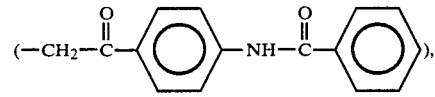

β-naphthoylmethyl

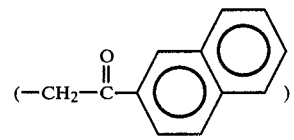

and dibenzoyl methyl

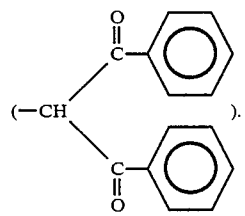

As examples of the case when $R_2$ is $C_lH_{2l}$—B′, there may be cited —$CH_2$—C≡C—$CH_3$, —$CH_2$—C≡C—$C_2H_5$,

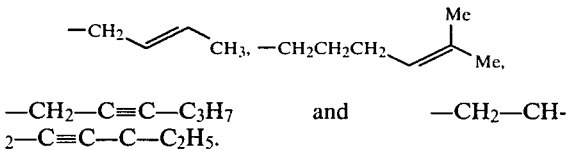

—CH$_2$—C≡C—C$_3$H$_7$ and —CH$_2$—CH$_2$—C≡C—C—C$_2$H$_5$.

As specific examples when R$_2$ represents

there may be cited 1,3-dimethoxy-2-propyl

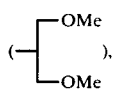

1,3-diethoxy-2-propyl

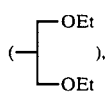

1-methoxy-3-stearoyloxy-2-propyl

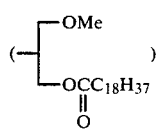

and 1,3-diacetoxy-2-propyl

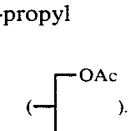

As specific examples when Ar$_1$ is substituted phenyl group, there may be cited p-chlorophenyl, p-bromophenyl, p-fluorophenyl, m-chlorophenyl, m-fluorophenyl, 3,4-dichlorophenyl, p-(trifluoromethyl)phenyl, p-tolyl, 3,4-dimethylphenyl, p-anisyl, 3,4-dimethoxyphenyl, 4-phenoxyphenyl, p-benzoylaminophenyl, p-acetaminophenyl, p-carbamoylaminophenyl and p-nitrophenyl.

As specific examples of —z—Ar$_2$, there may be cited phenyl, p-chlorophenyl, p-bromophenyl, p-fluorophenyl, 3,4-dichlorophenyl, m-fluorophenyl, m-trifluoromethylphenyl, p-trifluoromethylphenyl, p-nitrophenyl, p-anisyl, 3,4-dimethoxyphenyl, p-tolyl, m-tolyl, o-tolyl, p-ethylphenyl, p-propylphenyl, p-butylphenyl, 3,4-dimethyl phenyl, 2,4-dimethylphenyl, 3-chloro-4-methylphenyl, 3-fluoro-4-methylphenyl, 4-biphenyl, p-phenoxyphenyl, p-phenoxy-3-chlorophenyl, benzyl, p-chlorobenzyl, m-chlorobenzyl, p-methoxybenzyl, o-methoxybenzyl, p-methylbenzyl, p-ethylbenzyl, p-propylbenzyl, p-nitrobenzyl, 3,4-dichlorobenzyl, α-methylbenzyl, α,α'-dimethylbenzyl, phenethyl, p-chlorophenethyl, p-bromophenethyl, p-fluorophenethyl, m-chlorophenethyl, m-fluorophenethyl, o-chlorophenethyl, p-methyl phenethyl, p-methoxyphenethyl, 3,4-dimethoxyphenethyl, p-ethyl phenethyl, α-methylphenethyl, β-methylphenethyl, α,α'-dimethyl phenethyl, β,β'-dimethylphenethyl, 3-phenylpropyl, 3-(p-chloro phenyl)propyl, 3-(p-fluorophenyl)propyl, 3-(p-bromophenyl)propyl, 3-(m-chlorophenyl)propyl, 3-(3,4-dichlorophenyl)propyl, 3-(p-tolyl)propyl, 3-(p-ethylphenyl)propyl, 4-phenylbutyl, 4-(p-chlorophenyl)butyl, 4-(3,4-dichlorophenyl)butyl, 4-(p-tolyl)butyl and 5-phenylpentyl.

As examples when R$_{11}$ or R$_{12}$ denotes an alkyl group having 1-10 carbon atoms, specifically there may be cited methyl, ethyl, propyl, octyl and decyl. As examples when R$_{11}$ or R$_{12}$ denotes a cycloalkyl group having 3-12 carbon atoms, there may be cited cyclopropyl, cyclopentyl, cyclohexyl, cyclooctyl and cyclododecyl.

As examples when R$_{11}$ or R$_{12}$ denotes a substituted phenyl group, what is the same as the case wherein A$_{r2}$ denotes a substituted phenyl is illustrated. As examples when R$_{11}$ or R$_{12}$ denotes an aralkyl group having 7-12 carbon atoms, specifically there may be cited benzyl, phenethyl, 3-phenylpropyl, p-methylbenzyl, p-ethylbenzyl, p-propylbenzyl and 3,4-dimethylbenzyl.

As specific examples when R$_8$ denotes an acyl group having 1-12 carbon atoms, there may be cited acetyl, propionyl, butyroyl, octanoyl and dodecanoyl. As specific examples when R$_8$ denotes an aroyl group having 6-12 carbon atoms, there may be cited benzoyl, phenylacetyl, 3-phenylpropionyl, p-phenylbenzoyl, α-naphthoyl and β-nahthoyl.

As specific examples when R$_7$ denotes a straight chain alkyl group having 1-30 carbon atoms, there may be cited methyl, ethyl, propyl, butyl, pentyl, hexyl, octyl, hexadecanyl and octaeicosanyl. As specific examples when R$_7$ denotes an acyl group having 1-30 carbon atoms, there may be cited acetyl, octanoyl, palmitoyl, eicosanoyl and hexaeicosanoyl.

Specific examples when R$_9$ or Y denotes an alkyl groups having 1-4 carbon atoms include methyl, ethyl, propyl and butyl.

Specific examples when R$_{10}$ is straight chain alkyl having 4-10 carbon atoms include n-butyl, n-pentyl, n-hexyl, n-heptyl, n-octyl and n-decyl.

As specific examples when R$_{13}$ is branched alkyl having 5-10 carbon atoms, there may be cited 1,1-dimethylpentyl, 1-methylpentyl, 2-methylpentyl, 3-metylpentyl, 1,1-dimenthylhexyl, 2-methylhexyl and 1,1-dimethyl-2-methylhexyl.

As specific examples when R$_{14}$ denotes straight chain or branched alkyl having 1-5 carbon atoms, there may be cited methyl, ethyl, n-propyl, n-butyl, n-pentyl, isobutyl and 3-methylbutyl.

As specific examples of C$_t$H$_{2t}$, there may be cited methylene, ethylene, propylene, butylene, 1,1-dimethyl methylene, 1,1-dimethylethylene, 1,1-dimethylpropylene and 3-methylpropylene.

The compound represented by the aforesaid general formula (I) obtained according to the present invention is a PGI$_2$ derivative having a novel skeleton converting the structure of the exoenol ether part which is a chracteristic structure of PGI$_2$ to an inter-m-phenylene type.

This compound is characterized in that drawbacks recognized in PGI$_2$ in general are sharply improved. Namely, the compound represented by the general formula (I) is very stable in an aqueous solution, in addition, its physiological action is very continuous even if it is inside an organism. Further, the compound represented by the general formula (I) has excellent properties in the aspect of having the multi-facet physiological activities possessed by PGI$_2$ in a more selective form, wherein lies its merit from the viewpoint of its utilization as a medicine.

The compound represented by the aforesaid general formula (I) obtained according to the present invention can be named in accordance with the nomencloture of prostaglandin and prostacyclene-analog proposed by N. A. Nelson et al. [N. A. Nelson, "J. Med. Chem.," "17, 911 (1974) and R. A. Johnson, D. R. Morton, N. A. Nelson, "Prostaglandins," 15, 737 (1974)]. The most fundamental compound converting the exoenol ether structure part of PGI$_2$ to inter-m-phenylene is represented by the following formula, numbered as shown and named 5,6,7-trinor-4,8-inter-m-phenylene PGI$_2$.

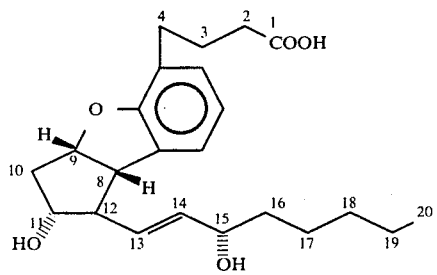

According to this nomenclature, the compound of the following formula included in the present invention is named 5,6,7-trinor-4,8-inter-m-phenylene-13,14-didehydro-16,17,18,19,20-pentanor-15-cyclohexyl PGI$_2$.

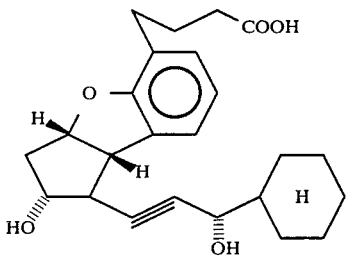

Further, when there is a substituent in a phenylene group to be inserted, there is no properly proposed nomenclature, however, by expanding the aforesaid nomenclature, it is named as follows. Namely, number of a phenylene group at a position bonding to 4-position is named 1' and said number at a position bonding to 8-position carbon is named 3'.

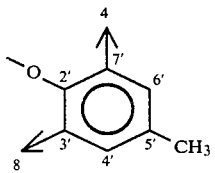

Thus, such compound is named 5,6,7-trinor-4-,8-inter-(5'-methyl-m-phenylene) or 5,6,7-trinor-4,8-inter-(5'-methyl-1',3'-phenylene).

According to this nomenclature, the compound of the following formula included in the present invention

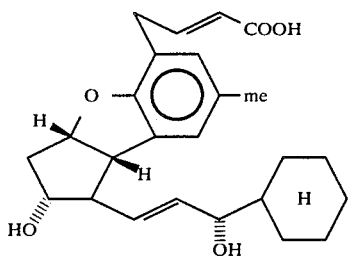

is named 5,6,7-trinor-4,8-inter-(5'-methyl-m-phenylene)-2,3-didehydro-16,17,18,19,20-pentanor-15-cyclohexyl PGI$_2$. This compound according to the formal nomenclature, is named after cyclopental[b]benzofuran ring as a substituent. According to this method, the name of this compound is

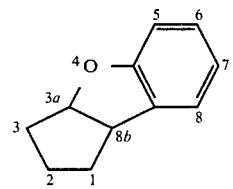

[1,2,3a,8b]-tetrahydro-3a,8b-cis-2-endo-hydroxy-7-metyl-1-exo-(3-cyclohexyl-3-hydroxypyopen-1-yl)-5-cyclopenta[b]benzofuranyl-2,3-didehydrobutanoic acid. However, in this specification, the compound is named according to the aforesaid simple nomenclature excluding the synthetic intermediate.

When the most preferable compounds included in the present invention are shown according to the aforesaid nomenclature, the following compounds may be cited.
5,6,7-trinor-4,8-inter-m-phenylene-16(S)-methyl PGI$_2$,
5,6,7-trinor-4,8-inter-m-phenylene-16(R)-methyl PGI$_2$,
5,6,7-trinor-4,8-inter-m-phenylene-16-methyl-ω-homo PGI$_2$,
5,6,7-trinor-4,8-inter-m-phenylene-17(S)-methyl-ω-homo PGI$_2$,
5,6,7-trinor-4,8-inter-m-phenylene-13,14-didehydro-16,17,18,19,20-pentanor-15-cyclohexyl PGI$_2$,
5,6,7-trinor-4,8-inter-m-phenylene-13,14-didehydro-ω-homo PGI$_2$,
5,6,7-trinor-4,8-inter-m-phenylene-2,3-didehydro-17(S)-methyl PGI$_2$,
5,6,7-trinor-4,8-inter-m-phenylene-2,3-didehydro-17(S)-methyl-ω-homo PGI$_2$,
5,6,7-trinor-4,8-inter-m-phenylene-2,3-didehydro-16,17,18,19,20-pentanor-15-cyclopentyl PGI$_2$,
5,6,7-trinor-4,8-inter-m-phenylene-2,3-didehydro-16,17,18,19,20-pentanor-15-cyclohexyl PGI$_2$, The following compounds are also preferable ones.
5,6,7-trinor-4,8-inter-m-phenylene-16,16-dimethyl PGI$_2$,
5,6,7-trinor-4,8-inter-m-phenylene-16-methyl PGI$_2$,
5,6,7-trinor-4,8-inter-m-phenylene-16(S)-methyl-ω-homo PGI$_2$,
5,6,7-trinor-4,8-inter-m-phenylene-16(R)-methyl-ω-homo PGI$_2$,
5,6,7-trinor-4,8-inter-m-phenylene-17(S)-methyl PGI$_2$,
5,6,7-trinor-4,8-inter-m-phenylene-17(R)-methyl PGI$_2$,
5,6,7-trinor-4,8-inter-m-phenylene-17(R)-methyl-ω-homo PGI$_2$, 5,6,7-trinor-4,8-inter-m-phenylene-13,14-didehydro-PGI$_2$,
5,6,7-trinor-4,8-inter-m-phenylene-13,14-didehydro-17(S)-methyl PGI$_2$,
5,6,7-trinor-4,8-inter-m-phenylene-13,14-didehydro-17(R)-methyl PGI$_2$,
5,6,7-trinor-4,8-inter-m-phenylene-13,14-didehydro-17(S)-methyl-ω-homo PGI$_2$,
5,6,7-trinor-4,8-inter-m-phenylene-13,14-didehydro-17(R)-methyl-ω-homo PGI$_2$,
5,6,7-trinor-4,8-inter-m-phenylene-13,14-didehydro-16,17,18,19,20-pentanor-15-cyclopentyl PGI$_2$,
5,6,7-trinor-4,8-inter-m-phenylene-13,14-didehydro-16,17,18,19,20-pentanor-15-(2-methylcyclopentyl) PGI$_2$,
5,6,7-trinor-4,8-inter-m-phenylene-13,14-didehydro-16,17,18,19,20-pentanor-15-(3-methylcyclopentyl) PGI$_2$,
5,6,7-trinor-4,8-inter-m-phenylene-13,14-didehydro-16,17,18,19,20-pentanor-15-(2-methylcyclohexyl) PGI$_2$,
5,6,7-trinor-4,8-inter-m-phenylene-13,14-didehydro-16,17,18,19,20-pentanor-15-(3-methylcyclohexyl) PGI$_2$,
5,6,7-trinor-4,8-inter-m-phenylene-13,14-didehydro-16,17,18,19,20-pentanor-15-(4-methylcyclohexyl) PGI$_2$,
5,6,7-trinor-4,8-inter-m-phenylene-13,14-didehydro-16,17,18,19,20-pentanor-15-phenyl PGI$_2$,
5,6,7-trinor-4,8-inter-m-phenylene-13,14-didehydro-16,17,18,19,20-pentanor-15-(p-tolyl) PGI$_2$,
5,6,7-trinor-4,8-inter-m-phenylene-17,18,19,20-tetranor-16-phenoxy PGI$_2$,
5,6,7-trinor-4,8-inter-m-phenylene-18-oxa PGI$_2$,
5,6,7-trinor-4,8-inter-m-phenylene-2,3-didehydro PGI$_2$,
5,6,7-trinor-4,8-inter-m-phenylene-2,3-didehydro-ω-homo PGI$_2$,
5,6,7-trinor-4,8-inter-m-phenylene-2,3-didehydro-16,16-dimethyl PGI$_2$,
5,6,7-trinor-4,8-inter-m-phenylene-2,3-didehydro-17(R)-methyl PGI$_2$,
5,6,7-trinor-4,8-inter-m-phenylene-2,3-didehydro-17(R)-methyl-ω-homo PGI$_2$,
5,6,7-trinor-4,8-inter-m-phenylene-2,3-didehydro-16,17,18,19,20-pentanor-15-(4-methylhexyl) PGI$_2$,
5,6,7-trinor-4,8-inter-m-phenylene-2,3-didehydro-16,17,18,19,20-pentanor-15-phenyl PGI$_2$,
5,6,7-trinor-4,8-inter-m-phenylene-2,3-didehydro-17,18,19,20-tetranor-16-phenyl PGI$_2$,
5,6,7-trinor-4,8-inter-m-phenylene-2,3-didehydro-18,19,20-trinor-17-phenyl PGI$_2$,
5,6,7-trinor-4,8-inter-m-phenylene-2,3-didehydro-17,18,19,20-tetranor-16-phenoxy PGI$_2$,
5,6,7-trinor-4,8-inter-m-phenylene-2,3-didehydro-18-oxa PGI$_2$,
5,6,7-trinor-4,8-inter-m-phenylene-2,3,13,14-tetradehydro PGI$_2$
5,6,7-trinor-4,8-inter-m-phenylene-2,3,13,14-tetradehydro-16,17,18,19,20-pentanor-15-cyclohexyl PGI$_2$,
5,6,7-trinor-4,8-inter-m-phenylene-2,3,13,14-tetradehydro-16,17,18,19,20-pentanor-15-cyclopentyl PGI$_2$,
5,6,7-trinor-4,8-inter-m-phenylene-2,3,13,14-tetradehydro-16,17,18,19,20-pentanor-15-phenyl PGI$_2$,
and the corresponding methyl ester, ethyl ester, benzyl ester, phenyl ester, methoxy methyl ester, carbomethoxy methyl ester, phenacyl ester, 1,3-diacetoxy-2-propyl ester, phenethyl ester, amide, butyl amide, cyclohexyl amide, (N-methanesulfonyl)amide and morpholine amide may be cited.

Further, as compounds included in the present invention, the following compounds may be cited.

5,6,7-trinor-4,8-inter-m-phenylene-16,16-dimethyl-ω-homo PGI$_2$,
5,6,7-trinor-4,8-inter-m-phenylene-18-methyl PGI$_2$,
5,6,7-trinor-4,8-inter-m-phenylene-19-methyl PGI$_2$,
5,6,7-trinor-4,8-inter-m-phenylene-15-methyl-17(S)-methyl PGI$_2$,
5,6,7-trinor-4,8-inter-m-phenylene-13,14-didehydro-15-methyl PGI$_2$,
5,6,7-trinor-4,8-inter-m-phenylene-13,14-didehydro-16,16-dimethyl PGI$_2$,
5,6,7-trinor-4,8-inter-m-phenylene-13,14-didehydro-17,18,19,20-tetranor-16-cyclopentyl PGI$_2$,
5,6,7-trinor-4,8-inter-m-phenylene-2,3-didehydro-17,18,19,20-tetranor-16-cyclohexyl PGI$_2$,
5,6,7-trinor-4,8-inter-m-phenylene-13,14-didehydro-18,19,20-trinor-17-cyclopentyl PGI$_2$,
5,6,7-trinor-4,8-inter-m-phenylene-13,14-didehydro-18,19,20-trinor-17-cyclohexyl PGI$_2$,
5,6,7-trinor-4,8-inter-m-phenylene-13,14-didehydro-16,17,18,19,20-pentanor-15-(p-chlorophenyl) PGI$_2$,
5,6,7-trinor-4,8-inter-m-phenylene-13,14-didehydro-16,17,18,19,20-pentanor-15-(m-chlorophenyl) PGI$_2$,
4,6,7-trinor-4,8-inter-m-phenylene-13,14-didehydro-16,17,18,19,20-pentanor-15-(3,4-dichlorophenyl) PGI$_2$,
5,6,7-trinor-4,8-inter-m-phenylene-13,14-didehydro-16,17,18,19,20-pentanor-15-(p-methoxyphenyl) PGI$_2$,
5,6,7-trinor-4,8-inter-m-phenylene-13,14-didehydro-17,18,19,20-tetranor-16-phenyl PGI$_2$,
5,6,7-trinor-4,8-inter-m-phenylene-13,14-didehydro-17,18,19,20-tetranor-16-(p-chlorophenyl) PGI$_2$,
5,6,7-trinor-4,8-inter-m-phenylene-13,14-didehydro-17,18,19,20-tetranor-16-(m-chlorophenyl) PGI$_2$,
5,6,7-trinor-4,8-inter-m-phenylene-13,14-didehydro-17,18,19,20-tetranor-16-(p-tolyl) PGI$_2$,
5,6,7-trinor-4,8-inter-m-phenylene-13,14-didehydro-18,19,20-trinor-17-phenyl PGI$_2$,
5,6,7-trinor-4,8-inter-m-phenylene-13,14-didehydro-18,19,20-trinor-17-(p-chlorophenyl) PGI$_2$,
5,6,7-trinor-4,8-inter-m-phenylene-13,14-didehydro-18,19,20-trinor-17-(m-chlorophenyl) PGI$_2$,
5,6,7-trinor-4,8-inter-m-phenylene-13,14-didehydro-18,19,20-trinor-17-(3,4-dichlorophenyl) PGI$_2$,
5,6,7-trinor-4,8-inter-m-phenylene-13,14-didehydro-16,17,18,19,20-pentanor-15-(p-trifluoromethylphenyl) PGI$_2$,
5,6,7-trinor-4,8-inter-m-phenylene-13,14-didehydro-16,17,18,19,20-pentanor-15-(m-trifluoromethylphenyl) PGI$_2$,
5,6,7-trinor-4,8-inter-m-phenylene-13,14-didehydro-16,17,18,19,20-pentanor-15-(m-fluorophenyl) PGI$_2$,
5,6,7-trinor-4,8-inter-m-phenylene-13,14-didehydro-19,20-dinor-18-phenyl PGI$_2$,
5,6,7-trinor-4,8-inter-m-phenylene-17,18,19,20-tetranor-16-(m-chlorophenoxy) PGI$_2$,
5,6,7-trinor-4,8-inter-m-phenylene-17,18,19,20-tetranor-16-(p-chlorophenoxy) PGI$_2$,
5,6,7-trinor-4,8-inter-m-phenylene-17,18,19,20-tetranor-16-(p-trifluoromethylphenyl) PGI$_2$,
5,6,7-trinor-4,8-inter-m-phenylene-17,18,19,20-tetranor-16-(m-trifluoromethylphenyl) PGI$_2$,
5,6,7-trinor-4,8-inter-m-phenylene-17-oxa PGI$_2$,
5,6,7-trinor-4,8-inter-m-phenylene-16,17-dimethyl-18-oxa PGI$_2$, 5,6,7-trinor-4,8-inter-m-phenylene-17-oxa-ω-homo PGI$_2$,
5,6,7-trinor-4,8-inter-m-phenylene-17,18,19,20-tetranor-16-cyclohexyloxy PGI$_2$,
5,6,7-trinor-4,8-inter-m-phenylene-17,18,19,20-tetranor-cyclopentyloxy PGI$_2$,
5,6,7-trinor-4,8-inter-m-phenylene-2,3-didehydro-16,17,18,19,20-pentanor-15-cycloheptyl PGI$_2$,
5,6,7-trinor-4,8-inter-m-phenylene-2,3-didehydro-16,17,18,19,20-pentanor-15-cyclooctyl PGI$_2$,
5,6,7-trinor-4,8-inter-m-phenylene-2,3-didehydro-17,18,19,20-tetranor-16-cyclohexyl PGI$_2$,
5,6,7-trinor-4,8-inter-m-phenylene-2,3-didehydro-17,18,19,20-tetranor-16-cyclopentyl PGI$_2$,
5,6,7-trinor-4,8-inter-m-phenylene-2,3-didehydro-18,19,20-trinor-17-cyclohexyl PGI$_2$,
5,6,7-trinor-4,8-inter-m-phenylene-2,3-didehydro-16,17,18,19,20-pentanor-15-(p-tolyl) PGI$_2$,
5,6,7-trinor-4,8-inter-m-phenylene-2,3-didehydro-16,17,18,19,20-pentanor-15-(p-chlorophenyl) PGI$_2$,
5,6,7-trinor-4,8-inter-m-phenylene-2,3-didehydro-16,17,18,19,20-pentanor-15-(m-chlorophenyl) PGI$_2$,
5,6,7-trinor-4,8-inter-m-phenylene-2,3-didehydro-16,17,18,19,20-pentanor-15-(m-fluorophenyl) PGI$_2$,
5,6,7-trinor-4,8-inter-m-phenylene-2,3-didehydro-16,17,18,19,20-pentanor-15-(p-fluorophenyl) PGI$_2$,
5,6,7-trinor-4,8-inter-m-phenylene-2,3-didehydro-16,17,18,19,20-pentanor-15-(p-trifluoromethylphenyl) PGI$_2$,
5,6,7-trinor-4,8-inter-m-phenylene-2,3-didehydro-16,17,18,19,20-pentanor-15-(m-trifluoromethylphenyl) PGI$_2$,
5,6,7-trinor-4,8-inter-m-phenylene-2,3-didehydro-16,16-dimethyl-18-oxa PGI$_2$,
5,6,7-trinor-4,8-inter-m-phenylene-2,3-didehydro-17-oxa-ω-homo PGI$_2$,
5,6,7-trinor-4,8-inter-m-phenylene-2,3,13,14-tetradehydro-17,18,19,20-tetranor-16-phenyl PGI$_2$,
5,6,7-trinor-4,8-inter-m-phenylene-3,4-didehydro PGI$_2$,
5,6,7-trinor-4,8-inter-m-phenylene-3,4-didehydro-16,17,18,19,20-pentanor-15-phenyl PGI$_2$,
5,6,7-trinor-4,8-inter-m-phenylene-3,4-didehydro-16,17,18,19,20-pentanor-15-cyclohexyl PGI$_2$,
5,6,7-trinor-4,8-inter-m-phenylene-3-oxa PGI$_2$,
5,6,7-trinor-4,8-inter-m-phenylene-3-oxa-16,17,18,19,20-pentanor-15-phenyl PGI$_2$,
5,6,7-trinor-4,8-inter-m-phenylene-3-oxa-16,17,18,19,20-pentanor-15-cyclohexyl PGI$_2$,
5,6,7-trinor-4,8-inter-m-phenylene-3-oxa-13,14-didehydro-16,17,18,19,20-pentanor-15-cyclohexyl PGI$_2$,
5,6,7-trinor-4,8-inter-m-phenylene-3-oxa-13,14-didehydro-16,17,18,19,20-pentanor-15-cyclopentyl PGI$_2$,
5,6,7-trinor-4,8-inter-m-phenylene-3-oxa-13,14-didehydro PGI$_2$,
5,6,7-trinor-4,8-inter-m-phenylene-3-oxa-13,14-didehydro-16,17,18,19,20-pentanor-15-phenyl PGI$_2$,
5,6,7-trinor-4,8-inter-m-phenylene-3-oxa-13,14-didehydro-16,17,18,19,20-pentanor-15-cyclohexyl PGI$_2$,
5,6,7-trinor-4,8-inter-m-phenylene-2,3-didehydro-13,14-dihydro-16,17,18,19,20-pentanor-15-phenyl PGI$_2$,
5,6,7-trinor-4,8-inter-m-phenylene-2,3-didehydro-13,14-dihydro-16,17,18,19,20-pentanor-15-cyclohexyl PGI$_2$,
5,6,7-trinor-4,8-inter-m-phenylene-2,3-didehydro-13,14-dihydro-17,18,19,20-tetranor-16-phenoxy PGI$_2$,
5,6,7-trinor-4,8-inter-m-phenylene-2,3-didehydro-13,14-dihydro-17(S)-methyl PGI$_2$,
5,6,7-trinor-4,8-inter-m-phenylene-2,3-didehydro-13,14-dihydro-17(R)-methyl PGI$_2$,
5,6,7-trinor-4,8-inter-m-phenylene-2,3-didehydro-13,14-dihydro-17(S)-methyl-ω-homo PGI$_2$,
5,6,7-trinor-4,8-inter-m-phenylene-2,3-didehydro-13,14-dihydro-17(R)-methyl-ω-homo PGI$_2$,
5,6,7-trinor-4,8-inter-(5'-methyl-m-phenylene)-16,17,18,19,20-pentanor-15-phenyl PGI$_2$,
5,6,7-trinor-4,8-inter-(5'-bromo-m-phenylene)-16,17,18,19,20-pentanor-15-cyclohexyl PGI$_2$,
5,6,7-trinor-4,8-inter-(5'-methyl-m-phenylene)-3-oxa PGI$_2$,
5,6,7-trinor-4,8-inter-(5'-methyl-m-phenylene)-13,14-didehydro-16,17,18,19,20-pentanor-15-cyclohexyl PGI$_2$,
5,6,7-trinor-4,8-inter-(5'-methyl-m-phenylene)-13,14-didehydro- PGI$_2$,
5,6,7-trinor-4,8-inter-(5'-methyl-m-phenylene)-13,14-didehydro-17(S)-methyl PGI$_2$,
5,6,7-trinor-4,8-inter-(5'-methyl-m-phenylene)-13,14-didehydro-17(R)-methyl-ω-homo PGI$_2$,
5,6,7-trinor-4,8-inter-(5'-methyl-m-phenylene)-13,14-didehydro-16,17,18,19,20-pentanor-15-cyclohexyl PGI$_2$, and the corresponding methyl ester, ethyl ester, benzyl ester, phenyl ester, methoxy methyl ester, carbomethoxy methyl ester, phenacyl ester, 1,3-diacetoxy-2-propyl ester, phenethyl ester, amide, butyl amide, cyclohexyl amide, (N-methanesulfonyl)amide and morpholine amide may be cited, however, such compounds are not limited thereto.

The compounds of the present invention may be easily produced by the processes mentioned hereinbelow.

The compounds wherein A is —(CH$_2$)$_3$—, B is

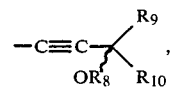

R$_1$ is COOH and R$_8$ is hydrogen are produced by the synthesizing processes shown in chart A.

chart A

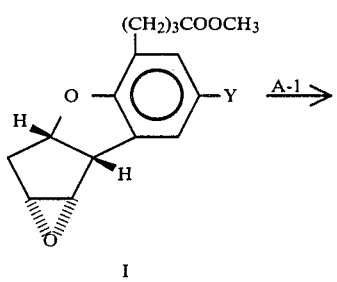

I

-continued
chart A

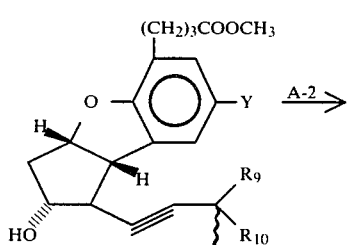
II

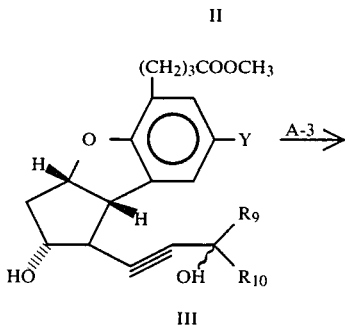
III

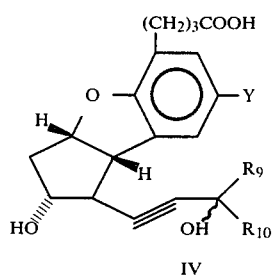
IV

The step A-1 is easily achieved by reacting an aluminium compound represented by the general formula

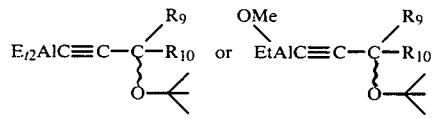

(wherein R$_9$ and R$_{10}$ are the same as defined above) with the compound I in a hydrocarbon solvent such as benzene, toluene and xylene. The reaction temperature ranges from −50° C. to 50° C., however, in a normal practice, a preferable result is obtained when the reaction temperature ranges from −20° C. to 30° C. The aluminium compound used in the reaction may be obtained by the reaction shown by formula (a) or (b).

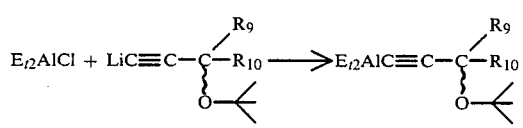

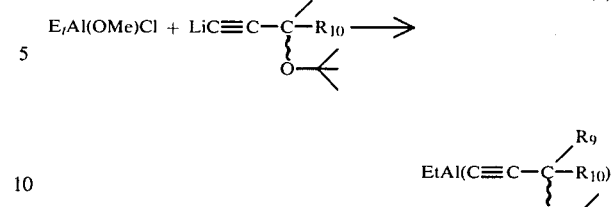

These aluminium compounds are normally not isolated, but generated per se in the system and used. An aluminium compound of a further complicated composition or a mixture of aluminium compounds may be generated in the system and used. Such aluminium compound is generated in the system by, for example, dissolving 1 equivalent of E$_{t2}$AlCl in toluene, adding 0.2–0.5 equivalent of MeOH to the resultant solution and subsequently adding thereto 1 equivalent of

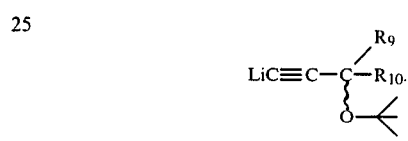

The step A-2 is a step of removing the protective group of alcohol (at 15-position). Normally, an acid is employed in this step and especially trifluoroacetic acid is preferably employed. A solvent may or may not be used, however, when it is used, a halogenated hydrocarbon such as methylene chloride is preferably used. The reaction temperature ranges from −70° C. to 50° C., however, a sufficiently preferable result is obtained at a temperature ranging from −20° C. to 30° C. in an ordinary practice of the reaction.

The step A-3 is a step of hydrolyzing an ester.

For the hydrolysis of an ester, a base is preferably employed and for an ordinary practice, sodium hydroxide, potassium hydroxide, sodium carbonate and potassium carbonate are employed. As the solvent, aqueous methanol, aqueous ethanol, aqueous dioxane and aqueous dimethyl sulfoxide are employed, however, ordinarily, employment of aqueous methanol brings about a sufficiently preferable result.

The process for preparing the starting material I is shown in B.

chart B

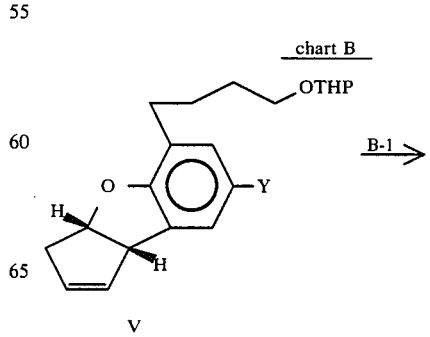
V

-continued
chart B

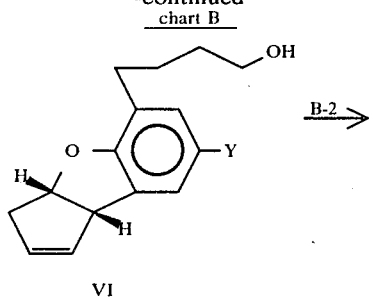

VI

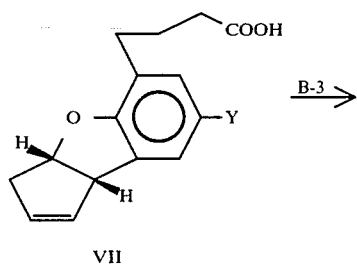

VII

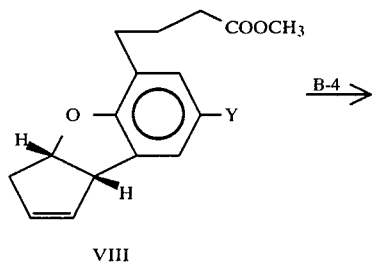

VIII

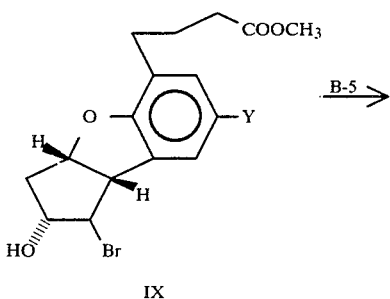

IX

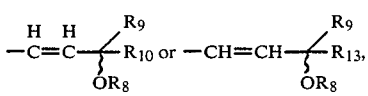

I

The step B-1 is a step of eliminating a tetrahydropyranyl group by an acid catalyst to obtain a hydroxy group. As this acid catalyst, a proper amount of hydrochloric acid, hydrobromic acid, acetic acid, p-toluenesulfonic acid or phosphoric acid may be added into a proper solvent, but the acid catalyst is not limited to these acids. As the solvent, mainly a water-containing solvent system such as acetonitrile-water, THF-acetic acid-water, acetic acid and water or methanol or ethanol is employed. For an ordinary practice, by heating the compound V in an acetic acid-water (2:1) mixture to 40° C., a preferable result is obtained.

The step B-2 is a step of oxidizing an alcohol, and as an oxidizing reagent, an ordinary oxidizing agent of an alcohol is employed, however, chromium trioxide and pyridinium dichromate ($Na_2Cr_2O_7PY$) are preferably employed, when chromium trioxide is employed, aqulous pyridine is preferable as solvent, and when pyridinium dichromate is employed dimethyl formamide is especially preferably employed as solvent, ordinarily, when pyridinium dichromate is employed in dimethyl formamide, a preferable result is obtained.

The reaction temperature ranges from $-40°$ C. to $100°$ C., however, ordinarily a preferable reaction rate is obtained at the reaction temperature ranging from $0°$ C. to $50°$ C.

The step B-3 is a methyl esterification step, which is easily achieved ordinarily by bringing the compound VII into contact with the ether solvent of diazomethane.

The step B-4 is practiced by dissolving the compound VIII in a dimethyl sulfoxide-water solvent system and treating with N-bromosuccinimide (NBS).

The step B-5 is a step of treating bromohydrin IX with a base to convert the fomer to epoxide. Ordinarily, suffices it to treat the compound IX in anhydrous methanol with potassium carbonate employed as the base.

A process for preparing the compound V wherein Y is hydrogen was made public by an already filed patent application the inventors of which were the present inventors (Japanese Patent Application No. 111709/1979), however, even when Y is not hydrogen, by using what has a substituent Y at the para-position as a starting phenol compounds, said compound V is prepared via a similar step.

A compound wherein A is $-(CH_2)_3-$, B is

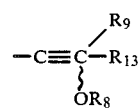

$R_1$ is COOH and $R_8$ is hydrogen, is synthesized by steps similar to chart A.

A compound wherein A is $-CH_2O-CH_2-$, B is $$\begin{array}{c}H\ \ H\ \ \diagup R_9\\-C=C-\!\!\!-\!\!\!\diagdown R_{10}\\ \ \ \ \ \ \ \ \ \ \ \ OR_8\end{array} \text{ or } \begin{array}{c}\diagup R_9\\-CH=CH-\!\!\!-\!\!\!\diagdown R_{13},\\ \ \ \ \ \ \ \ \ \ \ \ OR_8\end{array}$$

$R_1$ is COOH and $R_8$ is hydrogen is also synthesized by steps similar to chart A. However, in this case, the necessary starting compound XIV is prepared by steps shown in chart C.

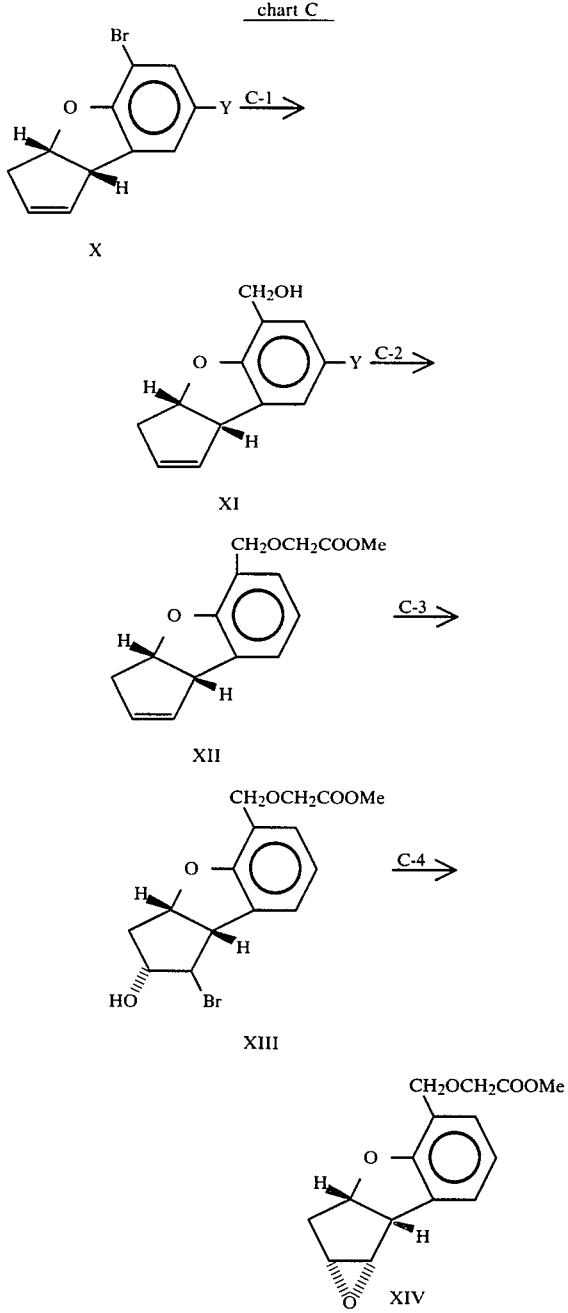

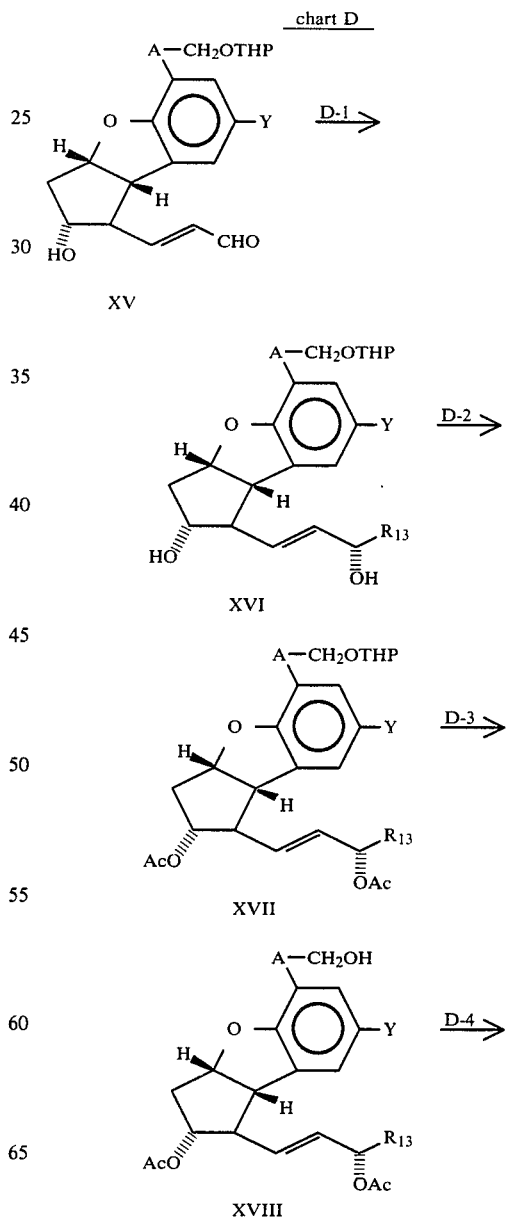

this end, the compound XI is at first reacted with sodium hydride to make the corresponding alkoxy anion and subsequently methyl bromoacetate is added thereto and reacted therewith.

The step C-3 is carried out in the same manner as in the step B-4 and the step C-4 is carried out in the same manner as in the step B-5.

A compound wherein A is (i) —$(CH_2)_3$— to or (iv) —$CH_2$—O—$CH_2$—, $R_8$ and $R_9$ are hydrogen, X is —CH=CH— (trans) and $R_{13}$ is either branched alkyl having 5–10 carbon atoms or

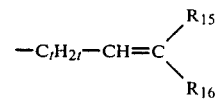

is prepared by steps shown in chart D.

The step C-1 is a step of substituting bromine of the compound X to a hydroxy methyl group. For this end, the compound X is treated with a base to make the former the corresponding phenyl anion and subsequently anhydrous formalin may be reacted therewith.

As the base ordinarily, butyl lithium, phenyl lithium, cyclohexyl magnesium bromide and isopropyl magnesium bromide are employed, however, said base is not limited thereto.

Ordinarily, when phenyl lithium is employed and the reaction is carried out in tetrahydrofuran at a temperature ranging from −40° C. to 20° C., a preferable result is obtained.

The step C-2 is a step of carbomethoxy methyl etherification of a hydroxy group of the compound XI. For -continued
chart D

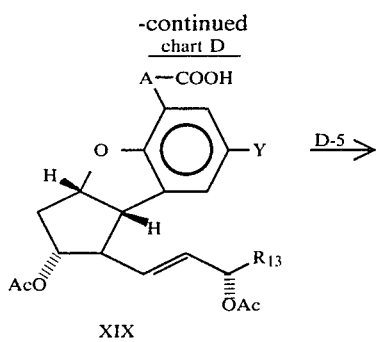

XIX

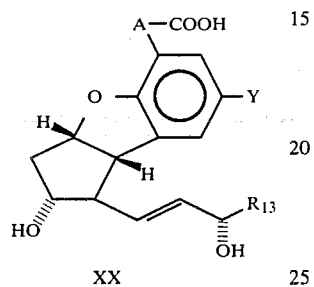

XX

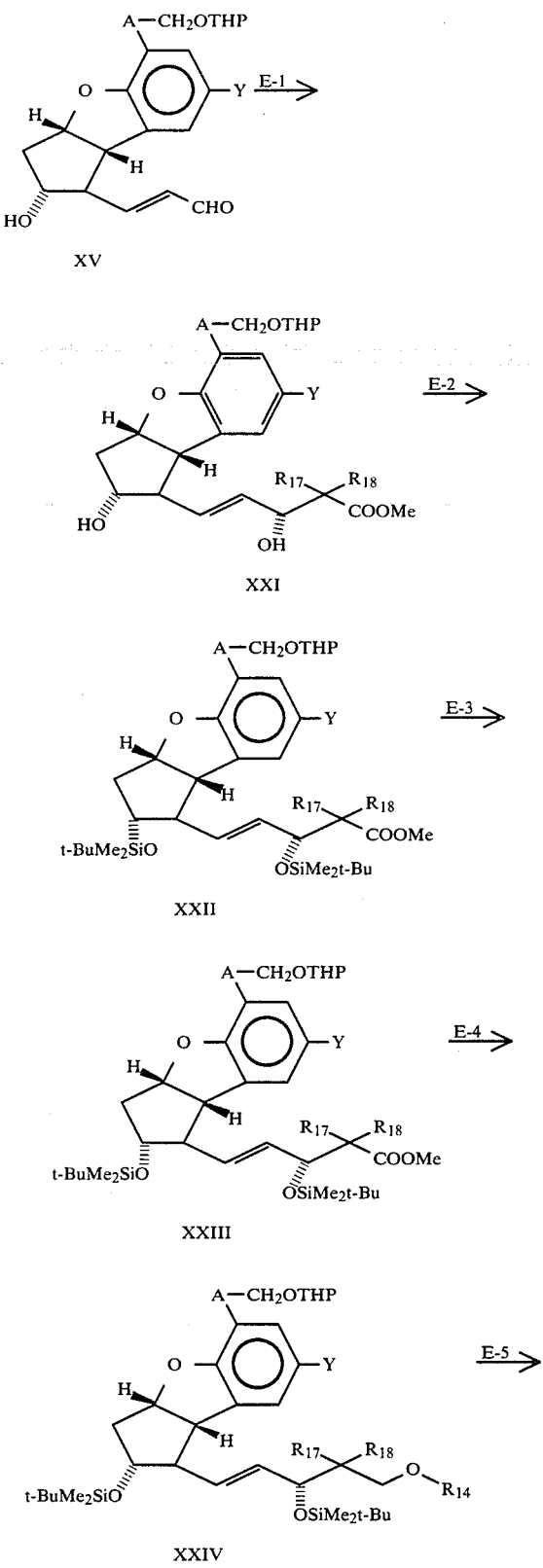

group having 2 carbon atoms in the main chain, said compound is prepared by steps shown in E.

The step D-1 is an alkylating step, which is practiced by reacting $R_{13}MgCl$ or $R_{13}MgBr$ with the compound XV. As said $R_{13}MgCl$ and $M_{13}MgBr$, there may be cited 2-(2-methyl)hexylmagnesium chloride, 2-(2-methyl)heptyl magnesium chloride, 2-methylpentyl magnesium chloride, 2(R)methylpentyl magnesium chloride, 2(S)-methylpentyl magnesium chloride, 2-methylhexyl magnesium chloride, 2-(R)-methylhexyl magnesium chloride, 2(S)-methylhexyl magnesium chloride, 3-methylpentyl magnesium chloride, 2-methylpentyl magnesium bromide, 6-methyl-5-heptyl magnesium bromide and 2-pentenyl magnesium chloride, however, it goes without saying that said $R_{13}MgCl$ and $R_{13}MgBr$ are not limited to these compounds. The practice of the reaction is very easy, ordinarily, the compound XV is dissolved in a solvent and an equimolar amount or excess amount of a THF or ether solution of the aforesaid Grignard reagent may be added dropwise thereto at a temperature ranging from $-70°$ to $50°$ C.

As the solvent, a solvent of the ether series such as tetrahydrofuran, ether and dimethoxy ethane is preferably employable.

The step D-2 is a step of acetylating a free hydroxyl group, which is ordinarily practiced by reacting the compound XV1 with acetic anhydride in pyridine.

The step D-3 is practiced in the same manner as in the step B-1.

The step D-4 is practiced, using the oxidizing agent described in connection with the step B-2 under the same conditions as in the step B-2. The step D-5 is a hydrolyzing step of an ester, and basically is practiced, using the same base as in the step A-3 under the same conditions as in the step A-3.

A compound wherein A is (i) $-(CH_2)_3-$ or (iv) $-CH_2-O-CH_2-$, $R_9$ is hydrogen, X is $-CH=CH-$ (trans), $R_{13}$ is $-C_tH_{2t}OR_{14}$ and $C_tH_{2t}$ is not an alkylene group having 2 carbon atoms in the main chain, employing $LiC_tH_{2t}OR_{14}$ or $ClMgC_tH_{2t}OR_{14}$ instead of the alkylating agent employed in the step D-1 as an alkylating agent, is prepared by practicing the steps D-2, 3, 4 and 5 in this order thereafter. When $C_tH_{2t}$ is an alkylene

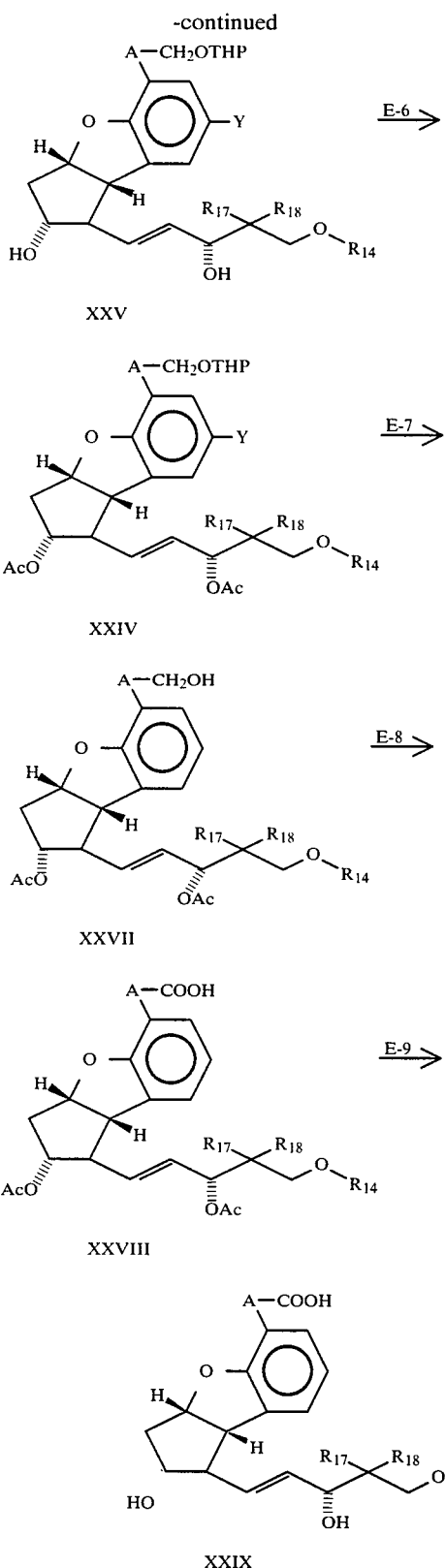

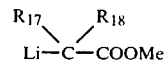

(wherein $R_{17}$ denotes hydrogen, methyl and ethyl, and $R_{18}$ denotes hydrogen, methyl and ethyl) at a temperature ranging from $-80°$ C. to $0°$ C. As a solvent, for an ordinary practice, tetrahydrofuran is preferably employed, however, the solvent is not limited thereto.

The step E-2 is a step of converting free hydroxy group, to dimethyl t-butyl silyl ether, which is ordinarily achieved by adding imidazole as a catalyst to a dimethyl formamide solution of the compound XXI and subsequently adding to the resultant mixture, dimethyl t-butyl silyl chloride (and reacting the mixture). The reaction temperature is ordinarily ranging from $0°$ C. to $50°$ C. and a preferable reaction rate is obtained at such temperature.

The step E-3 is a step of reducing a methoxy carbonyl group to a hydroxymethyl group and is practiced using a reducing agent ordinarily employed for this purpose. As the reducing agent, ordinarily lithium aluminium hydride and diisobutyl aluminium hydride are employed, however, for an ordinary practice, lithium aluminium hydride is economical and preferably employed. In case lithium aluminium hydride is employed as the reducing agent, it is preferable that a solvent of the ether system such as ether and tetrahydrofuran is employed and in case diisobutyl aluminium hydride is employed as the reducing agent, hydrocarbon such as benzene and toluene is preferably employed as the solvent.

The step E-4 is a step of alkylating a free hydroxy group, and as an alkylating agent, ordinarily what is known as an alkylating agent of an alcohol is utilized. For an ordinary practice, the compound XXIII may be converted to the corresponding alkoxy anion with sodium hydride and subsequently $R_{14}I$ (wherein $R_{14}$ is the same as defined above, however, when the step E is applied, Z is not to be valence bond) may be acted thereon. As a solvent, tetrahydrofuran, dimethylformamide, dimethylsulfoxide and dimethoxyethane are preferably employed. The reaction temperature is preferably within the range of $0°-80°$ C.

The step E-5 is a step of removing a dimethyl t-butyl silyl group which is a protective group of an alcohol, which is ordinarily achieved by treating XXIV with tetraalkyl ammonium fluoride. As said tetraalkyl ammonium fluoride, anything will do, however, ordinarily suffices it to use easily available tetrabutyl ammonium fluoride.

As a reaction solvent, tetrahydrofuran, dimethoxyethane and dimethyl formamide are preferably employed.

The step E-6 is practiced in the same manner as in the step D-2. The step E-7 is practiced in the same manner as in the step D-3. The step E-9 is practiced in the same manner as in the step D-5.

A compound wherein A is (i) $-(CH_2)_3-$ or (iv) $-CH_2-O-CH_2-$, both $R_8$ and $R_9$ are hydrogen, X is $-CH=CH-$ (trans), $R_{13}$ is $-C_tH_{2t}OR_{14}$ and the number of the main chain carbon atoms of $-C_tH_{2t}$ is 2, further, $R_{14}$ is The step E-1 is a so-called aldol condensation step, which may be practiced by treating the compound XV with

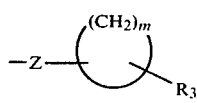

or —Z—A$_{r2}$ and Z denotes valence bond, is produced by tosylating or halogenating the compound XXIII instead of the step E-4 of E, thereafter, acting alkoxy anion or phenoxy anion or substituted phenoxy anion obtained by treating R$_{14}$OH with sodium hydride or potassium hydride on said compound to introduce the same to the compound XXIV and subsequently practicing the steps E-5 to E-9 in the same manner.

A compound wherein A is —CH$_2$—CH=CH—, R$_1$ is COOH and R$_8$ is hydrogen is produced by the synthetic processes shown in F.

The step F-1 is a step of introducing a phenylseleno group to the α-position of a methoxy carbonyl group. This step is practiced by treating the compound XXX with diisopropylamido lithium to generate an anion at the α-position of a methoxy carbonyl group and subsequently adding diphenyl diselenide or phenyl selenyl bromide to the anion.

chart F

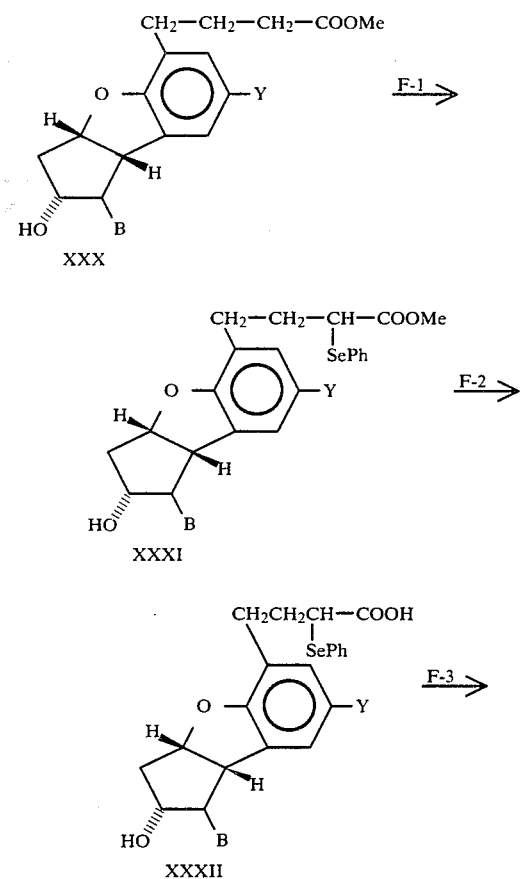

-continued
chart F

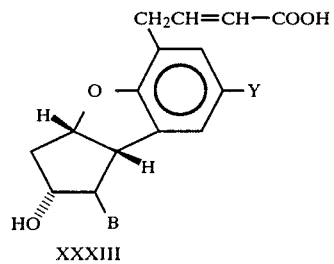

XXXIII

For producing anion at the α-position of a methoxy carbonyl group, ordinarily diisopropyl amido lithium is used in a solvent of the ethers such as tetrahydrofuran and dimethoxy ethane at a temperature ranging from −80° C. to 50° C. A reaction after adding diphenyl diselenide is achieved by allowing the reaction mixture to stand at a temperature ranging from −78° C. to 30° C. or stirring the reaction mixture at the same temperature for 10–120 minutes.

The step F-2 is a step of hydrolyzing an ester and is practiced in the same manner as in the step A-3.

The step F-3 contains a step of oxidizing selen of the compound XXXII to selenoxide and a step of producing olefin by eliminating phenylseleninic acid by heating, however, since elimination of phenylseleninic acid easily takes place at room temperature, the selenoxide of the compound XXXI does not isolated and the compound XXXIII is obtained.

For oxidizing a phenyl seleno group, a sufficiently preferable result is ordinarily obtained when hydrogen peroxide is employed.

A compound wherein A is —CH=CH—CH$_2$—, R$_1$ is COOH and R$_8$ is hydrogen may be produced by steps shown in chart G.

The step G-1 is practiced in the same manner as in the step F-3.

The step G-2 is practiced in a similar manner as in the step A-3. In this alkaline hydrolysis step, Δ$^{2.3}$ double bond is easily isomerized to Δ$^{3.4}$ double bond.

chart G

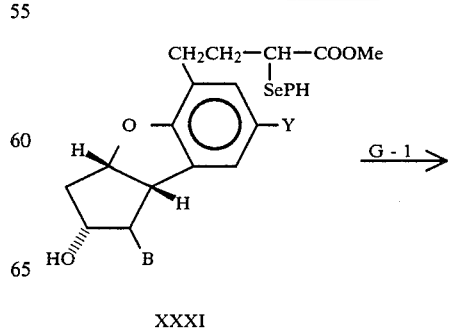

XXXI

-continued
chart G

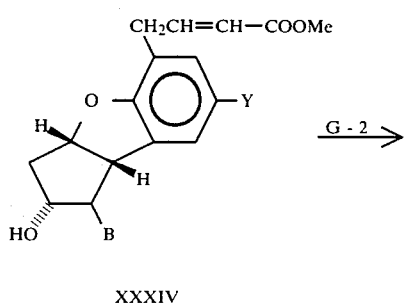

XXXIV

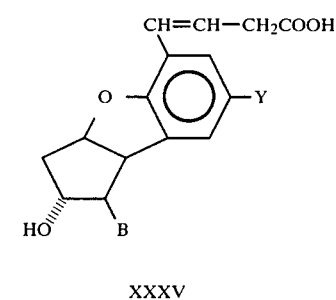

XXXV

Of the compounds of the general formula (I) a compound wherein $R_1$ is —$COOR_2$ and $R_2$ is not hydrogen or cation, namely, $R_2$ is an ester residue, is produced by esterification (when the corresponding $R_2$ is a hydrogen carboxylic acid). As the esterification process, various processes are known, however, a process of using diazoalkane, a process of treating a silver salt or tertiary amine salt of a carboxylic acid with active halide and a mixed acid anhydride method are especially preferably employed for producing the compound of the present invention.

In a process employing diazoalkane, this object may be easily achieved by bringing a carboxylic acid into contact with diazoalkane in a solvent. As such diazoalkane, diazomethane, diazoethane, diazopropane and diazodecane may be cited, however, the diazoalkane is of course not limited thereto. The second process is ordinarily practiced by reacting the silver salt or tertiary amine salt of a carboxylic acid in an aprotic polar solvent such as dimethyl formamide or acetonitrile. As examples of said active halide, there may be cited benzyl chloride, benzyl bromide, p-bromo benzyl bromide, p-methoxy benzyl bromide, p-bromo benzyl bromide phenacyl bromide, p-nitrophenacyl bromide and α-benzoyl phenacyl bromide, however, it goes without saying that such active halide is not limited thereto. The third process of a mixed acid anhydride is the broadest in its applicable scope and the greater part of the ester compounds of the present invention is produced by this process. This process comprises at first treating ethyl chlorocarbonate, pivaloyl chloride or p-toluenesulfonl chloride with a carboxylate to produce a mixed acid anhydride, adding thereto an excess amount of an alcohol $R_2OH$ (wherein $R_2$ is the same as defined above, but not being hydrogen or cation) and heating the resultant mixture. Specific examples of said alcohol include methanol, ethanol, propanol, butanol, octanol, decanol, isopropanol, 2-ethylhexanol, benzyl alcohol, p-bromobenzyl alcohol, phenethyl alcohol, cyclopentyl alcohol, cyclopentylmethyl alcohol, 2-methoxy ethanol, 2-(2-methoxy ethoxy)ethanol, hydroxy acetic acid methyl ester, lactic acid ethyl ester γ-hydroxybutyric acid methyl ester, 2-butyne-1-ol, 2-pentyne-1-ol, 1,3-di-(O)-methyl glycerine, 1,3-diacetyl glycerine, phenol, p-bromophenol, p-fluorophenol, m-chlorophenol, m-fluorophenol, 3,4-dichlorophenol, p-(trifluoromethyl)-phenol, p-methylphenol, 3,4-dimethylphenol, p-methoxyphenol, 4-phenoxyphenol and p-benzoylaminophenol, but said alcohol is not limited thereto.

Of the compounds represented by the general formula (I), a compound wherein $R_1$

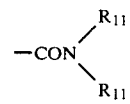

(wherein $R_{11}$ is the same as defined above, two $R_{11}$ may be the same or different, however, $R_{11}$ is not —$SO_2R_{12}$) is obtained by a step H-1 amidizing a compound represented by the general formula wherein $R_1$ is COOH.

chart H

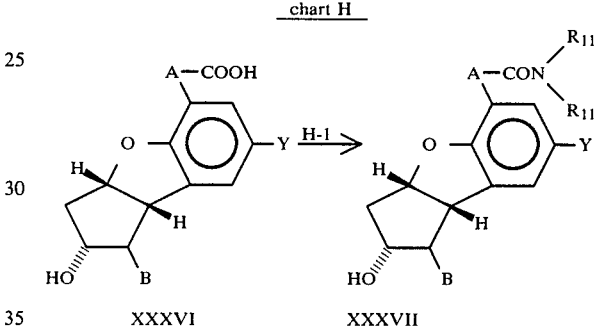

XXXVI        XXXVII

The step H-1 is a step converting a carboxylic acid to the corresponding amide, which is ordinarily achieved by treating a tertiary amine with a carboxylic acid of the compound represented by the general formula XXXVI to make a tertiary ammonium salt of a carboxylic acid, subsequently reacting it with ethyl chlorocarbonate or p-toluenesulfonic acid chloride to make a mixed acid anhydride, adding thereto an amine of

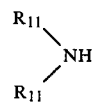

and heating the resultant mixture. Specific examples of said amine include ammonia, N-methylamine, N-ethylamine, N-butylamine, N,N-dimethylamine, N,N-diethylamine, aniline, p-bromoaniline, cyclohexylamine, cyclopentylamine, N-benzylamine, phenethyl amine, morpholine and piperidine, however, said amine is not limited thereto.

Of the compounds represented by the general formula (I), a compound wherein $R_1$ is

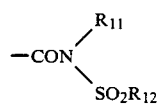

and $R_8$ is hydrogen, is produced by a step shown in chart I.

chart I

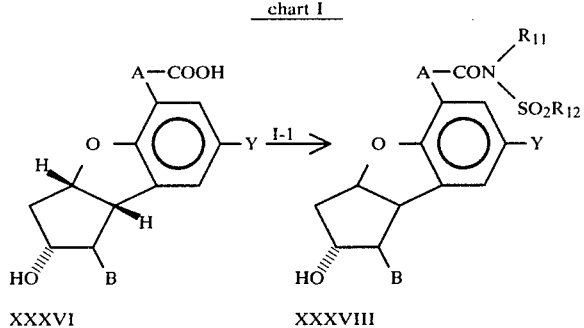

XXXVI  XXXVIII

The step I-1 is achieved by converting the compound (XXXVI) to a mixed acid anhydride, thereafter, reacting therewith a lithium sulfoneamide reagent represented by

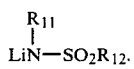

A compound wherein A is $-(CH_2)_n-$, Y is hydrogen, alkyl having 1-4 carbon atoms or methoxy and X is $-CH_2CH_2-$, is obtained by hydrogenating a compound wherein the corresponding X is $-CH=CH-$. Hydrogenation ordinarily employs palladium black, palladium on carbon, palladium on barium sulfate and Raney nickel as catalysts and a preferable result is obtained ordinarily under atmospheric pressure.

Another compound of the present invention wherein X is $-CH_2-CH_2-$, is obtained by employing, instead of the compound of the general formula XV, a compound represented by the general formula XXXIX

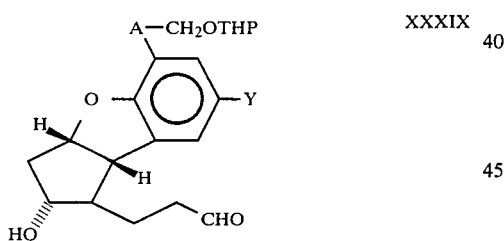

XXXIX and then practicing the steps shown in chart D.

A compound wherein $R_1$ is $CH_2OH$, is obtained by reducing a compound represented by the general formula XL or XLI with lithium aluminium hydride or alkaline hydrolysis of the compound of the general formula XVIII.

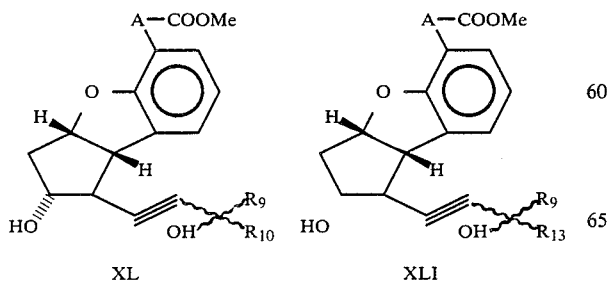

XL  XLI

A compound wherein $R_9$ is an alkyl group having 1-4 carbon atoms, X is $-CH=CH-$ and $R_1$ is $-COOH$, is synthesized by steps shown in J.

The step J-1 is a step of converting alkyl alcohol to α,β-unsaturated ketone, wherein ordinarily active manganese dioxide is employed as an oxidizing agent and said alcohol may be reacted in dichloromethane as a solvent.

The step J-2 is a step of trialkyl silylating a hydroxyl group. In the general formula XLV, $R_{17}$ denotes a straight chain or branched alkyl group having 1-10 carbon atoms and three $R_{17}$ may be the same or different. As specific examples of $R_{17}$, there may be cited methyl, ethyl, propyl, butyl, octyl, isopropyl, t-butyl and 2-ethylhexyl, but $R_{17}$ is not limited thereto.

chart J

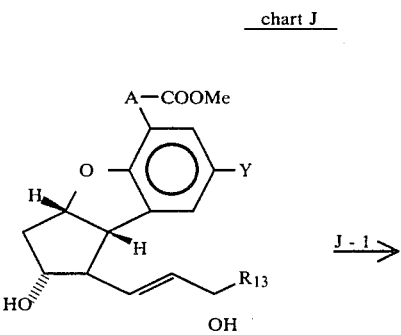

XLII

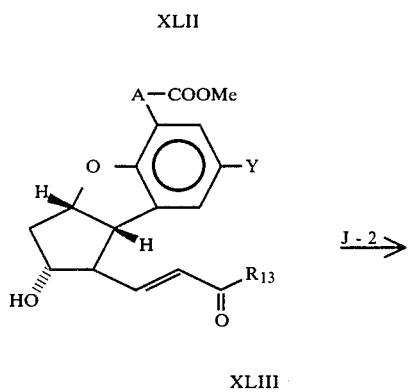

XLIII

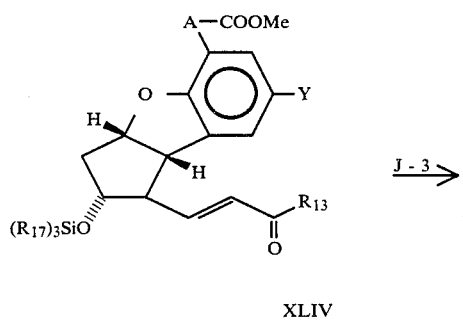

XLIV

-continued
chart J

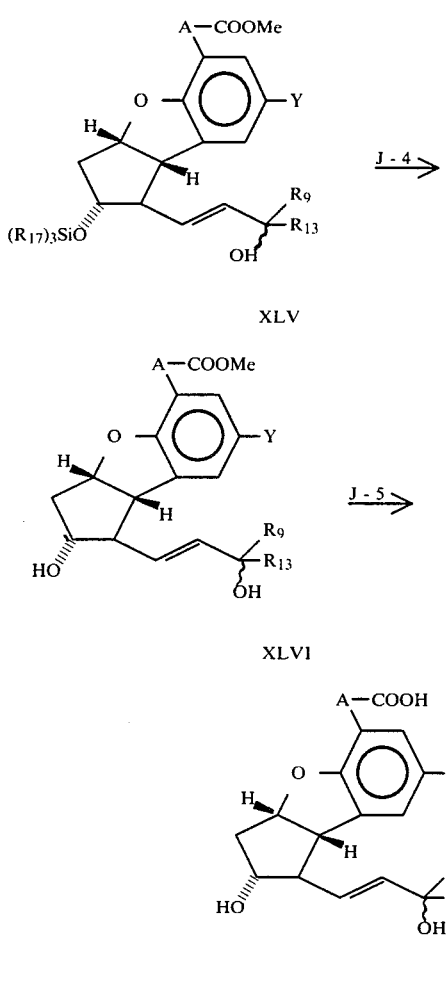

XLV

XLVI

XLVII

For silylating a hydroxy group, general methods described in, for example, "Protective Groups in Organic Chemistry," compiled and written by J. F. W. McOmie, p 103–104, Plenum Press (London and New York) 1973 and literatures cited therein, are applicable.

Ordinarily trimethyl silylation or t-butyl dimethyl silylation is most simply used. For trimethyl silylation, trimethyl chlorosilane in the presence of a tertiary amine base such as pyridine and triethyl amine or a mixture of hexamethyldisilazane and trimethyl chlorosilane can be used. For t-butyl dimethyl silylation, ordinarily a method of using imidazole as a base is preferable.

Other general trialkyl silylation may react the corresponding trialkyl silyl chloride in the presence of a base such as pyridine and triethyl amine.

The step J-3 is achieved by treating XLIV with a Grignard reagent such as $R_9MgCl$, $R_9MgBr$ or $R_9MgI$ (wherein $R_9$ is the same as defined above) in ether or tetrahydrofuran. In this case, the Grignard reagent is used in an amount within the range of 0.8–1.5 mol equivalent based on the compound XLIV. Ordinarily, the product XLV is not isolated, but is used as a material of the step J-4.

The step J-4 is a step of removing a trialkyl silyl group which is a protective group of a hydrokyl group, which is ordinarily achieved by dissolving the trialkyl silyl group in an acidic aqueous solvent and heating the resulting solution.

Examples of said acidic aqueous solvent, is, inclusive acetic acid-water, acetic acid-tetrahydrofuran-water, acetic acid-ethanol water and ethanol-0.01N hydrochloric acid mixtures.

Ordinarily, the object is achieved when the trialkyl silyl group is allowed to stand in a solvent composed of an ethanol/water (10:1) mixture added with a drop of acetic acid at a temperature ranging from 0° C. to 50° C. for 0.5–5 hours. Further, as another method, a tetraalkyl ammonium fluoride may be acted on the compound XLV.

Ordinarily, when tetrabutyl ammonium fluoride is employed as said tetraalkyl ammonium fluoride, a sufficiently preferable result may be obtained.

The step J-5 is a step of alkaline hydrolysis and practiced in similar manner to the step A-3.

The methods of production mentioned so far are practiced in the same manner in the production of anyone of d form, l form or dl form, however, especially upon producing the d form or l form, it is possible to produce the same in accordance with the earlier mentioned method of production from the corresponding optically active starting material.

The compound represented by the general formula (I) obtained in accordance with the present invention has a strong platelet aggregation inhibiting activity and blood pressure lowering activity besides a strong gastric mucous membrane protecting action and or gastric juice secretion inhibiting activity. More particularly, blood collected from man or an anesthetized rabbit was prevented from coagulation with a 1/10 volume of 3.8% sodium citrate solution and centrifuged for 10 minutes, at 200xg, the resultant platelet rich plasma was aggregated with arachidonic acid, adenosine-2-phosphoric acid (ADP) and collagen as aggregating agents according to Born's method ("Nature," 1962, 194, 927) using aggregometer. The anti-aggregatory effect by the pretreatment with the compounds (6), (9), (19), (48), (49), (55) and (97) of the present invention, was a comparable or stronger anti-aggregatory effect with or than that of prostaglandin $E_1$.

Under anesthesia with pentobarbital, the arterial pressure of rats was measured and the solutions of the compounds (6), (9), (19), (48), (49), (55) and (97) of the present invention were injected through a catheter into a vein. The blood pressure reducing activity of the compounds was 1–2 times that of prostglandin $E_1$, but with more prolonged duration.

As for the protecting action of the gastric mucous membrane, tests on the gastric mucous membrane lesion due to alcohol in a rat, accdording to Robert's method ("Gastroenterology," 1979, 77, 433), proved that the compounds (19), (76) and (97) of the present invention had the activity of 0.3–1 times that of prostaglandin $E_2$, i.e. 10–30 μg/kg administered orally strongly inhibited the lesion.

The result of the gastric juice secretion inhibiting effect according to Shay's method ("Gastroenterology," 1954, 25, 906), by subcutaneous injection of the compounds (19), (76), (60), (65) and (97) of the present invention shows the effective dose of 0.3–1 mg/kg, which is 0.1–0.3 times of the dose of prostaglandin $E_2$, in inhibiting the gastric juice.

The compounds of the present invention, especially the compounds (6), (9), (19), (48), (49), (55) and (97) do not exhibit the diarrhoea inducing actions recognized in prostaglandin $E_1$ and $E_2$ up to the dose of 3 mg/kg by subcutaneous administration in a rat.

Accordingly, in application as medicines of the compounds of the present invention, an anti-ulcer agent, an anti-thrombotic agents, and a blood pressure reducing agent are conceivable, further, an anti-asthma medicine is conceivable based on the action of relaxing the bronchial smooth muscle. In application as an anti-thrombotic agent, application to extracorporeal circulation, treatment of Buerger's disease, prevention and treatment of muocardinal infarction and angina prectoris, prevention and treatment of cerebral infarction, prevention TIA and treatment of diabetic thrombosis are conceivable.

More particularly, for example, in an object of treating gastric ulcer, 0.01-100 mg/man is administered 1-3 times a day orally, subcutaneously, intramuscularlly or intra-rectally.

Further, the application as an anti-thrombotic agent or a blood pressure reducing agent is expectative. More particularly, for example, when treatment of Buerger's disease, by intravenous injection of 0.001-100 ng/kg/min, when used as an anti-thrombotic agent, by orally administering 0.01-50 mg/man 1-3 times a day, and when used as a blood pressure reducing agent, by orally administering 0.01-5.0 mg/man 1-3 times a day.

The compounds of the present invention may be orally administered in the form of a solid material containing an additives such as starch, lactose, sucrose, a kind of clay and a taste curing agent. Or these can be administered parenterally in the form of a sterile solution, or these can contain other solute such as sodium chloride or glucose in an amount sufficient to make the solution isotonic.

Because the compound of the present invention has stable chemical structure, it has no difficulty in making a medicine and it can be applied in a broad range of administration routes such as the aforementioned medicine for oral administration, various kinds of injections and suppositories. Hereinbelow, the present invention will be explained by reference to examples.

REFERENTIAL EXAMPLE 1

3,5-cis-bis(2,6-dibromophenoxy)cyclopentene

To a nitrogen-substituted 500 ml flask, 5.6 g (0.117 mol) of sodium hydride in mineral oil dispersion was added and the sodium hydride was washed with n-hexane to remove mineral oils. To the flask, 100 ml of 1,2-dimethoxyethane was added and while the resulting mixture was being stirred at 0° C., 29.4 g (0.117 mol) of 2,6-dibromophenol which had been dissolved in 150 ml of 1,2-dimethoxyethane was slowly added thereto. When foaming calmed down, 280 mg (1.06 mmol, 2 mol % based on 3,5-dibromocyclopentene) of 18-crown-6 and 12 g (0.053 mol) of 3,5-dibromocyclopentene were added. The obtained mixture was stirred at room temperature for 3 days. The reaction mixture was filtered to give a solid substance, which was washed with 20 ml of water 3 times.

Further, the solid substance was dissolved in 1.5 liters of chloroform, the resulting mixture was dried over magnesium sulfate and concentrated to obtain 22.6 g (75%) of roughly pure white solid, which was 3,5-cis-bis(2,6-dibromophenoxy)cyclopentene, white needle-crystals, mp 205.0°-206.0° C.

Elemental analysis. Calculated for $C_{17}H_{12}Br_4O_2$: C: 35.95, H: 2.13. Found: C: 35.86, H: 2.19.

($C_{17}H_{12}Br_4O_2$, mw 567.93):

MS (m/e) 572, 571,570, 569, 568, 567, 566, 565, 564 ($M^+$).

IR (KBr disk) $\nu cm^{-1}$: 1550, 960, 740.

NMR (CDCl$_3$) $\delta$ ppm: 2.90 (dt, 1H), 3.12 (dt, 1H), 5.10 (dd, 2H) 6.31 (s, 2H), 6.83 (t, 2H), 7.52 (d, 4H).

REFERENTIAL EXAMPLE 2

3,5-cis-bis(2,6-dibromophenoxy)cyclopentene

To a solution of 227.6 g of 2,6-dibromophenol in 350 ml of ethanol was added a solution of 59 g of potassium hydroxide in 390 ml of ethanol.

The resulting mixture was stirred for 10 minutes and thereafter concentrated under reduced pressure.

The obtained crystals were dissolved in 1.2 liter of anhydrous DME, 2.2 g of 18-crown-6 was added and the resulting mixture was stirred.

Subsequently, 36.8 g of cyclopentadiene was dissolved in methylene chloride which had been cooled to −50° C., while the obtained solution was being stirred, a solution of 68.8 g of bromine in 10 ml of methylene chloride was added thereto dropwise, further, 15 g of sodium hydrogen carbonate was added and the obtained mixture was stirred for 10 minutes.

This reaction mixture was added to the above-prepared DME solution of a potassium salt of 2,6-dibromophenol and the resulting mixture was stirred at room temperature for 2 days. The separated crystals were filtered and the obtained crystals were washed 3 times with water, once with ether and once with petroleum ether, thereafter, when the washed crystals were dried under reduced pressure, 95.3 g of a roughly pure product was obtained. Further, when the aforesaid mother liquor was concentrated, the separated crystals were washed 2 times with water, once with ether and 2 times with petroleum ether and dried to give 22.9 g of a roughly pure product. The total yield was 118.2 g, mp 205°-206° C.

IR (KBr) $\nu cm^{-1}$: 1550, 1470, 820, 750.

NMR (CDCl$_3$) $\delta$: 2.90 (1H, dt, J=16.0 Hz, 8.0 Hz), 3.12 (1H, dt, J=16.0 Hz, 8.0 Hz), 5.10 (2H, dd, J=8.0 Hz, 7.0 Hz), 6.31 (2H, s), 6.83 (2H, t, J=8.0 Hz) 7.52 (4H, d, J=8.0 Hz).

Elemental analysis: Calculated for $C_{17}H_{12}Br_4O_2$: C: 35.95, H: 2.13. Found: C: 35.86, H: 2.19.

In a similar manner, when 2,6-dibromo-p-chlorophenol was employed instead of 2,6-dibromophenol, 3,5-cis-bis(2,6-dibromo-4-chlorophenoxy)cyclopentene is obtained.

REFERENTIAL EXAMPLE 3

3,5-cis(2,4,6-tribromophenoxy)cyclopentene

To a solution of 193 g of 2,4,6-tribromophenol in 600 ml of ethanol was added dropwise a solution of 45 g of potassium hydroxide in 250 ml of ethanol, the resulting solution was stirred for 10 minutes and thereafter concentrated under reduced pressure. Ethanol was added to the residue, the resulting mixture was again evaporated to dryness, and the obtained crystals were dried under reduced pressure. To a solution of 2,4,6-tribromophenol potassium salt in 1200 ml of anhydrous DME, 2 g of 18-crown-6 was added and the resulting mixture was stirred at room temperature. Subsequently, a solution of 22.8 g of cyclopentadiene in methylene chloride was cooled to −50° C. and while the resulting solution was being stirred at −50° C., a solution of 42.4 g of bromine in 10 ml of methylene chloride was added dropwise thereto. This reaction mixture was added to the above-prepared DME solution of 2,4,6-tribromophenol potassium salt and the resulting mixture was stirred at room temperature for 2 days. The separated crystals were filtered, the obtained crystals were washed 3 times with water, once with ether and 2 times with petroleum ether, and thereafter when they were dried under reduced pressure, 109.6 g of roughly pure crystals was obtained. Further, when the aforesaid mother liquor was concentrated, the separated crystals were filtered and washed with petroleum ehter, 2 times with water, once with ether and 2 times with petroleum ether to yield 13.1 g of roughly pure crystals. The total yield was 123.4 g.

IR (KBr) $\nu cm^{-1}$: 1570, 1600, 1470, 805, 780.

In a similar manner, when instead of 2,4,6-tribromophenol, 2,4-dichloro-6-bromophenol is employed, 3,5-cis-bis(2,4-dichloro-6-bromophenoxy)cyclopentene is obtained, and, 2,6-dibromo-4-methoxyphenol is employed, 3,5-cis-bis(2,6-dibromo-4-methoxyphenyl)cyclopentene is obtained.

REFERENTIAL EXAMPLE 4

3,5-cis-bis(2,4-dibromophenoxy)cyclopentene

To a solution of 407 g of 2,4-dibromophenol in 400 ml of ethanol, was added a solution of 90.7 g of potassium hydroxide in 600 ml of ethanol, the resulting solution was stirred for 10 minutes and thereafter, concentrated under reduced pressure. Operations of dissolving the residue in DME and concentrating the resulting solution were repeated 2 times and thereafter, the obtained residue was well dried under reduced pressure. The so obtained potassium salt of 2,4-dibromophenol was dissolved in 2000 ml of anhydrous DME, 4 g of 18-crown-6 was added and the resulting solution was stirred at room temperature.

Subsequently, 63 g of cyclopentadiene was dissolved in 80 ml of anhydrous methylene chloride, the resulting solution was cooled to −50° C. under argon atmosphere, and while it was being stirred, a solution of 37.9 g of bromine in 20 ml of methylene chloride was added dropwise thereto. To the reaction solution 10 g of sodium hydrogen carbonate was added and thereafter, the mixture was stirred for 10 minutes. This reaction mixture was added to the aboveprepared DME solution of the potassium salt of 2,4-dibromophenol, and the resulting mixture was stirred at room temperature for 2 days.

Crystals separated from this reaction mixture were filtered, the obtained crystals were washed 3 times with water, once with ether and 2 times with petroleum ether and dried to yield 71.9 g of crystals. Further, when the aforesaid mother liquor was concentrated, the separated crystals were washed with petroleum ether, 2 times with water, once with ether and 2 times with petroleum ether thereafter, when they were dired, 159.1 g of crystals was obtained. The total yield was 231 g.

IR (KBr) $\nu cm^{-1}$: 1575, 1600, 1470, 805, 780.

In a similar manner, when phenol is employed instead of 2,4-dibromophenol, 3,5-cis-bisphenoxycyclopentene is obtained.

REFERENTIAL EXAMPLE 5

3,5-cis-bis(2,6-dibromo-4-methylphenoxy)cyclopentene

To a solution of 176 g of 2,6-dibromo-p-cresol in 210 ml of ethanol was added a solution of 43 g of potassium hydroxide in 280 ml of ethanol, the resulting solution was stirred for 10 minutes and thereafter concentrated. The residue was dissolved in 900 ml of anhydrous DME, 155 g of 18-crown-6 was added, and the resulting solution was stirred at room temperature.

Subsequently, the solution of 27 g of cyclopentadiene in 50 ml of methylene chloride had been cooled to −50° C. and while the resulting solution was being stirred, the solution of 50.5 g of bromine in 10 ml of methylene chloride was added dropwise thereto, 5 g of sodium hydrogen carbonate was added to the resulting solution and the resulting mixture was stirred for 10 minutes. This reaction mixture was added to the aboveprepared DME solution of the potassium salt of 2,6-dibromo-p-cresol, and the resulting mixture was stirred at room temperature for 2 days. The separated crystals were filtered, the obtained crystals were washed 2 times with water, once with ether and 2 times with petroleum ether, thereafter, when they were dried under reduced pressure, 165.8 g of a roughly pure product was obtained. Further, the aforesaid mother liquor was concentrated, the separated crystals were washed 2 times with water, once with ether and 2 times with petroleum ether and thereafter, when they were dried under reduced pressure, 22.5 of a roughly pure product was obtained. The total yield was 188.3 g.

IR (KBr) $\nu cm^{-1}$: 1590, 850, 800, 745.

NMR (CDCl$_3$) δ: 2.38 (6H,s), 2.80 (1H, dd, J=14.0 Hz, 5.0 Hz), 3.10 (1H, dd, J=14.0 Hz, 7.0 Hz), 5.08 (2H, dd, J=5.0 Hz, 7.0 Hz), 6.32 (2H, s), 7.36 (4H, s).

REFERENTIAL EXAMPLE 6

3,5-cis-bis(o-bromophenoxy)cyclopentene

In a similar manner as in Referential Example 2, when o-bromophenol was employed instead of 2,6-dibromophenol, 6.0 g of 3,5-cis-bis(o-bromophenoxy)cyclopentene, mp 138°–138.5° C., was obtained from 6.2 g of 3,5-cis-dibromocyclopentene.

IR (KBr) $\nu cm^{-1}$: 1585, 1570, 1165, 992, 790.

NMR (CDCl$_3$) δ: 2.21 (1H, dd, J=14.0 Hz, 5.0 Hz), 3.08 (1H, dd, J=14.0 Hz, 7.0 Hz), 5.20 (2H, dd, J=7.0 Hz, 5.0 Hz), 6.30 (2H, s), 6.80–7.50 (8H, m).

Calculated for C$_{17}$H$_{14}$O$_2$Br$_2$: C: 49.66, H: 3.68. Found: C: 49.76, H: 3.56.

REFERENTIAL EXAMPLE 7

3a,8b-cis-dihydro-3H-5-bromo-cyclopenta[b]benzofuran

In an argon-substituted 50 ml flask, 515 mg (0.906 mmol) of 3,5-cis-bis(2,6-dibromophenoxy)cyclopentene was placed, which was dissolved in 11 ml of anhydrous tetrahydrofuran, and the resulting solution was cooled to −78° C. To the solution 0.72 ml (1.44 mmol) of n-butyl lithium (about 2.0M) was added dropwise in about 15 minutes, and the resulting solution was stirred at −10° C. for about 3 hours. To the reaction mixture 5 ml of a saturated aqueous solution of ammonium chloride was added and the resulting solution was extracted with ether (30 ml×3 times). The organic layer was dried over anhydrous magnesium sulfate and concentrated. When the concentrate was purified by column chromato-graphy (silica gel 7 g, developing solvent: cyclohexane/ethyl acetate 97:3), 98.6 mg (0.416 mmol, 45.9%) of a colorless oily substance was obtained.

TLC: Rf=0.6 (cyclohexane:ethyl acetate 97:3).

IR (liquid film method) $\nu cm^{-1}$: 3060, 2950, 1600, 1585, 945, 750.

NMR (CDCl$_3$) δ ppm: 2.9 (m, 2H) 4.8 (m, 1H), 5.54 (m, 1H), 5.66 (m, 2H), 6.70 (t, 1H), 7.2 (m, 2H).

MS (m/e): 238, 236 (M$^+$), 209, 211, 128.

Thereafter, in a similar manner, when 3,5-cis-bis(2-bromo-6-chlorophenoxy)cyclopentene is employed instead of 3,5-cis-bis(2,6-dibromophenoxy)cyclopentene, 3a,8b-cis-dihydro-3H-5-chlorocyclopenta[b]benzofuran is obtained.

REFERENTIAL EXAMPLE 8

3a,8b-cis-dihydro-3H-5-bromo-cyclopenta[b]benzofuran

To a stirred suspension of 87.1 g of 2,5-cis-bis(2,6-dibromophenoxy)cyclopentene in 300 ml of anhydrous THF at 40° C. was added 140 ml of cyclohexylmagnesiumbromide (2.18N) dropwise, and the resulting solution was stirred for 30 minutes. The temperature of this reaction mixture was allowed to cool to room temperature, 0.58 g of cuprous iodide was added and the resulting mixture was further stirred for 30 minutes. Precipitates existing in the reaction mixture were filtered, the filtrate was concentrated, and the residue was dissolved in cyclohexane. The resulting solution was washed with a 5% aqueous solution of sodium hydroxide, dried and thereafter concentrated to yield 60 g of an oily substance. When this oily substance was distilled (bp 60° C./10$^{-3}$ mm Hg) on a molecular distillation apparatus, 20 g of crude crystals was obtained.

The spectrum data were the same as those of Referential Example 7.

REFERENTIAL EXAMPLE 9

3a,8b-cis-dihydro-3H-cyclopenta[b]benzofuran

In a similar manner as in Referential Example 7, instead of 3,5-cis-bis(2,6-dibromophenoxy)cyclopentene, 6.0 g of 3,5-cis-bis(o-bromophenoxy)cyclopentene was employed to give 1.84 g of the subject compound.

IR (neat) $\nu cm^{-1}$: 3060, 1602, 1585.

NMR (CDCl$_3$) δ: 2.80 (1H, dd, J=2.2, 0.5 Hz), 2.82 (1H, dd, J=5.2, 0.5 Hz), 4.35 (1H, d, J=7.8 Hz), 5.43 (1H, ddd, J=7.8, 5.2, 2.2 Hz), 5.71 (2H, s), 6.95 (4H, m).

Mass: 158 (M$^+$).

REFERENTIAL EXAMPLE 10

3a,8b-cis-dihydro-3H-5,7-dibromo-cyclopenta[b]benzofuran

In a similar manner as in Referential Example 7, instead of 3,5-cis-bis(2,6-dibromophenoxy)cyclopentene, 50 g of 3,5-cis-bis(2,4,6-tribromophenoxy)cyclopentene was employed to give 10 g of 3a,8b-cis-dihydro-3H-5,7-dibromo-cyclopenta[b]benzofuran (mp 110°-112° C.).

IR (KBr) $\nu cm^{-1}$: 3070, 2980, 2920, 1595, 1570, 865, 830, 740, 720.

NMR (CDCl$_3$) δ: 2.90 (2H, m), 4.48 (1H, m), 5.60 (1H, m), 5.80 (2H, m), 7.25 (1H, d, J=2.0 Hz), 7.40 (1H, d, J=2.0 Hz).

Mass: 314 (M$^+$), 316 (M+2), 318 (M+4).

REFERENTIAL EXAMPLE 11

3a,8b-cis-dihydro-3H-7-bromo-cyclopenta[b]benzofuran

Under argon atmosphere, 2.0 g of 3,5-cis-bis(2,4-dibromophenoxy)cyclopentene was dissolved in 4 ml of 1,2-dimethoxyethane, 3,8 ml of an ether solution (1.5M) of phenyllithium was added, and the resulting mixture was stirred at 40° C. for 3 hours and at 70° C. for 12 hours.

The temperature was allowed to cool to room temperature, 5 ml of a saturated aqueous solution of ammonium chloride was added to the reaction solution, the resulting solution was extracted with ether (20 ml×3) and the extracted liquid was washed with 10 ml of a 5% aqueous solution of sodium hydroxide and 10 ml of saturated brine and dried. After concentration, 1.8 g of an oily substance thus obtained was purified by column chromatography [silica gel; cyclohexane:chloroform (3:1)] to give 540 mg of the subject compound.

IR (CHCl$_3$) $\nu cm^{-1}$: 3060, 1602, 1583.

NMR (CDCl$_3$) δ ppm: 2.81 (2H, m), 4.36 (1H, d, J=8.0), 5.48 (1H, ddd, J=2.6, 5.2 7.8), 5.76 (2H, m), 6.62 (1H, d, J=8.0), 7.19 (1H, dd, J=8.0, 2.0), 7.30 (1H d, J=2.0).

Mass: 236 (M$^+$), 238 (M+2).

REFERENTIAL EXAMPLE 12

3a,8b-cis-dihydro-3H-5-bromo-7-methylcyclopenta[b]benzofuran

Under argon atmosphere, 13.45 g of 3,5-cis-bis(2,6-dibromo-4-methylphenoxy)cyclopentene was placed in a 300 ml flask and dissolved in 100 ml of tetrahydrofuran, which was cooled to 40° C. To the resulting sultion, 55 ml of a tetrahydrofuran solution (0.83M) of cyclohexyl magnesium bromide was added dropwise over 45 minutes, and the resulting solution was stirred for 1 hour, 449 mg of cuprous iodide was added, the temperature was allowed to cool to room temperature, and the resulting mixture was stirred for 40 minutes. The reaction mixture was added to 100 ml of a vigrously stirred saturated aqueous solution of ammonium chloride, the resulting solution was extracted with ether (100 ml and 20 ml×3), the extracted liquid was washed with a 5% aqueous solution of sodium hydroxide (20 ml×3) and saturated brine (20 ml) and dried. After concentration, the obtained oily substance was purified by column chromatography (silica gel 300 g; cyclohexane/methylene chloride 100:1→20:1) to obtain 4,45 g (78%) of a white solid. When it was recrystallized from a cyclohexane-petroleum ether mixed solvent, 4.1 g of colorless needles (mp 182°-184° C.) was obtained.

IR (KBr) $\nu cm^{-1}$: 1605, 1585, 940, 780, 740, 710.

NMR (CDCl$_3$) δ: 2.22 (3H, s), 2.84 (2H, m), 4.38 (1H, d, J=8.0 Hz), 5.48 (1H, dt, J=8.0, 4.0 Hz), 5.72 (2H, m), 6.90 (1H, s), 7.03 (1H, s).

Mass: 250 (M$^+$), 252 (M+2).

In a similar manner, when instead of 3,5-cis-bis(2,6-dibromo-4-methylphenoxy)cyclopentene, 3,5-cis-bis(2-bromo-6-chloro-4-methylphenoxy)cyclopentene is employed, 3a,8b-cis-dihydro-3H-5-chloro-7-methylcyclopenta[b]benzofuran is obtained, and when 3,5-cis-bis(2-bromo-4-methylcyclopenta[b]benzofuran) is employed, 3,8b-cis-dihydro-3H-7-methylbenzofuran is obtained.

REFERENTIAL EXAMPLE 13

3a,8b-cis-dihydro-3H-5-bromo-7-chlorocyclopenta[b-]benzofuran

In a similar manner as in Referential Example 7, instead of 3,5-cis-bis-(2,6-dibromophenoxy)cyclopentene, 1.10 g of 3,5-cis-bis(2,6-dibromo-4-chlorophenoxy)cyclopentene was employed to obtain 211 mg of the subject compound.

IR (CHCl$_3$) $\nu$cm$^{-1}$: 3060, 1605.

Mass: 270 (M+), 272 (M+2), 274 (M+4).

In a similar manner, instead of 3,5-cis-bis(2,6-dibromo-4-chlorophenoxy)cyclopentene, when 3,5-cis-bis(2-bromo-4-chlorophenoxy)cyclopentene is employed, 3a,8b-cis-dihydro-3H-7-chlorocyclopenta[b-]benzofuran is obtained, and when 3,5-cis-bis(2-bromo-4,6-dichlorrophenoxy)cyclopentene is employed, 3a,8b-cis-dihydro-3H-5,7-dichlorocyclopenta[b]benzofuran is obtained.

REFERENTIAL EXAMPLE 14

3a,8b-cis-dihydro-3H-5-(4-tetrahydropyranyloxy-n-butyl)cyclopenta[b]benzofuran

To a solution of 150 mg (0.632 mmol) of 3a,8b-cis-dihydro-3H-5-bromocyclopenta[b]benzofuran in 7 ml of THF, was added dropwise at −78° C. 0.32 ml of n-butyl lithium (2.0M). After stirring the resulting solution for 15 minutes, 215 mg (0.758 mmol, 1.2 equiv.) of 4-iodobutyl-tetrahydropyranyl ether was added thereto, and the resulting mixture was stirred at −78° C. for 2 hours and at −12° C. for 2 hours, 5 ml of saturated brine was added and the mixture was extracted with 50 ml of ether. After drying, it was concentrated to obtain 230 mg of an oily crude product, which was purified by high-speed liquid chromatography to obtain 171 mg (86.2%) of the subject compound as an oily substance.

IR (liquid film method) $\nu$cm$^{-1}$: 3040, 2920, 1590, 748.

NMR (CDCl$_3$) $\delta$ ppm: 1.3–2.0 (m, 10H) 2.58 (t, 2H), 2.84 (m, 2H), 3.4 (m, 2H), 3.8 (m, 2H), 4.37 (d, 1H), 4.56 (s, 1H), 5.44 (m, 1H), 5.74 (s, 2H), 6.7–7.1 (m, 3H).

MS (m/e): 314 (M+), 230, 214, 171.

REFERENTIAL EXAMPLE 15

1,2,3a,8b-cis-tetrahydro-5-(4-tetrahydropyranyloxy-n-butyl)-1-exo-bromo-2-endo-hydroxy-cyclopenta[b]benzofuran To a solution of 720 mg (2.3 mmol) of 3a,8b-cis-dihydro-3H-5-(4-tetrahydropyranyloxy-n-butyl)-cyclopenta[b]benzofuran in a mixture of 20 ml of dimethyl sulfoxide/water (18/1) and 3 ml of THF, 573 mg (3.2 mmol, 1.4 equiv.) of N-bromosuccinimide was added, followed by stirring for 1.5 hours at 0°–5° C. 5 ml of saturated aqueous solution of sodium hydrogen carbonate was added thereto and the resultant mixture was extracted with 200 ml of ether, dried and concentrated. The resulting crude substance was purified by column chromatography to yield 459 mg of the captioned compound.

REFERENTIAL EXAMPLE 16

1,2,3a,8b-cis-tetrahydro-5-(4-tetrahydropyranyloxy-n-butyl)-1,2-syn-epoxy-3H-cyclopenta[b]benzofuran To a solution of 450 mg (1.09 mmol) of 1,2,3a,8b-cis-tetrahydro-5-(4-tetrahydropyranyloxy-n-butyl)-1-exo-bromo-2-endo-hydroxy-cyclopenta[b]benzofuran in 5 ml of methanol was added 322 mg of potassium carbonate and the mixture was stirred at 0° C. for 1.5 hours, methanol was distilled off under a reduced pressure therefrom, the remaining mixture was extracted with 20 ml of ether, dried and thereafter, concentrated. By column chromatography, 320 mg (0.97 mmol, 89%) of the subject compound was obtained.

IR (neat) $\nu$cm$^{-1}$: 3030, 2920, 1590, 1470, 1220, 1130, 965, 840, 745.

NMR (CDCl$_3$) $\delta$ ppm: 1.4–1.8 (m, 10H) 2.2 (dd, 1H), 2.5 (m, 3H), 3.5 (m, 2H), 3.64 (bs, 2H), 3.7 (m, 2H), 3.84 (d, 1H), 4.56 (bs, 1H), 5.3 (t, 1H), 6.7–7.3 (m 3H).

MS (m/e): 330 (M+), 246, 227.

REFERENTIAL EXAMPLE 17

1,2,3a,8b-cis-tetrahydro-5-(4-tetrahydropyranyloxy-n-butyl)-1-exo-(2-formylvinyl)-2-endo-hydroxy-3H-cyclopenta[b]benzofuran To a solution of 315 mg (0.95 mmol) of 1,2,3a,8b-cis-tetrahydro-5-(4-tetrahydropyranyloxy-n-butyl)-1,2-syn-epoxy-cyclopenta[b]benzofuran in 2 ml of THF at −78° C. was added solution of separately synthesized 1,3-bis(-methylthio)allyl anion (2.4 mmol) in THF.

The resulting solution was stirred for 2 hours, and 1 ml of methanol and 3 ml of a saturated aqueous solution of ammonium chloride was added and extracted with 100 ml of ether. The ether extract was dried over anhydrous sodium sulfate and concentrated.

2.7 g (10 mmol) of mercuric chloride, 1.6 g (1.6 mmol) of calcium carbonate, 12 ml of acetonitrile, 3 ml of water and 2 ml of THF, was added to the resulting oily substance and the resulting mixture was heated to 40° C. under argon atmosphere, which was stirred with heating overnight, the reaction solution was filtered, and the precipitate was washed with 50 ml of ether, the ether layer was washed with 10 ml of saturated brine, dried and thereafter purified by column chromatography to obtain 151 mg (41%) of the subject compound and 187 mg (51%) of the position isomer.

IR (neat) $\nu$cm$^{-1}$: 3600–3300, 2930, 1687, 1635, 1590, 750.

NMR (CDCl$_3$) $\delta$ ppm: 1.5–1.8 (m, 10H) 2.1 (m, 1H), 2.6 (m, 1H), 2.6 (t, 2H), 2.83 (q, 1H), 3.1 (bs, 1H), 3.4 (m, 2H), 3.62 (t, 1H), 3.8 (m, 2H), 4.1 (m, 1H), 4.56 (m, 1H) 5.2 (m, 1H), 6.24 (dd, 1H), 6.7–7.1 (m, 4H), 9.6 (d, 1H).

MS (m/e): 386 (M+), 302, 284.

REFERENTIAL EXAMPLE 18

3a,8b-cis-dihydro-3H-5-(4-tetrahydropyranyloxy-n-butyl)-7-methylcyclopenta[b]benzofuran To a solution of 507 mg (2.02 mmol) of 3a,8b-cis-dihydro-5-bromo-7-methylcyclopenta[b]benzofuran in 0.6 ml of THF at −20° C. under argon atmosphere, 2.15 ml (0.963M ether solution, 2.06 mmol) of phenyl lithium was added dropwise. After 1 hour a solution of 601 mg (2.11 mmol) of 4-iodobutyl tetrahydropyranyl ether in 2 ml of THF was added, and the resulting solution was stirred for 3 hours. Further, it was stirred for a time in which the temperature was allowed to raise to 15° C., thereafter, the reaction solution was added to 3 ml of a saturated aqueous solution of ammonium chloride, the solution was extracted from the water layer with ether (5 ml×5), the organic layer was dried and thereafter concentrated to obtain 904 mg of an oily substance, after it was purified by column chromatography (Merck Lobar Column B, cyclohexane:ethyl acetate 3:1), 537 mg (81%) of 2 in an oily state was obtained.

IR (neat) νcm⁻¹: 3060, 3010, 2930, 2860, 1610, 1210, 1080, 760, 720.

NMR (CDCl₃) δ: 1.64 (10H m), 2.24 (3H, s), 2.54 (2H, m), 2.78 (2H, m), 3.44 (2H, m), 3.80 (2H, m), 4.31 (1H, d, J=8.0 Hz), 4.56 (1H, m), 5.41 (1H, m) 5.72 (2H, m), 6.73 (1H, s), 6.83 (1H, s).

Mass (m/e): 328 (M⁺).

REFERENTIAL EXAMPLE 19

3a,8b,-cis-dihydro-3H-5-(4-tetrahydropyranyloxy-n-butyl)-7-bromocyclopenta[b]benzofuran In a similar manner as in Referential Example 18, 500 mg of 3a,8b-cis-dihydro-3H-5,7-dibromocyclopenta[b]benzofuran was employed instead of 3a,8b-cis-dihydro-3H-5-bromo-7-methylcyclopenta[b]benzofuran to obtain 200 mg of 3a,8b-cis-dihydro-3H-5-(4-tetrahydropyranyloxy-n-butyl)-7-bromocyclopenta[b]benzofuran.

IR (neat) νcm⁻¹: 3060, 2930, 1610, 760.

In a similar manner, when 3a,8b,-cis-dihydro-3H-5-bromo-7-chlorocyclopenta[b]benzofuran is employed instead of 3a,8b-cis-dihydro-3H-5,7-dihydrocyclopenta[b]benzofuran, 3a,6b-cis-dihydro-3H-5-(4-tetrahydropyranyloxy-n-butyl)-7-chlorocyclopenta[b]benzofuran is obtained.

REFERENTIAL EXAMPLE 20

3a,8b,-cis-dihydro-3H-5-(4-hydroxy-n-butyl)-7-bromocycropenta[b]benzofuran

To a solution of 260 mg of 3a,8b-cis-dihydro-3H-5-(4-tetrahydropyranyloxy-n-butyl)-7-bromocyclopenta[b]benzofuran in 2 ml of acetonitrile and 2 ml of THF, was added at 0° C. 2 ml of 1/10N hydrochloric acid, and the resulting solution was stirred at room temperature for 14 hours, triethyl amine and a saturated aqueous solution of sodium hydrogen carbonate was added, and the resulting mixture was extracted with ether 3 times. The combined ether layer were washed with saturated brine, dried and concentrated, to afford 348 mg of an oil substance. The oily substance was purified by column chromatography [(silica gel: cylcohexane:ethyl acetate (7:3)] to yield 140 mg of a pure product.

IR (neat) νcm⁻¹: 3600–2300, 1590, 1050, 750.

Mass (m/e): 308, 310 (M⁺).

In a similar manner, when instead of 3a,8b-cis-dihydro-3H-5-(4-tetrahydropyranyloxy-n-butyl)-7-bromocyclopenta[b]benzofuran, 3a,8b-cis-dihydro-3H-5-(4-tetrahydropyranyloxy-n-butyl)-7-methylcyclopenta[b]benzofuran is employed, 3a,8b-cis-dihydro-3H-5-(4-hydroxy-n-butyl)-7-methylcyclopenta[b]benzofuran is obtained, and 3a,8b-cis-dihydro-3H-5-(4-tetra-n-hydropyranyloxy-n-butyl)-7-chlorocyclopenta[b]benzofuran is employed, 3a,8b-cis-dihydro-3H-5-(4-hydroxy-n-butyl)-7-chlorocyclopenta[b]benzofuran is obtained.

REFERENTIAL EXAMPLE 21

3a,8b-cis-dihydro-3H-5-(3-carboxy-n-propyl)-7-bromocyclopenta[b]benzofuran

To a solution of 330 mg of 3a,8b-cis-dihydro-3H-5-(4-hydroxy-n-butyl)-7-bromocyclopenta[b]benzofuran in 7.5 ml of DMF was added 1.9 g of pyridinium dichromate, and the resulting mixture was stirred at room temperature for 14 hours. Water was added and the mixture was extracted with ether 5 times, the combined ether layers were washed with saturated brine, dried and concentrated to give 340 mg of an oil substance.

The oily substance was purified by column chromatography [silica gel (which had been treated with acetic acid); ethyl acetate:cyclohexane (1:1)] to afford 260 mg of a carboxylic acid.

IR (neat) νcm⁻¹: 3600–2300, 1705, 1605, 1580, 1190, 1000, 830, 710.

NMR (CDCl₃) δ: 1.94 (2H, quintet, J=7.0 Hz), 2.37 (2H, t, J=7.0 Hz), 2.62 (2H, t, J=7.0 Hz), 2.80 (2H, m), 4.38 (1H, d, J=7.0 Hz), 5.42 (1H, m), 5.64 (2H, m), 7.03 (1H, d, J=1.5 Hz), 7.16 (1H, d, J=1.5 Hz).

Mass (m/e): 322, 324 (M⁺).

In a similar manner, instead of 3a,8b-cis-dihydro-3H-5-(4-hydroxy-n-butyl)-7-bromocyclopenta[b]benzofuran, when 3a,8b-cis-dihydro-3H-5-(4-hydroxy-n-butyl)-7-chlorocyclopenta[b]benzofuran is employed, 3a,8b-cis-dihydro-3H-5-(3-carboxy-n-propyl)-7-chlorocyclopenta[b]benzofuran is obtained, and when 3a,8b-cis-dihydro-3H-5-(4-hydroxy-n-butyl)-7-methylcyclopenta[b]benzofuran is employed, 3a,8b-cis-dihydro-3H-5-(3-carboxy-n-propyl)-7-methylcyclopenta[b]benzofuran is obtained.

REFERENTIAL EXAMPLE 22

3a,8b-cis-dihydro-3H-5-(3-carbomethoxy-n-propyl)-7-bromocyclopenta[b]benzofuran

To a solution of 100 mg of 3a,8b-cis-dihydro-3H-5-(3-carboxy-n-propyl)-7-bromocyclopenta[b]benzofuran in 2 ml of ethyl acetate was added either solution of a large excess of diazomethane. The resulting solution was well stirred, allowed to stand for 5 minutes and concentrated to afford 102 mg of a roughly pure methyl ester.

IR (neat) νcm⁻¹: 1738, 1605, 1580, 1190, 1000, 830, 710.

NMR (CDCl₃) δ: 1.90 (2H, quintet, J=7.0 Hz), 2.30 (2H, t, J=7.0 Hz), 2.55 (2H, t, J=7.0 Hz), 2.80 (2H, m), 3.66 (3H, s), 4.35 (1H, m), 5.45 (1H, m), 5.65 (2H, m), 7.03 (1H, d, J=2.0 Hz), 7.16 (1H, d, J=2.0 Hz).

Mass (m/e): 336, 338 (M⁺).

Thereafter, in a similar manner, instead of 3a,8b-cis-dihydro-3H-5-(3-carboxy-n-propyl)-7-bromocyclopenta[b]benzofuran, when 3a,8b-cis-dihydro-3H-5-(3-carboxy-n-propyl)-7-chlorocyclopenta[b]benzofuran is employed, 3a,8b-cis-dihydro-3H-5-(3-carbomethoxy-n-propyl)-7-chlorocyclopenta[b]benzofuran is obtained, and when 3a,8b-cis-dihydro-3H-5-(3-carboxy-n-propyl)-7-methylcyclopenta[b]benzofuran is employed 3a,8b-cis-dihydro-3H-5-(3-carbomethoxy-n-propyl)-7-methylcyclopenta[b]benzofuran is obtained.

REFERENTIAL EXAMPLE 23

3a,8b-cis-dihydro-3H-5-(3-carboethoxy-n-propyl)-7-bromocyclopenta[b]benzofuran

In a similar manner as in Referential Example 22, but by using diazoethane instead of diazomethane, 102 mg of 3a,8b-cis-dihydro-3H-5-(3-carboethoxy-n-propyl)-7-bromocyclopenta[b]benzofuran was obtained from 100 mg of 3a,8b-cis-dihydro-3H-5-(3-carboxy-n-propyl)-7-bromocyclopenta[b]benzofuran.

IR (neat) νcm⁻¹: 1738, 1605, 1580, 1190, 1000, 830, 710.

Mass (m/e): 350, 352 (M⁺).

Thereafter, in a similar manner, instead of 3a,8b-cis-dihydro-3H-5-(3-carboxy-n-propyl)-7-bromocyclopenta[b]benzofuran, when 3a,8b-cis-dihydro-3H-5-(3-carboxy-n-propyl)-7-chlorocyclopenta[b]benzofuran is employed, 3a,8b-cis-dihydro-3H-5-(3-carboethoxy-n-propyl)-7-chlorocyclopenta[b]benzofuran is obtained, and when 3a,8b-cis-dihydro-3H-5-(3-carboxy-n-propyl)-7-methylcyclopenta[b]benzofuran is employed, 3a,8b-cis-dihydro-3H-5-(3-carboethoxy-n-propyl)-7-methylcyclopenta[b]benzofuran is obtained.

REFERENTIAL EXAMPLE 24

3a,8b-cis-dihydro-3H-5-(3-carbobenzyloxy-n-propyl)-7-bromocyclopenta[b]benzofuran To an ice-cooled solution of 150 mg of 3a,8b-cis-dihydro-3H-5-(3-carboxy-n-propyl)-7-bromocyclopenta[b]benzofuran in 5 ml of DMF, was added 0.05 ml of triethyl amine and 0.05 ml of benzyl bromide, and the resulting solution was stirred at room temperature for 14 hours. Ether was added, and the resulting mixture was washed with water and brine, dried and concentrated to afford 200 mg of an oily substance. The oily substance was purified by column chromatography [silica gel; cyclohexane:ethyl acetate (9.5:0.5)] to give 160 mg of pure product.

IR (neat) $\nu cm^{-1}$: 1738, 1605, 1585, 1190, 1000, 830, 710.

Mass (m/e): 412, 414 (M+).

Thereafter, in a similar manner, instead of 3a,8b-cis-dihydro-3H-5-(3-carboxy-n-propyl)-7-methylcyclopenta[b]benzofuran, when 3a,8b-cis-dihydro-3H-5-(3-carboxy-n-propyl)-7-chlorocyclopenta[b]benzofuran is employed, 3a,8b-cis-dihydro-3H-5-(3-carbobenzyloxy-n-propyl)-7-chlorocyclopenta[b]benzofuran is obtained, and when 3a,8b-cis-dihydro-3H-5-(3-carboxy-n-propyl)-7-methylcyclopenta[b]benzofuran is employed, 3a,8b-cis-dihydro-3H-5-(3-carbobenzyloxy-n-propyl)-7-methylcyclopenta[b]benzofuran is obtained.

REFERENTIAL EXAMPLE 25

3a,8b-cis-dihydro-3H-7-bromo-5-hydroxymethylcyclopenta[b]benzofuran

To a solution of 1.38 g (4.37 mmol) of 3a,8b-cis-dihydro-3H-5,7-dibromocyclopenta[b]benzofuran in 5 ml of tetrahydrofuran under argon atmosphere was added a solution of 10.0 ml (0.76M, 7.6 mmol, 1.7 equiv.) of cyclohexyl magnesium bromide in THF, and the resulting mixture was stirred at 40° C. for 2 hours. This solution was slowly added dropwise to a tetrahydrofuran solution of formaldehyde (which had been prepared from 21 g of para-formaldehyde) which had been cooled to −70° C. After the resulting solution was stirred at −78° C. for 30 minutes, white solids adhered to the vessel wall were smashed, 100 ml of water was added to the reaction solution, and the mixture was extracted with ethyl acetate (20 ml×5) and the extracts were dried over anhydrous sodium sulfate. After concentration, 150 mg of an oily crude product obtained was purified by column chromatography to give 913 mg (3.42 mmol, 78.2%) of a white solid. Recrystallization of the solid from 5 ml of cyclohexane petroleum ether (3:2) mixture afforded 800 mg of needles (mp 98°-102° C.)

IR (KBr) $\nu cm^{-1}$: 3300, 2980, 2930, 1180, 1010, 995, 945, 870, 830, 760, 710.

NMR (CDCl₃) δ: 2.16 (1H, s), 2.78 (2H, m), 4.34 (1H, d, J=8.0 Hz), 4.57 (2H, s), 5.49 (1H, m), 5.63 (2H, m), 7.22 (2H, s).

Mass (m/e): 266 (M+), 268.

Thereafter, in a similar manner, instead of 3a,8b-cis-dihydro-3H-5,7-dibromocyclopenta[b]benzofuran, when 3a,8b-cis-dihydro-3H-5-bromo-7-chlorocyclopenta[b]benzofuran is employed, 3a,8b-cis-dihydro-3H-7-chloro-5-hydroxymethylcyclopenta[b]benzofuran is obtained, and when 3a,8b-cis-dihydro-3H-5-bromo-7-methylcyclopenta[b]benzofuran is employed, 3a,8b-cis-dihydro-3H-5-hydroxymethyl-7-methylcyclopenta[b]benzofuran is obtained.

REFERENTIAL EXAMPLE 26

Methyl 3a,8b-cis-dihydro-3H-7-bromo-5-cyclopenta[b]benzofuranylmethyloxyacetate

To a suspension of 49.4 mg (2.06 mmol) of sodium hydride in 1 ml of dimethoxyethane, at 0° C. under argon atmosphere was added dropwise a solution of 256 mg (0.598 mmol) of 3a,8b-cis-dihydro-3H-7-bromo-5-hydroxymethyl-cyclopenta[b]benzofuran in 3 ml of DME and the resulting solution was stirred at 0° C. for 30 minutes. This solution was added to a solution of 456 mg (2.98 mmol) of methyl α-bromoacetate in 1 ml of a dimethoxyethane which had been cooled to −78° C. in advance, the temperature was raised to 0° C. and the resulting solution was stirred for 6 hours. 2 ml of a saturated aqueous solution of ammonium chloride was slowly added at 0° C., the resulting solution was extracted with ether (10 ml×3) and the extracts were dried over anhydrous sodium sulfate. 361 mg of an oily substance obtained after concentration was purified by column chromatography (Merck Co.'s Lobar Column, cyclohexane-ethyl acetate 4:1) to obtain 290.6 mg (0.957 mmol, 89.5%) of a white solid. Recrystallization from a cyclohexane-ethyl acetate mixture afforded 250 mg of needles (mp 81.5°-82.5° C.).

IR (KBr) $\nu cm^{-1}$: 2960, 2910, 1760, 1600, 1455, 1440, 1220, 1190, 1120, 995, 980, 940, 900, 870, 830, 760, 720.

NMR (CDCl₃) δ: 2.80 (2H, m), 3.76 (3H, s), 4.13 (2H, s), 4.36 (1H, d, J=8.0 Hz), 4.55 (1H, d, J=12.0 Hz), 4.57 (1H, d, J=12.0 Hz), 5.50 (1H, m), 5.76 (2H, m), 7.29 (2H, m).

Mass (m/e): 338, 340 (M+).

Thereafter, in a similar manner, instead of 3a,8b-cis-dihydro-3H-7-bromo-5-hydroxymethylcyclopenta[b]benzofuran, when 3a,8b-cis-dihydro-3H-7-chloro-5-hydroxymethyl-cyclopenta[b]benzofuran is employed, methyl 3a,8b-cis-dihydro-3H-7-chloro-5-cyclopenta[b]benzofuranylmethyl-oxyacetate is obtained, and when 3a,8b-cis-dihydro-3H-7-methyl-5-hydroxymethylcyclopenta[b]benzofuran is employed, methyl 3a,8b-cis-dihydro-3H-7-methyl-5-cyclopenta[b]benzofuranylmethyl-oxyacetate is obtained.

REFERENTIAL EXAMPLE 27

Methyl 3a,8b-cis-dihydro-3H-7-bromo-5-cyclopenta[b]benzofuranylmethyloxyacetate

To a suspension of 49.4 mg (2.06 mmol) of sodium hydride 1 ml of dimethoxy ethane at 0° C. under argon atmosphere to which was added dropwise solution of 256 mg (0.958 mmol) of 3a,8b-cis-dihydro-3H-7-bromo-5-hydroxymethylcyclopenta[b]benzofuran in 3 ml of dimethoxyehtane and the resulting solution was stirred at 0° C. for 30 minutes. This solution was added to a solution of 456 mg (2.98 mmol) of methyl α-bromocetate in 1 ml of dimethoxyethane which had been cooled to −78° C., the temperature was raised to 0° C. and the resulting solution was stirred for 6 hours. Two ml of a saturated aqueous solution of ammonium chloride was slowly added at 0° C., the solution was extracted with ether (10 ml×3) and the extracts were dried over anhydrous sodium sulfate. After concentration, 361 mg of an oily substance obtained was purified by column chromatography (Merck C.'s Lobar Column, cyclohexane-ethyl acetate 4:1) to give 290.6 mg (0.857 mmol, 89.5%) of a white solid 2. This solid was recrystallized from a cyclohexane—ethyl acetate mixture to yield 250 mg of needles (mp 81.5°–82.5° C.).

IR (KBr) $\nu$cm$^{-1}$: 2960, 2910, 1760, 1600, 1455, 1440, 1220, 1190, 1120, 995, 980, 940, 900, 870, 830, 760, 720.

NMR (CDCl$_3$) δ: 2.80 (2H, m), 3.76 (3H, s), 4.13 (2H, s), 4.36 (1H, d, J=8.0 Hz), 4.55 (1H, d, J=12.0 Hz), 4.57 (1H, d, J=12.0 Hz), 5.50 (1H, m), 5.76 (2H, m) 7.29 (2H, m).

Mass (M/e): 338, 340 (M+).

Thereafter, in a similar manner, instead of 3a,8b-cis-dihydro-3H-7-bromo-3-hydroxymethylcyclopenta[b]benzofuran, when 3a,8b-cis-dihydro-3H-7-chloro-5-hydroxymethylcyclopenta[b]benzofuran is employed, methyl 3a,8b-cis-dihydro-3H-7-chloro-5-cyclopenta[b]benzofuranylmethyloxyacetate is obtained, and when 3a,8b-cis-dihydro-3H-7-methyl-5-hydroxymethylcyclopenta[b]benzofuran is employed, methyl 3a,8b-cis-dihydro-3H-7-methyl-5-cyclopenta[b]benzofuranylmethyloxy-acetate is obtained.

REFERENTIAL EXAMPLE 28

Ethyl 3a,8b-cis-dihydro-3H-7-bromo-5-cyclopenta[b]benzofuranylmethyloxyacetate

In a similar manner as in Referential Example 27, when ethylbromoacetate was employed instead of methyl α-bromoacetate, from 250 mg of 3a,8b-cis-dihydro-3H-7-bromo-5-hydroxymethylcyclopenta[b]benzofuran, 250 mg of an ester body was obtained.

IR (neat) $\nu$cm$^{-1}$: 2960, 2915, 1760, 1600, 1455, 1220, 1190, 995, 980, 940, 900, 870, 760.

Mass (m/e): 352, 354 (M+).

Thereafter, in a similar manner, instead of 3a,8b-cis-dihydro-3H-7-bromo-5-hydroxymethylcyclopenta[b]benzofuran, when 3a,8b-cis-dihydro-3H-7-chloro-5-hydroxymethylcyclopenta[b]benzofuran is employed, ethyl 3a,8b-cis-dihydro-3H-7-chloro-5-cyclopenta[b]benzofuranylmethyloxyacetate is obtained, and when 3a,8b-cis-dihydro-3H-7-methyl-5-cyclopenta[b]benzofuran is employed, ethyl 3a,8b-cis-dihydro-3H-7-methyl-5-cyclopenta[b]benzofuranylmethyloxyacetate is obtained.

REFERENTIAL EXAMPLE 29

Benzyl 3a,8b-cis-dihydro-3H-7-bromo-5-cyclopenta[b]benzofuranylmethyloxyacetate

In a similar manner as in Referential Example 27, when benzyl α-bromoacetate was employed instead of methyl α-bromoacetate, from 250 mg of 3a,8b-cis-dihydro-3H-7-bromo-5-hydroxymethylcyclopenta[b]benzofuran, 260 mg of the subject compound was obtained.

IR (neat) $\nu$cm$^{-1}$: 2960, 2910, 1760, 1600, 1455, 1220, 1190, 995, 980, 830, 720.

Mass (m/e): 414,416 (M+).

Thereafter, in a similar manner, instead of 3a,8b-cis-dihydro-3H-7-bromo-5-hydroxymethylcyclopenta[b]benzofuran, when 3a,8b-cis-dihydro-3H-7-chloro-5-hydroxymethylcyclopenta[b]benzofuran is employed, 3a,8b-cis-dihydro-3H-7-chloro-cyclopenta[b]benzofuranylmethyloxyacetate is obtained, and when 3a,8b-cis-dihydro-3H-7-methyl-5-hydroxymethylcyclopenta[b]benzofuran is employed, benzyl 3a,8b-cis-dihydro-3H-7-methyl-5-cyclopenta[b]benzofuranylmethyloxy-acetate is obtained.

REFERENTIAL EXAMPLE 30

5-(3a,8b-cis-dihydro-3H-7-bromocyclopenta[b]benzofuranylmethyloxy)acetic acid

In a similar manner as in Referential Example 27, when sodium α-bromoacetate was employed instead of methyl α-bromoacetate, from 250 mg of 5-(3a,8b-cis-dihydro-3H-7-bromo-5-hydroxymethylcyclopenta[b]benzofuran, 250 mg of 5-(3a,8b-cis-dihydro-3H-7-bromo-cyclopenta[b]benzofuranylmethyloxy)acetic acid was obtained.

IR (neat) $\nu$cm$^{-1}$: 3600–2300, 1710, 1600, 1190, 1120, 995, 940, 830, 750.

Mass (m/e): 324, 326 (M+).

Thereafter, in a similar manner, instead of 3a,8b-cis-dihydro-3H-7-bromo-5-hydroxymethylcyclopenta[b]benzofuran, when 3a,8b-cis-dihydro-3H-7-chloro-5-hydroxymethylcyclopenta[b]benzofuran is employed, 5-(3a,8b-cis-dihydro-3H-7-chlorocyclopenta[b]benzofuranyl)methyloxyacetic acid is obtained, and when 3a,8b-cis-dihydro-3H-7-methyl-5-hydroxymethylcyclopenta[b]benzofuran is employed, 3a,8b-cis-dihydro-3H-7-methyl-5-cyclopenta[b]benzofuranylmethyloxyacetic acid is obtained.

REFERENTIAL EXAMPLE 31

3a,8b-cis-dihydro-3H-7-bromo-5-(2-hydroxyethyloxy)-methylcyclopenta[b]benzofuran To a suspension of 200 mg of lithium aluminium hydride in 5 ml of anhydrous THF, at 0° C. under argon atmosphere was added a solution of 200 mg of methyl 3a,8b-cis-dihydro-3H-7-bromo-5-cyclopenta[b]benzofuranylmethoxyacetate in 5 ml of anhydrous THF and the resulting mixture was stirred at room temperature for 2 hours. Ethyl acetate and a saturated aqueous solution of sodium potassium tartarate was added and the produced precipitate was filtered. The filtrate was dried and thereafter concentrated to give 200 mg of an oily substance. This oily substance was purified by column chromatography [silica gel; cyclohexane:ethyl acetate (1:7)] to yield 150 mg of the alcohol.

(IR (neat) $\nu$cm$^{-1}$: 3400, 1600, 1190, 1120, 1010, 995, 830, 730.

Mass (m/e): 310, 312 (M+).

Thereafter, in a similar manner, instead of methyl 3a,8b-cis-dihydro-3H-7-bromocyclopenta[b]benzofuranylmethoxyacetate, when methyl 3a,8b-cis-dihydro-3H-7-chloro-5-cyclopenta[b]benzofuranylmethoxyacete is employed, 3a,8b-cis-dihydro-3H-7-chloro-5-(2-hydroxyethyloxy)methylcyclopenta[b]benzofuran is obtained, and when methyl 3a,8b-cis-dihydro-3H-7-methyl-5-cyclopenta[b]benzofuranylmethoxyacetate is employed, 3a,8b-cis-dihydro-3H-7-methyl-5-(2-hydroxyethyloxy)methylcyclopenta[b]benzofuran was obtained.

REFERENTIAL EXAMPLE 32

3a,8b-cis-dihydro-3H-7-bromo-5-(2-tetrahydropyranyloxyethyloxy)methylcyclopenta[b]benzofuran To a solution of 500 mg of 3a,8b-cis-dihydro-3H-7-bromo-5-hydroxyethyloxymethylcyclopenta[b]benzofuran in 2.5 ml of methylene chloride, was added 400 mg of dihydropyran. 0.25 ml of a solution of 1.8 g of p-toluenesulfonic acid in 50 ml of THF dried with a molecular sieve was added to the above mentioned solution under ice cold conditions, and the resulting mixture was stirred at room temperature for 10 minutes.

Pyridine was added and the resulting mixture was stirred for 30 minutes, thereafter, washed with 50% brine and saturated brine and dried and concentrated to give 600 mg of an oily substance.

This oily substance was purified by column chromatography [silica gel; ethyl acetate:cyclohexane (4:1)] to yield 500 mg of an oily substance.

IR (neat) $\nu cm^{-1}$: 1590, 1440, 1340, 1065, 1010, 855, 810, 748.

Mass (m/e): 394, 396 (M+).

Thereafter, in a similar manner, instead of 3a,8b-cis-dihydro-3H-7-bromo-5-(2-hydroxyethyloxy)methylcyclopenta[b]benzofuran, when 3a,8b-cis-dihydro-3H-7-chloro-5-(2-hydroxyethyloxy)methylcyclopenta[b]benzofuran is employed, 3a,8b-cis-dihydro-3H-7-chloro-5-(2-tetrahydropyranyloxyethyloxy)methyloxycylopenta[b]benzofuran is obtained, and when 3a,8b-cis-dihydro-3H-7-methyl-5-(2-hydroxyethyloxy)methylcyclopenta[b]benzofuran is employed, 3a,8b-cis-dihydro-3H-7-methyl-5-(2-tetrahydropyranyloxyethyloxy)-methyl-cyclopenta[b]benzofuran is obtained.

REFERENTIAL EXAMPLE 33

Methyl 1,2,3a,8b-cis-tetrahydro-7-bromo-1,2-syn-epoxy-5-cyclopenta[b]benzofuranylmethyloxyacetate To a solution of 274 mg (0.809 mmol) of methyl 3a,8b-cis-dihydro-3H-7-bromocyclopenta[b]benzofuranylmethyloxyacetate in 5 ml of a dimethyl sulfoxide—water (19:1) mixture and 0.9 ml of tetrahydrofuran was added, 218 mg (1.11 mmol, 1.5 equiv.) of imide N-bromosuccinate and the resulting mixture was stirred at room temperature for 3.5 hours, subsequently, 330 mg (2.39 mmol, 3.0 equiv.) of potassium carbonate and 8 ml of methanol and 8 ml of water were added to make the resulting mixture homogeneous, which was further stirred for 15 hours. After the solvent was distilled off under reduced pressure, 4 ml of saturated brine was added and the mixture was extracted with ethyl acetate (20 ml × 5) and the extracts were dried over anhydrous sodium sulfate. After concentration 461 mg of an oily substance obtained was purified by column chromatography [Merck Co.'s Lobar Column: cyclohexane-ethyl acetate (1:2)] to give 185 mg of crude crystals. This crude crystals were recrystallized from an ethyl acetate—cyclohexane mixture to yield 150 mg of needles (mp 100°–102° C.).

IR (KBr) $\nu cm^{-1}$: 3050, 3950, 1760, 1600, 1455, 1190, 1140, 975, 870, 840, 760, 710.

NMR (CDCl$_3$) δ: 2.25 (1H, ddd, J=0.5 Hz, 7.0 Hz, 16.0 Hz), 2.45 (1H, d, J=16.0 Hz), 3.68 (3H, m), 3.73 (3H, s), 4.09 (2H, s), 4.50 (1H, d, J=12.0 Hz), 4.52 (1H, d J=12.0 Hz), 5.30 (1H, t, J=7.0 Hz), 7.31 (1H, d, J=2.0 Hz), 7.34 (1H, d, J=2.0 Hz).

Mass (m/e): 354, 356 (M+).

Thereafter, in a similar manner, instead of methyl 3a,8b-cis-dihydro-3H-7-bromo-5-cyclopenta[b]benzofuranylmethyloxyacetate, when methyl 3a,8b-cis-dihydro-3H-7-chloro-5-cyclopenta[b]benzofuranylmethyloxyacetate is employed, methyl 1,2,3a,8b-cis-tetrahydro-7-chloro-1,2-syn-epoxy-5-cyclopenta[b]benzofuranylmethyloxyacetate is obtained, and when methyl 3a,8b-cis-dihydro-3H-7-methyl-5-cyclopenta[b]benzofuranylmethyloxyacetate is employed, methyl 1,2,3a,8b-cis-tetrahydro-7-methyl-1,2-syn-epoxy-5-cyclopenta[b]benzofuranylmethyloxyacetate is obtained.

REFERENTIAL EXAMPLE 34

Ethyl 1,2,3a,8b-cis-tetrahydro-7-bromo-1,2-syn-epoxy-5-cyclopenta[b]benzofuranylmethyloxyacetate In a similar manner as in Referential Example 33, when 250 mg of ethyl 3a,8b-cis-dihydro-3H-7-bromo-5-cyclopenta[b]benzofuranylmethoxyacetate was employed instead of methyl 3a,8b-cis-dihydro-3H-7-bromo-5-cyclopenta[b]benzofuranylmethoxyacetate, 150 mg of ethyl 1,2,3a,8b-cis-tetrahydro-7-bromo-1,2-syn-epoxy-5-cyclopenta[b]benzofuranylmethyloxyacetate was obtained.

IR (neat) $\nu cm^{-1}$: 3050, 2950, 1760, 1600, 1455, 1190, 1140, 975, 870, 840, 760, 710.

Mass (m/e): 368, 370 (M+).

Thereafter, in a similar manner, instead of ethyl 3a,8b-cis-dihydro-3H-7-bromo-5-cyclopenta[b]benzofuranylmethoxyacetate, when ethyl 3a,8b-cis-dihydro-3H-7-chloro-5-cyclopenta[b]benzofuranylmethyloxyacete is employed, ethyl 1,2,3a,8b-cis-tetrahydro-7-chloro-1,2-syn-epoxy-5-cyclopenta[b]benzofuranylmethyloxyacetate is obtained, and when ethyl 3a8b-cis-dihydro-3H-7-methyl-5-cyclopenta[b]benzofuranylmethyloxyacetate is employed, ethyl 1,2,3a,8b-cis-tetrahydro-7-methyl-1,2-syn-epoxy-5-cyclopenta[b]benzofuranylmethyloxyacetate is obtained.

REFERENTIAL EXAMPLE 35

Benzyl 1,2,3a,8b-cis-tetrahydro-7-bromo-1,2-syn-epoxy-5-cyclopenta[b]benzofuranylmethyloxyacetate In a similar manner as in Referential Example 33, when 250 mg of benzyl 3a,8b-cis-dihydro-3H-7-bromo-5-cyclopenta[b]benzofuranylmethoxyacetate was employed instead of methyl 3a,8b-cis-dihydro-3H-7-bromo-5-cyclopenta[b]benzofuranylmethoxyacetate, 250 mg of benzyl 1,2,3a,8b-cis-tetrahydro-7-bromo-1,2-syn-epoxy-5-cyclopenta[b]benzofuranylmethyloxyacetate was obtained.

IR (neat) $\nu cm^{-1}$: 3050, 2950, 1760, 1600, 1190, 975, 870, 845, 760, 710.

Mass (m/e): 430, 432 (M+).

Thereafter, in the same manner, instead of benzyl 3a,8b-cis-dihydro-3H-7-bromo-5-cyclopenta[b]benzofuranylmethyloxyacetate, when benzyl 3a,8b-cis-dihydro-3H-7-chloro-5-cyclopenta[b]benzofuranylmethoxyacetate is employed, benzyl 1,2,3a8b-cis-tetrahydro-7-chloro-1,2-syn-epoxy-5-cyclopenta[b]benzofuranylmethyloxyacetate is obtained, and when benzyl 3a,8b-cis-dihydro-3H-7-methyl-5-cyclopenta[b]benzofuranylmethyloxyacetate is employed, benzyl 1,2,3a,8b-cis-tetrahydro-7-methyl-1,2-syn-epoxy-5-cyclopenta[b]benzofuranylmethyloxyacetate is obtained.

REFERENTIAL EXAMPLE 36

1,2,3a,8b-cis-tetrahydro-7-bromo-1,2-syn-epoxy-5-hydroxyethyloxymethylcyclopenta[b]benzofuran In the same manner as in Referential Example 33, when 200 mg of 3a,8b-cis-dihydro-3H-7-bromo-5-hydroxyethyloxymethylcyclopenta[b]benzofuran is employed instead of methyl 3a,8b-cis-dihydro-3H-7-bromo-5-cyclopenta[b]benzofuranylmethyloxyacetate, 150 mg of 1,2,3a,8b-cis-tetrahydro-7-bromo-1,2-syn-epoxy-5-hydroxyethyloxymethylcyclopenta[b]benzofuran is obtained.

IR (neat) νcm⁻¹: 3400, 1600, 1190, 1120, 1010, 995, 850, 830, 730.

Mass (m/e): 326, 328 (M+).

Thereafter, in a similar manner, instead of 3a,8b-cis-dihydro-3H-7-bromo-5-hydroxyethyloxymethylcyclopenta[b]benzofuran, when 3a8b-cis-dihydro-3H-7-chloro-5-hydroxyethyloxymethylcyclopenta[b]benzofuran is employed, 1,2,3a,8b-cis-tetrahydro-7-chloro-1,2-syn-epoxy-5-hydroxyethyloxymethylcyclopenta[b]benzofuran is obtained, and when 3a,8b-cis-dihydro-3H-7-methyl-5-hydroxyethylcyclopenta[b]benzofuran is employed, 1,2,3a,8b-cis-tetrahydro-7-methyl-1,2-syn-epoxy-5-hydroxyethyloxymethylcyclopenta[b]benzofuran is obtained.

REFERENTIAL EXAMPLE 37

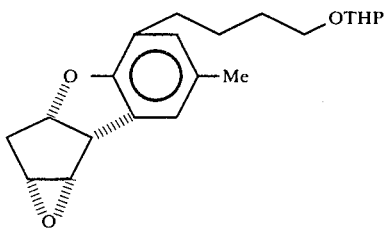

1,2,3a,8b-cis-tetrahydro-5-(4-tetrahydropyranyloxy-n-butyl)-7-methyl-1,2-syn-epoxycyclopenta[b]benzofuran To a solution of 9.13 g (27.8 mmol) of 3a,8b-cis-dihydro-3H-5-(4-tetrahydropyranyloxy-n-butyl)-7-methyl-cyclopenta[b]benzofuran in 230 ml of a dimethyl sulfoxide-water (18:1) mixture was added 40 ml of THF and 26.7 g (150 mmol, 5.4 equiv.) of imide N-bromosuccinate, and the resulting mixture was stirred at 0°-5° C. for 1 hour.

After confirming the loss of the starting material by TLC, 100 ml of methanol and 70 ml of water and 41.0 g (297 mmol, 10.7 equiv.) of potassium carbonate were added, and the resulting mixture was stirred at room temperature for 2.5 hours. After distilling off the solvent at a temperature less than 50° C., 100 ml of saturated brine was added and the mixture was extracted with 250 ml (50 ml×5) of ether, the combined organic layers were washed with 50 ml of saturated brine. After distilling off the solvent, when the resulting residue was purified by column chromatography (Merck silica gel, Art 7734 500 g, cyclohexane:ethyl acetate 50:1→3:1), 8.08 g of an oily substance was obtained.

IR (neat) νcm⁻¹: 3020, 2930, 2860, 1610, 1475, 1215, 1200, 1140, 1120, 1035, 870, 850, 780, 740.

NMR (CDCl₃) δ: 1.64 (10H, m), 1.98 (1H, ddd, J=15.0 Hz, 3.0 Hz, 2.0 Hz), 2.28 (3H, s), 2.55 (2H, m), 2.62 (1H, dd, J=1.50 Hz, 8.0 Hz), 3.45 (2H, m), 3.52 (1H, t, J=2.0 Hz), 3.69 (1H, d, J=2.0 Hz), 3.82 (2H, m), 4.11 (1H, d, J=8.0 Hz), 4.58 (1H, m), 4.99 (1H, dt, J=8.0 Hz, 3.0 Hz), 6.82 (1H, s), 6.90 (1H, s).

Mass (m/e): 344 (M+).

REFERENTIAL EXAMPLE 38

1,2,3a,8b-cis-tetrahydro-5-(4-tetrahydropyranyloxy-n-butyl)-7-bormo-1,2-syn-epoxycyclopenta[b]benzofuran In a similar manner as in Referential Example 37, from 1 g of 3a,8b-cis-dihydro-3H-5-(4-tetrahydropyranyloxy-n-butyl)-7-bromocyclopenta[b]benzofuran, 800 mg of 1,2,3a,8b-cis-tetrahydro-3H-5-(4-tetrahydropyranyloxy-n-butyl)-7-bromo-1,2-syn-epoxycyclopenta[a]benzofuran was obtained.

IR (neat) νcm⁻¹: 1605, 1590, 1195, 1035, 845, 735, 755.

NMR (CDCl₃) δ: 1.4~1.8 (10H, m,), 2.50 (3H, m), 3.40 (2H, m), 3.64 (4H, m), 3.80 (2H, m) 4.60 (1H, m), 5.34 (1H, t, J=8.0 Hz), 7.12 (1H, d, J=20 Hz), 7.21 (1H, d, J=2.0 Hz).

Mass (m/e): 408, 410 (M+).

Thereafter, in a similar manner, when 3a,8b-cis-dihydro-3H-5-(4-tetrahydropyranyloxy-n-butyl)-7-chlorocyclopenta[b]benzofuran is employed instead of 3a,8b-cis-dihydro-3H-5-(tetrahydropyranyloxy-butyl)-7-bromocyclopenta[b]benzofuran, 1,2,3a,8b-cis-tetrahydro-5-(4-tetrahydropyranyloxy-n-butyl)-7-chloro-1,2-syn-epoxycyclopenta[b]benzofuran is obtained.

REFERENTIAL EXAMPLE 39

1,2,3a,8b-cis-tetrahydro-5-tetrahydropyranyloxyethyloxymethyl-7-bromo-1,2-syn-epoxycyclopenta[b]benzofuran In a similar manner as in Referential Example 37, from 1 g of 3a,8b-cis-dihydro-3H-5-tetrahydropyranyloxyethyloxymethyl-7-bromo-cyclopenta[b]benzofuran, 800 mg of the subject compound was obtained.

IR (neat) νcm⁻¹: 1605, 1590, 1195, 1035, 845, 735, 755.

Mass (m/e): 410, 412 (M+).

Thereafter, in a similar manner, instead of 3a,8b-cis-dihydro-3H-tetrahydropyranyloxyethyloxymethyl-7-bromocyclopenta[b]benzofuran, when 3a,8b-cis-dihydro-3H-5-tetrahydropyranyloxyetthyloxymethyl-7-chlorocyclopenta[b]benzofuran is employed, 1,2,3a,8b-cis-tetrahydro-5-tetrahydropyranyloxyethyloxymethyl-7-chloro-1,2-syn-epoxycyclopenta[b]benzofuran is obtained, and when 3a,8b-cis-dihydro-3H-5-tetrahydropyranyloxyethyloxy-7-methylcyclopenta[b]benzofuran is employed, 1,2,3a,8b-cis-tetrahydro-5-tetrahydropyranyloxyethyloxymethyl-7-methyl-1,2-syn-epoxycyclopenta[b]benzofuran is obtained.

REFERENTIAL EXAMPLE 40

1,2,3a,8b-cis-tetrahydro-5-(4-hydroxy-n-butyl)-7-bromo-1,2-syn-epoxycyclopenta[b]benzofuran In a similar manner as in Referential Example 37, from 1 g of 3a,8b-cis-dihydro-3H-5-(4-hydroxy-n-butyl)-7-bromocyclopenta[b]benzofuran, 700 mg of the subject compound was obtained.

IR (neat) νcm⁻¹: 3400, 1600, 1190, 1010, 850, 730.

NMR (CDCl₃) δ: 1.4~1.9 (5H, m), 2.22 (1H, dd, J=16.0 Hz, 6.6 Hz), 2.50 (3H, m) 3.40-4.00 (5H, m), 5.32 (1H, t, J=8.0 Hz), 7.10 (1H, d, J=2.0 Hz), 7.20 (1H, d, J=2.0 Hz).

Mass (m/e): 324, 326 (M+).

Thereafter, in a similar manner, instead of 3a,8b-cis-dihydro-3H-5-(4-hydroxy-n-butyl)-7-bromocyclopenta[b]benzofuran, when 3a,8b-cis-dihydro-3H-5-(4- hydroxy-n-butyl)-7-chlorocyclopenta[b]benzofuran is employed, 1,2,3a,8b-cis-tetrahydro-5-(4-hydroxy-n-butyl)-7-chloro-1,2-syn-epoxycyclopenta[b]benzofuran is obtained, and when 3a,8b-cis-dihydro-3H-5-(4-hydroxy-n-butyl)-7-methylcyclopenta[b]benzofuran is employed, 1,2,3a,8b-cis-tetrahydro-5-(4-hydroxy-n-butyl)-7-methyl-1,2-syn-epoxycyclopenta[b]benzofuran is obtained.

REFERENTIAL EXAMPLE 41

1,2,3a,8b-cis-tetrahydro-5-(3-carbomethyoxy-n-propyl)-7-bromo-1,2-syn-epoxycyclopenta[b]benzofuran In a similar manner as in Referential Example 37, from 1 g of 3a,8b-cis-dihydro-3H-5-(3-carbomethoxy-n-propyl)-7-bromo-cyclopenta[b]benzofuran, 700 mg of the epoxide was obtained.

IR (neat) $\nu cm^{-1}$: 1738, 1605, 1580, 1190, 1000, 850, 710.

Mass (m/e): 352, 354 (M+).

Thereafter, in a similar manner, instead of 3a,8b-cis-dihydro-3H-5-(3-carbomethoxy-n-propyl)-7-bromocyclopenta[b]benzofuran, when 3a,8b-cis-dihydro-3H-5-(3-carbomethoxy-n-propyl)-7-chlorocyclopenta[b]benzofuran is employed, 1,2,3a,8b-cis-tetrahydro-5-(3-carbomethoxy-n-propyl)-7-chloro-1,2-syn-epoxycyclopenta[b]benzofuran is obtained, and when 3a,8b-cis-dihydro-3H-5-(3-carbomethoxy-n-propyl)-7-methyl cyclopenta[b]benzofuran is employed, 1,2,3a,8b-cis-tetrahydro-5-(3-carbomethoxy-n-propyl)-7-methyl-1,2-syn-epoxycyclopenta[b]benzofuran is obtained.

REFERENTIAL EXAMPLE 42

1,2,3a,8b-cis-tetrahydro-5-(3-carboethoxy-n-propyl)-7-bromo-1,2-syn-epoxycyclopenta[b]benzofuran In a similar manner as in Referential Example 37, from 1 g of 3a,b 8b-cis-dihydro-3H-5-(3-carboethoxy-n-propyl)-7-bromocyclopenta[b]benzofuran, 800 mg of the epoxide was obtained.

IR (neat) $\nu cm^{-1}$: 1738, 1605, 1580, 1190, 1000, 850, 710.

Mass (m/e): 366, 368 (M+).

Thereafter, in a similar manner, from 3a,8b-cis-dihydro-3H-5-(3-carboethoxy-n-propyl)-7-chlorocyclopenta[b]benzofuran, 1,2,3a,8b-cis-tetrahydro-5-(3-carboethoxy-n-propyl)-7-chloro-1,2-syn-epoxycyclopenta[b]benzofuran is obtained, and from 3a,8b-cis-dihydro-3H-5-(3-carboethoxy-n-propyl)-7-methylcyclopenta[b]benzofuran, 1,2,3a,8b-cis-tetrahydro-5-(3-carboethoxy-n-propyl)-7-methyl-1,2-syn-epoxycyclopenta[b]benzofuran is obtained.

REFERENTIAL EXAMPLE 43

1,2,3a,8b-cis-tetrahydro-5-(3-carbobenzyloxy-n-propyl)-7-bromo-1,2-syn-epoxycyclopenta[b]benzofuran In a similar manner as in Referential Example 37, from 1 g of 3a,8b-cis-dihydro-3H-5-(3-carbobenzyloxy-n-propyl)-7-bromocyclopenta[b]benzofuran, 700 mg of the epoxide was obtained.

IR (neat) $\nu cm^{-1}$: 1739, 1609, 1580, 1190, 1000, 890, 710.

Mass (m/e): 428, 430 (M+).

Thereafter, in a similar manner, from 3a,8b-cis-dihydro-3H-5-(3-carbobenzyloxy-n-propyl)-7-chlorocyclopenta[b]benzofuran, 1,2,3a,8b-cis-tetrahydro-5-(3-carbobenzyloxy-n-propyl)-7-chloro-1,2-syn-epoxycyclopenta[b]benzofuran is obtained, and from 3a,8b-cis-dihydro-3H-5-(3-carbobenzyloxy-n-propyl)-7-methylcyclopenta[b]benzofuran, 1,2,3a,8b-cis-tetrahydro-5-(3-carbobenzyloxy-n-propyl)-7-methyl-1,2-syn-epoxycyclopenta[b]benzofuran is obtained.

REFERENTIAL EXAMPLE 44

1,2,3a,8b-cis-tetrahydro-5-(3-carboxy-n-propyl)-7-bromo-1,2-syn-epoxycyclopenta[b]benzofuran To a solution of 250 mg of 3a,8b-cis-dihydro-3H-5-(3-carboxy-n-propyl)-7-bromocyclopenta[b]benzofuran in 5 ml of a DMSO-Water (19:1) mixture and 0.5 ml of THF, was added 218 mg of NBS and the resulting mixture was stirred at room temperature for 3.5 hours. To the mixture were added 330 mg of potassium carbonate, 8 ml of methanol and 8 ml of water and the resulting mixture was further stirred for 15 hours. The reaction mixture was concentrated, water was added and the PH value of the mixture was adjusted to 3-4 with 1N hydrochloric acid under ice cold conditions and the mixture was extracted 3 times with ethyl acetate. The combined organic layer was washed with water and saturated brine, dried and thereafter, when it was concentrated, 460 mg of an oily substance was obtained. When this oily substance was purified by column chromatography [silica gel (which had been treated with acetic acid): ethyl acetate:cyclohexane (2:1)], 170 mg of the subject compound was obtained.

IR (neat) $\nu cm^{-1}$: 3600-2300, 1705, 1605, 1585, 1190, 1000, 850, 710.

NMR (CDCl$_3$) δ: 1.95 (2H, m) 2.30 (2H, t, J=7.0 Hz), 2.55 (2H, t, J=7.0 Hz), 2.10–2.60 (2H, m), 3.66 (2H, s), 3.72 (1H, m), 5.25 (1H, t, J=7.0 Hz), 7.07 (1H, d, J=1.5 Hz), 7.25 (1H, d, J=1.5 Hz).

Mass (m/e): 338, 340 (M+).

Thereafter, in a similar manner, when 3a,8b-cis-dihydro-3H-5-(3-carboxy-n-propyl)-7-chlorocyclopenta[b]benzofuran is employed, 1,2,3a,8b-cis-tetrahydro-5-(3-carboxy-n-propyl)-7-chloro-1,2-syn-epoxycyclopenta[b]benzofuran is obtained, and when 3a,8b-cis-dihydro-3H-5-(3-carboxy-n-propyl)-7-methylcyclopenta[b]benzofuran is employed, 1,2,3a,8b-cis-tetrahydro-5-(3-carboxy-n-propyl)-7-methyl-1,2-syn-epoxycyclopenta[b]benzofuran is obtained.

REFERENTIAL EXAMPLE 45

1,2,3a,8b-cis-tetrahydro-7-bromo-1,2-syn-epoxy-5-cyclopenta[b]benzofuranylmethyloxyacetic acid In a similar manner as in Referrential Example 44, from 250 mg of 5-(3a,8b-cis-dihydro-3H-7-bromocyclopenta[b]benzofuranylmethoxy) acetic acid, 150 mg of the subject compound was obtained.

IR (neat) $\nu cm^{-1}$: 3600-2300, 1705, 1605, 1585, 1190, 1140, 1050, 1000, 845, 710.

Mass (m/e): 340, 342 (M+).

Thereafter, in a similar manner, from 3a,8b-cis-dihydro-3H-7-chloro-5-cyclopenta[b]benzofuranylmethyloxyacetic acid, 1,2,3a,8b-cis-tetrahydro-7-chloro-1,2-syn-epoxy-5-cyclopenta[b]benzofuranyl methyloxyacetic acid was obtained, and from 3a,8b-cis-dihydro-3H-7-methyl-5-cyclopenta[b]benzofuranylmethyloxyacetic acid, 1,2,3a,8b-cis-tetrahydro-7-methyl-1,2-syn-epoxycyclopenta[b]benzofuranylmethyloxy acetic acid was obtained.

REFERENTIAL EXAMPLE 46

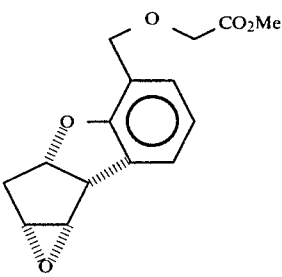

Methyl 1,2,3a,8b-cis-tetrahydro-1,2-syn-epoxycyclopenta[b]benzofuranylmethyloxyacetate To a solution of 247 mg (0.695 mmol) of methyl 1,2,3a,8b-cis-tetrahydro-7-bromo-1,2-syn-epoxy-5-cyclopenta[b]benzofuranylmethoxyacetate and 205 mg (2.45 mmol) of sodium acetate in 30 ml of methanol was added 147 mg of 5% palladium-barium sulfate, and the resulting mixture was vigorously stirred at room temperature under hydrogen atomosphere for 1.5 hours. Palladium was removed by filtration, methanol was distilled off under reduced pressure, 5 ml of saturated brine and 5 ml of a saturated aqueous solution of sodium bicarbonate was added, and the mixture was extracted with ethyl acetate (10 ml×5). The combined extracts were dried over anhyrous sodium sulfate. After concentration, when 200 mg of an oily substance obtained was purified by column chromatography (Merck Co.'s Lobar Column; cyclohexane-ethyl acetate 1:2), 183 mg of a white solid was obtained. This solid was recrystallized from a cyclohexane-ether mixture to yield 150 mg of the subject compound as needles (mp 60°–62° C.).

IR (KBr) $\nu cm^{-1}$: 3020, 2950, 1750, 1600, 1260, 1120, 1030, 1000, 970, 860, 845, 780, 755.

NMR (CDCl$_3$) δ: 2.29 (1H, dd, J=15.0 Hz, 7.0 Hz), 2.50 (1H, d, J=16.0 Hz), 3.72 (3H, m), 3.74 (3H, s), 4.10 (2H, s), 4.59 (1H, t, J=12.0 Hz), 4.62 (1H, d, J=12.0 Hz), 5.35 (1H, t, J=7.0 Hz), 6.87 (1H, dd, J=8.0 Hz, 6.0 Hz), 7.23 (1H, d, J=6.0 Hz), 7.24 (1H, d, J=8.0 Hz).

Mass (m/e): 276 (M+).

REFERENTIAL EXAMPLE 47

Ethyl 1,2,3a,8b-cis-tetrahydro-1,2-syn-epoxycyclopenta[b]benzofuranylmethyloxyacetate In a similar manner as in Referential Example 46, from 250 mg of ethyl 3a,8b-cis-tetrahydro-7-bromo-1,2-syn-epoxy-5-cyclopenta[b]benzofuranylmethyloxyacetate, 153 mg of the debrominated compound was obtained.

IR (neat) $\nu cm^{-1}$: 3020, 2950, 1760, 1600, 1260, 1030, 970, 845, 860, 780.

Mass (m/e): 290 (M+).

REFERENTIAL EXAMPLE 48

Benzyl 1,2,3a,8b-cis-tetrahydro-1,2-syn-epoxycyclopenta[b]benzofuranylmethyloxyacetate In a similar manner as in Referential Example 46, from 250 mg of benzyl 1,2,3a,8b-cis-tetrahydro-7-bromo-1,2-syn-epoxycyclopenta[b]benzofuranylmethoxyacetate, 120 mg of the debrominated compound was obtained.

IR (neat) $\nu cm^{-1}$: 3020, 2950, 1760, 1600, 1260, 1120, 1030, 970, 845, 780.

Mass (m/e): 352 (M+).

REFERENTIAL EXAMPLE 49

1,2,3a,8b-cis-tetrahydro-1,2-syn-epoxy-5-hydroxyethyloxymethylcyclopenta[b]benzofuran In a similar manner as in Referential Example 46, from 250 mg of 1,2,3a,8b-cis-tetrahydro-7-bromo-1,2-syn-epoxy-5-hydroxyethyloxymethylcyclopenta[b]benzofuran, 150 mg of the debrominated compound was obtained.

IR (neat) $\nu cm^{-1}$: 3400, 1600, 1190, 1120, 1010, 995 850, 830, 730.

Mass (m/e): 248 (M+).

REFERENTIAL EXAMPLE 50

1,2,3a8b-cis-tetrahydro-5-tetrahydropyranyloxyethyloxymethyl-1,2-syn-epoxycyclopenta[b]benzofuran In a similar manner as in Referential Example 46, from 250 mg of 1,2,3a,8b-cis-tetrahydro-5-tetrahydropyranyloxyethyloxymethyl-7-bromo-1,2-syn-epoxycyclopenta[b]benzofuran, 120 mg of the debrominated compound was obtained.

IR (neat) $\nu cm^{-1}$: 1605, 1590, 1195, 1035, 845, 735, 755.

Mass (m/e): 332 (M+).

REFERENTIAL EXAMPLE 51

1,2,3a,8b-cis-tetrahydro-5-(3-carbomethoxy-n-propyl)-1,2-syn-epoxycyclopenta[b]benzofuran In a similar manner as in Referential Example 46, from 250 mg of 1,2,3a,8b-cis-tetrahydro-5-(3-carbomethoxy-n-propyl)-7-bromo-1,2-syn-epoxycyclopenta[b]benzofuran, 140 mg of the debrominated compound was obtained.

IR (neat) $\nu cm^{-1}$: 1738, 1605, 1580, 1190, 1000, 850, 710.

NMR (CDCl$_3$) δ: 1.60 (2H, m) 1.90 (2H, t, J=7.0 Hz), 2.00–2.70 (4H, m), 3.62 (3H, s), 3.68 (2H, s), 3.77 (1H, d, J=8.0 Hz), 5.20 (1H, t, J=7.0 Hz), 6.80 (1H, t, J=7.0 Hz), 7.04 (1H, dd, J=7.0 Hz, 1.5 Hz), 7.14 (1H, dd, J=7.0 Hz, 1.5 Hz).

Mass (m/e): 274 (M+).

REFERENTIAL EXAMPLE 52

1,2,3a,8b-cis-tetrahydro-5-(3-carboethoxy-n-propyl)-1,2-syn-epoxycyclopenta[b]benzofuran In a similar manner as in Referential Example 46, from 250 mg of 1,2,3a,8b-cis-tetrahydro-5-(3-carboethoxy-n-propyl)-7-bromo-1,2-syn-epoxycyclopenta[b]benzofuran, 160 mg of the debrominated compound was obtained.

IR (neat) $\nu cm^{-1}$: 1738, 1605, 1580, 1000, 850, 710.

Mass (m/e): 288 (M+).

REFERENTIAL EXAMPLE 53

1,2,3a,8b-cis-tetrahydro-5-(3-carbobenzyloxy-n-propyl)-1,2-syn-epoxycyclopenta[b]benzofuran In a similar manner as in Referential Example 46, from 250 mg of 1,2,3a,8b-cis-tetrahydro-5-(3-carbobenzyloxy-n-propyl)-7-bromo-1,2-syn-epoxycyclopenta[b]benzofuran, 100 mg of the debrominated compound was obtained.

IR (neat) νcm$^{-1}$: 1738, 1605, 1580, 1000, 850, 710.
Mass (m/e): 350 (M+).

REFERENTIAL EXAMPLE 54

1,2,3a,8b-cis-tetrahydro-5-(4-hydroxy-n-butyl)-1,2-syn-epoxycyclopenta[b]benzofuran In a similar manner as in Referential Example 46, from 250 mg of 1,2,3a,8b-cis-tetrahydro-5-(4-hydroxy-n-butyl)-7-bromo-1,2-syn-epoxy-cyclopenta[b]benzofuran, 160 mg of the debrominated compound was obtained.

IR (neat) νcm$^{-1}$: 3400, 1600, 1190, 1010, 850, 730.
Mass (m/e): 246 (M+).

REFERENTIAL EXAMPLE 55

1,2,3a,8b-cis-tetrahydro-5-(4-tetrahydropyranyloxy-n-butyl)-1,2-syn-epoxycyclopenta[b]benzofuran In a similar manner as in Referential Example 46, from 250 mg of 1,2,3a-8b-cis-tetrahydro-5-(4-tetrahydropyranyloxy-n-butyl)-7-bromo-1,2-syn-epoxycyclopenta[b]benzofuran, 150 mg of the debrominated compound was obtained.

IR (neat) νcm$^{-1}$: 3030, 2920, 2850, 1590, 1470, 1445, 1220, 1180, 1130, 1110, 1065, 1025, 965, 840, 745.

(NMR (CDCl$_3$) δ: 1.40–1.80 (10H, m), 2.20 (1H, dd, J=160 Hz, 6.6 Hz), 2.50 (3H, m), 3.50 (2H, m), 3.64 (2H, m), 3.70 (2H, m), 3.84 (1H, m), 4.56 (1H, s), 5.30 (1H, t, J=8.0 Hz), 6.70–7.30 (3H, m).

Mass (m/e): 330 (M+).

REFERENTIAL EXAMPLE 56

1,2,3a,8b-cis-tetrahydro-5-(3-carboxy-n-propyl)-1,2-syn-epoxycyclopenta[b]benzofuran To a solution of 250 mg of 1,2,3a,8b-cis-tetrahydro-3H-5-(3-carboxy-n-propyl)-7-bromo-1,2-syn-epoxycyclopenta[b]benzofuran in 30 ml of methanol, were added 205 mg of sodium acetate and 147 mg of 5% palladium-barium sulfate, and the resulting mixture was stirred at room temperature under H$_2$ atmosphere for 1.5 hours. Palladium was filtered, the filtrate was concentrated, water was added, and the pH of the mixture was adjusted to 3–4 with 0.5M hydrochloric acid under ice cold conditions. The mixture was extracted 3 times with ethyl acetate and the combined organic layer was washed with water and saturated brine, dried, and thereafter concentrated to give 180 mg of an oily substance. This oily substance was purified by column chromatography [silica gel (which had been treated with acetic acid); cyclohexane:acetic acid (1:2)] to yield 150 mg of the pure carboxylic acid.

IR (neat) νcm$^{-1}$: 3600–2300, 1705, 1590, 1185, 850.

NMR (CDCl$_3$) δ: 1.95 (2H, m) 2.30 (2H, t, J=7.0 Hz), 2.55 (2H, t, J=7.0 Hz), 2.10–2.60 (2H, m), 3.66 (2H, s), 3.72 (1H, m), 5.25 (1H, t, J=7.0 Hz), 6.78 (1H, t, J=7.0 Hz), 6.94 (1H, dd, J=7.0 Hz, 1.2 Hz), 7.20 (1H, dd, J=7.0 Hz, 1.2 Hz).

Mass (m/e): 260 (M+).

REFERENTIAL EXAMPLE 57

5-(1,2,3a,8b-cis-tetrahydro-1,2-syn-epoxycyclopenta[b]benzofuranylmethoxy)acetic acid In a similar manner as in Referential Example 56, from 250 mg of 5-(1,2,3a,8b-cis-tetrahydro-7-bromo-1,2-syn-epoxycyclopenta[b]benzofuranylmethoxy)acetic acid, 160 mg of the debrominated compound was obtained.

IR (neat) νcm$^{-1}$: 3600–2300, 1705, 1590, 1185, 850.
Mass (m/e): 262 (M+).

REFERENTIAL EXAMPLE 58

Preparation of 3a,8b-cis-dihydro-3H-5-carbomethoxycyclopenta[b]benzofuran

To a stirred solution 3 g of 3a,8b-cis-dihydro-3H-5-bromo-cyclopenta[b]benzofuran in 60 ml of anhydrous THF, at −78° C. under argon atmosphere added dropwise 10.2 ml of n-butyl lithium (1.5N), and the resulting solution was stirred at −78° C. for 35 minutes, while carbon dioxide generated from dry ice was being passed thereinto. The temperature was gradually raised to −10° C., the solution was stirred at −10° C. for 1 hour. Solid ammonium chloride was added, the resulting mixture was stirred at room temperature for 5 minutes and thereafter THF was removed under reduced pressure. Benzene was added, the mixture was washed once with a saturated aqueous solution of sodium hydrogen carbonate and 2 times with water, thereafter, the pH value of the combined water layer was adjusted to 2 with 2N hydrochloric acid and the mixture was extracted 3 times with ethyl acetate. The combined ethyl acetate layers were washed with water and saturated brine, dired and thereafter concentrated to give 2.1 g of 3a,8b-cis-3H-5-carboxy-cyclopenta[b]benzofuran. This carboxylic acid was suspended in ethyl acetate, the suspension was methylated with an ether solution of diazomethane, which was concentrated to afford 2.2 g of a crude oily substance. This oily substance was purified by column chromatography [silica gel; ethyl acetate:cyclohexane (1:3)] to yield 1.9 g of 3a,8b-cis-dihydro-3H-5-carbomethoxy-cyclopenta[b]benzofuran (Yield 7.5%).

IR (neat) ν: 1720, 1605 cm$^{-1}$.

NMR (CDCl$_3$) δ: 2.90 (2H, m) 3.89 (3H, s), 4.18 (1H, dd, J=8.0 Hz, 0.3 Hz), 5.60 (1H, dt, J=8.0 Hz, 4.0 Hz), 5.75 (2H, m), 6.84 (1H, t, J=8.0 Hz), 7.24 (1H, dd, J=8.0 Hz, 1.2 Hz), 7.70 (1H, dd, J=8.0 Hz, 1.2 Hz).

Mass (m/e): 216 (M+).

REFERENTIAL EXAMPLE 59

Preparation of 3a,8b-cis-dihydro-3H-5-carbomenthyloxycyclopenta[b]benzofuran

To a suspension of 300 mg of 3a,8b-cis-dihydro-3H-5-carboxy-cyclopenta[b]benzofuran in 5 ml of anhydrous benzene was added 0.8 ml of oxalyl chloride and the resulting solution was stirred at 60° C. for 1 hour. The reaction mixture was concentrated and dried, the air was substituted by argon, the residue was dissolved in anhydrous pyridine, and 600 mg of 1-menthol was added and the mixture was stirred at 60° C. for 1.5 hours. The reaction solution was concentrated, ethyl acetate was added, the mixture was washed with a saturated aqueous solution of sodium hydrogen carbonate, water and saturated brine and concentrated. The obtained oily substance was purified by column chromatography [silica gel; ethyl acetate:cyclohexane (1:9)] to give 470 mg of 3a,8b-cis-dihydro-3H-5-carbomenthyloxy-cyclopenta[b]benzofuran was obtained (yield 90%).

IR (neat) ν: 1705, 1605, 1260, 1385, 1140, 1060, 1040, 1015 cm$^{-1}$.

REFERENTIAL EXAMPLE 60

Resolution of 3a,8b-cis-dihydro-3H-5-carbomenthyloxycyclopenta[b]benzofuran

When 300 mg of 3a,8b-cis-dihydro-3H-5-carbomenthyloxycyclopenta[b]benzofuran obtained in Referential Example 59 was separated and purified by column chromatography [silica gel; ethyl acetate:cyclohexane (0.5:9.5)], 73.7 mg of a less polar portion and 86.3 mg of a polar portion were obtained.

Analytical data of the less polar portion:

IR (neat) $\nu$: 1705, 1605, 1260, 1285, 1140, 1060, 1040, 1015 cm$^{-1}$.

NMR (CDCl$_3$) $\delta$: 0.78 (3H,d, J=8.0 Hz), 0.90 (6H, d, J=7.0 Hz), 1.4~1.9 (10H, m), 2.90 (1H, m), 4.40 (1H, d, J=8.0 Hz), 4.92 (1H dt, J=11.0 Hz, 4.0 Hz), 5.70 (3H, m), 6.84 (1H, t, J=8.0 Hz), 7.34 (1H, dd, J=8.0 Hz, 1.2 Hz), 7.74 (1H, dd, J=8.0 Hz, 1.2 Hz).

Mass (m/e): 340 (M$^+$).

$[\alpha]_D^{MeOH} = -116$.

Analytical data of the polar portion:

IR (neat) $\nu$: 1705, 1603, 1260, 1285, 1138, 1058, 1040, 1015 cm$^{-1}$.

NMR (CDCl$_3$) $\delta$: 0.80 (3H, d, J=6.5 Hz), 0.94 (6H, d, J=7.0 Hz) 1.4~1.9 (10H, m), 2.94 (1H, m), 4.38 (1H, d, J=8.0 Hz), 4.90 (1H, dt, J=10.0 Hz, 4.0 Hz), 5.70 (3H, m), 6.84 (1H, t, J=8.0 Hz), 7.34 (1H, dd, J=8.0 Hz, 1.2 Hz), 7.70 (1H, dd, J=8.0 Hz, 1.2 Hz).

Mass (m/e): 340 (M$^+$).

$[\alpha]_D^{MeOH} = +11.5$.

REFERENTIAL EXAMPLE 61

Preparation of 3a,8b-cis-dihydro-3H-5-carboxy-cyclopenta[b]benzofuran (optical active compound)

63 mg of the compound ($[\alpha]_D^{MeOH} = -116$) resoluted in Referential Example 60 was dissolved in 2 ml of methanol, 1 ml of 3N sodium hydroxide was added, and the resulting solution was stirred at 60° C. for 14 hours. The reaction mixture was concentrated, an ether-benzene (2:1) mixture was added and the mixture was extracted with water 3 times. The water layer was combined the pH of which was adjusted to 2 with 6N hydrochloric acid and extracted with ethyl acetate 3 times. The combined ethyl acetate layer was washed with water and saturated brine, dried and thereafter, concentrated to give 34.6 mg of the optically active carboxylic acid (mp 147°-148° C.).

IR (KBr) $\nu$: 3600-2400, 1690, 1605 cm$^{-1}$.

Mass (m/e): 202 (M$^+$).

$[\alpha]_D^{MeOH} = -104$.

Under the similar conditions, when 76 mg of the compound whose $[\alpha]_D^{MeOH}$ was +11.5 was employed, 42 mg of the optically active carboxylic acid (mp 148°-150° C.) was obtained.

IR (KBr) $\nu$: 3600-2400, 1690, 1605 cm$^{-1}$.

Mass (m/e): 202 (M$^+$).

$[\alpha]_D^{MeOH} = +105$.

REFERENTIAL EXAMPLE 62

Preparation of 3a,8b-cis-dihydro-3H-5-hydroxymethylcyclopenta[b]benzofuran

To a solution of 300 mg of 3a,8b-cis-dihydro-3H-5-carbomethoxycyclopenta[b]benzofuran in 7 ml of anhydrous toluene at −78° C. was added, 0.298 ml of diisobutyl aluminium hydride and the resulting mixture was stirred at −78° C. for 3 hours. Methanol was added and the mixture was stirred at room temperature for 5 minutes, thereafter, 50% brine was added and the mixture was extracted with ether 3 times. The combined ether layer was washed with saturated brine and water, dried over magnesium sulfate and concentrated to give 300 mg of an oily substance. This oily substance was separated and purified by column chromatography [silica gel; ethyl acetate:cyclohexane (1:4)] to yield 230 mg of the alcohol (yield 88%).

IR (neat) $\nu$: 3245, 1598, 1000 cm$^{-1}$.

REFERENTIAL EXAMPLE 63

Preparation of 3a,8b-cis-dihydro-3H-5-formyl-cyclopenta[b]benzofuran

To a solution of 230 mg of 3a,8b-cis-dihydro-3H-5-hydroxymethylcyclopenta[b]benzofuran in 5 ml of methylene chloride was added 5 g of active manganese dioxide, and the resulting mixture was stirred at room temperature under argon atmosphere for 2 hours. The reaction mixture was passed through a short column made of silica gel to filter manganese dioxide, and the column washed well with methylene chloride. The combined methylene chloride solution was concentrated to give 210 mg of a roughly pure aldehyde (mp 59°-60° C.) (yield 91%).

IR (neat) $\nu$: 2730, 1680, 1605 cm$^{-1}$.

NMR (CDCl$_3$) $\delta$: 2.90 (2H, m), 4.40 (1H, d, J=7.0 Hz), 5.70 (3H, m), 6.90 (1H, t, J=8.0 Hz), 7.41 (1H, dd, J=8.0 Hz, 1.2 Hz), 7.58 (1H, dd, J=8.0 Hz, 1.2 Hz), 10.10 (1H,s).

Mass (m/e): 186 (M$^+$).

REFERENTIAL EXAMPLE 64

Preparation of 3a,8b-cis-dihydro-3H-5-formyl-1,2-syn-epoxycyclopenta[b]benzofuran To an ice cooled solution of 100 mg of 3a,8b-cis-dihydro-3H-5-formyl-cyclopenta[b]benzofuran in 2.8 ml of a dimethyl sulfoxide-water (18:1) mixture and 0.42 ml of THF, was added, 180 mg of imide N-bromosuccinate and the resulting mixture was stirred for 4 hours. To the reaction mixture was added 300 mg of potassium carbonate and 0.5 ml of water, and the resulting mixture was stirred under ice cold conditions for 2 hours. Water was added to the reaction mixture, and the mixture was extracted with ether 5 times. The combined ether layer was washed with water, dried and concentrated to afford 130 mg of an oily substance. This oily substance was purified by column chromatography [silica gel; ethyl acetate:cyclohexane (1:1)] to give 105 mg of crude crystals. This crude crystals were recrystallized from a benzene-hexane mixture to yield 90 mg of a pure compound (mp 100°-101° C.).

IR (KBr) $\nu$: 2730, 1680, 1605, 845 cm$^{-1}$.

NMR (CDCl$_3$) $\delta$: 2.30 (1H, dd, J=16.0 Hz, 7.0 Hz), 2.68 (1H, d, J=16.0 Hz), 3.82 (1H, d, J=8.0 Hz), 6.96 (1H, t, J=8.0 Hz), 7.50 (1H, dd, J=8.0 Hz, 1.2 Hz), 7.64 (1H, dd, J=8.0 Hz, 1.2 Hz), 10.18 (1H, s).

Mass (m/e): 202 (M$^+$).

REFERENTIAL EXAMPLE 65

Preparation of
1,2,3a,8b-cis-tetrahydro-5-(4-tetrahydropyranyloxy-1-hydroxy-n-butyl)-1,2-syn-epoxy-cyclopenta[b]benzofuran To a stirred solution of 10 mg of 1,2,3a,8b-cis-tetrahydro-5-formyl-1,2-syn-epoxy-cyclopenta[b]benzofuran in anhydrous THF was added at −60° C., a large excess of a THF solution of a Grignas reagent produced from 3-bromo-n-propyl-tetrahydropyranylether, and the resulting solution was stirred at −30° C. to −40° C. for 1.5 hours. Solid ammonium chloride was added, and the resulting mixture was stirred at −40° C. for 20 minutes, thereafter, water was added, and the mixture was extracted with ether 3 times, the extract was washed with saturated brine, dried and thereafter, concentrated. The obtained oily substance was purified by column chromatography [silica gel; ethyl acetate:cyclohexane (1:1)] to give 13 mg of a pure product.

IR (neat) ν: 3430, 1595, 1025, 845 cm$^{-1}$.

REFERENTIAL EXAMPLE 66

Preparation of
1,2,3a,8b-cis-tetrahydro-5-(4-tetrahydropyranyloxy-1-acetoxy-n-butyl)-1,2-syn-epoxy-cyclopenta[b]benzofuran 13 mg of 1,2,3a,8b-cis-tetrahydro-5-(4-tetrahydropyranyloxy-1-hydroxy-n-butyl)-1,2-syn-epoxy-cyclopenta[b]benzofuran was dissolved, in 1 ml of acetic anhydride and 0.5 ml of anhydrous pyridine, and the resulting solution was stirred at room temperature for 14 hours. The reaction solution was concentrated to dryness, the residue was dissolved in toluene and concentrated, and this operation was repeated. The obtained oily substance was refined by column chromatography [silica gel; ethyl acetate:cyclohexane (1:1)] to give 13 mg of a pure product.

IR (neat) ν: 1738, 1595, 1230, 1030, 845 cm$^{-1}$.

NMR (CDCl$_3$) δ: 2.05 (3H, s), 3.68 (2H, s), 3.20–3.90 (5H, m), 4.58 (1H, m), 5.37 (1H, t, J=7.0 Hz), 5.93 (1H, J=7.0 Hz), 6.86 (1H, t, J=8.0 Hz), 7.20 (2H, m).

Mass (m/e): 388 (M+).

REFERENTIAL EXAMPLE 67

Preparation of
1,2,3a,8b-cis-tetrahydro-5-(4-tetrahydropyranyloxy-n-butyl)-1,2-syn-epoxycyclopenta[b]benzofuran To a solution of 6 mg of 1,2,3a,8b-cis-tetrahydro-5-(4-tetrahydropyranyloxy-1-acetoxy-n-butyl)-1,2-syn-epoxycyclopenta[b]benzofuran in 0.5 ml of ethyl acetate was added, 15 mg of a 10% palladium-carbon was added, and the resulting mixture was stirred at room temperature under hydrogen atmosphere for 3 hours. The catalyst was filtered off and the filtrate was concentrated to afford 6 mg of an oily substance. This oily substance was separated and purified by column chromatography [silica gel; ethyl acetate:cyclohexane (1:2)] to give 3 mg of a pure product. The compound obtained herein was completely identical with the compound obtained in Referential Example 16 in IR, Mass and Rf value of TLC.

REFERENTIAL EXAMPLE 68

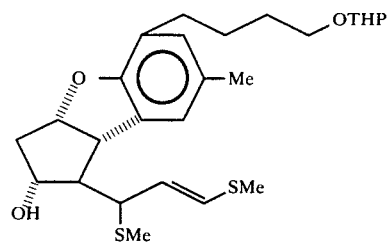

1,2,3a,8b-cis-tetrahydro-1-exo-(1,3-bismethylthio-2-propenyl)-2-endo-hydroxy-7-methyl-5-(4-tetrahydropyranyloxy-n-butyl)cyclopenta[b]benzofuran To a 170 ml of THF solution of 1,3-bismethylthio-1-propenyl lithium (0.16M, 27.2 ml, 1.45 equiv.) was added dropwise at −78° C. under argon atmosphere a solution of 6.43 g (18.7 mmol) of 1,2,3a,8b-cis-tetrahydro-7-methyl-5-(4-tetrahydropyranyloxybutyl)-1,2-syn-epoxycyclopenta[b]benzofuran in 40 ml of THF, and the resulting solution was stirred for 2 hours. The reaction solution was poured into 100 ml of a saturated aqueous solution of ammonium chloride, and products was extracted with ethyl acetate (20 ml×5) and the combined organic layers were dried. After concentration, the resulting 10.1 g of a crude products was purified by column chromatography (silica gel 400 g; cyclohexane:ethyl acetate 5:1→3:2) to afford 4.15 g (8.68 mmol, 46%) of polar 4 and 4.53 g (9.48 mmol, 51%) of the less polar position isomer, 2 kinds of oily substances.

NMR (CDCl$_3$) δ: 1.62 (m, 10H), 1.80–2.66 (m, 15H), (At 2.06, 2.14, 2.25, 2.29 and 2.31, five singlet could be confirmed), 3.22 (dd, J=8, 10 Hz, 1H), 3.53 (m, 2H), 3.80 (m, 2H), 4.14 (dd, J=6, 7 Hz, 1H), 4.20 (broad singlet, 1H), 4.56 (m, 1H), 5.06 (m, 1H), 5.32 (dd, J=15, 10 Hz, 1H), 6.17 (d, J=15 Hz, 1H), 6.77 (s, 1H), 6.88 (s, 1H).

IR (neat): 3450 (3650–3150), 2970, 2930, 2860, 1600, 1475, 1435, 1215, 1200, 1140, 1120, 1075, 1030, 970, 865, 815, 740, 700.

Mass spectrum: M+ 478.

In a similar manner of Referential Example 68 1,2,3a,8b-cis-tetrahydro-7-bromo-5-(4-tetrahydropyranyloxybutyl)-1,2-syn-epoxycyclopenta[b]benzofuran; 1,2,3a,8b-cis-tetrahydro-7-chloro-5-(4-tetrahydropyranyloxybutyl)-1,2-syn-epoxycyclopenta[b]benzofuran or 1,2,3a,8b-cis-tetrahydro-7-methoxy-5-(4-tetra-hydropyranyloxybutyl)-1,2-syn-epoxycyclopenta[b]benzofuran is employed as the starting material to give 1,2,3a,8b-cis-tetrahydro-1-exo-(1,3-bismethylthio-2-propenyl)-2-endo-hydroxy-7-bromo-5-(4-tetrahydropyranyloxybutyl)cyclopenta[b]benzofuran; 1,2,3a,8b-cis-tetrahydro-1-exo-(1,3-bismethylthio-2-propenyl)-2-endo-hydroxy-7-chloro-5-(4-tetrahydropyranyloxybutyl)cyclopenta[b]benzofuran or 1,2,3a,8b-cis-tetrahydro-1-exo-(1,3-bismethylthio-2-propenyl)-2-endo-hydroxy-7-methoxy-5-(4-tetrahydropyranyloxybutyl)cyclopenta[b]benzofuran.

REFERENTIAL EXAMPLE 69

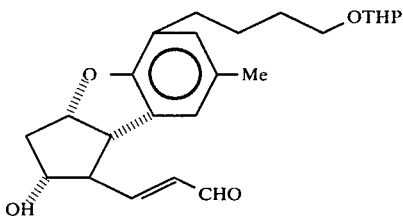

1,2,3a,8b-cis-tetrahydro-1-exo-(2-formylethenyl)-3-endo-hydroxy-7-methyl-5-(4-tetrahydropyranyloxybutyl)cyclopenta[b]benzofuran The mixture of 861 mg (5.05 mmol, 2.5 equiv.) of cupric chloride dihydrate, 2.00 g (20 mmol, 10 equiv.) of calcium carbonate and 5 ml of acetone was cooled to 0° C. To this suspension was added a solution of 954 mg (2.00 mmol) of 1,2,3a,8b-cis-tetrahydro-3H-1-exo-(1,3-bismethylthio-2-propenyl)-2-endo-hydroxy-7-methyl-5-(4-tetrahydropyranyloxy-n-butyl)cyclopenta[b]benzofuran in 6 ml of acetone and the resulting mixture was stirred at 0°–5° C. for 6 hours. After distilling off acetone, 50 ml of ether was added, the inorganic salt was filtered off, and the filtrate was washed with a saturated aqueous solution of ammonium chloride (1 ml×4) and dried. After concentration, 72.7 mg of the residue was purified by column chromatography (silica gel 70 g, cyclohexane:ethyl acetate 1:2→ethyl acetate) to afford to 528 mg (7.32 mmol, 66%) of 5 and 66 mg (0.21 mmol, 10%) of the aldehyde which a tetrahydropyranyl group of 5 was eliminated.

NMR (CDCl$_3$) δ: 1.63 (m, 10H), 2.64 (m, 1H), 2.22 (s, 3H), 2.54 (m, 3H), 2.74 (t, J=8, 1H), 3.08 (wide one -double line, 1H), 3.44 (m, 3H), 3.80 (m, 2H), 4.03 (m, 1H), 4.55 (m, 1H), 5.11 (q, J=7 Hz, 1H), 6.24 (dd, J=16, 8 Hz, 1H), 6.80 (m, 3H), 9.55 (d, J=8 Hz, 1H).

IR (neat) νcm$^{-1}$: 3400 (3600–3100), 2930, 2860, 1680, 1640, 1475, 1220, 1200, 1130, 1070, 1030, 975, 860, 740.

Mass spectrum: M+ 400.

In a similar manner of Referential Example 69, 1,2,3a,8b-cis-tetrahydro-1-exo-(1,3-bismethylthio-2-propenyl)-2-endo-hydroxy-7-bromo-5-(4-tetrahydropyranyloxybutyl)cyclopenta[b]benzofuran; 1,2,3a,8b-cis-tetrahydro-1-exo-(1,3-bismethylthio-2-propenyl)-2-endo-hydroxy-7-chloro-5-(4-tetrahydropyranyloxybutyl)cyclopenta[b]benzofuran or 1,2,3a,8b-cis-tetrahydro-1-exo-(1,3-bismethylthio-2-propentyl)-2-endo-hydroxy-7-methoxy-5-(4-tetrahydropyranyloxybutyl)cyclopenta[b]benzofuran is employed as the starting material to give 1,2,3a,8b-cis-tetrahydro-1-exo-(2-formylethenyl)-3-endohydroxy-7-bromo-5-(4-tetrahydropyranyloxybutyl)cyclopenta[b]benzofuran; 1,2,3a,8b-cis-tetrahydro-1-exo-(2-formylethenyl)-3-endohydroxy-7-chloro-5-(4-tetrahydropyranyloxybutyl)cyclopenta[b]benzofuran or 1,2,3a,8b-cis-tetrahydro-1-exo-(2-formylethenyl)-3-endohydroxy-7-methoxy-5-(4-tetrahydropyranyloxybutyl)cyclopenta[b]benzofuran.

REFERENTIAL EXAMPLE 70

1-t-butyldimethylsiloxy-1-phenyl-2-propyne

To a solution of 5.0 g (37.9 mmol) of 1-phenyl-2-propyne-1-ol in 20 ml of dimethyl formamide were added 6.9 g (45.8 mmol) of t-butyl dimethylsilyl chloride and 6.2 g (91.1 mmol) of imidazole, and the resulting mixture was stirred at room temperature for 3 hours, 50 ml of water was added and the mixture was extracted with a pentane-ether (1:1) mixture (4×30 ml). The organic layer was washed with water (30 ml) and saturated brine, dried over anhydrous magnesium sulfate (30 mg) and thereafter concentrated. The residue was purified by column chromatography (silica gel 100 g, cyclohexane-ethyl acetate) and further distilled (dp 98° C./1 mm Hg) to give 5.7 g (24.7 mmol, 65%) of the subject compound.

IR (neat) νcm$^{-1}$: 3300, 3060, 3030, 2960, 2930, 2880, 2850, 2110, 1600, 1460, 1250, 1090, 1065, 840, 780, 695.

GLC glass column 3 mm×2 m
liq phase silicon SE52
2% Gaschrom Q80/100
temp. column 150° C.
injection 200° C.
carrier gas N$_2$ 60 ml/min
detector FID
instrument Shimadzu GC-5A
retention time 6.5 min

REFERENTIAL EXAMPLE 71

6-methyl-5-heptene-1-ol

To a stirred suspension 77 g of isopropyltriphenylphosphonium iodide in 200 ml of anhydrous DMSO at −78° C. was added 57 ml of dimethyl-sulfinylcarbanion (prepared from 15 g of sodium hydride (55%) in mineral oil dispersion and 100 ml of anhydrous DMSO), and the resulting mixture was stirred at room temperature for 10 minutes. A solution of 6 g of 2-hydroxytetrahydropyran in 10 ml of anhydrous DMSO was added dropwise, and the resulting mixture was stirred at room temperature for 1 hour. Ice and water were added, and the mixture was extracted 3 times with n-hexane, the combined organic layers were washed with a 10% aqueous solution of sulfuric acid, a saturated aqueous solution of sodium hydrogen carbonate and water, thereafter dried and concentrated to give 10 g of an oily substance. This oily substance was distilled (bp 110° C./30 mmHg) to yield 5 g of a pure alcohol.

IR (neat) νcm$^{-1}$: 3400, 1160, 830.

NMR (CDCl$_3$) δ: 1.60 (3H, s), 1.68 (3H, s), 2.00 (2H, q, J=7.0 Hz), 2.54 (1H, s), 3.60 (2H, t, J=6.0 Hz), 5.12 (1H, tq, J=7.0 Hz, 2.0 Hz).

Mass (m/e): 128 (M+).

Anal. Calcd for C$_8$H$_{16}$O: C; 74.94; H; 12.58. Found: C; 74.88, H; 12.52.

REFERENTIAL EXAMPLE 72

6-methyl-5-heptenyl tosylate

To an ice cooled solution of 5 g of 6-methyl-5-heptene-1-ol in 20 ml of anhydrous pyridine was added, 11.5 g of tosyl chloride and the resulting mixture was stirred under ice cold conditions for 2 hours. Ice was added and the mixture was extracted with n-hexane 3 times, the combined organic layers were washed 2 times with 2N hydrochloric acid, water and a saturated aqueous solution of copper sulfate, dried and thereafter, concentrated to give 11 g of roughly pure tosylate.

IR (neat) νcm$^{-1}$: 1595, 1440, 1355, 1175, 810.

NMR (CDCl$_3$) δ: 1.56 (3H, s), 1.67 (3H, s), 1.96 (2H, q, J=7.0 Hz), 2.26 (3H, s), 4.04 (2H, t, J=6.0 Hz), 5.04 (1H, tq, J=8.0 Hz, 2.0 Hz), 7.36 (2H, d, J=8.0 Hz), 7.80 (2H, d, J=8.0 Hz).

Mass (m/e): 282 (M+).

Anal. Calcd for $C_{15}H_{22}O_3S$: C; 63.83, H; 7.80. Found: C; 63.78, H; 7.75.

REFERENTIAL EXAMPLE 73

6-methyl-5-heptenyl bromide

A solution of 11 g of 6-methyl-5-heptenyl tosylate in 100 ml of THF were added 10 ml of HMPA, 50 g of potassium bromide and 300 mg of 18-crown-6, and the resulting mixture was refluxed for 5 hours. After cooling, water was added, and the mixture was concentrated, the residue was extracted with pentane 3 times, the combined organic layers were washed with a saturated aqueous solution of sodium hydrogen carbonate water and saturated brine, dried and concentrated to give 8 g of an oily substance. This oily substance was distilled (bp 70° C./5 mm Hg) to yield 5.7 g of a pure bromide.

IR (neat) $\nu cm^{-1}$: 1245, 840.

NMR ($CDCl_3$) δ: 1.61 (3H, s), 1.70 (3H, s), 3.40 (2H, t, J=7.0 Hz), 5.10 (1H, tq, J=7.8 Hz, 2.0 Hz).

Anal. Calcd for $C_8H_{15}Br$: C; 50.00, H; 7.81. Found: C; 49.98, H; 7.80.

REFERENTIAL EXAMPLE 74

2-methylpentyl bromide

To an ice cooled solution of 6 g of 2-methylpentyl alcohol in 30 ml of anhydrous pyridine was added 16 g of tosyl chloride, and the resulting mixture was stirred for 40 minutes. Ice was added under ice cold conditions, and the mixture was extracted 3 times with n-hexane, the combined hexane layers were washed 2 times with 2N hydrochloric acid, once water and once a saturated aqueous solution of copper sulfate, dried and concentrated to afford 14 g of a roughly pure tosylate. To a stirred solution of the tosylate in 100 ml of THF were added 30 ml of HMPA, 50 g of potassium bromide and 5 g of 18-crown-6, the resulting mixture was refluxed for 14 hours. The reaction mixture was cooled, ice was added, and the mixture was extracted 3 times with pentane, the extract was washed 2 times with water and 2 times with saturated brine and thereafter concentrated to give 14 g of an oily substance. This oily substance was distilled (bp 54° C./30 mm Hg) to yield 6 g of a pure bromide.

NMR ($CDCl_3$) δ: 0.98 (3H, t, J=7.0 Hz), 1.02 (3H, d, J=6.8 Hz), 1.36 (4H, m), 1.80 (1H, octet J=6.8 Hz), 3.38 (2H, dd, J=5.0 Hz, 2.5 Hz).

Mass (m/e): 166, 164 (M+), 123, 121.

Anal. Calcd. for $C_6H_{13}Br$: C; 43.64; H; 7.88. Found: C; 43.51, H; 7.80.

REFERENTIAL EXAMPLE 75 l-citronelol-tetrahydropyranylether

To an ice cooled solution of 50 g of l-citronelol in 250 ml of anhydrous methylene chloride were added 40 g of dihydropyran and 25 ml of a THF solution of p-toluenesulfonic acid which was prepared by dissolving 1.8 g of p-toluenesulfonic acid in 50 ml of THF and drying the solution over a molecular sieve, and the resulting mixture was stirred under ice cold conditions for 10 minutes. Two ml of pyridine was added, the resulting solution was stirred at room temperature for 30 minutes, thereafter, washed with saturated brine:water (1:1) mixture and saturated brine, thereafter, dried and concentrated to give 76 g of a roughly pure ether body.

IR (neat) $\nu cm^{-1}$: 1670, 1140, 1120, 1080, 1030, 870, 820.

NMR ($CDCl_3$) δ: 0.90 (3H, d, J=6.0 Hz), 1.00–1.90 (5H, m), 1.60 (3H, s), 1.68 (3H, s), 1.99 (2H, q, J=8.0 Hz), 3.50 (2H, m), 3.80 (2H, m), 4.57 (1H, m), 5.10 (1H, tq, J=8.0 Hz, 1.0 Hz).

Mass (m/e): 240 (M+).

REFERENTIAL EXAMPLE 76

3(s)-methyl-6-tetrahydrofuranyloxyhexanal

Into a stirred solution of 35 g of l-citroneloltetrahydrofuranylether in 500 ml of methanol at −78° C. was passed a stream of ozone. After 2.5 hours, a nitrogen stream was vigorously bubbled through the solution for 1 hour to remove the excess ozone. Two hundred ml of dimethyl sulfide was added, the temperature was allowed to warm to room temperature over 1 hour, and resulting mixture was concentrated. The residue was dissolved in pentane, a small amount of ethyl acetate was added, and the mixture was washed with saturated brine, dried and thereafter concentrated to give 36 g of an oily substance. This oily substance was used in the following reaction without further purification.

IR (neat) $\nu cm^{-1}$: 1728, 1140, 1125, 1080, 1030, 870, 819.

NMR ($CDCl_3$) δ: 0.94 (3H, d, J=5.0 Hz), 2.45 (2H, m), 1.20–2.00 (5H, m), 3.50 (2H, m), 3.80 (2H, m), 4.58 (1H, m), 10.00 (1H, t, J=2.0 Hz).

Mass (m/e): 241 (M+).

REFERENTIAL EXAMPLE 77

3(s)-methyl-7-heptene-1-ol tetrahydropyranylether

To a stirred solution of 30 g of methyltriphenylphosphonium bromide in 100 ml of anhydrous DMSO, under water cooled conditions was added 20 ml of dimethylsulfinylcarbanion (prepared from 6.6 g of sodium hydide (50% mineral oil dispersion) and 40 ml of anhydrous DMSO), the resulting solution was stirred for 10 minutes, thereafter, 10 g of 3(S)-methyl-6-tetrahydrofuranyloxyhexanal was added, and the resulting mixture was stirred at room temperature for 30 minutes. The reaction mixture was cooled with ice, and ice and water were added, and the mixture was extracted 3 times with n-pentane. The combined pentane layers were washed with water and saturated brine, dried and thereafter concentrated to afford 10 g of an oily substance. This oily substance was purified by column chromatography (silica gel; chloroform) to give 9 g of a pure product.

IR (neat) $\nu cm^{-1}$: 1640, 1120, 1075, 1030, 990, 905.

NMR ($CDCl_3$) δ: 0.92 (3H, d, J=6.0 Hz), 1.10–1.90 (5H, m), 2.10 (2H, q, J=7.5 Hz), 3.50 (2H, m), 3.80 (2H, m), 4.60 (1H, m), 5.00 (2H, m), 5.80 (1H, m).

Mass (m/e): 212 (M+).

REFERENTIAL EXAMPLE 78

3(s)-methyl-heptene-1-ol

To a solution of 3 g of 3(S)-methyl-7-heptene-1-ol tetrahydropyranylether in 84 ml of acetonitrile were added 42 ml of THF and 42 ml of ¼N hydrochloric acid, and the resulting solution was stirred at room temperature for 14 hours. Ether was added, and the mixture was shaken, the water layer was removed, the organic layer was washed with saturated aqueous solution of sodium hydrogen carbonate, dried and thereafter concentrated to give 3 g of an oily substance. This oily substance was purified by column chromatography (silica gel, 2% ethyl acetate-chloroform) to yield 1.5 g of the alcohol.

IR (neat) $\nu cm^{-1}$: 3330, 1640, 1050, 990, 910.

NMR (CDCl$_3$) δ: 0.92 (3H, d, J=6.0 Hz), 1.10-2.00 (5H, m), 2.10 (2H, m), 3.67 (2H, t, J=8.0 Hz), 5.00 (2H, m), 5.80 (1H, m).

Mass (m/e): 128 (M+).

REFERENTIAL EXAMPLE 79

3(S)-methylheptanol

To a solution of 8 g of 3(s)-methyl-7-heptene-1-ol in 50 ml of a 2% potassium hydroxide-methanol mixture was added 1 g of platinum oxide, and the resulting mixture was stirred at room temperature under hydrogen atmosphere for 3 hours. The reaction mixture was filtered, the filtrate was concentrated, the residue was treated with water and the mixture was extracted 3 times with ether. The combined ether layers were washed with water and saturated brine, dried and thereafter concentrated to give 7.9 g of the saturated alcohol in a roughly pure form.

IR (neat), $\nu$ cm$^{-1}$: 3300, 1120, 1055.

NMR (CDCl$_3$) δ: 0.90 (6H, m), 3,67 (2H, t, J=7.0 Hz), 1,00-2.90 (9H, m), 2,10 (2H, s).

Mass (m/e): 130 (M+).

REFERENTIAL EXAMPLE 80

3 (S)-methylheptanoic acid

To a solution of 1 g of 3(s)-methylheptanol in 3 ml of anhydrous DME was added 14 g of pyridinium dichromate, and the resulting mixture was stirred at room temperature for 14 hours. The reaction mixture was treated with water and the mixture was extracted 5 times with ether. The combined ether layers were washed with 2N hydrochloric acid, water and a saturated aqueous solution of copper sulfate and concentrated. The residue was dissolved in n-hexane, the solution was washed once with a saturated aqueous solution of sodium hydrogen carbonate and 6 times with water, the pH value of the water layer was adjusted to 2 with 2N hydrochloric acid and the layer was extracted with 5 times chloroform. The combined chloroform layer were washed with water, dried and thereafter concentrated to give 700 mg of the roughly pure carboxylic acid.

IR (neat) $\nu$ cm$^{-1}$: 3600-2300, 1710, 1100.

NMR (CDCl$_3$) δ: 0.90 (3H, t, J=7.0 Hz), 0.98 (3H, d, J=6.8 Hz), 1.10-1.60 (7H, m), 2.96 (2H, d, J=7.0 Hz).

Mass (m/e): 144 (M+).

REFERENTIAL EXAMPLE 81

2(S)-methylhexyl chloride

To a solution 6 g of 3(s)-methylheptanoic acid in 100 ml of benzene under argon atmosphere were added 9.6 g of acetic acid, 0.9 ml of water and 20 g of lead tetraacetate, the resulting mixture was stirred at room temperature for 30 minutes, thereafter, 1.9 g of lithium chloride was added thereto under argon atmosphere, and the resulting mixture was stirred at 80° C. for 3 hours. The benzene layer was decanted, washed with diluted hyrochloric acid and an aqueous solution of sodium carbonate, dried and thereafter concentrated to give 8 g of an oily substance. This oily substance was purified by column chromatography (silica gel; hexane) to yield 34 g of the chloride.

NMR (CDCl$_3$) δ: 0.90-1.10 (6H), 1.10-1.60 (6H), 1.60-2.00 (1H), 3.00-3.50 (2H).

Mass (m/e): 134, 136.

EXAMPLE 1

5,6,7-trinor-4,8-inter-m-phenylene-13,14-didehydro PGI$_2$ methyl ester 15-t-butylether (1)

To a solution of 1.515 g (8.32 mmol) of 3-t-butyloxy-1-octyne in 5 ml of dry toluene at 0° C. under argon atmosphere, was slowly added 5 ml of a hexane solution of n-butyl lithium (1.54M, 7.7 mmol), and the resulting solution was stirred for 15 minutes.

To the solution was added 3.7 ml (7.25 mmol) of a toluene solution (1.96M) of a mixture of diethyl aluminium chloride and ethyl methoxy aluminium chloride (3:1), and the resulting solution was stirred at 0° C. for 1 hour. A solution of 302 mg (1.1 mmol) of methyl 4-(3a,8b-cis-dihydro-3H-1,2-syn-epoxycyclopenta[b]benzofuran-5-yl)butanoate in 7 ml of dry toluene was added, and the resulting solution was stirred at room temperature for 1 hour in an ice bath and 30 ml of saturated brine was slowly added thereto. The resulting solution was extracted with 50 ml of ether and the ether layer was washed with saturated brine, dried over anhydrous sodium sulfate, thereafter, concentrated. After the excess 3-t-butyloxy-1-octyne was distilled off, the residue was purified by chromatography [Merck Lobar Column B; cyclohexane:ethyl acetate (2:1)] to give 160 mg (32%) of the subject compound and 140 mg (28%) of the position isomer.

Spectrum data of the subject compound:

IR (neat, $\nu$ cm$^{-1}$): 3450, 2950, 2855, 2220, 1740, 1595, 1450, 1370, 1255, 1195, 1035, 750.

NMR (CDCl$_3$, δ ppm): 0.90 (t, 6 Hz, 3H), 1.26 (s, 9H), 1.2-1.7 (m, 6H), 1.8-2.45 (m, 9H), 2.60 (t, 7 Hz, 2H), 2.88 (td, 6 Hz, 2 Hz, 1H), 3.64 (s, 3H), 3.80 (dd, 8 Hz, 5 Hz, 1H), 4.02-4.22 (m, 2H), 5.26 (m, 1H), 6.79 (t, 7 Hz, 1H), 6.95 (dd, 7 Hz, 2 Hz, 1H), 7.14 (dd, 7 Hz, 2 Hz, 2 Hz, 1H).

MS (m/e): 456, 382, 297, 279, 232, 201, 156, 144.

Spectrum data of the position isomer:

IR (neat, $\nu$ cm$^{-1}$): 3450, 2950, 2855, 2220, 1740, 1595, 1450, 1370, 1255, 1195, 1050, 750.

NMR (CDCl$_3$, δ ppm): 0.88 (r, 6 Hz, 3H), 1.23 (s, 9H), 1.2-1.7 (m, 10H), 1.7-2.1 (m, 3H), 2.33 (t, 7 Hz, 2H), 2.42 (m, 1H), 2.60 (t, 7 Hz, 2H), 3.65 (s, 3H), 3.96 (t, 8 Hz, 1H), 4.10 (t, 6 Hz, 1H), 4.23 (t, 8 Hz, 1H), 5.18 (dd, 8 Hz, 5 Hz, 1H), 6.78 (t, 7 Hz, 1H), 6.99 (dd, 7 Hz, 2 Hz, 1H), 7.13 (dd, 7 Hz, 2 Hz, 1H).

MS (m/e): 456 (M+) 400, 382, 325, 297, 201.

EXAMPLE 2

5,6,7-trinor-4,8-inter-m-phenylene-13,14-didehydro PGI$_2$ methyl ester (12)

To 185 mg (0.406 mmol) of 5,6,7-trinor-4,8-inter-m-phenylene-13,14-didehydro-PGI$_2$ methyl ester 15-t-butylether was added 1 ml of trifluoroacetic acid, and the resulting mixture was stirred for 2 hours in an ice bath. Trifluoroacetic acid was distilled off under reduced pressure and the residue was purified by chromatography (Lobar Column B, cyclohexane-ethyl acetate 1:2) to give 65 mg (0.163 mmol) of the subject compound.

IR (neat $\nu$ cm$^{-1}$): 3400, 2930, 2855, 2230, 1740, 1600, 1460, 1255, 1195, 1005, 865, 755.

NMR (CDCl$_3$, δ ppm): 0.91 (t, 7 Hz, 3H), 1.2-2.5 (m, 14H), 2.30 (t, 7 Hz, 2H), 2.60 (t, 7 Hz, 2H), 2.84 (td, 6

Hz, 2 Hz, 1H), 3.65 (s, 3H), 3.80 (dd, 8 Hz, 5 Hz, 1H), 4.24 (q, 5 Hz, 1H), 4.40 (td, 6 Hz, 2 Hz, 1H), 5.13 (m, 1H), 6.79 (t, 7 Hz, 1H), 6.98 (dd, 7 Hz, 2 Hz, 1H), 7.14 (dd, 7 Hz, 2 Hz, 1H).

MS (m/e): 400 (M+), 392, 232, 158.

The above mentioned procedure was followed except the use of 163 g (0.357 mmol) of the position isomer of (1), in place of (1) to give 88 mg (0.221 mmol, 62%) of the position isomer of the subject compound.

IR (neat, $\nu$ cm$^{-1}$): 3400, 2930, 2850, 2230, 1740, 1595, 1460, 1250, 1195 1005, 865, 755.

NMR (CDCl$_3$, δ ppm): 0.88 (t, 6 Hz, 3H), 1.16-1.80 (m, 10H), 1.92 (m, 2H), 2.32 (t, 7 Hz, 2H), 2.41 (m, 1H), 2.59 (t, 7 Hz, 2H), 2.67 (x, 2H), 3.64 (s, 3H), 3.92 (t, 8 Hz, 1H), 4.21 (t, 8 Hz, 1 Hz), 4.30 (td, 6 Hz, 2 Hz, 1H), 5.16 (dd, 8 Hz, 5 Hz, 1H), 6.76 (t, 7 Hz, 1H), 6.98 (dd, 7 Hz, 2 Hz, 1H), 7.12 (dd, 7 Hz, 2 Hz, 1H).

MS (m/e): 400 (M+), 325, 293, 233, 201.

EXAMPLE 3

5,6,7-trinor-4,8-inter-m-phenylene-13,14-didehydro-PGI$_2$ (3)

To a solution of 27.2 mg (0.0685 mmol) of 5,6,7-trinor-4,8-inter-m-phenylene-13,14-didehydro-PGI$_2$ methyl ester in 3 ml of MeOH was added 1 ml of an aqueous solution of 1N sodium hydroxide and the solution was stirred at room temperature for 2 hours. Methanol was distilled off and the residue was washed with 5 ml of an n-hexane:ether (2:1) mixture.

The residue was cooled with ice, 1N hydrochloric acid was added to adjust pH to 3 and the mixture was extracted with ethyl acetate (3×10 ml). The organic layer was dried over sodium sulfate and concentrated to give 26.4 mg (0.0684 mmol, 100%) of the subject compound as an oily substance.

IR (neat, $\nu$ cm$^{-1}$): 3600-2500, 2930, 2850, 2230, 1710, 1595, 1450, 1250, 1190, 1030, 865, 745.

NMR (CDCL$_3$, δ ppm): 0.90 (t, 6 Hz, 3H), 1.2-1.8 (m, 8H), 2.2-2.6 (m, 4H), 2.31 (t, 7 Hz, 2H), 2.62 (t, 7 Hz, 2H), 2.80 (td, 6 Hz, 2 Hz, 1H), 3.77 (dd, 8 Hz, 6 Hz, 1H). 4.11 (q, 6 Hz, 1H), 4.40 (td, 6 Hz, 2 Hz, 1H), 5.10 (b, 4H), 6.78 (t, 7 Hz, 1H), 6.97 (dd, 7 Hz, 1 Hz, 1H), 7.12 (dd, 7 Hz, 1 Hz, 1H).

MS (m/e): 386 (M+), 368, 218, 158.

The above mentioned procedure was followed except the use of 56.4 mg (0.141 mmol) of the position isomer of (2) in place of (2) to give 51.4 mg (0.133 mmol, 94%) of the position isomer of the subject compound.

IR (neat, $\nu$ cm$^{-1}$): 3600-2500, 2930, 2850, 2230, 1710, 1595, 1450, 1250, 1190, 1000, 865, 750. NMR (CDCl$_3$, δ ppm): 0.89 (t, 6 Hz, 3H), 1.1-1.8 (m, 10H), 1.93 (q, 6 Hz, 2H), 2.30 (m, 1H), 2.35 (t, 7 Hz, 2H), 2.62 (t, 7 Hz, 2H), 3.92 (t, 8 Hz, 1H), 4.22 (t, 8 Hz, 1H), 4.30 (td, 6 Hz, 1 Hz, 1H), 5.17 (dd, 8 Hz, 5 Hz, 1H), 5.42 (bs, 3H), 6.77 (t, 7 Hz, 1H), 6.99 (dd, 7 Hz, 2 Hz, 1H), 7.14 (dd, 7 Hz, 2 Hz, 1H).

EXAMPLE 4

5,6,7-trinor-4,8-inter-m-phenylene-13,14-didehydro-20-methyl PGI$_2$ methyl ester 15-t-butylether (4)

The procedure of Example 1 was followed except the uses of 2.912 g (14.85 mmol) of 3-t-butyloxy-1-nonyne and 563 mg (2.055 mmol) of methyl 4-(3a,8b-cis-dihydro-3H-1,2-syn-epoxycyclopenta[b]benzofuran-5-yl)butanoate in place of 3-t-butyloxy-1-octyne and methyl 4-(3a,8b-cis-dihydro-3H-1,2-syn-epoxycyclopenta[b]benzofuran-5-yl)butanoate to give 208 mg (0.441 mmol, 22%) of the subject compound and 210 mg (0.446 mmol, 22%) of the position isomer.

Spectrum data of the subject compound:

IR (neat, $\nu$ cm$^{-1}$): 3450, 2930, 2855, 2230, 1745, 1595, 1450, 1370, 1255, 1195, 1040, 865, 750.

NMR (CDCl$_3$, δ ppm): 0.89 (t, 6 Hz, 3H), 1.26 (s, 9H), 1.1-2.2 (m, 15H), 2.29 (t, 7 Hz, 2H), 2.59 (t, 7 Hz, 2H), 2.89 (td, 6 Hz, 2 Hz, 1H), 3.64 (s, 3H), 3.85 (dd, 8 Hz, 5 Hz, 1H), 4.12 (td, 6 Hz, 2 Hz, 1H), 4.25 (q, 5 Hz, 1H), 5.25 (m, 1H), 6.88 (t, 7 Hz, 1H), 6.96 (dd, 7 Hz, 2 Hz, 1H), 7.12 (dd, 2 Hz, 7 Hz, 1H).

MS (m/e): 470 (M+), 396, 297, 279, 232, 158.

Spectrum data of the position isomer:

IR (neat, $\nu$ cm$^{-1}$): 3450, 2930, 2855, 2230, 1754, 1595, 1450, 1370, 1255, 1190, 1045, 1010, 865, 750.

NMR (CDCl$_3$, δ ppm): 0.98 (t, 6 Hz, 3H), 1.23 (s, 9H), 1.1-1.7 (m, 12H), 1.8-2.1 (m, 3H), 2.32 (t, 7 Hz, 2H), 2.42 (m, 1H), 2.60 (t, 7 Hz, 2H), 3.65 (s, 3H), 3.95 (t, 8 Hz, 1H), 4.10 (td, 6 Hz, 1 Hz, 1H), 4.16 (t, 8 Hz, 1H), 5.18 (dd, 8 Hz, 5 Hz, 1H), 6.78 (t, 7 Hz, 1H), 6.98 (dd, 7 Hz, 2 Hz, 1H), 7.14 (dd, 7 Hz, 2 Hz, 1H).

MS (m/e): 470 (M+), 414, 396, 297, 231, 201.

EXAMPLE 5

5,6,7-trinor-4,8-inter-m-phenylene-13,14-didehydro-20-methyl-PGI$_2$ methyl ester (5)

The procedure of Example 2 was followed except the use of 196 mg (0.416 mmol) of 5,6,7-trinor-4,8-inter-m-phenylene-13,14-didehydro-20-methyl PGI$_2$ methyl ester 15-t-butylether in place of (1) to give 75 mg (0.180 mmol, 43%) of the subject compound.

IR (neat, $\nu$ cm$^{-1}$): 3400, 2930, 2850, 2225, 1740, 1595, 1450, 1250, 1190, 1030, 860, 750.

NMR (CDCl$_3$, δ ppm): 0.90 (t, 6 Hz, 3H), 1.2-2.4 (m, 16H), 2.30 (t, 7 Hz, 2H) 2.60 (t, 7 Hz, 2H), 2.86 (td, 6 Hz, 2 Hz, 1H), 3.65 (s, 3H), 3.82 (dd, 8 Hz, 6 Hz, 1H) 4.25 (q, 6 Hz, 1H), 4.40 (td, 6 Hz, 2 Hz, 1H), 5.24 (m, 1H), 6.89 (t, 7 Hz, 1H), 6.97 (dd, 7 Hz, 2 Hz, 1H), 7.13 (dd, 7 Hz, 2 Hz, 1H).

MS (m/e): 414 (M+), 396, 232, 158.

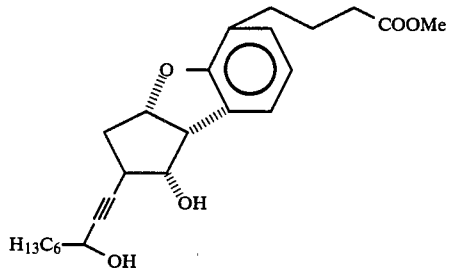

The above mentioned procedure was followed except the use of 168 mg (0.357 mmol) of the position isomer of (4) in place of (4) to give 88 mg (0.212 mmol, 59%) of the position isomer of the subject compound.

IR (neat, $\nu$ cm$^{-1}$): 3400, 2930, 2850, 2230, 1740, 1595, 1450, 1250, 1190, 1000, 860, 750.

NMR (CDCl$_3$, δ ppm): 0.89 (t, 6 Hz, 3H), 1.1-1.8 (m, 12H), 1.92 (m, 2H), 2.08 (bs, 2H), 2.34 (t, 7 Hz, 2H), 2.43 (m, 1H), 2.60 (t, 7 Hz, 2H), 3.65 (s, 3H), 3.95 (t, 8 Hz, 1H), 4.22 (t, 8 Hz, 1H), 4.32 (td, 6 Hz, 2 Hz 1H), 5.18 (dd, 8 Hz, 5 Hz, 1H), 6.78 (t, 7 Hz, 1H), 7.00 (dd. 7 Hz, 2 Hz, 1H), 7.14 (dd, 7 Hz, 2 Hz, 1H).

MS (m/e): 414 (M+), 396, 375, 293, 233, 201.

EXAMPLE 6

5,6,7,-trinor-4,8-inter-m-phenylene-13,14-didehydro-20-methyl-PGI₂ (6)

The procedure of Example 3 was followed except the use of 55.5 mg (0.134 mmol) of 5,6,7-trinor-4,8-inter-m-phenylene-13,14-didehydro-20-methyl-PGI₂ methyl ester in place of (2) to give 47.0 mg (0.118 mmol 88%) of the subject compound.

IR (neat, ν cm⁻¹): 3600–2500, 2930, 2850, 2225, 1710, 1595, 1450, 1250, 1190, 1030, 860, 745.

NMR (CDCl₃, δ ppm): 0.89 (t, 6 Hz, 3H), 1.1–2.2 (m, 14H), 2.31 (t, 7 Hz, 2H), 2.62 (t, 7 Hz, 2H), 2.82 (td, 6 Hz, 2 Hz, 1H), 3.88 (dd, 8 Hz, 6 Hz, 1H), 4.23 (q, 6 Hz, 1H), 4.39 (td, 6 Hz, 2 Hz, 1H), 4.64 (bs, 3H), 5.20 (m, 1H), 6.88 (t, 7 Hz, 1H), 6.96 (dd, 7 Hz, 2 Hz, 1H), 7.12 (dd, 7 Hz, 2 Hz, 1H).

MS (m/e): 400 (M+), 218, 158.

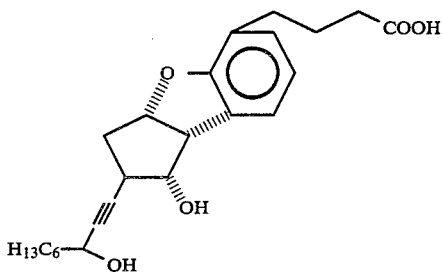

The above mentioned procedure was followed except the use of 64.7 mg (0.156 mmol) of the position isomer of (5) in place of (5) to give 58 mg (0.145 mmol, 93%) of the position isomer of the subject compound.

IR (neat, ν cm⁻¹): 3600–2500, 2925, 2830, 2230, 1710, 1595, 1450, 1250, 1190, 1000, 865, 750.

NMR (CDCl₃, δ ppm): 0.90 (t, 6 Hz, 3H), 1.1–1.8 (m, 12H), 1.98 (q, 7 Hz, 2H), 2.36 (t, 7 Hz, 2H), 2.40 (m, 1H), 2.62 (t, 7 Hz, 2H), 3.94 (t, 8 Hz, 1H), 4.22 (t, 8 Hz, 1H), 4.32 (td, 7 Hz, 2 Hz, 1H), 4.54 (bs, 3H), 5.16 (dd, 8 Hz, 5 Hz, 1H), 6.78 (t, 7 Hz, 1H), 7.00 (dd, 7 Hz, 2 Hz, 1H), 7.14 (dd, 7 Hz, 2 Hz, 1H).

MS (m/e): 400 (M+), 311, 217, 201.

EXAMPLE 7

5,6,7-trinor-4,8-inter-m-phenylene-13,14-didehydro-15-cyclohexyl-16,17,18,19,20-pentanor PGI₂ methyl ester 15-t-butylether (7)

The procedure of Example 1 was followed except the use of 2.965 g (15.28 mmol) of 3-t-butyloxy-3-cyclohexyl-1-propyne and 552 mg (2.015 mmol) of methyl 4-(3a,8b-cis-dihydro-3H-1,2-syn-epoxy-cyclopenta[b]benzofuran-5-yl)butanoate in place of 3-t-butyloxy-1-octyne and methyl 4-(3a,8b-cis-dihydro-3H-1,2-syn-epoxy-cyclopenta[b]benzofuran-5-yl)butanoate to give 196 mg (0.419 mmol, 21%) of the subject compound and 210 mg (0.449 mmol, 22%) of the position isomer.

Spectrum data of the subject compound:
IR (neat, ν cm⁻¹): 3450, 2930, 2850, 1740, 1595, 1450, 1365, 1255, 1195, 1040, 1020, 865, 745.

NMR (CDCl₃, δ ppm): 0.9–1.4 (m, 6H), 1.24 (s, 9H), 1.5–2.1 (m, 11H), 2.30 (t, 7 Hz, 2H), 2.59 (t, 7 Hz, 1H), 2.88 (td, 5 Hz, 2 Hz, 1H), 3.64 (s, 3H), 3.94 (m, 2H), 4.26 (q, 5 Hz, 1H), 5.30 (m, 1H), 6.79 (t, 7 Hz, 1H), 6.96 (dd, 7 Hz, 2 Hz, 1H), 7.12 (dd, 7 Hz, 2 Hz, 1H).

MS (m/e): 468 (M+), 329, 299, 279, 154.

Spectrum data of the position isomer:
IR (neat, ν cm⁻¹): 3450, 2930, 2850, 1740, 1595, 1450, 1365, 1255, 1195, 1045, 1010, 865, 750.

NMR (CDCl₃, δ ppm): 0.9–1.2 (m, 6H), 1.22 (s, 9H), 1.6–2.1 (m, 11H), 2.34 (t, 7 Hz, 2H), 2.43 (m, 1H), 2.61 (t, 7 Hz, 1H), 3.64 (s, 3H), 3.86 (dd, 6 Hz, 1 Hz, 1H), 3.97 (t, 8 Hz, 1H), 4.12 (m, 1H), 5.18 (dd, 8 Hz, 6 Hz, 1H), 6.79 (t, 7 Hz, 1H), 7.00 (dd, 7 Hz, 2 Hz, 1H), 7.14 (dd, 7 Hz, 2 Hz, 1H).

MS (m/e): 468 (M+), 329, 297, 279, 201.

EXAMPLE 8

5,6,7,-trinor-4,8-inter-m-phenylene-13,14-didehydro-15-cyclohexyl-16,17,18,19,20-pentanor PGI₂ methyl ester (8)

The procedure of Example 2 was followed except the use of 193 mg (0.412 mmol) of 5,6,7-trinor-4,8-inter-m-phenylene-13,14-didehydro-15-cyclohexyl-16,17,18,19,20-pentanor PGI₂ methyl ester 15-t-butylether in place of (1) to give 99 mg (0.240 mmol, 58%) of the subject compound.

IR (neat, ν cm⁻¹): 3380, 2925, 2850, 2230, 1730, 1595, 1450, 1250, 1190, 1025, 865, 745.

NMR (CDCl₃, δ ppm): 1.0–1.4 (m, 6H), 1.6–2.4 (m, 11H), 2.30 (t, 7 Hz, 2H), 2.59 (t, 7 Hz, 2H), 2.83 (td, 5 Hz, 2 Hz, 1H), 3.64 (s, 3H), 3.81 (dd, 8 Hz, 5 Hz, 1H), 4.18 (dd, 5 Hz, 2 Hz, 1H), 4.24 (q, 5 Hz, 1H), 5.24 (m, 1H), 6.79 (t, 7 Hz, 1H), 6.96 (dd, 7 Hz, 1 Hz, 1H), 7.14 (dd, 7 Hz, 1 Hz, 1H).

MS (m/e): 412 (M+), 394, 232, 158.

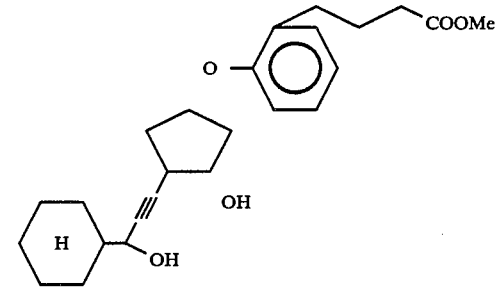

The above mentioned procedure was followed except the use of 162 mg (0.345 mmol) of the position isomer of (7), in place of (7) to give 68 mg (0.165 mmol, 48%) of the position isomer of the subject compound was obtained.

IR (neat, ν cm⁻¹): 3380, 2925, 2850, 2225, 1730, 1595, 1440, 1250, 1190, 1005, 860, 750.

NMR (CDCl₃, δ ppm): 0.9–1.4 (m, 6H), 1.6–2.2 (m, 11H), 2.34 (t, 7 Hz, 2H), 2.43 (m, 1H), 2.59 (t, 7 Hz, 2H), 3.64 (s, 3H), 3.94 (t, 8 Hz, 1H), 4.11 (dd, 5 Hz, 1 Hz, 1H), 4.22 (t, 8 Hz, 1H), 5.17 (dd, 8 Hz, 5 Hz, 1H), 6.77 (t, 7 Hz, 1H), 6.97 (dd, 7 Hz, 2 Hz, 1H), 7.12 (dd, 7 Hz, 2 Hz, 1H).

MS (m/e): 412 (M+), 396, 201, 176.

EXAMPLE 9

5,6,7,-trinor-4,8-inter-m-phenylene-13,14-didehydro-15-cyclohexyl-16,17,18,19,20-pentanor PGI₂ (9)

The procedure of Example 3 was followed except the use of 79.1 mg (0.192 mmol) of 5,6,7-trinor-4,8-inter-m-phenylene-13,14-didehydro-15-cyclohexyl-16,17,18,19,20-pentanor PGI₂ methyl ester, in place of (2) to give 61.5 mg (0.155 mmol, 81%) of the subject compound.

IR (neat, ν cm⁻¹): 3600-2500, 2930, 2850, 2225, 1705, 1595, 1450, 1260, 1190, 1080, 1020, 860, 740.

NMR (CDCl$_3$, δ ppm): 0.8-1.5 (m, 6H), 1.5-2.2 (m, 9H), 2.31 (t, 7 Hz, 2H), 2.61 (t, 7 Hz, 2H), 2.80 (td, 5 Hz, 1 Hz, 1H), 3.79 (dd, 8 Hz, 5 Hz, 1H), 4.16 (dd, 6 Hz, 2 Hz, 1H), 4.22 (q, 5 Hz, 1H), 4.90 (bs, 3H), 5.18 (m, 1H), 6.78 (t, 7 Hz, 1H), 6.95 (dd, 7 Hz, 1 Hz, 1H), 7.12 (dd, 7 Hz, 1 Hz, 1H).

MS (m/e): 398 (M+), 380, 297, 279, 218, 158.

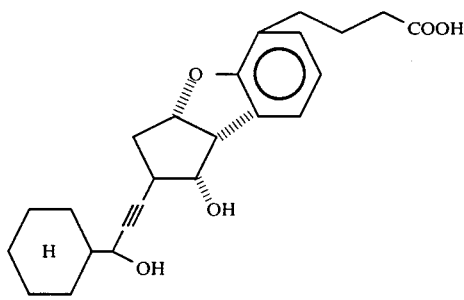

The above mentioned procedure was followed except the use of 49.9 mg (0.121 mmol) of the position isomer of (8), in place of (8) to give 43.7 mg (0.110 mmol, 91%) of the position isomer of the subject compound.

IR (neat, ν cm⁻¹): 3600-2500, 2925, 2850, 2225, 1705, 1595, 1450, 1250, 1190, 1090, 1000, 865, 750.

NMR (CDCl$_3$, δ ppm): 0.8-1.5 (m, 6H), 1.5-2.2 (m, 9H), 2.36 (t, 7 Hz, 2H), 2.50 (m, 1H), 2.63 (t, 7 Hz, 2H), 3.95 (t, 8 Hz, 1H), 4.0-4.6 (m, 5H), 5.19 (dd, 8 Hz, 5 Hz, 1H), 6.78 (t, 7 Hz, 1H), 7.00 (dd, 7 Hz, 1 Hz, 1H), 7.14 (dd, 7 hz, 1 Hz, 1H).

MS (m/e): 398 (M+), 380, 337, 297, 217, 201, 176.

EXAMPLES 10-18

The procedure of Example 1 are followed except the uses of 3-t-butyloxy-3-(4-methylcyclohexyl)-1-propyne; 3-t-butyloxy-3-(3-methyl-cyclohexyl)-1-propyne; 3-t-butyloxy-3-(2,2-dimethyl-4-methylcyclohexyl)-1-propyne; 3-t-butyloxy-3-(2-methylcyclohexyl)-1-propyne; 3-t-butyloxy-3-cyclopentyl-1-propyne; 3-t-butyloxy-3-(2-methylcyclopentyl)-1-propyne; 3-t-butyloxy-4-cyclohexyl-1-butyne; 3-t-tutyloxy-4-cyclopentyl-1-butyne or 3-t-butyloxy-5-cyclohexyl-1-pentyne in place of 3-t-butyloxy-1-octyne and the procedures of Example 2 and 3 are followed successively except the uses of the resulting compounds to give 5,6,7-trinor-4,8-inter-m-phenylene-13,14-didehydro-16,17,18,19,20-pentanor-15-(4-methyl-cyclohexyl) PGI$_2$ (10), 5,6,7-trinor-4,8-inter-m-phenylene-13,14-didehydro-16,17,18,19,20-pentanor-15-(3-methylcyclohexyl) PGI$_2$ (11), 5,6,7-trinor-4,8-inter-m-phenylene-13,14-didehydro-16,17,18,19,20-pentanor-15-(2,2-dimethyl-4-methylcyclohexyl) PGI$_2$ (12), 5,6,7-trinor-4,8-inter-m-phenylene-13,14-didehydro-16,17,18,19,20-pentanor-15-(2-methylcyclohexyl) PGI$_2$ (13), 5,6,7-trinor-4,8-inter-m-phenylene-13,14-didehydro-16,17,18,19,20-pentanor-15-cyclopentyl PGI$_2$ (14), 5,6,7-trinor-4,8-inter-m-phenylene-13,14-didehydro-16,17,18,19,20-pentanor-15-(2-methylcyclopentyl) PGI$_2$ (15), 5,6,7-trinor-4,8-inter-m-phenylene-13,14-didehydro-17,18,19,20-tetranor-16-cyclohexyl PGI$_2$ (16), 5,6,7-trinor-4,8-inter-m-phenylene-13,14-didehydro-17,18,19,20-tetranor-16-cyclopentyl PGI$_2$ (17), or 5,6,7-trinor-4,8-inter-m-phenylene-13,14-didehydro-18,19,20-trinor-17-cyclohexyl PGI$_2$ (18).

The infrared spectra and mass spectra of the compounds (10)-(18) are shown in Table 1.

TABLE 1

| Example | Compound | Mass spectrum (m/e, M+) | Infrared spectrum cm⁻¹ |
|---|---|---|---|
| 10 | 10 | 412 | 3600-2500, 2930, 2850, 1705, 1595, 1450, 1262, 1190, 1080, 860, 740 |
| 11 | 11 | 412 | 3600-2500, 2930, 2852, 1705, 1595, 1452, 1260, 1192, 1080, 862, 740 |
| 12 | 12 | 440 | 3600-2500, 2932, 2850, 1704, 1595, 1448, 1260, 1190, 1082, 860, 742 |
| 13 | 13 | 412 | 1705, 1596, 1448, 1260, 1190, 1080, 860, 740 |
| 14 | 14 | 382 | 1705, 1596, 1450, 1265, 1190, 1080, 860, 740 |
| 15 | 15 | 398 | 1706, 1595, 1451, 1260, 1190, 1080, 860, 740 |
| 16 | 16 | 412 | 1705, 1596, 1450, 1260, 1190, 1080, 860, 740 |
| 17 | 17 | 398 | 1705, 1596, 1450, 860 |
| 18 | 18 | 426 | 1705, 1596, 1450, 860, 742 |

EXAMPLE 19

5,6,7-trinor-4,8-inter-m-phenylene-13,14-didehydro-15-phenyl-16,17,18,19,20-pentanor PGI$_2$ methyl ester (19)

To a solution of 4.461 g (19.36 mmol) of t-butyldimethylsiloxyphenyl-1-propyne in 10 ml of dry toluene at −50° C. under argon was added 11.5 ml (19.11 mmol) of a hexane solution (1.62M) of n-butyl lithium, and the resulting solution was stirred for 20 minutes. 8.5 ml (16.66 mmol) of a toluene solution (1.96M) of a diethylaluminium chloride:ethylmethoxyaluminium chloride (3:1) mixture was added, the resulting solution was stirred for 10 minutes, thereafter, the temperature was allowed to warm to 0° C. and stirring was carried out for 1 hour. A solution of 518 mg (1.89 mmol) of methyl 4-(3a,8b-cis-dihydro-3H-1,2-syn-epoxycyclopenta[b-]benzofuran-5-yl)butanoate in 6 ml of toluene was added, and the resulting solution was stirred at 60° C. for 12 hours.

Methanol (2 ml) and further 20 ml of saturated brine under ice cold conditions were added. The resulting solution was extracted with ether (200 ml), the ether layer was washed with saturated brine (3×30 ml), dried and thereafter concentrated.

The residue was purified by chromatography (Merck Lobar B, cyclohexane-ethyl acetate 5:2) to afford crude a 15-t-butyldimethylsilyl ether and the position isomer thereof. This silylether was dissolved in 5 ml of an acetic acid:water:THF (3:1:1) mixture and stirred at room temperature for 15 hours. The solvent was distilled off under a reduced pressure and the residue was purified by chromatography (Merck Lobar B, cyclohexane-ethyl acetate 1:3) to give 22.2 mg (0.0547 mmol, 29%) of the subject compound.

IR (neat, ν cm⁻¹): 3400, 3040, 2930, 2850, 2220, 1720, 1590, 1445, 1260, 1190, 1075, 1020 735, 695.

NMR (CDCl$_3$, δ ppm): 1.8-2.5 (m, 6H), 2.30 (t, 7 Hz, 2H), 2.60 (t, 7 Hz, 2H), 2.93 (dd, 5 Hz, 2 Hz, 1H), 3.64

(s, 3H), 3.87 (dd, 8 Hz, 5 Hz, 1H), 4.31 (q, 5 Hz, 1H), 5.26 (m, 1H), 5.51 (d, 2 Hz, 1H), 6.79 (t, 7 Hz, 1H), 6.97 (dd, 7 Hz, 2 Hz, 1H), 7.13 (dd, 7 Hz, 2 Hz, 1H), 7.30–7.70 (m, 5H).

MR (m/e): 406 (M+), 388, 232, 158, 131, 105.

The above mentioned procedure was followed to give 29.9 mg (0.0736 mmol, 3.9%) of the position isomer.

Spectrum data of the position isomer:

IR (neat, $\nu$ cm$^{-1}$): 3380, 3020, 2930, 2850, 2225, 1730, 1590, 1445, 1240, 1190, 995, 750, 695.

NMR (CDCl$_3$, δ ppm): 1.84–2.14 (m, 4H), 2.32 (t, 7 Hz, 2H), 2.43 (m,1H), 2.59 (t, 7 Hz, 2H), 2.78 (bs, 2H), 3.64 (s, 3H), 3.90 (t, 8 Hz, 1H), 4.24 (t, 8 Hz, 1H), 5.15 (dd, 8 Hz, 5 Hz, 1H), 5.42 (s, 1H), 6.77 (t, 7 Hz, 1H), 6.98 (dd, 7 Hz, 1 Hz, 1H), 7.11 (dd, 7 Hz, 1 Hz, 1H), 7.12–7.65 (m, 5H).

MS (m/e): 406 (M+), 388, 200, 163, 144, 105.

EXAMPLE 20

5,6,7-trinor-4,8-inter-m-phenylene-13,14-didehydro-15-phenyl-16,17,18,19,20-pentanor-PGI$_2$ (20)

The procedure of Example 3 was followed except the use of 14.2 mg (0.0350 mmol) of 5,6,7-trinor-4,8-inter-m-phenylene-13,14-didehydro-15-phenyl-16,17,18,19,20-pentanor PGI$_2$ methyl ester in place of (2) to give 12.6 mg (0.0321 mmol, 92%) of the subject compound.

IR (neat, $\nu$ cm$^{-1}$): 3600–2500, 2925, 2850, 2220, 1700, 1595, 1450, 1240, 1190, 1075, 1025, 860, 745, 695.

NMR (CDCl$_3$, δ ppm): 1.9–2.1 (m, 4H), 2.30 (t, 7 Hz, 2H), 2.52 (t, 7 Hz, 2H), 2.89 (td, 6 Hz, 2 Hz, 1H), 3.84 (dd, 8 Hz, 6 Hz, 1H), 4.25 (q, 6 Hz, 1H), 4.3 (bs, 3H), 5.23 (m, 1H), 5.49 (d, 2 Hz, 1H), 6.78 (t, 7 Hz, 1H), 6.96 (dd, 7 Hz, 2 Hz, 1H), 7.11 (dd, 7 Hz, 2 Hz, 1H), 7.30–7.70 (m, 5H).

MS (m/e): 392 (M+), 374, 218, 158.

The above mentioned procedure was followed except the use of 27.5 mg (0.0677 mmol) of the position isomer of (19) in place of (19) to give 19.4 mg (0.0495 mmol, 73%) of the position isomer of the subject compound.

IR (neat, $\nu$ cm$^{-1}$): 3600–2500, 2920, 2850, 2225, 1700, 1590, 1450, 1240, 1190, 1100, 1040, 990, 850, 745, 695.

NMR (CDCl$_3$, δ ppm): 1.8–2.15 (m, 4H), 2.34 (t, 7 Hz, 2H), 2.43 (m, 1H), 2.61 (t, 7 Hz, 2H), 3.91 (t, 8 Hz, 1H), 4.24 (t, 8 Hz, 1H), 4.53 (bs, 3H), 5.15 (dd, 8 Hz, 5 Hz, 1H), 5.41 (s, 1H), 6.76 (t, 7 Hz, 1H), 6.97 (dd, 7 Hz, 2 Hz, 1H), 7.10 (dd, 7 Hz, 2 Hz, 1H), 7.24–7.64 (m, 5H).

MS (m/e): 392 (M+), 374, 170.

EXAMPLES 21–28

The procedure of Example 19 is followed except the uses of 3-(t-butyldimethylsiloxy)-3-(p-chlorophenyl)-1-propyne, 3-(t-butyldimethylsiloxy)-3-(m-chlorophenyl)-1-propyne, 3-(t-butyldimethylsiloxy)-3-(p-tolyl)-1-propyne, 3-(t-butyldimethylsiloxy)-3-(p-methoxyphenyl)-1-propyne, 3-(t-butyldimethylsiloxy)-3-(m-trifluoromethylphenyl)-1-propyne, 3-(t-butyldimethylsiloxy)-4-phenyl-1-butyne, 3-(t-butyldimethylsiloxy)-5-phenyl-1-pentyne, or 3-(t-butyldimethylsiloxy)-3-(β-naphthyl)-1-propyne in place of 3-t-butyldimethylsiloxy-3-phenyl-1-propyne, and the procedure of Example 20 is followed except the use of the each resulting compound to give 5,6,7-trinor-4,8-inter-m-phenylene-13,14-didehydro-16,17,18,19,20-pentanor-15-(p-chlorophenyl) PGI$_2$ (21), 5,6,7-trinor-4,8-inter-m-phenylene-13,14-didehydro-16,17,18,19,20-pentanor-15-(m-chlorophenyl) PGI$_2$ (22), 5,6,7-trinor-4,8-inter-m-phenylene-13,14-didehydro-16,17,18,19,20-pentanor-15-(p-tolyl) PGI$_2$ (23), 5,6,7-trinor-4,8-inter-m-phenylene-13,14-didehydro-16,17,18,19,20-pentanor-15-(p-methoxyphenyl) PGI$_2$ (24), 5,6,7-trinor-4,8-inter-m-phenylene-13,14-didehydro-16,17,18,19,20-pentanor-15-(m-trifluoromethylphenyl) PGI$_2$ (25), 5,6,7-trinor-4,8-inter-m-phenylene-13,14-didehydro-17,18,19,20-tetranor-16-phenyl PGI$_2$ (26), 5,6,7-trinor-4,8-inter-m-phenylene-13,14-didehydro-18,19,20-trinor-17-phenyl PGI$_2$ (27), or 5,6,7-trinor-4,8-inter-m-phenylene-13,14-didehydro-16,17,18,19,20-pentanor-15-(β-naphthyl) PGI$_2$ (28). The spectral data of the compounds (21)–(28) are shown in Table 2.

TABLE 2

| Example | Compound | Mass spectrum (m/e) | Infrared spectrum cm$^{-1}$ |
|---|---|---|---|
| 21 | 21 | 426 | 3600–2500, 2925, 2850, 1700, |
|    |    | 428 | 1595, 1400, 1240, 1190, 1075, 860 |
| 22 | 22 | 426 | 1700, 1595, 1450, 1242, 1190, |
|    |    | 428 | 1075, 860, 730 |
| 23 | 23 | 406 | 1700, 1595, 1450, 1242, 1190, 1075, 860, 815, 730 |
| 24 | 24 | 422 | 1700, 1598, 1455, 1240, 1190, 1075, 860 |
| 25 | 25 | 460 | |
| 26 | 26 | 406 | 1700, 1595, 1450, 1240, 1190, 1075, 1025, 860, 740, 695 |
| 27 | 27 | 420 | 1700, 1240, 1190, 860, 740, 695 |
| 28 | 28 | 442 | 1700, 1240, 1190 |

EXAMPLE 29–33

The procedure of Example 1 is followed except the uses of 3-t-butyloxy-5-methyl-1-octyne, 3-t-butyloxy-5-methyl-1-nonyne, 3-t-butyloxy-4,4-dimethyl-1-octyne, 3-t-butyloxy-4,4-dimethyl-1-nonyne, or 3-t-butyloxy-9-methyl-8-decene-1-yn in place of 3-t-butyloxy-1-octyne, and the procedures of Examples 2 and 3 are followed successively except the uses of the resulting compounds to give 5,6,7-trinor-4,8-inter-m-phenylene-13,14-didehydro-17-methyl PGI$_2$ (29), 5,6,7-trinor-4,8-inter-m-phenylene-13,14-didehydro-17-methyl-ω-homo PGI$_2$ (30), 5,6,7-trinor-4,8-inter-m-phenylene-13,14-didehydro-16,16-dimethyl PGI$_2$ (31), 5,6,7-trinor-4,8-inter-m-phenylene-13,14-didehydro-16,16-dimethyl-ω-homo PGI$_2$ (32), or 5,6,7-trinor-4,8-inter-m-phenylene-13,14-didehydro-20-isopropylidene PGI$_2$ (33). The spectral data of these compounds are shown in Table 3.

TABLE 3

| Example | Compound | Mass spectrum (m/e) | Infrared spectrum cm$^{-1}$ |
|---|---|---|---|
| 29 | 29 | 400 | 1710, 1595, 1450, 1250, 1190, 1030, 865, 745 |
| 30 | 30 | 414 | 1708, 1597, 1452, 1250, 1190, 1025 |
| 31 | 31 | 428 | 1710, 1595, 1450, 1250, 1190 |
| 32 | 32 | 442 | 1710, 1595, 1450, 1250, 1190 |
| 33 | 33 | 426 | 1705, 1595, 1450, 1250, 1190, 862, 740 |

EXAMPLE 34

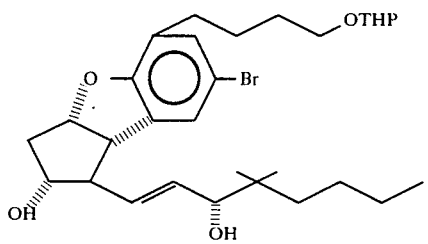

2-decarboxy-2-tetrahydropyranyloxymethyl-5,6,7-trinor-4,8-inter-(5-bromo-1,3-phenylene)-16,16-dimethyl PGI₂ (34)

To a solution of 183 mg (0.394 mmol) of 1,2,3a,8b-cis-tetrahydro-7-bromo-1-exo-(2-formylethenyl)-2-endo-hydroxy-5-(4-tetrahydropyranyloxy-butyl)cyclopenta[b]benzofuran in 3 ml of THF −78° C. was added 1.9 ml (0.85M, 1.61 mmol, 4.1 equiv.) of a solution of 2-(2-methyl)hexylmagnesium chloride in THF, and the resulting solution was stirred for 30 minutes. After TLC analysis revealed completion, 2 ml of a saturated aqueous solution of ammonium chloride was added, and the mixture was extracted with ethyl acetate (10 ml×6). The organic layer was dried and thereafter concentrated to obtain 196 mg of an oily crude product. This crude product was purified by column chromatography (Merck Co.'s Lobar Column B; cyclohexane:ethyl acetate 1:3) to give 60 mg (27%) of the polar subject compound and 29 mg (13%) of a less polar 15-epimer.

IR (neat) ν cm⁻¹: 3400 (3650–3000), 2930, 2860, 1600, 1350, 1255, 1190, 1135, 1115, 1070, 1020, 965, 860, 745.

NMR (CDCl₃ solution) δ ppm: 0.87 (s, 3H), 0.91 (s, 3H), 0.91 (t, J=6 Hz, 3H), 1.28 (m, 6H), 1.64 (m, 10H), 1.97 (m, 1H), 2.59 (m, 4H), 3.00 (broad s, 2H), 3.39 (m, 3H), 3.81 (m, 4H), 4.57 (m, 1H), 5.07 (m, 1H), 5.64 (m, 2H), 6.94 (s, 1H), 7.09 (s, 1H).

Mass spectrum (m/e): M⁺ 564.

| Anal. Calcd. for C₃₀H₄₅O₅Br | Found |
|---|---|
| C: 63.71% | 63.69% |
| H: 8.02% | 8.03% |
| Br: 14.13% | 14.11% |

EXAMPLE 35

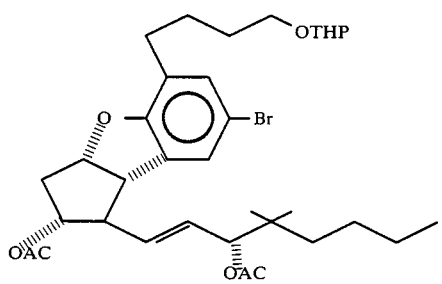

2-decarboxy-2-tetrahydropyranyloxymethyl-5,6,7-trinor-4,8-inter-(5-bromo-1,3-phenylene)-16,16-dimethyl PGI₂ diacetate (35)

Under nitrogen atmosphere, to a solution of 132 mg (0.234 mmol) of 2-decarboxy-2-tetrahydropyranyloxymethyl-5,6,7-trinor-4,8-(5-bromo-1,3-phenylene)-16,16-dimethyl PGI₂ in 1 ml of pyridine was added acetic anhydride, and the resulting solution was stirred at room temperature for 15 hours. After TLC analysis revealed completion, the solution was concentrated to give 145 mg (0.223 mmol, 95.3%) of the subject compound as an oil.

NMR (CDCl₃ solution) δ ppm: 0.89 (m, 9H), 1.25 (m, 6H), 1.67 (m, 10H), 1.75 (s, 3H), 2.03 (m, 1H), 2.07 (s, 3H), 2.56 (m, 3H), 2.82 (m, 1H), 3.56 (m, 3H), 3.81 (m, 2H), 4.58 (m, 1H), 4.93 (q, J=6 Hz, 1H), 5.08 (m, 1H), 5.20 (m, 1H), 5.62 (m, 2H), 6.93 (s, 1H), 7.08 (s, 1H).

IR (neat, ν cm⁻¹): 2930, 2860, 1735, 1450, 1365, 1235, 1130, 1120, 965, 900, 860, 750.

Mass (m/e): 648 (M⁺), 650 (M+2).

| Anal. Calcd. for C₃₄H₄₉O₇Br | Found |
|---|---|
| C = 62.86% | 62.83% |
| H = 7.60% | 7.59% |

EXAMPLE 36

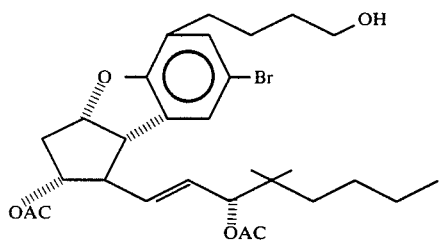

2-decarboxy-2-hydroxymethyl-5,6,7-trinor-4,8-inter-(5-bromo-1,3-phenylene)-16,16-dimethyl PGI₂ 11(0), 15(0)-diacetate (36)

To a solution of 145 mg (0.223 mmol) of 2-decarboxy-2-tetrahydro-pyranyloxymethyl-5,6,7-trinor-4,8-inter-(5-bromo-1,3-phenylene)-16,16-dimethyl PGI₂ diacetate in 1 ml of THF and 2 ml of acetontirile was added 1 m of 0.25N hydrochloric acid, and the resulting solution was stirred at room temperature for 7 hours. The reaction solution was cooled to 0° C., 3 ml of a saturated aqueous solution of sodium bicarbonate was added and the mixture was extracted with ethyl acetate (10 ml×5). The organic layer was dried over anhydrous Na₂SO₄, concentrated and 153 mg of an oily substance obtained was purified by column chromatography (Merck Co.'s Lobar Column; cyclohexane:ethyl acetate 2:3) to give 101 mg (0.179 mmol, 80.2%) of 36 as an oil.

NMR (CDCl₃ solution) ν ppm: 0.89 (m, 9H), 1.25 (m, 6H), 1.64 (m, 4H), 1.74 (s, 3H), 2.03 (m, 1H), 2.07 (s, 3H), 2.12 (broad s, 1H), 2.55 (m, 3H), 2.80 (m, 1H), 3.61 (m, 3H), 4.93 (q, J=6 Hz, 1H), 5.07 (m, 1H), 5.20 (m, 1H), 5.60 (m, 2H), 6.92 (s, 1H), 7.07 (s, 1H).

IR (neat, ν cm⁻¹): 3450, (3650–3000), 2930, 2860, 1735, 1600, 1450, 1370, 1235, 1190, 1050, 1020, 970, 910, 860, 740.

Mass (m/e): 564 (M⁺), 566 (M+2).

| Anal. Calcd. for C29H41O6Br | Found |
|---|---|
| C = 61.59% | 61.55% |
| H = 7.30% | 7.28% |

EXAMPLE 37

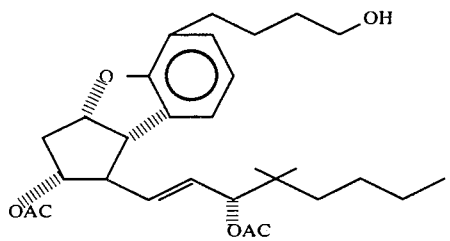

2-decarboxy-2-hydroxymethyl-5,6,7-trinor-4,8-inter-m-phenylene-16,16-dimethyl PGI₂ 11(0), 15(0)-diacetate (37)

To a solution of 92 mg (0.162 mmol) of 2-decarboxy-2-hydroxymethyl-5,6,7-trinor-4,8-inter-(5-bromo-1,3-phenylene)-16,16-dimethyl-PGI₂ diacetate and 1 mg of 2,2'-azobisisobutyronitrile in 6 ml of benzene under argon atmosphere was added 300 mg (1.03 mmol, 6.4 equiv.) of tri-n-butyltin hydride, and the resulting mixture was stirred at 50° C. for 26 hours. To the mixture 1 ml of a saturated aqueous solution of sodium bicarbonate and 1 ml saturated brine were added and the mixture was extracted with ethyl acetate (10 ml×3). The organic layer was dried over anhydrous Na₂SO₄ and thereafter concentrated. When 343 mg of an oily substance obtained was purified by column chromatography (Merck Co.'s Lobar Column; cyclohexane:ethyl acetate 1:2), 69 mg (0.142 mmol, 87.6%) of 37 was obtained in an oily state.

NMR (CDCl₃ solution) δ ppm: 0.89 (m, 9H), 1.25 (m, 6H), 1.64 (m, 4H), 1.74 (s, 3H), 2.03 (m, 1H), 2.07 (s, 3H), 2.55 (m, 3H), 2.80 (m, 1H), 3.10 (broad s, 1H), 3.61 (m, 3H), 4.93 (q, J=6 Hz, 1H), 5.07 (m, 1H), 5.20 (m, 1H), 5.60 (m, 2H), 6.76 (dd, J=7, 8 Hz, 1H), 6.89 (d, J=7 Hz, 1H), 6.90 (d, J=8 Hz, 1H).

IR (neat, ν cm⁻¹): 3450 (3650–3000), 2930, 2860, 1735, 1600, 1450, 1370, 1235, 1190, 1050, 1020, 970, 860, 760, 740.

Mass (m/e): 486 (M+).

| Anal. Calcd. for C29H42O6 | Found |
|---|---|
| C = 71.58% | 71.56% |
| H = 8.63% | 8.63% |

EXAMPLE 38

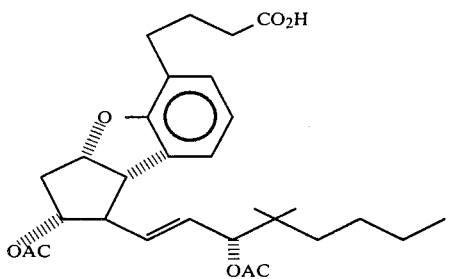

5,6,7-trinor-4,8-inter-m-phenylen-16,16-dimethyl PGI₂ diacetate (38)

To a solution of 66.0 mg (0.136 mmol) of 2-decarboxy-2-hydroxymethyl-5,6,7-trinor-4,8-inter-m-phenylene-16,16-dimethyl PGI₂ diacetate in 1 ml of N,N-dimethylformamide was added 412 mg (1.10 mmol, 8.1 equiv.) of pyridinium dichromate, and the resulting mixture was stirred at room temperature for 7 hours. Five ml of water was added and the mixture was extracted with ethyl acetate (10 ml×3), the organic layer was washed with saturated brine (1 ml×2) and dried over anhydrous Na₂SO₄. After concentration, 194 mg of the obtained crude product was purified by column chromatography (Merck Co.'s Lobar Column cyclohexane: ACOEt 2:1) to give 64.0 mg (0.128 mmol, 94.1%) of 38.

NMR (CDCl₃ solution) δ ppm: 0.89 (m, 9H), 1.25 (m, 6H), 1.74 (s, 3H), 1.99 (m, 1H), 2.08 (s, 3H), 2.10 (m, 2H), 2.39 (t, J=7 Hz, 2H), 2.60 (m, 3H), 2.82 (m, 1H), 3.60 (dd, J=6, 8 Hz, 1H), 4.95 (q, J=6 Hz, 1H), 5.09 (m, 1H), 5.22 (m, 1H), 5.62 (m, 2H), 6.76 (dd, J=7, 8 Hz, 1H), 6.89 (d, J=7 Hz, 1H), 6.90 (d, J=8 Hz, 1H).

IR (neat, ν cm⁻¹): 3200 (3600–2300), 2960, 2930, 2860, 1735, 1710, 1600, 1450, 1370, 1235, 1190, 1020, 965, 860, 760, 740.

Mass (m/e): 500 (M+).

| Anal. Calcd. for C29H40O9 | Found |
|---|---|
| C = 69.58% | 69.29% |
| H = 8.05% | 7.82% |

EXAMPLE 39

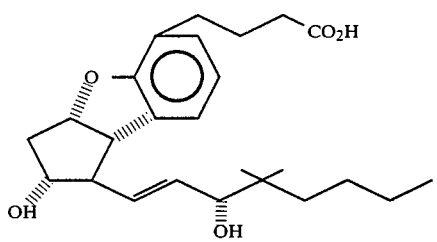

5,6,7-trinor-4,8-inter-m-phenyelene-16,16-dimethyl PGI₂ (39)

To a solution of 48.0 mg (0.096 mmol) of 5,6,7-trinol-4,8-inter-m-phenylene-16,16-dimethyl PGI₂ diacetate in 2 ml of methanol was added 0.5 ml (0.50 mmol, 5.2 equiv.) of 1N sodium hydroxide, and the resulting solution was stirred at room temperature for 24 hours. The solution was cooled to 0° C., 1N HCl was added slowly to adjust the pH of the reaction solution to 3, thereafter, the mixture was extracted with ethyl acetate (10 ml×5), and the organic layer was washed with saturated brine (1 ml×2) and thereafter dried over anhydrous $Na_2SO_4$. After evaporation of the solvent, 400 mg (0.096 mmol, 100%) of 39 was obtained.

NMR ($CDCl_3$ solution) δ ppm: 0.89 (m, 9H), 1.27 (m, 6H), 1.96 (m, 3H), 2.34 (m, 3H), 2.62 (m, 3H), 3,38 (t, J=9 Hz, 1H), 3.85 (m, 2H), 5.07 (non-dissociated quartet, J=8 Hz, 1H), 5.40 (broad singlet 3H), 5.63 (m, 2H), 6.74 (dd, J=8, 6 Hz, 1H), 6.94 (m, 2H).

IR (neat, ν $cm^{-1}$): 3400 (3600–2220), 2960, 2930, 2860, 1710, 1600, 1450, 1250, 1190, 1070, 1020, 970, 910, 860, 765, 735.

Mass (m/e): 416 (M+).

| Anal. Calcd. for $C_{25}H_{36}O_5$ | Found |
|---|---|
| C = 72.09% | 71.98% |
| H = 8.70% | 8.66% |

EXAMPLE 40

2-decarboxy-2-tetrahydropyranyloxymethyl-5,6,7-trinor-4,8-inter-m-phenylene-17-methyl $PGI_2$ (40, 41)

To a solution of 1 g of 1,2,3a,8b-cis-tetrahydro-5-(4-tetrahydropyranyloxymethyl)-1-exo-(2-formylethenyl)-2-endo-hydroxy cyclopenta(b)benzofuran in 20 ml of anhydrous THF cooled in ice bath was added dropwise 5 ml of 2-methylpentyl magnesium bromide (1N), and the resulting solution was stirred for 30 minutes. Ammonium chloride, methanol and water were added, and the mixture was extracted 3 times with ether. The combined ether layers were washed with water and saturated brine, dried and thereafter concentrated to afford 1.5 g of an oily substance. The oily substance was purified by column chromatography (silica gel; ethyl acetate) to give 196 mg of a less polar substance and 200 mg of a polar substance.

The less polar substance (17-α-methyl isomer) (40).

IR (neat) ν$cm^{-1}$: 3350, 1595, 970, 765, 745.

NMR ($CDCl_3$) δ: 0.90 (6H, m), 3.40 (4H, m), 3.80 (4H, m) 4.20 (1H, m), 4.57 (1H, m), 5.10 (1H, m), 5.62 (2H, m), 6.72 (1H, t, J=7.0 Hz), 6.94 (1H, d, J=7.0 Hz), 6.96 (1H, d, J=7.0 Hz).

Mass (m/e): 472, 454, 436.

The polar substance (17-β-methyl isomer) (41).

IR (neat, ν$cm^{-1}$): 3350, 1595, 970, 765, 745.

NMR ($CDCl_3$) δ: 0.90 (6H, m), 3.40 (4H, m), 3.80 (4H, m), 4.20 (1H, m), 4.60 (1H, m), 5.10 (1H, m), 5.60 (2H, m). 6.72 (1H, t, J=7.0 Hz), 6.94 (1H, d, J=7.0 Hz), 6.96 (1H, d, J=7.0 Hz).

Mass (m/e): 472, 454, 436.

| | As $C_{29}H_{44}O_5$ | |
|---|---|---|
| Anal. Calcd. for $C_{29}H_{44}O_5$ | | Found |
| C = 73.69% | | 73.61% |
| H = 9.36% | | 9.32% |

EXAMPLE 41

2-decarboxy-2-tetrahydropyranyloxymethyl-5,6,7-trinor-4,8-inter-m-phenylene-11,15-dideoxy-11,15-diacetoxy-17-α-methyl $PGI_2$ (42)

A solution of 170 mg of 2-decarboxy-2-tetrahydropyranyloxymethyl-5,6,7-trinor-4,8-inter-m-phenylene-17-α-methyl $PGI_2$ in 10 ml of acetic anhydride and 5 ml of anhydrous pyridine was stirred at room temperature for 2 hours. When the reaction solution was concentrated and the residue was treated azeotropically twice with toluence and once with benzene to give 200 mg of a nearly pure diacetate.

IR (neat, ν$cm^{-1}$): 1740, 1595, 1235, 970, 760, 750.

NMR ($CDCl_3$) δ: 0.90 (5H,m), 1.72 (3H, s), 2.06 (3H, s), 2.60 (3H, s), 2.80 (1H, q, J=7.0 Hz), 3.20–4.00 (5H, m), 4.60 (1H, m), 4.92 (1H, m), 5.30 (2H, m), 5.60 (2H, m), 6.74 (1H, dd, J=8.0 Hz, 7.0 Hz), 6.96 (1H, d, J=8.0 Hz), 6.98 (1H, d, J=6.0 Hz).

Mass (m/e): 556 (M+).

| Anal. Calcd. for $C_{33}H_{48}H_7$ | Found |
|---|---|
| C = 71.19% | 71.10% |
| H = 8.69% | 8.60% |

EXAMPLE 42

2-decarboxy-2-tetrahydropyranyloxymethyl-5,6,7-trinor-4,8-inter-m-phenylene-11,15dideoxy-11,15-diacetoxy-17-β-methyl $PGI_2$ (43)

The procedure of Example 41 was followed except the use of 180 mg of 2-decarboxy-2-tetrahydropyranyloxymethyl-5,6,7-trinol-4,8-inter-m-phenylene-17-methyl $PGI_2$ in place of (40) to give 200 mg of a diacetate.

IR (neat) ν$cm^{-1}$: 1740, 1595, 1235, 970, 760, 750.

NMR ($CDCl_3$) δ: 0.90 (6H, m), 1.73 (3H, s), 2.04 (3H, s), 2.60 (3H, s), 2.80 (1H, q, J=6.0 Hz), 3.20–4.00 (4H, m), 4.60 (1H, m), 4.92 (1H, m), 5.30 (2H, m), 5.60 (2H, m), 6.74 (1H, dd, J=8.0 Hz, 6.0 Hz), 6.96 (1H, d, J=6.0 Hz), 6.98 (1H, d, J=8.0 Hz).

Mass (m/e): 556 (M+).

| Anal. Calcd. for $C_{33}H_{48}O_7$ | Found |
|---|---|
| C = 71.19% | 71.02% |
| H = 8.69% | 8.58% |

EXAMPLE 43

2-decarboxy-2-hydroxymethyl-5,6,7-trinor-4,8-inter-m-phenylene-11,15-didehydroxy-11,15-diacetoxy-17-α-methyl $PGI_2$ (44)

To a solution of 200 mg of 2-decarboxy-2-tetrahydropyranyloxymethyl-5,6,7-trinor-4,8-inter-m-phenylene-11,15-didehydroxy-11,15-diacetoxy-17-α-methyl $PGI_2$ in 5.6 ml of acetonitrile were added ¼N hydrochloric acid and 2.6 ml of THF, and the resulting solution was stirred at room temperature for 4 hours. Water was added, and the mixture was extracted 3 times with ether, the combined ether layers were washed with water and saturated brine, dried and thereafter concentrated to afford 220 mg of an oily substance. The oily substance was purified by column chromatography

[silica gel; ethyl acetate:cyclohexane (2:1)] to give 142 mg of the alcohol.

IR (neat) νcm⁻¹: 3450, 1740, 1595, 1240, 970, 760, 750.

NMR (CDCl₃) δ: 0.90 (6H, m), 1.63 (3H, s), 2.06 (3H, m), 2.60 (3H, m), 2.80 (1H, q, J=6.0 Hz), 3.65 (3H, m), 4.92 (1H, m), 5.30 (2H, m), 5.60 (2H, m), 6.78 (1H, dd, J=10.0 Hz, 6.0 Hz), 6.93 (1H, d, J=6.0 Hz), 6.95 (1H, d, J=10.0 Hz).

Mass (m/e): 472 (M+).

| Anal. Calcd. for $C_{28}H_{40}O_6$ | Found |
|---|---|
| C = 71.16% | 71.11% |
| H = 8.53% | 8.48% |

EXAMPLE 44

2-decarboxy-2-hydroxymethyl-5,6,7-trinor-4,8-inter-m-phenylene-11,15-didehydroxy-11,15-diacetoxy-17-β-methyl PGI₂ (45)

The procedure of Example 43 was followed except the use of 180 mg of 2-decarboxy-2-tetrahydropyranyloxymethyl-5,6,7,-trinor-4,8-inter-m-phenylene-11,15-didehydroxy-11,15-diacetoxy-17-β-methyl PGI₂ in place of (42) to give 120 mg of the alcohol.

IR (neat) νcm⁻¹: 3450, 1740, 1595, 1240, 970, 760, 750.

NMR (CDCl₃) δ: 0.92 (6H, m), 1.74 (3H, s), 2.05 (3H, s), 2.60 (3H, m), 2.80 (1H, q, J=6.0 Hz), 3.65 (3H, m), 4.92 (1H, m), 5.30 (2H, m), 5.60 (2H, m), 6.78 (1H, dd, J=10.0 Hz, 6.0 Hz), 6.93 (1H, d, J=6.0 Hz), 6.95 (1H, d, J=10.0 Hz).

Mass (m/e): 472 (M+).

| Anal. Calcd. for $C_{28}H_{40}O_6$ | Found |
|---|---|
| C = 71.16% | 70.01% |
| H = 8.53% | 8.41% |

EXAMPLE 45

5,6,7-trinor-4,8-inter-m-phenylene-11,15-dideoxy-11,15-diacetoxy-17-α-methyl PGI₂ (46)

To a solution of 129 mg of 2-decarboxy-2-hydroxymethyl-5,6,7-trinor-4,8-inter-m-phenylene-11,15-didehydroxy-11,15-diacetoxy-17-α-methyl PGI₂ in 3.3 ml of anhydrous DMF was added 820 mg of pyridinium dichromate, and the resulting mixture was stirred at room temperature for 16 hours. Water was added and the mixture was extracted 5 times with ether, the combined ether layers were washed with water and saturated brine, dried and thereafter concentrated to afford 140 mg of an oily substance. The oily substance was purified by column chromatography [silica gel (which had been treated with acetic acid) ethyl acetate:cyclohexane (1:2)], to give 98.8 mg of the carboxylic acid.

IR (neat) νcm⁻¹: 3600-2300, 1740, 1710, 1595, 1240, 970, 760, 740.

NMR (CDCl₃) δ: 0.87 (3H, t, J=5.0 Hz), 0.90 (3H, d, J=6.0 Hz), 1.72 (3H, s), 2.06 (3H, s), 2.40 (2H, t, J=8.0 Hz), 2.63 (2H, t, J=7.5 Hz), 2.84 (1H, 1, J=6.0 Hz), 3.62 (1H, dd, J=10.0 Hz, 6.0 Hz), 4.92 (1H, q, J=6.0 Hz), 5.30 (2H, m), 5.60 (2H, m), 6.77 (1H, dd, J=8.0 Hz, 6.0 Hz), 6.95 (1H, d, J=6.0 Hz), 6.97 (1H, d, J=8.0 Hz).

Mass (m/e): 486 (M+).

| Anal. Calcd. for $C_{28}H_{38}O_7$ | Found |
|---|---|
| C = 69.11% | 68.91% |
| H = 7.87% | 7.69% |

EXAMPLE 46

5,6,7-trinor-4,8-inter-m-phenylene-11,15-dideoxy-11,15-diacetoxy-17-β-methyl PGI₂ (47)

The procedure of Example 45 was followed except the use of 100 mg of 2-decarboxy-2-hydroxymethyl-5,6,7-trinor-4,8-inter-m-phenylene-11,15-dideoxy-11,15-diacetoxy-17-β-methyl PGI₂ in place of (44) to give 85 mg of a carboxylic acid (47).

IR (neat) νcm⁻¹: 3600-2300, 1740, 1710, 1595, 1240, 970, 760, 740.

NMR (CDCl₃) δ: 0.90 (6H, m), 1.72 (3H, s), 2.05 (3H, s), 2.40 (3H, t, J=7.0 Hz), 2.60 (3H, t, J=7.0 Hz), 2.85 (1H, t, J=6.0 Hz), 3.60 (1H, dd, J=6.0 Hz, 6.0 Hz), 4.82 (1H, q, J=6.0 Hz), 5.30 (2H, m), 5.60 (2H, m), 6.76 (1H, t, J=7.0 Hz), 6.98 (2H, d, J=7.0 Hz).

Mass (m/e): 486 (M+).

| Anal. Calcd. for $C_{28}H_{38}O_7$ | Found |
|---|---|
| C = 69.11% | 68.97% |
| H = 7.87% | 7.80% |

EXAMPLE 47

5,6,7-trinor-4,8-inter-m-phenylene-17-α-methyl PGI₂ (48)

To a solution of 88 mg of 5,6,7,-trinor-4,8-inter-m-phenylene-11,15-dideoxy-11,15-diacetoxy-17-α-methyl PGI₂ in 5 ml of methanol was added 1 ml of 1N sodium hydroxide, and the resulting solution was stirred at room temperature for 2 hours. The reaction solution was concentrated, water was added, the pH of the mixture cooled in an ice bath was adjusted to 3 with 1N hydrochloric acid and the mixture was extracted 3 times with ethyl acetate. The combined organic layers were washed with water and saturated brine, dried and thereafter concentrated to give 68 mg of the pure diol.

IR (neat) νcm⁻¹: 3600-2300, 1710, 1595, 970, 760, 740.

NMR (CDCl₃) δ: 0.90 (6H, m), 3.37 (1H, t, J=8.0 Hz), 3.83 (1H, m), 4.16 (2H, m), 5.05 (1H, m), 5.60 (5H, m), 6.72 (1H, dd, J=8.0 Hz, 6.0 Hz), 6.92 (1H, d, J=6.0 Hz), 6.94 (1H, d, J=8.0 Hz).

Mass (m/e): 402 (M+).

| Anal. Calcd. for $C_{24}H_{34}O_5$ | Found |
|---|---|
| C = 71.61% | 71.55% |
| H = 8.51% | 8.48% |

EXAMPLE 48

5,6,7-trinor-4,8-inter-m-phenylene-17-β-methyl PGI₂ (49)

The procedure of Example 47 was followed except the use of 70 mg of 5,6,7-trinor-4,8-inter-m-phenylene-11,15-dideoxy-11,15-diacetoxy-17-β-methyl PGI₂ in place of (46) to give 57 mg of the diol (49).

IR (neat) $\nu cm^{-1}$: 3600–2300, 1710, 1595, 970, 760, 740.

NMR (CDCl$_3$) δ: 0.90 (6H, m), 2.33 (2H, t, J=7.0 Hz), 2.63 (2H, t, J=7.0 Hz), 3.36 (1H, t. J=8.0 Hz), 3.88 (1H, m), 4.17 (1H, m), 5.06 (1H, m), 5.53 (5H, m), 6.70 (1H, t, J=7.2 Hz), 6.95 (2H, m).

Mass (m/e): 402 (M+).

| Anal. Calcd. for C$_{24}$H$_{34}$O$_5$ | Found |
|---|---|
| C = 71.61% | 71.52% |
| H = 8.51% | 8.42% |

EXAMPLE 49

2-decarboxy-2-tetrahydropyranyloxymethyl-5,6,7-trinor-4,8-inter-m-phenylene-17-α-methyl-20 -homo PGI$_2$ (50) (51)

To a solution of 2 g of 3a,8b-cis-tetrahydro-1H-5-(4-tetrahydropyranyloxymethyl)-1-β-(2-formylethenyl)-2-α-hydroxycyclopenta[b]benzofuran in 40 ml of anhydrous THF cooled in an ice bath was added dropwise 11 ml of 2(s)-methylhexyl magnaesium chloride (0.9N), and the resulting solution was stirred for 30 minutes. Ammonium chloride, methanol and water were added, and the mixture was extracted 3 times with ether. The combined ether layers were washed with water and saturated brine, dried and thereafter concentrated to afford 3 g of an oily substance. The oily substance was purified by column chromatography (silica gel; ethyl acetate) to give 400 mg a less polar substance and 203 mg of a polar substance.

The less polar substance (17-α-isomer, 50).

IR (neat) $\nu cm^{-1}$: 3350, 1595, 970, 765, 745.

NMR (CDCl$_3$) w: 0.85–1.10 (6H, m) 1.00–3.00 (25H), 3.00–4.00 (8H), 4.00–4.40 (1H), 4.40–5.00 (1H), 4.90–4.30 (1H), 5.40–5.80 (2H), 6.60–7.10 (3H).

Mass (m/e): 486.

The polar substance (17-β-isomer, 51).

IR (neat) $\nu cm^{-1}$: 3350, 1595, 970, 765, 745.

NMR (CDCl$_3$) w: 0.70–1.10 (6H), 1.00–3.00 (25H), 3.00–4.40 (9H), 4.40–4.90 (1H), 4.90–5.40 (1H), 5.40–5.90 (2H), 6.40–7.20 (3H).

Mass (m/e): 486.

EXAMPLE 50

2-decarboxy-2-tetrahydropyranyloxymethyl-5,6,7-trinor-4,8-inter-m-phenylene-11,15-dideoxy-11,15-diacetoxy-17-α-methyl-20 -homo PGI$_2$ (52)

2-decarboxy-2-tetrahydropyranyloxymethyl-5,6,7-trinor-4,8-inter-m-phenylene-17-α-methyl-20-homo PGI$_2$ 320 mg was dissolved in 20 ml of acetic anhydride and 10 ml of anhydrous pyridine and the solution was stirred at room temperature for 2 hours. The reaction solution was concentrated and the resulting residue was azeotropically treated with toluene and benzene to give 390 mg of a nearly pure diacetate.

IR (neat) $\nu cm^{-1}$: 1740, 1595, 1235, 970, 760, 750.

NMR (CDCl$_3$) δ: 0.70–1.10 (9H), 1.00–3.00 (25H), 1.60–1.80 (3H), 1.90–2.20 (3H), 3.00–4.10 (4H), 4.40–5.00 (2H), 5.00–6.00 (4H), 6.50–7.10 (3H).

Mass (m/e): 570 (M+).

EXAMPLE 51

2-decarboxy-2-hydroxymethyl-5,6,7-trinor-4,8-inter-m-phenylene-11,15-didehydro-11,15-diacetoxy-17-α-methyl-20 -homo PGI$_2$ (53)

To a solution of 400 mg of 2-decarboxy-2-tetrahydropyranyloxymethyl-5,6,7-trinor-4,8-inter-m-phenylene-11,15-didehydroxy-11,15-diacetoxy-17-α-methyl-20 -homo PGI$_2$ in 11.2 ml of acetonitrile were added 5.2 ml of ¼N hydrochloric acid and 5.2 ml of THF, and the resulting solution was stirred at room temperature for 4 hours. Water was added the mixture was extracted with ether 3 times, the combined ether layers were washed with water and saturated brine, dried and thereafter concentrated to afford 400 mg of an oily substance. The oily substance was purified by column chromatography [silica gel; ethyl acetate:cyclohexane (2:1)] to give 270 mg of the alcohol.

IR (neat) $\nu cm^{-1}$: 3450, 1740, 1595, 1240, 970, 760, 750.

NMR (CDCl$_3$) δ: 0.70–1.10 (6 Hz), 1.00–3.00 (19H), 1.60–1.80 (3H), 1.90–2.20 (3H), 3.50–3.90 (3H), 4.70–6.00 (5H), 6.70–7.10 (3H).

Mass (m/e): 486 (M+).

EXAMPLE 52

5,6,7-trinor-4,8-inter-m-phenylene-11,15-dideoxy-11,15-diacetoxy-17-α-methyl-20-homo PGI$_2$ (54)

To a solution of 270 mg of 2-decarboxy-2-hydroxymethyl-5,6,7-trinor-4,8-inter-m-phenylene-11,15-didehydroxy-11,15-diacetoxy-17-α-methyl-20 -homo PGI$_2$ in 3.3 ml of anhydrous DMF was added 1.6 g of pyridinium dichromate, and the resulting mixture was stirred at room temperature for 14 hours. Water was added, and the mixture was extracted 5 times with ether, the combined ether layers were washed with water and saturated brine, dried and thereafter concentrated to give 270 mg of an oily substance. The oily substance was purified by column chromatography [silica gel (which had been treated with acetic acid) ethyl acetate:cyclohexane (1:2)] to yield 180 mg of a carboxylic acid.

IR (neat) $\nu cm^{-1}$: 3600–2300, 1740, 1710, 1595, 1240, 970, 760, 740.

NMR (CDCl$_3$) δ: 0.70–1.10 (6H), 1.10–3.00 (17H), 3.40–4,00 (1H), 4.60–6.00 (5H), 6.50–7.20 (3H).

Mass (m/e): 500 (M+).

EXAMPLE 53

5,6,7-trinor-4,8-inter-m-phenylene-17-α-methyl-20-homo PGI$_2$ (55)

To a solution of 160 mg of 5,6,7-trinor-4,8-inter-m-phenylene-11,15-dideoxy-11,15-diacetoxy-17-α-methyl-20 -homo PGI$_2$ in 10 ml of methanol was added 2 ml of 1N sodium hydroxide, and the resulting solution was stirred at room temperature for 2 hours. The reaction solution was concentrated, water was added, the pH of the mixture cooled in an ice bath was adjusted to 3 with 1N hydrochloric acid and the mixture was extracted 3 times with ethyl acetate. The combined organic layers were washed with water and saturated brine, dried and thereafter concentrated to give 130 mg of the pure diol.

IR (neat) $\nu cm^{-1}$: 3600–2300, 1710, 1595, 970, 760, 740.

NMR (CDCl$_3$) δ: 0.70–1.10 (9H), 1.00–3.00 (17H), 3.00–4.50 (4H), 4.80–5.90 (6H), 6.50–7.20 (3H).

Mass (m/e): 416 (M+).

EXAMPLE 54

2-decarboxy-2-tetrahydropyranyloxymethyl-5,6,7-trinor-4,8-inter-m-phenylene-17,18,19,20-tetranor-16-phenoxy PGI$_2$ (56)

To a solution of 2 g of (phenoxymethyl) tri-n-butylstannane in 20 ml of anhydrous THF at −78° C. was added 3.3 ml of n-butyllithium (1.5N) and the resulting solution was stirred for 8 minutes, a solution of 700 mg of 3a,8-b-cis-2,3,3a,8b-tetrahydro-1H-5-(4-tetrahydropyranyloxybutyl)-β-(2-formylethenyl)-2-α-hydroxycyclopenta[b]benzofuran in 4 ml of anhydrous THF was added dropwise. After stirring at −78° C. for 1 hour, methanol and solid ammonium chloride were added, the resulting mixture was stirred at −78° C. for 20 minutes and at room temperature for 20 minutes, thereafter, water was added and the mixture was extracted 3 times with ether. The combined ether layers were washed with saturated brine, dried and thereafter concentrated to give a crude oily substance. When this oily substance was purified by column chromatography [silica gel; ethyl acetate:cyclohexane (4:1)], 440 mg of the diol (15α) was obtained.

IR (neat) νcm$^{-1}$: 3400, 1600, 1585, 970, 760.

NMR (CDCl$_3$) δ: 3.45 (4H, m), 3.90 (6H, m), 4.58 (2H, m), 5.10 (1H, m), 5.80 (2H, m) 6.75 (1H, t, J=6.0 Hz), 6.96 (5H, m), 7.26 (2H, m).

Mass (m/e): 494 (M+).

| Anal. Calcd. for C$_{30}$H$_{38}$O$_6$ | Found |
|---|---|
| C = 72.87% | 72.80% |
| H = 7.69% | 7.55% |

EXAMPLE 55

2-decarboxy-2-tetrahydropyranyloxymethyl-5,6,7-trinor-4,8-inter-m-phenylene-11,15-didehydroxy-11,15-diacetoxy-17,18,19,20-tetranor-16-phenoxy-PGI$_2$ (57)

To a solution of 420 mg of 2-decarboxy-2-tetrahydropyranyloxymethyl-5,6,7-trinor-4,8-inter-m-phenylene-17,18,19,20-tetranor-16-phenoxy PGI$_2$ in 10 ml of acetic anhydride was added 5 m of anhydrous pyridine, and the resulting solution was stirred at room temperature for 2 hours. This reaction mixture was concentrated under reduced pressure by a vacuum pump, the obtained residue was azeotropically treated 3 times with toluene and once with benzene to give 495 mg of a nearly pure diacetate.

IR (neat) νcm$^{-1}$: 1740, 1595, 1585, 1230, 968, 758, 695.

NMR (CDCl$_3$) δ: 1.75 (3H, s), 2.10 (3H, s).

Mass: 578 (M+), 494.

| Anal. Calcd. for C$_{34}$H$_{42}$O$_8$ | Found |
|---|---|
| C = 70.59% | 70.27% |
| H = 7.27% | 7.21% |

EXAMPLE 56

2-decarboxy-2-hydroxymethyl-5,6,7-trinor-4,8-inter-m-phenylene-11,15-didehydroxy-11,15-diacetoxy-17,18,19,20-tetranor-16-phenoxy-PGI$_2$ (58)

To a solution of 480 mg of 2-decarboxy-2-tetrahydropyranyloxymethyl-5,6,7-trinor-4,8-inter-m-phenylene-11,15-didehydroxy-11,15-diacetoxy-17,18,19,20-tetranor-16-phenoxy PGI$_2$ in 10 ml of acetonitrile were added 5 ml of THF and 5 ml of ¼N hydrochloric acid, and the resulting solution was stirred at room temperature for 3 hours. Ether and water were added, and the mixture was extracted 3 times with ether. The combined ether layers were washed with water, a saturated aqueous solution of sodium hydrogen carbonate and saturated brine, dried and thereafter concentrated to afford 480 mg of an oily substance. The oily substance was purified by column chromatography [silica gel; ethyl acetate:cyclohexane (2:1)] to give 340 mg of the alcohol (58).

IR (neat) ν cm$^{-1}$: 3450, 1730, 1595, 1585, 1230, 960, 758, 690.

NMR (CDCl$_3$) δ: 1.76 (3H, s), 2.10 (3H, s), 3.65 (3H, m), 4.10 (2H, d, J=5.0 Hz), 4.97 (1H, m), 5.20 (1H, m), 5.60 (1H, m), 5.78 (2H, m), 6.70 (1H, t, J=6.0 Hz), 6.95 (4H, m), 7.25 (3H, m).

Mass (m/e): 494 (M+).

| Anal. Calcd. for C$_{29}$H$_{24}$O$_7$ | Found |
|---|---|
| C = 70.45% | 70.44% |
| H = 6.88% | 6.85% |

EXAMPLE 57

5,6,7-trinor-4,8-inter-m-phenylene-11,15-didehydroxy-11,15-diacetoxy-17,18,19,20-tetranor-16-phenoxy PGI$_2$ (59)

To a solution of 330 mg of 2-decarboxy-2-hydroxymethyl-5,6,7-trinor-4,8-inter-m-phenylene-11,15-didehydroxy-11,15-diacetoxy-17,18,19,20-tetranol-16-phenoxy PGI$_2$ in 7.5 ml of anhydrous DMF was added 1.9 g of pyridinium dichromate, and the resulting mixture was stirred at room temperature for 14 hours. Water was added, and the mixture was extracted 5 times with ether, the combined organic layers were washed with saturated brine, thereafter dried and concentrated to afford 350 mg of an oily substance. The oily substance was purified by column chromatography (silica gel (Lobar Column which had been treated with acetic acid); ethyl acetate:cyclohexane (2:1)) to give 250 mg of a carboxylic acid.

IR (neat) ν cm$^{-1}$: 3600–2400, 1740, 1710, 1598, 1589, 1230, 965, 760, 690.

NMR (CDCl$_3$) δ: 1.74 (3H, s), 2.10 (3H, s), 3.60 (1H, dd, J=9.0 Hz, 5.0 Hz), 4.10 (2H, d, J=4.5 Hz), 4.95 (1H, m), 5.20 (1H, m), 5.60 (1H, m), 5.80 (2H, m), 6.75 (1H, t, J=6.0 Hz), 6.95 (4H, m), 7.30 (3H, m).

Mass (m/e): 508 (M+).

| Anal. Calcd. for C$_{29}$H$_{32}$O$_8$ | Found |
|---|---|
| C = 68.50% | 68.42% |
| H = 6.30% | 6.25% |

EXAMPLE 58

5,6,7-trinor-4,8-inter-m-phenylene-17,18,19,20-tetranor-16-phenoxy PGI$_2$ (60)

To a solution of 250 mg of 5,6,7-trinor-4,8-inter-m-phenylene-11,15-didehydroxy-11,15-diacetoxy-17,18,19,20-tetranor-16-phenoxy PGI$_2$ in 15 ml of methanol was added 3 ml of 1N NaOH, and the resulting solution was stirred at room temperature for 2 hours.

The reaction mixture was concentrated under a reduced pressure, water was added, the pH of the mixture cooled in an ice bath was adjusted to 3 by 1N hydrochloric acid and the mixture was extracted 3 times with ethyl acetate. The combined organic layers were washed with water and saturated brine, thereafter dried and concentrated to give 204 mg of the nearly pure diol.

IR (neat) ν cm$^{-1}$: 3600–2400, 1710, 1595, 1585, 970, 858, 690.

NMR (CDCl$_3$) δ: 3.40 (1H, t, J=9 Hz), 4.00 (3H, m), 4.20 (4H, m) 5.10 (1H, m), 5,80 (2H, m), 6.75 (1H, t, J=6.0 Hz), 6.95 (4H, m), 7.30 (3H, m).

Mass (m/e): 424 (M+).

| Anal. Calcd. for C$_{25}$H$_{28}$O$_6$ | Found |
|---|---|
| C = 70.75% | 70.67% |
| H = 6.60% | 6.54% |

EXAMPLE 59

2-decarboxy-2-tetrahydropyranyloxymethyl-5,6,7-trinor-4,8-inter-m-phenylene-17,18,19,20-tetranor-16-m-chlorophenoxy PGI$_2$ (61)

To a solution of 2.2 g of (m-chlorophenoxymethyl)-tributylstannane in 20 ml of annydrous THF at −78° C. was added 3.4 ml of n-butyl lithium (1.5N), and the resulting solution was stirred at −78° C. for 8 minutes. A solution of 650 mg of 3a,8b-cis-2,3,3a,8b-tetrahydro-1H-5-(4-tetrahydropyranyloxybutyl)-1-β-(2-formylethenyl)-2-α-hydroxycyclopenta[b]benzofuran in 4 ml of anhydrous THF was added. After stirring at −78° C. for 30 minutes, solid ammonium chloride and methanol were added, the resulting mixture was stirred at −78° C. for 10 minutes and at room temperature for 10 minutes, thereafter, water was added and the mixture was extracted 3 times with ether. The combined ether layers were washed with saturated brine, dried and thereafter concentrated to yield 3 g of an oily substance. The oily substance was purified by column chromatography [silica gel; ethyl acetate:cyclohexane (4:1)] to give 425 mg of the pure product (61).

IR (neat) ν cm$^{-1}$: 3350, 1590, 1580, 965, 770, 745, 680.

NMR (CDCl$_3$) δ: 3.42 (3H, m), 3.90 (4H, m), 4.56 (2H, m), 5.10 (1H, m), 5.80 (2H, m), 6.74 (1H, t, J=8.0 Hz), 6.96 (5H, m), 7.20 (1H, t, J=8.0 Hz).

Mass (m/e): 528, 530 (M+).

| Anal. Calcd. for C$_{30}$H$_{27}$O$_6$Cl | Found |
|---|---|
| C = 68.18% | 68.02% |
| H = 7.01% | 6.88% |

EXAMPLE 60

2-decarboxy-2-tetrahydropyranyloxymethyl-5,6,7-trinor-4,8-inter-m-phenylene-11,15-didehydroxy-11,15-diacetoxy-17,18,19,20-tetranor-16-m-chlorophenoxy PGI$_2$ (62)

A solution of 400 mg of 2-decarboxy-2-tetrahydropyranyloxymethyl-5,6,7-trinol-4,8-inter-m-phenylene-17,18,19,20-tetranol-16-m-chlorophenoxy PGI$_2$ in 10 ml of acetic anhydride and 5 ml of pyridine was stirred at room temperature for 14 hours. The reaction mixture was concentrated under a reduced pressure by a vacuum pump and the resulting residue was azeotropically treated with toluene 2 times to give 464 mg of the roughly pure diacetate (62).

IR (neat) ν cm$^{-1}$: 1740, 1592, 1500, 965, 775, 750, 680.

NMR (CDCl$_3$) δ: 1.75 (3H, s), 2.10 (3H, s), 3.40–4.00 (4H, m), 4.08 (2H, d, J=4.0 Hz), 4.60 (1H, m), 4.98 (1H, m), 5.20 (1H, m), 5.60 (1H, m) 5.78 (2H, m), 6.62–7.10 (6H, m), 7.20 (1H, t, J=8.0 Hz).

Mass (m/e): 612, 614 (M+).

| Anal. Calcd. for C$_{34}$H$_{41}$O$_8$Cl | Found |
|---|---|
| C = 66.67% | 66.58% |
| H = 6.70% | 6.62% |

EXAMPLE 61

2-decarboxy-2-hydroxymethyl-5,6,7-trinor-4,8-inter-m-phenylene-11,15-didehydroxy-11,15-diacetoxy-17,18,19,20-tetranor-16-m-chlorophenoxy PGI$_2$ (63)

To a solution of 400 mg of 2-decarboxy-2-tetrahydropyranyloxymethyl-5,6,7-trinor-4,8-inter-m-phenylene-11,15-didehydroxy-11,15-diacetoxy-17,18,19,20-tetranor-16-m-chlorophenoxy PGI$_2$ in 10 ml of acetonitrile and 5 ml of THF was added 5 ml of ¼N hydrochloric acid and the resulting solution was stirred at room temperature for 4 hours. Ether and water were added, and the mixture was extracted 3 times with ether. The combined ether layers were washed with water, a saturated aqueous solution of sodium hydrogen carbonate and saturated brine, dried and thereafter concentrated to yield 400 mg of an oily substance. The oily substance was purified by column chromatography [silica gel; ethyl acetate:cyclohexane (2:1)] to give 314 mg of the alcohol (63).

IR (neat) ν cm$^{-1}$: 3400, 1730, 1595, 1580, 965, 775, 680.

NMR (CDCl$_3$) δ: 1.72 (3H, s), 2.10 (3H, s), 3.62 (3H, s), 4.08 (2H, d, J=6.0 Hz), 4.95 (1H, dd, J=12.0 Hz, 5.0 Hz), 5.20 (1H, m), 5.60 (1H, dd, J=5.0 Hz, 2.0 Hz), 5.78 (2H, m), 6.60–7.00 (6H, m), 7.20 (1H, t, J=8.0 Hz).

Mass (m/e): 528, 530 (M+).

| Anal. Calcd. for C$_{29}$H$_{33}$O$_7$Cl | Found |
|---|---|
| C = 65.90% | 65.78% |
| H = 6.25% | 6.09% |

EXAMPLE 62

5,6,7-trinor-4,8-inter-m-phenylene-11,15-didehydroxy-11,15-diacetoxy-17,18,19,20-tetranor-16-m-chlorophenoxy PGI$_2$ (64)

To a solution of 300 mg of 2-decarboxy-2-hydroxymethyl-5,6,7-trinor-4,8-inter-m-phenylene-11,15-didehydroxy-11,15-diacetoxy-17,18,19,20-tetranol-16-m-chlorophenoxy PGI$_2$ in 7.5 ml of DMF was added 1.9 g of pyridinium dichromate, and the resulting mixture was stirred at room temperature for 14 hours. Ether and water were added and the mixture was extracted 5 times with ether. The combined ether layers were washed with saturated brine, dried and thereafter concentrated to afford 300 mg of an oily substance. The oily substance was purified by column chromatography [silica gel (Lobar Column which had been treated with acetic acid); ethyl acetate:cyclohexane (2:1)] to give 210 mg of a carboxylic acid (64).

IR (neat) ν cm⁻¹: 3600–2400, 1730, 1710, 1595, 1580, 965, 775, 745, 680.

NMR (CDCl₃) δ: 1.74 (3H, s), 2.10 (3H, s), 3.60 (1H, m), 4.05 (2H, d, J=6.0 Hz), 4.90 (1H, m), 5.20 (1H, m), 5.60 (1H, m), 5.75 (2H, m), 6.60–7.00 (6H, m), 7.20 (1H, t, J=8.0 Hz).

Mass (m/e): 542, 544 (M⁺).

| Anal. Calcd. for C₂₉H₃₁O₈Cl | Found |
|---|---|
| C = 64.21% | 64.18% |
| H = 5.72% | 5.68% |

EXAMPLE 63

5,6,7-trinor-4,9-inter-m-phenylene-17,18,19,20-tetranor-16-m-chlorophenoxy PGI₂ (65)

To a solution of 160 mg of 4,6,7-trinor-4,8-inter-m-phenylene-11,15-didehydroxy-11,15-diacetoxy-17,18,19,20-tetranor-16-m-chlorophenoxy PGI₂ in 10 ml of methanol was added 2 ml of 1N sodium hydroxide, and the resulting solution was stirred at room temperature for 1 hour. The reaction solution was concentrated, water was added, the pH of the mixture cooled in an ice bath was adjusted to 3 with 1N hydrochloric acid, the mixture was extracted 3 times with ethyl acetate. The combined organic layers were washed with water and saturated brine and thereafter concentrated to yield 125 mg of nearly pure crystals. The crystals were recrystallized from an ethyl acetate-hexane mixture to afford 80 mg of pure crystals (65), mp 103°–105° C.

IR (KBr) ν cm⁻¹: 3600–2400, 1700, 1690, 1680, 965, 770, 740, 680.

NMR (CDCl₃) δ: 3.40 (1H, t, J=9.0 Hz), 3.94 (3H, m), 4.52 (1H, m), 5.05 (1H, m), 5.75 (2H, m), 6.60–7.10 (6H, m), 7.20 (1H, t, J=8.0 Hz).

| Anal. Calcd. for C₂₉H₂₇O₆Cl | Found |
|---|---|
| C = 65.50% | 65.44% |
| H = 5.90% | 5.81% |

EXAMPLES 64–68

The procedure of Example 54 was followed except the use of (n-propoxymethyl)tri-n-butyl stannane, (n-butoxymethyl)tri-n-butylstannane, (cyclopentyloxymethyl)tri-n-butylstannane, (cyclohexyloxymethyl)tri-n-butylstannane, or (cycloheptyloxymethyl)tri-n-bulylstannane in place of (phenoxymethyl)tri-n-butyl stannane, and the procedures of Examples 55–58 are followed successively except the uses of the each resulting compounds to give 5,6,7-trinor-4,8-inter-m-phenylene-17,18,19,20-tertranor-16-propoxy PGI₂ (66), 5,6,7-trinor-4,8-inter-m-phenylene-17,18,19,20-tetranor-16-butoxy PGI₂ (67), 5,6,7-trinor-4,8-inter-m-phenylene-17,18,19,20-tetranor-16-cyclopentyloxy PGI₂ (68), 5,6,7-trinor-4,8-inter-m-phenylene-17,18,19,20-tetranor-16-cyclohexyloxy PGI₂ (69), or 5,6,7-trinor-4,8-inter-m-phenylene-17,18,19,20-tetranor-16-cycloheptyloxy PGI₂ (70). In Table 4, the spectral data of these compounds are shown.

TABLE 4

| Example | Compound | Mass spectrum (m/e M⁺) | Infrared spectrum cm⁻¹ |
|---|---|---|---|
| 64 | 66 | 390 | 3600–2300, 1710, 1595, 1200, 970, 765, 745 |
| 65 | 67 | 404 | 1710, 1595, 970, 745 |
| 66 | 68 | 416 | 1710, 1595, 970, 745 |
| 67 | 69 | 430 | 1705, 1598, 970, 745 |
| 68 | 70 | 444 | 1710, 1594, 970, 945 |

REFERENTIAL EXAMPLE 82

2-decarboxy-2-tetrahydropyranyloxymethyl-5,6,7-trinor-4,8-inter-m-phenylene-17,18,19,20-tetranor-16,16-dimethyl-16-methoxycarbonyl PGI₂

To a solution of 0.9 ml of diisopropylamine in 20 ml of anhydrous THF was at −78° C. under argon atmosphere added dropwise 3.9 ml of n-butyl lithium (1.5N) and the resulting solution was stirred at that temperature for 15 minutes. A solution of 0.7 ml of isobutyric acid in 2 ml of anhydrous THF at −78° C. was added dropwise, the resulting solution was stirred for 30 minutes, thereafter, a solution of 500 mg of 3a,8b-cis-2,3,3a,8b-tetrahydro-1H-5-(4-tetrahydropyranyloxybutyl)-1-β-(2-formylethenyl)-2-α-hydroxycyclopenta[b]benzofuran in 2 ml of anhydrous THF was added dropwise thereto. The reaction mixture was stirred at −78° C. for 20 minutes, thereafter, methanol was added, the resulting mixture was stirred at room temperature for 10 minutes, water was added and the mixture was extracted 3 times with ether. The combined ether layers were washed with water and saturated brine, dried and thereafter concentrated to give 600 mg of an oily substance. The oily substance was purified by column chromatography [silica gel; ethyl acetate:cyclohexane (4:1)] to afford 205 mg of an oily substance.

IR (neat) ν cm⁻¹: 3375, 1725, 1592, 1250, 970, 775, 745.

NMR (CDCl₃) δ: 1.10 (3H, s), 1.12 (3H, s), 2.60 (4H, m), 3.82 (3H, m), 4.57 (1H, m), 5.10 (1H, m), 5.66 (2H, m), 6.76 (1H, t, J=7.0 Hz), 6.94 (2H, m).

Mass (m/e): 488 (M⁺), 404 (—THP).

| Anal. Calcd. for C₂₈H₄₀O₇ | Found |
|---|---|
| C = 68.83% | 68.80% |
| H = 8.25% | 8.21% |

REFERENTIAL EXAMPLE 83

2-decarboxy-2-tetrahydropyranyloxymethyl-5,6,7-trinor-4,8-inter-m-phenylene-11,15,dideoxy-11,15-bis(t-butyldimethylsilyloxy)-17,18,19,20-tetranor-16,16-dimethyl-16-methoxycarbonyl PGI₂

To a solution of 300 mg of 2-decarboxy-2-tetrahydropyranyloxymethyl-5,6,7-trinor-4,8-inter-m-phenylene-17,18,19,20-tetranor-16,16-dimethyl-16-carbomethoxy PGI₂ in 1.3 ml of anhydrous DMF were added 390 mg of imidazole and 458 mg of t-butyldimethylsilyl chloride, and the resulting mixture was stirred for 30 hours. A pentane-ether (1:1) mixture and water were added, and the mixture was extracted 3 times with a pentane-ether (1:1) mixture. The combined organic layers were washed with a saturated aqueous solution of sodium hydrogen carbonate, water and saturated brine, dried and thereafter concentrated to give 400 mg of an oily substance.

The oily substance was purified by column chromatography [silica gel; ethyl acetate:cyclohexane (1:16)] to afford 360 mg of an oily substance.

IR (neat) ν cm$^{-1}$: 1730, 1692, 1250, 970, 835, 780, 745.

NMR (CDCl$_3$) δ: 0.75 (9H, s), 0.87 (9H, s), 1.09 (3H, s), 1.17 (3H, s) 2.56 (4H, m), 3.50 (4H, m), 3.66 (3H, s), 3.90 (1H, m), 4.36 (1H, d, J=6.0 Hz), 4.60 (1H, m), 5.10 (1H, m), 5.60 (2H, m), 6.77 (1H, t, J=7.0 Hz), 6.94 (1H, d, J=7.0 Hz), 7.00 (1H, d, J=7.0 Hz).

Mass (m/e): 716 (M+), 632 (—THP).

| Anal. Calcd. for C$_{40}$H$_{68}$O$_7$Si$_2$ | Found |
|---|---|
| C = 67.04% | 66.91% |
| H = 9.50% | 9.28 |

REFERENTIAL EXAMPLE 84

2-decarboxy-2-tetrahydropyranyloxymethyl-5,6,7-trinor-4,8-inter-m-phenylene-11-deoxy-11-t-butyldimethylsilyloxy-16,16-dimethyl-18,19,20-trinor-17-hydroxy PGI$_2$ To a stirred suspension of 200 mg of lithium aluminium hydride in 2 ml of anhydrous THF cooled in an ice bath was added dropwise a solution of 340 mg of 2-decarboxy-2-tetrahydropyranyloxymethyl-5,6,7-trinor-4,8-inter-m-phenylene-11,15-deoxy-11,15-bis(dimethyl-t-butylsilyloxy)-17,18,19,20-tetranor-16,16-dimethyl-16-methoxycarbonyl PGI$_2$ in 4 ml of anhydrous THF. The reaction mixture was stirred at room temperature for 2 hours, thereafter, a saturated aqueous solution of sodium potassium tartarate was added, and the separated precipitate was filtered, the filtrate was dried and thereafter concentrated to give 276 mg of a nearly pure product. This compound was used in the following reaction without purification.

IR (neat) ν cm$^{-1}$: 3375, 1592, 1250, 970, 835, 775, 740.

NMR (CDCl$_3$) δ: 0.80 (9H, s), 0.92 (3H, s), 0.94 (3H, s), 2.04 (3H, s), 2.54 (5H, m), 3.50 (4H, m), 3.90 (4H, m), 4.60 (1H, m), 5.10 (1H, m), 5.70 (2H, m), 6.76 (1H, dd, J=9.0 Hz, 6.0 Hz), 6.96 (1H, d, J=6.0 Hz), 6.98 (1H, d, J=9.0 Hz).

Mass (m/e): 574 (M+), 526.

| Anal. Calcd. for C$_{33}$H$_{54}$O$_6$Si | Found |
|---|---|
| C = 68.99% | 68.91% |
| H = 9.41% | 9.37% |

EXAMPLE 69

2-decarboxy-2-tetrahydropyranyloxymethyl-5,6,7-trinor-4,8-inter-m-phenylene-11-deoxy-11-t-butyldimethylsilyloxy-16,16-dimethyl-18,19,20-trinor-17-ethoxy PGI$_2$ (71)

Sodium hydride (500 mg of 50% mineral oil dispersion) was washed 3 times with n-hexane, hexane was removed under reduced pressure, and 2 ml of anhydrous DME was added under argon atmosphere. To the stirred suspension cooled in an ice bath was added dropwise a solution of 260 mg of 2-decarboxy-2-tetrahydropyranyloxymethyl-5,6,7-trinor-4,8-inter-m-phenylene-11-deoxy-11-t-butyldimethylsilyloxy-18,19,20-trinor-16,16-dimethyl-17-hydroxy PGI$_2$ in 5 ml of anhydrous DME. The reaction mixture was stirred at room temperature for 1 hour, thereafter, 0.5 ml of ethyl iodide was added, and the resulting mixture was stirred at room temperature for 1 hour. Ammonium chloride, methanol and water were added, and the mixture was stirred at room temperature for 20 minutes. The reaction mixture was extracted 3 times with ether, the combined ether layers were washed with water and saturated brine, dried and thereafter concentrated to give 300 mg of an oily substance. The oily substance purified by column chromatography [silica gel; ethyl acetate:cyclohexane (1:5)] to afford 172 mg of an oily substance.

IR (neat) ν cm$^{-1}$: 3490, 1595, 1250, 970, 780, 745.

NMR (CDCl$_3$) δ: 0.80 (9H, s), 0.92 (3H, s), 0.96 (3H, s), 1.20 (3H, t, J=7.0 Hz), 2.60 (3H, m), 3.34 (2H, AB, J=8.0 Hz), 3.50 (4H, m), 3.58 (2H, q, J=7.0 Hz), 3.80 (3H, m), 4.60 (1h, m), 5.10 (1H, m), 5.66 (2H, m), 6.72 (1H, 5,J=7.0 Hz), 6.96 (1H, d, J=7.0 Hz), 6.98 (1H, d, J=7.0 Hz).

Mass (m/e): 602 (M+), 518 (—THP).

| Anal. Calcd. for C$_{35}$H$_{58}$O$_6$Si | Found |
|---|---|
| C = 69.77% | 69.66% |
| H = 9.63% | 9.60% |

EXAMPLE 70

2-decarboxy-2-tetrahydropyranyloxymethyl-5,6,7-trinor-4,8-inter-m-phenylene-16,16-dimethyl-18,19,20-trinor-17-ethoxy PGI$_2$ (72)

To a solution of 130 mg of 2-decarboxy-2-tetrahydropyranyloxymethyl-5,6,7-trinor-4,8-inter-m-phenylene-11-deoxy-11-t-butyldimethylsilyloxy-16,16-dimethyl-18,19,20-trinor-17-ethoxy PGI$_2$ in 5 ml of anhydrous THF was added 183 mg of tetrabutylammonium fluoride, and the resulting mixture was stirred at room temperature for 1 hour. Ether and a saturated aqueous solution of ammonium chloride were added, and the mixture was extracted 3 times with ether. The combined ether layers were washed with water and saturated brine, dried and thereafter concentrated to yield 106 mg of a nearly pure diol. This compound was used in the following reaction without purification.

IR (neat) ν cm$^{-1}$: 3450, 1595, 970, 770, 750.

NMR (CDCl$_3$) δ: 0.90 (3H, t, J=6.0 Hz), 0.92 (3H, s), 0.94 (3H, s), 1.10 (3H, t, J=7.0 Hz), 2.60 (5H,m), 3.40 (6H, m), 3.90 (4H, m), 4.58 (1H, m), 5.10 (1H, m), 5.65 (2H, m), 6.64 (1H, t, J=7.8 Hz), 6.96 (2H, d, J=7.8 Hz).

Mass (m/e): 488 (M+), 470 (—H$_2$O).

| Anal. Calcd. for C$_{29}$H$_{44}$O$_6$ | Found |
|---|---|
| C = 71.31% | 71.22% |
| H = 9.02% | 8.99% |

EXAMPLE 71

2-decarboxy-2-tetrahydropyranyloxymethyl-5,6,7-trinor-4,8-inter-m-phenylene-11,15-dideoxy-11,15-diacetoxy-16,16-dimethyl-18,19,20-trinor-17-ethoxy PGI$_2$ (73)

A solution of 130 mg of 2-decarboxy-2-tetrahydropyranyloxymethyl-5,6,7-trinor-4,8-inter-m-phenylene-16,16-dimethyl-18,19,20-trinor-17-ethoxy PGI in 3 ml of pyridine and 6 ml of acetic anhydride was stirred at room temperature for 14 hours. The reaction solution was concentrated and the resulting residue was azeotropically treated twice with toluene and once with benzene to give 155 mg of the nearly pure diacetate.

IR (liquid film method) $\nu$ cm$^{-1}$: 1740, 1595, 1240, 970, 745.

NMR (CDCl$_3$) $\delta$: 0.90 (3H, s), 0.94 (3H, s), 1.16 (3H, t, J=7.0 Hz), 1.74 (3H, s), 2.07 (3H, s), 2.60 (3H, s), 2.82 (1H, m), 3.44 (2H, q, J=7.0 Hz), 3.10–3.90 (6H, complicated forms), 4.60 (1H, m), 4.92 (1H, q, J=6.0 Hz), 5.27 (2H, m), 5.65 (2H, m), 6.76 (1H, dd, J=8.0 Hz, 6.0 Hz), 6.94 (1H, d, J=6.0 Hz), 6.96 (1H, d, J=8.0 Hz).

Mass (m/e): 572 (M+), 488 (—THP).

| Anal. Calcd. for C$_{33}$H$_{48}$O$_8$ | Found |
|---|---|
| C = 69.23% | 69.11% |
| H = 8.39% | 8.28% |

EXAMPLE 72

2-decarboxy-2-hydroxymethyl-5,6,7-trinor-4,8-inter-m-phenylene-11,15-dideoxy-11,15-diacetoxy-16,16-dimethyl-18,19,20-trinor-17-ethoxy PGI$_2$ (74)

To a solution of 140 mg of 2-decarboxy-2-tetrahydropyranyloxymethyl-5,6,7-trinor-4,8-inter-m-phenylene-11,15-dideoxy-11,15-diacetoxy-16,16-dimethyl-18,19,20-trinor-17-ethoxy PGI$_2$ in 3.5 ml of acetonitrile were added 1.7 ml of THF and 1.7 ml of 1.4H hydrochloric acid, and the resulting solution was stirred at room temperature for 8 hours. Water was added and the mixture was extracted 3 times with ether, the combined ether layers were washed with water and saturated brine, dried and thereafter concentrated to give 150 mg of an oily substance. The oily substance was purified by column chromatography [silica gel; ethyl acetate:cyclohexane (2:1)] to afford 103 mg of the pure alcohol (74).

IR (neat) $\nu$ cm$^{-1}$: 3450, 1740, 1595, 1240, 965, 760, 745.

NMR (CDCl$_3$) $\delta$: 0.90 (3H, s), 0.93 (3H, s), 1.16 (3H, d, J=7.0 Hz), 1.74 (3H, s), 2.07 (3H, s), 2.20–3.00 (3H, m) 3.15 (2H, s), 3.45 (2H, q, J=7.0 Hz), 3.65 (3H, m), 4.94 (1H, q, J=6.0 Hz), 5.20 (2H, m), 5.62 (2H, m), 6.77 (1H, dd, J=8.0 Hz, 6.0 Hz), 6.96 (1H, d, J=6.0 Hz), 6.98 (1H, d, J=8.0 Hz).

Mass (m/e): 488 (M+), 428, 368.

| Anal. Calcd. for C$_{28}$H$_{40}$O$_7$ | Found |
|---|---|
| C = 68.85% | 68.72% |
| H = 8.12% | 8.06% |

EXAMPLE 73

5,6,7-trinor-4,8-inter-m-phenylene-11,15-dideoxy-11,15-diacetoxy-16,16-dimethyl-18,19,20-trinor-17-ethoxy PGI$_2$ (75)

To a solution of 93 mg of 2-decarboxy-2-hydroxymethyl-5,6,7-trinor-4,8-inter-m-phenylene-11,15-dideoxy-11,15-diacetoxy-16,16-dimethyl-18,19,20-trinor-17-ethoxy PGI$_2$ in 2.5 ml of anhydrous DMF was added 630 mg of pyridinium dichromate, and the resulting solution was stirred at room temperature for 14 hours. Water was added and the mixture was extracted 5 times with ether. The combined ether layers were washed with water and saturated brine, dried and thereafter concentrated to give 100 mg of an oily substance. The oily substance was purified by column chromatography [silica gel (which had been treated with acetic acid); ethyl acetate:cyclohexane (1:1)] to afford 80 mg of the pure carboxylic acid.

IR (neat) $\nu$ cm$^{-1}$: 3600–2300, 1740, 1710, 1595, 1240, 965, 765, 745.

NMR (CDCl$_3$) $\delta$: 0.90 (3H, s), 0.94 (3H, s), 1.17 (3H, t, J=7.0 Hz), 2.08 (3H, s), 2.10 (3H, s), 2.40 (2H, t, J=7.0 Hz), 2.64 (2H, t, J=8.0 Hz), 2.87 (1H, q, J=6.0 Hz), 3.16 (2H, s), 3.42 (2H, q, J=7.0 Hz), 3.42 (1H, dd, J=8.0 Hz, 6.0 Hz), 4.94 (1H, q, J=6.0 Hz), 5.26 (2H, m), 5.62 (2H, m), 6.77 (1H, dd, J=8.0 Hz, 7.0 Hz), 6.96 (1H, d, J=7.0 Hz), 6.98 (1H, d, J=8.0 Hz).

Mass (m/e): 502 (M+), 442, 382.

| Anal. Calcd. for C$_{28}$H$_{38}$O$_8$ | Found |
|---|---|
| C = 66.93% | 66.82% |
| H = 7.57% | 7.49% |

EXAMPLE 74

5,6,7-trinor-4,8-inter-m-phenylene-16,16-dimethyl-18,19,20-trinor-17-ethoxy PGI$_2$ (76)

To a solution of 67 mg of 5,6,7-trinor-4,8-inter-m-phenylene-11,15-dideoxy-11,15-diacetoxy-16,16-dimethyl-18,19,20-trinor-17-ethoxy PGI$_2$ in 4.2 mml of methanol was added 0.85 ml of an aqueous solution of 1N sodium hydroxide, and the resulting solution was stirred at room temperature for 14 hours. The reaction solution was concentrated, water was added to the residue, the pH of the mixture was cooled in an ice bath was adjusted to 4 with in hydrochloric acid and the mixture extracted 3 times with ethyl acetate. The combined organic layers were washed with water and saturated brine, dried and thereafter concentrated to give 52 mg of the pure diol.

IR (neat) $\nu$ cm$^{-1}$: 3600–2300, 1710, 1595, 1200, 970, 765, 745.

NMR (CDCl$_3$) $\delta$: 0.93 (3H, s), 0.95 (3H, s), 1.20 (3H, d, J=7.0 Hz), 2.00 (3H, m), 2.36 (2H, t, J=8.0 Hz), 2.64 (3H, t, J=7.0 Hz), 2.62 (1H, m), 3.36 (2H, AB, J=8.5 Hz), 3.48 (2H, q, J=7.0 Hz), 3.40 (1H, m), 4.00 (2H, m), 5.00 (4H, m), 5.68 (2H, m), 6.60 (1H, dd, J=8.0 Hz, 6.0 Hz), 6.94 (1H, d, J=6.0 Hz), 6.98 (1H, d, J=8.0 Hz).

Mass (m/e): 418 (M+), 400, 382.

| Anal. Calcd. for C$_{24}$H$_{34}$O$_6$ | Found |
|---|---|
| C = 68.90% | 68.83% |
| H = 8.13% | 8.08% |

EXAMPLE 75

2-decarboxy-2-tetrahydropyranyloxymethyl-5,6,7-trinor-4,8-inter-m-phenylene-20-isopropylidene PGI$_2$ (77)

To a solution of 500 mg of 3a,8b-cis-2,3,3a,8b-tetrahydro-1H-5(4-tetrahydropyranyloxybutyl)-1-$\beta$-(2-formylethenyl)2-$\alpha$-hydroxycyclopenta[b]benzofuran in 10 ml of anhydrous THF cooled in an ice bath was added 2 ml of an ether solution (1.3N) of 6-methyl-5-heptenyl-magnesium bromide, and the resulting solution was stirred at 0° C. for 40 minutes. Ammonium chloride, methanol and water were added, and the mixture was extracted 3 times with ether. The combined ether layers were washed with water and saturated brine, dried and thereafter concentrated to give 600 mg of an oily substance. The oily substance was purified by column chromatography [silica gel; ethyl acetate:cyclohexane (5:1)] to give 300 mg of the diol (77).

IR (neat) ν cm⁻¹: 3350, 1952, 970, 810, 760, 740.

NMR (CDCl₃) δ: 1.62 (3H, s), 1.70 (3H, s), 3.42 (4H, m), 3.82 (4H, m), 5.12 (1H, m), 5.58 (1H, m), 5.14 (2H, m), 5.62 (2H, m), 6.66 (1H, t, J=8.0 Hz), 6.96 (2H, d, J=8.0 Hz).

| Anal. Calcd. for $C_{31}H_{46}O_5$ | Found |
|---|---|
| C = 74.66% | 74.55% |
| H = 9.30% | 9.22% |

EXAMPLE 76

2-decarboxy-2-tetrahydropyranyloxymethyl-5,6,7-trinor-4,8-inter-m-phenylene-11,15-dideoxy-11,15-diacetoxy-20-isopropylidene PGI₂ (78)

To a solution of 200 mg of 2-decarboxy-2-tetrahydropyranyloxymethyl-5,6,7-trinol-4,8-inter-m-phenylene-20-isopropylidene PGI₂ in 5 ml of acetic anhydride was added 2.6 ml of anhydrous pyridine and the resulting solution was stirred at room temperature for 3 hours. The reaction mixture was concentrated and the residue was azeotropically treated 2 times with toluene and with once benzene to give 2.33 mg of the nearly pure diacetate (78).

IR (neat) ν cm⁻¹: 1740, 1595, 1230, 970, 760, 745.

NMR (CDCl₃) δ: 1.60 (3H, s), 1.69 (3H, s), 1.74 (3H, s), 2.06 (3H, s), 2.60 (2H, m), 2.80 (1H, q, J=7.0 Hz), 3.20-4.00 (5H, m), 4.60 (1H, m), 4.92 (1H, m), 5.20 (3H, m), 5.60 (2H, m), 6.74 (1H, dd, J=0.9 Hz, 7.0 Hz), 6.94 (1H, d, J=7.0 Hz), 6.96 (1H, d, J=9.0 Hz).

Mass (m/e): 582 (M⁺).

| Anal. Calcd. for $C_{35}H_{50}O_7$ | Found |
|---|---|
| C = 72.13% | 72.00% |
| H = 8.65% | 8.42% |

EXAMPLE 77

2-decarboxy-2-hydroxymethyl-5,6,7-trinor-4,8-inter-m-phenylene-11,15-dideoxy-11,15-diacetoxy-20-isopropylidene PGI₂ (79)

To a solution of 220 mg of 2-decarboxy-2-tetrahydropyranyloxymethyl-5,6,7-trinor-4,8-inter-m-phenylene-11,15-dideoxy-11,15-diacetoxy-20-isopropylidene PGI₂ in 5.5 ml of acetonitrile were added 2.6 ml of THF and 2.6 ml of ¼N hydrochloric acid and the resulting mixture was stirred at room temperature for 5 hours. Water was added, and the mixture was extracted 3 times with ether, the combined ether layers were washed with water and saturated brine, dried and thereafter concentrated to give 230 mg of an oily substance. The oily substance was purified by column chromatography [silica gel; ethyl acetate:cyclohexane (2:1)] to give 138 mg of the alcohol (79).

IR (neat) ν cm⁻¹: 3450, 1735, 1595, 1240, 965, 840, 760, 745.

NMR (CDCl₃) δ: 1.60 (3H, s), 1.68 (3H, s), 1.72 (3H, s), 2.04 (3H, s), 2.60 (2H, m), 2.80 (1H, q, J=6.0 Hz), 3.62 (3H, m), 4.92 (1H, m), 5.20 (3H, m), 5.60 (2H, m), 6.76 (1H, dd, J=9.0 Hz, 6.0 Hz), 6.94 (1H, d, J=6.0 Hz), 6.98 (1H, d, J=9.0 Hz).

Mass (m/e): 498 (M⁺), 438, 378.

| Anal. Calcd. for $C_{30}H_{42}O_6$ | Found |
|---|---|
| C = 72.26% | 72.17% |
| H = 8.49% | 8.41% |

EXAMPLE 78

5,6,7-trinor-4,8-inter-m-phenylene-11,15-dideoxy-11,15-diacetoxy-20-isopropylidene PGI₂ (80)

To a solution of 122 mg of 2-decarboxy-2-hydroxymethyl-4,8-inter-m-phenylene-11,15-dideoxy-11,15-diacetoxy-20-isopropylidene PGI₂ in 3.3 ml of anhydrous DMF, was added 820 mg of pyridinium dichromate, and the resulting mixture was stirred at room temperature for 14 hours. Water was added, and the mixture was extracted 5 times with ether, the combined ether layers were washed with water and saturated brine, dried and thereafter concentrated to give 130 mg of an oily substance. The oily substance was separated and refined by column chromatography [silica gel (which had been treated with acetic acid) ethyl acetate:cyclohexane (1:2)] to afford 90 mg of a carboxylic acid (80).

IR (neat) ν cm⁻¹: 3600-2300, 1720 (br), 1595, 1230, 960, 830, 760, 745.

NMR (CDCl₃) δ: 1.60 (3H, s), 1.68 (3H, s), 1.72 (3H, s), 2.06 (3H, s), 2.40 (2H, t, J=7.0 Hz), 2.60 (2H, t, J=8.0 Hz), 2.80 (1H, m), 3.60 (1H, dd, J=9.0 Hz, 6.0 Hz), 4.94 (1H, m), 5.20 (3H, m), 5.60 (2H, m), 6.79 (1H, t, J=7.8 Hz), 6.96 (2H, d, J=7.8 Hz).

Mass (m/e): 512 (M⁺), 452, 392.

| Anal. Calcd. for $C_{30}H_{40}O_7$ | Found |
|---|---|
| C = 70.29% | 70.02% |
| H = 7.87% | 7.68% |

EXAMPLE 79

5,6,7-trinor-4,8-inter-m-phenylene-20-isopropylidene-PGI₂ (81)

To a solution of 78 mg of 5,6,7-trinor-4,8-inter-m-phenylene-11,15-dideoxy-11,15-diacetoxy-20-isopropylidene PGI₂ in 4.8 ml of methanol was added 1 ml of 1N sodium hydroxide, and the resulting solution was stirred at room temperature for 3 hours. The reaction solution was concentrated, water was added, the pH of the mixture cooled in an ice bath was adjusted to 3 with 1N hydrochloric acid and the mixture was extracted 3 times with ethyl acetate. The combined organic layers were washed with water and saturated brine, dried and thereafter concentrated to give 65 mg of the diol carboxylic acid (81).

IR (neat) ν cm⁻¹: 3600-2300, 1705, 1595, 970, 830, 765, 745.

NMR (CDCl₃) δ: 1.60 (3H, s), 1.68 (3H, s), 2.00 (4H, m), 2.32 (2H, t, J=7.0 Hz), 2.60 (2H, t, J=7.0 Hz), 3.40 (1H, t, J=9.0 Hz), 3.90 (1H, m), 4.10 (1H, m), 4.65 (3H, m), 5.10 (2H, m), 5.60 (2H, m), 6.72 (1H, dd, J=6.4 Hz, 8.4 Hz), 6.92 (1H, d, J=6.4 Hz), 6.93 (1H, d, J=6.6 Hz).

Mass (m/e): 428 (M⁺), 410, 382.

| Anal. Calcd. for $C_{26}H_{36}O_5$ | Found |
|---|---|
| C = 72.86% | 72.80% |

-continued

| Anal. Calcd. for $C_{26}H_{36}O_5$ | Found |
|---|---|
| H = 8.47% | 8.43% |

EXAMPLE 80

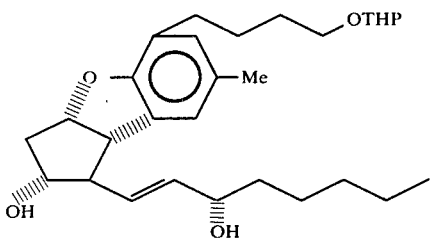

2-decarboxy-2-tetrahydropyranyloxymethyl-5,6,7-trinor-3,8-inter-(5-methyl-1,3-phenylene)-PGI$_2$ (82)

To a solution of 469 mg (1.17 mmol) of 1,2,3a,8b-cis-tetrahydro-1-exo-(2-formylethenyl)-2-endo-hydroxy-7-methyl-5-(4-tetrahydropyranyloxy-n-butyl)cyclopenta[b]benzofuran in 6 ml of THF at −78° C. under argon atmosphere was added 5.6 ml (0.63M, 3.53 mmol, 3.0 equiv.) of n-pentyl lithium, and resulting solution was stirred for 30 minutes. After confirming 2 products by thin layer chromatography, 2 ml of a saturated aqueous solution of ammonium chloride was added, the resulting solution was extracted with ethyl acetate (10 ml×5) and the organic layer was dried, and concentrated to afford 524 mg of a crude product. The product was purified by column chromatography (Merck Lobar Column; cyclohexane:ethyl acetate 1:5) to give 2 kinds of oily substances, 273 mg (49%) of the polar titled compound (82) and 139 mg (25%) of a less polar stereoisomer.

IR (neat) $\nu$ cm$^{-1}$: 3350 (3650–3100), 2930, 2860, 1610, 1470, 1200, 1135, 1120, 1070, 1030, 965, 860, 815, 730.

NMR (CDCl$_3$) δ: 0.91 (t, J=6 Hz, 3H), 1.35 (m, 8H), 1.35 (m, 8H), 1.65 (m, 10H), 1.85 (m, 1H), 2.22 (s, 3H), 2.24 (m, 1H), 2.55 (m, 3H), 3.40 (m, 5H), 3.80 (m, 3H), 4.08 (m, 1H), 4.57 (m, 1H), 5.03 (q, J=7 Hz, 1H), 6.72 (s, 1H), 6.76 (s, 1H).

Mass spectrum: M+ 472.

| Anal. Calcd. for $C_{29}H_{44}O_5$ | Found |
|---|---|
| C = 73.69% | 73.60% |
| H = 9.38% | 9.32% |

EXAMPLE 81

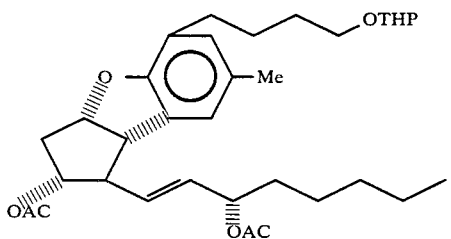

2-decarboxy-2-tetrahydropyranyloxymethyl-5,6,7-trinor-4,8-inter-(5-methyl-1,3-phenylene)PGI$_2$ diacetate (83)

To a solution of 240 mg (0.508 mmol) of 2-decarboxy-2-tetrahydropyranyloxymethyl-5,6,7-trinor-3,7-inter-(5-methyl-1,3-phenylene)PGI$_2$ in 8 ml of pyridine was added 10 ml of acetic anhydride, and the resulting mixture was stirred at room temperature for 2 hours. After confirming the loss of the material by thin-layer chromatography, the mixture was concentrated to give 258 mg (0.464 mmol, 91%) of (83).

IR (neat) $\nu$ cm$^{-1}$: 2930, 2860, 1740, 1470, 1370, 1235, 1200, 1130, 1115, 1065, 1020, 960, 860, 810, 740.

NMR (CDCl$_3$) δ: 0.89 (t, J=6 Hz, 3H), 1.30 (m, 8H), 1.66 (m, 10H), 1.77 (s, 3H), 1.90 (m, 1H), 2.06 (s, 3H), 2.24 (s, 3H), 2.54 (m, 3H), 2.80 (m, 1H), 3.50 (m, 3H), 3.80 (m, 2H), 4.58 (m, 1H), 4.92 (q, J=6 Hz, 1H), 5.22 (m, 2H), 5.62 (t, J=5 Hz, 2H), 6.76 (s, 2H).

Mass spectrum: M+ 566.

| Anal. Calcd. for $C_{33}H_{48}O_7$ | Found |
|---|---|
| C = 71.19% | 71.11% |
| H = 8.69% | 8.62% |

EXAMPLE 82

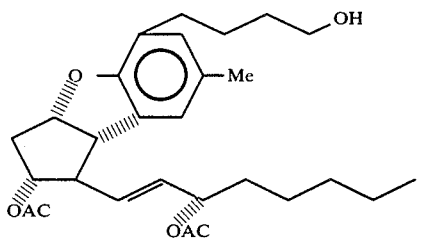

2-decarboxy-2-hydroxymethyl-5,6,7-trinor-4,8-inter-(5-methyl-1,3-phenylene)PGI$_2$ diacetate (84)

To a solution of 258 mg (0.464 mmol) of 2-decarboxy-2-tetrahydro-pyranyloxymethyl-5,6,7-trinor-4,8-inter-(5-methyl-1,3-phenylene)PGI$_2$ in 5 ml of THF were added 10 ml of acetonitrile and 4 ml of 0.25N hydrochloric acid, and the resulting mixture was stirred at room temperature. After confirming the loss of the material by thin-layer chromatography, 0.1 ml of trietyl amine, 3 ml of a saturated aqueous solution of sodium bicarbonate, and 3 ml of a saturated aqueous solution of sodium chloride were added and the resulting mixture was extracted with ethyl acetate (10 ml×5). The organic layer was dried and thereafter concentrated to give 365 mg of an oily substance. The oily substance was purified by column chromatography (Merck Lobar Column, cyclohexane:ethyl acetate 2:3) to afford 162 mg (0.343 mmol, 74%) of (84) as an oil.

IR (neat) $\nu$ cm$^{-1}$: 3400, (3600–3100), 2930, 2860, 1740, 1475, 1370, 1235, 1200, 1130, 1050, 1020, 960, 860, 730.

NMR (CDCl$_3$) δ: 0.91 (t, J=6 Hz, 3H), 1.31 (m, 6H), 1.66 (m, 8H), 1.78 (s, 3H), 1.78 (s, 3H), 2.03 (s, 3H), 2.08 (m, 1H), 2.25 (s, 3H), 2.56 (m, 3H), 2.79 (q, J=6 Hz, 1H), 3.55 (dd, J=8, 6Hz, 1H), 3.68 (m, 2H), 4.91 (q, J=6 Hz, 1H), 5.20 (m, 2H), 5.60 (dd, J=6, 5 Hz, 1H), 6.75 (s, 2H).

Mass spectrum: M+ 4.72.

| Anal. Calcd. for $C_{28}H_{40}O_6$ | Found |
|---|---|
| C = 71.16% | 69.97% |
| H = 8.53% | 8.46% |

EXAMPLE 83

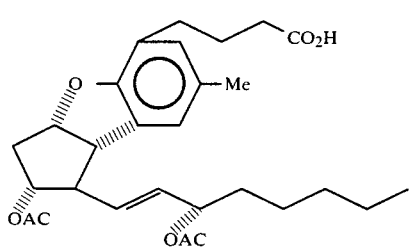

5,6,7-trinor-4,8-inter-(5-methyl-1,3-phenylene)PGI$_2$ diacetate (85)

and

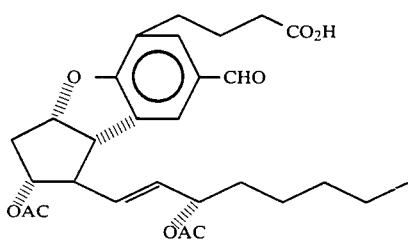

5,6,7-trinor-4,8-inter-(t-formyl-1,3-phenylene)PGI$_2$ diacetate (86)

To a solution of 160 mg (0.339 mmol) of 2-decarboxy-2-hydroxymethyl-5,6,7-trinor-4,8-inter-(5-methyl-1,3-phenylene)PGI$_2$ diacetate in 5 ml of N, N-dimethyl formamide at room temperature under argon atmosphere was added 1.027 g (2.73 mmol, 8 equiv.) of pyridinium dichromate, and the resulting mixture was stirred for 7 hours. Five ml of water was added, the mixture was extracted with ether (1 ml×2), the ether layer was washed with a saturated aqueous solution of sodium chloride, dried and thereafter concentrated to give 210 mg of an oily crude product. The product was purified by column chromatography (Merck Lobar Column, cyclohexane:ethyl acetate 2:1) to afford 111 mg (67%) of (85) and 27 mg (16%) of (86) as oils.

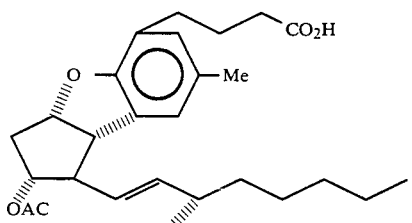

5,6,7-trinor-4,8-inter-(5-methyl-1,3-phenylene)PGI$_2$ diacetate (85)

| Anal. Calcd. for $C_{28}H_{38}O_7$ | Found |
|---|---|
| C = 69.11% | 68.82% |
| H = 7.87% | 7.59% |

NMR (CDCl$_3$) δ: 0.91 (t, J=6 Hz, 3H), 1.30 (m, 6H), 1.64 (m, 2H), 1.76 (s, 3H), 1.96 (m, 3H), 2.07 (s, 3H), 2.24 (s, 3H), 2.26 (m, 1H), 2.40 (t, J=8 Hz, 2H), 2.58 (t, J=8 Hz, 2H), 2.80 (t, J=6 Hz, 1H), 3.54 (dd, J=10, 6 Hz, 1H), 4.89 (q, J=6 Hz, 1H), 5.22 (m, 2H), 5.59 (dd, J=6,5 Hz, 2H), 6.73 (s, 3H).

IR (neat) ν cm$^{-1}$: 3300–2100, 2930, 2860, 1740, 1710, 1475, 1370, 1235, 1150, 1130, 1050, 1020, 960, 860.

Mass spectrum: M+ 486.

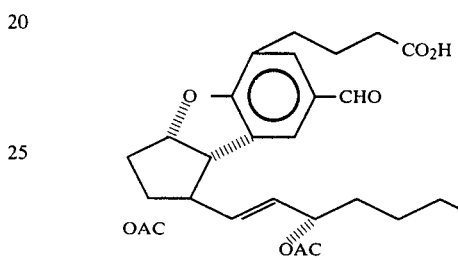

5,6,7-trinor-4,8-inter-(5-formyl-1,3-phenylene)PGI$_2$ diacetate (86)

| Anal. Calcd. for $C_{28}H_{36}O_8$ | Found |
|---|---|
| C = 67.18% | 67.00% |
| H = 7.25% | 7.01% |

NMR (CDCl$_3$) δ: 0.90 (t, J=6 Hz, 3H), 1.30 (m, 6H), 1.64 (m, 2H), 1.68 (s, 3H), 1.96 (m, 3H), 2.07 (s, 3H), 2.26 (m, 1H), 2.42 (t, J=8 Hz, 2H), 2.68 (t, J=8 Hz, 2H), 2.89 (m, 1H), 3.72 (dd, J=8, 4 Hz, 1H), 4.95 (q, J=4 Hz, 1H), 5.21 (m, 1H), 5.40 (m, 1H), 5.60 (m, 2H), 7.52 (s, 2H), 9.76 (s, 1H).

IR (neat) ν cm$^{-1}$: 3600–2200, 2930, 2860, 1740, 1690, 1600, 1430, 1370, 1235, 1110, 1050, 1020, 960.

Mass spectrum: M+ 500.

EXAMPLE 84

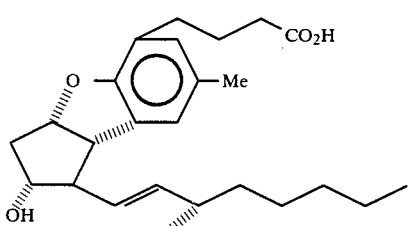

5,6,7-trinor-4,8-inter-(5-methyl-1,3-phenylene)PGI$_2$ (87)

To a solution of 103 mg (0.212 mmol) of 5,6,7-trinor-4,8-inter-(5-methyl-1,3-phenylene)PGI$_2$ diacetate was added 1 ml (ca 5 equiv.) of an aqueous solution of 1N sodium hydroxide and the mixture was stirred at room temperature for 2 hours. After evaporation of methanol, 1N hydrochloric acid was added to adjust the pH of the solution to 4 and the mixture was extracted with ethyl acetate (10 ml×7). The organic layer was washed with saturated brine (1 ml×2), dried and thereafter concentrated to give 84 mg (98.6%) of (87) as white crystals (mp; 129.5°–131° C.).

IR (KBr) $\nu$ cm$^{-1}$: 3400 (3600–2200), 2930, 2860, 1705, 1470, 1375, 1275, 1225, 1200, 1150, 1080, 980, 960, 870, 860, 740.

NMR (CDCl$_3$) δ: 0.90 (t, J=6 Hz, 3H), 1.34 (m, 8H), 1.96 (m, 3H), 2.22 (s, 3H), 2.33 (m, 3H), 2.59 (m 3H), 3.35 (t, J=8 Hz, 1H), 4.08 (m, 4H), 5.06 (m, 1H), 5.58 (m, 2H), 6.74 (s, 2H).

Mass spectrum: M+ 402.

EXAMPLE 85

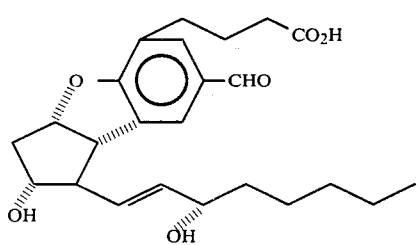

5,6,7-trinor-4,8-inter-(5-formyl-1,3-phenylene)PGI$_2$ (88)

The procedure of Example 84 was followed except the use of 16 mg of 5,6,7-trinor-4,8-inter -(5-formyl-1,3-phenylene)PGI$_2$ diacetate in place of (85), to give 12 mg (90%) of (88) as an oil.

| Anal. Calcd. for C$_{24}$H$_{32}$O$_6$ | Found |
|---|---|
| C = 69.21% | 69.11% |
| H = 7.74% | 7.62% |

NMR (CDCl$_3$) δ: 0.90 (t, J=6 Hz, 3H), 1.34 (m, 8H), 2.02 (m, 3H), 2.34 (m, 3H), 2.68 (m, 3H), 3.48 (t, J=8 Hz, 1H), 3.94 (m, 1H), 4.12 (m, 1H), 4.86 (a wide one-double line, 3H), 5.22 (m, 1H), 5.64 (m, 2H), 7.53 (s, 2H).

IR (neat) $\nu$ cm$^{-1}$: 3400 (3700–2200), 2930, 2860, 1710, 1690, 1600, 1470, 1435, 1280, 1220, 1125, 1080, 1025, 970, 890, 860, 740.

Mass (m/e): M+ 416.

EXAMPLE 86

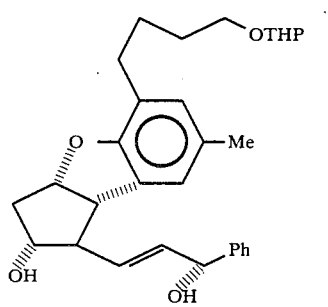

2-decarboxy-2-tetrahydropyranyloxymethyl-5,6,7-trinor-4,8-inter-(5-methyl-1,3-phenylene)-15-phenyl-16,17,18,19,20-petanor PGI$_2$ (89)

To a solution of 1.091 g (2.73 mmol) of 1,1,3a,8b-cis-tetrahydro-1-exo-(2-formylethenyl)-2-endo-hydroxy-7-methyl-5-(4-tetrahydropyranyloxy-n-butyl)cyclopenta[b]benzofuran in 16 ml of tetrahydrofuran at −78° C. under argon atmosphere was added 2.1 m (0.65M ether solution 13.7 mmol, 5 equiv.) of phenyl lithium, and the resulting solution was stirred for 2 hours. Five ml of a saturated aqueous solution of ammonium chloride was added, the temperature was allowed to warm to room temperature, and the mixture was extracted with ethyl acetate (10 ml×5), the combined organic layers were washed with 5 ml of saturated brine and dried over anhydrous Na$_2$SO$_4$. After concentration, the resulting 2.67 g of an oily substance was purified by column chromatography (Merck Co.'s Lobar Column, cyclohexane; ethyl acetate 1:4) to give 534 mg (1.12 mmol, 40.9%) of polar (89) and 325 mg (0.680 mmol, 24.9%) of less polar 15-epimer.

IR (neat) $\nu$ cm$^{-1}$: 3400 (3600–3100), 2930, 2850, 1600, 1470, 1450, 1200, 1135, 1115, 1070, 1020, 965, 860, 810, 760, 730, 700.

NMR (CDCl$_3$) δ: 1.62 (m, 10H), 1.94 (m, 1H), 2.14 (s, 3H), 2.45 (m, 1H), 2.53 (t, J=7 Hz, 2H), 2.65 (m, 1H), 2.60 (a wide one-double line, 2H), 3.23 (m, 1H), 3.36 (t, J=8 Hz, 2H), 3.84 (m, 3H), 4.53 (m, 1H), 5.21 (m, 1H), 5.43 (m, 1H), 5.77 (m, 2H), 6.62 (s, 1H), 6.73 (s, 1H), 7.36 (m, 5H).

Mass (m/e): 478 (M+).

| Anal. Calcd. for C$_{30}$H$_{38}$O$_5$ | Found |
|---|---|
| C = 75.29% | 75.21% |
| H = 8.00% | 7.93% |

EXAMPLE 87

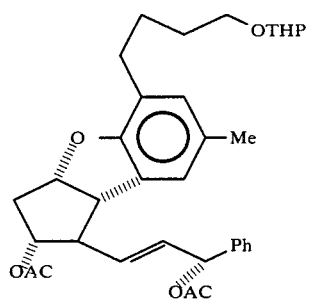

2-decarboxy-2-tetrahydropyranyloxymethyl-5,6,7-trinor-4,8-inter-(5-methyl-1,3-phenylene)-15-phenyl-16,17,18,19,20-pentanor PGI$_2$ (90)

To a solution of 510 mg of 2-decarboxy-2-tetrahydropyranyloxy-methyl-5,6,7-trinor-4,8-inter-(5-methyl-1,3-phenylene)-15-phenyl-16,17,18,19,20-pentanor PGI$_2$ in 10 ml of pyridine under nitrogen atmosphere was added 5 ml of acetic anhydride and the resulting solution was stirred at room temperature for 24 hours. Pyridine and acetic anhydride were evaporated to give 574 mg (1.02 mmol, 95.5%) of pure 2 as an oil.

IR (neat) ν cm$^{-1}$: 2930, 2850, 1740, 1600, 1475, 1370, 1230, 1135, 1110, 1060, 1020, 960, 860, 815, 760, 740, 700.

NMR (CDCl$_3$) δ: 1.63 (m, 10H), 1.77 (s, 3H), 2.00 (m, 1H), 2.11 (s, 3H), 2.20 (s, 3H), 2.54 (m, 3H), 2.75 (m, 1H), 3.48 (m, 3H), 3.89 (m, 2H), 4.57 (m, 1H), 4.92 (t, J=7 Hz, 1H), 5.14 (m, 1H), 5.76 (m, 2H), 6.65 (s, 1H), 6.76 (s, 1H), 7.16 (m, 5H).

Mass (m/e): 562 (M$^+$).

| Anal. Calcd. for C$_{34}$H$_{42}$O$_7$ | Found |
|---|---|
| C = 72.58% | 72.59% |
| H = 7.52% | 7.57% |

EXAMPLE 88

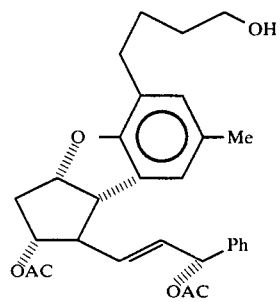

2-decarboxy-2-hydroxymethyl-5,6,7-trinor-4,8-inter-(5-methyl-1,3-phenylene)-15-phenyl-16,17,18,19,20-pentanor PGI$_2$ diacetate (91)

To a solution of 507 mg (0.902 mmol) of 2-decarboxy-2-tetrahydropyranyloxymethyl-5,6,7-trinor-4,8-inter-(5-methyl-1,3-phenylene)-15-phenyl-16,17,18,19,20-pentanor PGI$_2$ diacetate in 5 ml of tetrahydrofuran and 10 ml of acetonitrile was added 6 ml (1.5 mmol) of 0.25N hydrochloric acid, and the resulting solution was stirred at room temperature for 1.5 hours. After the solution was cooled to 0° C., 3 ml of saturated brine and 3 ml of a saturated aqueous solution of sodium bicarbonate were added, and the mixture was extracted with ethyl acetate (10 ml×4) and the organic layer was dried over anhydrous sodium sulfate. After concentration, the resulting 516 mg of an oily crude product was purified by column chromatography (Merck Co.'s Lobar Column, cyclohexane:ethyl acetate 1:2) to give 267 mg (0.559 mmol, 62%) of white solid (91), which was recrystallized from a cyclohexane:ethyl acetate (4:1) to give colorless needles (mp 76°-78° C.).

IR (KBr) ν cm$^{-1}$: 3450 (3650-3150), 2930, 2850, 1740, 1600, 1475, 1370, 1230, 1130, 1055, 1020, 960, 860, 760, 730, 700.

NMR (CDCl$_3$) δ: 1.64 (m, 5H), 1.78 (s, 3H), 1.97 (m, 1H), 2.11 (s, 3H), 2.20 (s, 3H), 2.54 (m, 3H), 2.78 (m, 1H), 3.52 (dd, J=8, 6 Hz, 1H), 3.66 (t, J=6 Hz, 2H), 4.86 (q, J=6 Hz, 1H), 4.96 (q, J=6 Hz, 1H), 5.17 (m, 1H), 5.76 (m, 2H), 6.30 (m, 1H), 6.68 (s, 1H), 6.76 (s, 1H), 7.37 (s, 5H).

Mass (m/e): 478 (M$^+$).

| Anal. Calcd. for C$_{29}$H$_{34}$O$_6$ | Found |
|---|---|
| C = 72.78% | 72.92% |
| H = 7.16% | 7.10% |

EXAMPLE 89

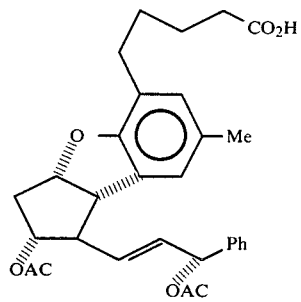

5,6,7-trinor-4,8-inter-(5-methyl-1,3-phenylene)-15-phenyl-16,17,18,19,20-pentanor PGI$_2$ diacetate (92)

To a solution of 219 mg (0.458 mmol) of 2-decarboxy-2-hydroxymethyl-5,6,7-trinor-4,8-inter-(5-methyl-1,3-phenylene)-15-phenyl-16,17,18,19,20-pentanor PGI$_2$ diacetate in 4 ml of anhydrous N,N-dimethyl formamide was added 688 mg (1,83 mmol, 4.0 equiv.) of pyridinium dichromate, and the resulting mixture was stirred at room temperature for 12 hours. Water was added, and the mixture was extracted with ether (20 ml×5), the ether layers were washed with saturated brine (1 ml×2) and dried over anhydrous sodium sulfate. After concentration, the resulting 238 mg of an oily substance was purified by column chromatography (Merck Co.'s Lobar Column, cyclohexane:ethyl acetate 1:2) to give 128 mg (0.260 mmol, 56.8%) of white crystals (92), which was recrystallized from 4 ml of a cyclohexane-ethyl acetate (4:1) to afford colorless needles (mp 111°-113° C.).

IR (KBr) ν cm$^{-1}$: 3450 (3650-2300), 2930, 2860, 1740, 1705, 1600, 1475, 1370, 1225, 1050, 1015, 955, 860, 765, 700.

NMR (CDCl$_3$) δ: 1.76 (s, 3H), 1.99 (m, 3H), 2.11 (s, 3H), 2.20 (s, 3H), 2.38 (m, 3H), 2.58 (t, J=8 Hz, 2H), 2.80 (m, 1H), 3.62 (dd, J=8, 6 Hz, 1H), 4.98 (q, J=7 Hz, 1H), 5.17 (m, 1H), 5.76 (m, 2H), 6.30 (m, 1H), 6.69 (0, 1H), 6.75 (s, 1H), 7.37 (s, 5H).

Mass (m/e): 492 (M$^+$).

| Anal. Calcd. for C$_{29}$H$_{32}$O$_7$ | Found |
|---|---|
| C = 70.72% | 70.46% |
| H = 6.54% | 6.50% |

EXAMPLE 90

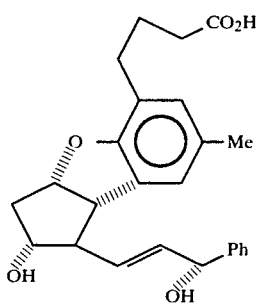

5,6,7-trinor-4,8-inter-(5-methyl-1,3-phenylene)-15-phenyl-16,17,18,19,20-pentanor PGI$_2$ (93)

To a solution of 110 mg (0.223 mmol) of 5,6,7-trinor-4,8-inter-(5-methyl-1,3-phenylene)-15-phenyl-16,17,18,19,20-pentanor PGI$_2$ diacetate in 3 ml of methanol was added 1.0 ml (4.5 equiv.) of 1N sodium hydroxide, and the resulting solution was stirred at room temperature for 2 hours. Methanol was evaporated (bath temperature less than 40° C.), and the mixture was cooled to 0° C., 0.25N hydrochloric acid was added to adjust the pH to 4. The two ml of saturated brine was added, the mixture was extracted with ethyl acetate (10 ml×5), and the organic layer was washed with saturated brine and dried over anhydrous sodium sulfate. Evaporation of the solvent afforded 91 mg (0.223 mmol, 100%) of white crystals (93), which was recrystallized from 4 ml of a cyclohexane-ethyl acetate (1:1) to give colorless prisms (mp 141°-144° C.).

IR (KBr) $\nu$ cm$^{-1}$: 3400 (3650-2200), 2960, 2930, 2850, 1705, 1675, 1600, 1475, 1410, 1300, 1280, 1220, 1195, 965, 860, 855, 760, 700.

NMR (CDCl$_3$) δ: 1.99 (m, 3H), 2.15 (s, 3H), 2.31 (m, 3H), 2.58 (t, J=8 Hz, 2H), 2.72 (m, 1H), 3.40 (m, 4H), 3.95 (m, 1H), 5.06 (m, 1H), 5.24 (m, 1H), 5.80 (m, 2H), 6.63 (s, 1H), 6.74 (s, 1H), 7.40 (m, 5H).

Mass (m/e): 408 (M$^+$).

| Anal. Calcd. for C$_{25}$H$_{28}$O$_5$ | Found |
|---|---|
| C = 73.51% | 73.71% |
| H = 6.91% | 6.93% |

EXAMPLES 91-92

The procedure of Example 86 is followed except the uses of 1,2,3a,8b-cis-tetrahydro-1-exo-(2-formylethenyl)-2-endohydroxy-7-bromo-5-(4-tetrahydropyranyloxybutyl)cyclopenta[b]benzofuran, or 1,2,3a,8b-cis-tetrahydro-1-exo-(2-formylethenyl)-2-endo-hydroxy-7-chloro-5-(4-tetrahydropyranyloxybutyl)cyclopenta[b]benzofuran and cyclohexylmagnesium chloride, in place of 1,2,3a-8b-cis-tetrahydro-1-exo-(2-formylethenyl)-2-endo-hydroxy-7-methyl-5-(4-tetrahydropyranyloxybutyl)cyclopenta[b]benzofuran and phenyl lithium, and the procedures of Examples 87-90 are followed successively except the uses of the each resulting compounds to give 5,6,7-trinor-4,8-inter-(5-bromo-1,3-phenylene)-16,17,18,19,20-pentanor-15-cyclohexyl PGI$_2$ (94), or 5,6,7-trinor-4,8-inter-(5-chloro-1,3-phenylene)-16,17,18,19,20-pentanor-15-cyclohexyl PGI$_2$ (95).

REFERENTIAL EXAMPLE 85

2-phenylseleno-5,6,7-trinor-4,8-inter-m-phenylene-16,17,18,19,20-pentanor-15-phenyl-PGI methyl ester To a solution of 0.15 ml of diisopropyl amine in 10 ml of anhydrous THF at $-78°$ C. was added 0.7 ml of 1.5N n-butyl lithium, and the resulting solution was stirred for 15 minutes. A solution of 90 mg of 5,6,7-trinor-4,8-inter-m-phenylene-16,17,18,19,20-pentanor-15-phenyl-PGI$_2$ methyl ester in 2 ml of anhydrous THF was added at $-78°$ C., the resulting solution was stirred at that temperature for 30 minutes, a solution of 200 mg of diphenylselenide in 1 ml of anhydrous HMPA was added, and the resulting solution was stirred at $-78°$ C. for 20 minutes. Solid ammonium chloride was added, and the mixture was stirred at $-78°$ C. for 20 minutes and at room temperature for 10 minutes, water was added and the mixture was extracted 3 times with ether. The combined organic layer was washed with water and saturated brine, dried and thereafter concentrated to give 100 mg of an oily substance. The oily substance was purified by column chromatography [silica gel; ethyl acetate:cyclohexane (3:1)] to afford 88 mg of the selenide.

IR (neat) $\nu$ cm$^{-1}$: 3350, 1730, 1590, 1500, 970, 748, 700.

NMR (CDCl$_3$) δ: 3.50 (m, 1H), 3.58 (s, 3H), 3.95 (m, 1H), 5.10 (m, 1H), 5.25 (dd, 1H, J=5.0 Hz, 3.0 Hz), 5.80 (m, 2H), 6.70 (1H, t, J=6.0 Hz), 6.88 (m, 2H), 7.32 (m, 3H), 7.55 (m, 2H).

Mass (m/e): 562 (M$^+$).

| Anal. Calcd. for C$_{31}$H$_{32}$O$_5$Se | Found |
|---|---|
| C = 66.61% | 66.55% |
| H = 5.68% | 5.69% |

EXAMPLE 93

Trans-2,3-didehydro-5,6,7-trinor-4,8-inter-m-phenylene-16,17,18,19,20-pentanor-15-phenyl-PGI$_2$ methyl ester (96)

To a solution of 40 mg of 2-phenylseleno-5,6,7-trinor-4,8-inter-m-phenylene-16,17,18,19,20-pentanor-15-phenyl-PGI$_2$ methyl ester in 5 ml of ethyl acetate was added 0.16 ml of 35% hydrogen peroxide, and the resulting mixture was stirred at room temperature for 1 hour. One ml of dimethyl sulfide and 200 mg of potassium acetate were added, and the mixture was stirred at room temperature for 10 minutes, thereafter, concentrated under reduced pressure. Water was added to the resulting residue, and the mixture was extracted 3 times with ethyl acetate, the extracts were washed with a saturated aqueous solution of sodium carbonate, water and saturated brine, dried and thereafter concentrated to give 40 mg of an oily substance. The oily substance was purified by column chromatography [silica gel; ethyl acetate:cyclohexane (2:1)] to afford 25 mg of the unsaturated ester (96).

IR (neat) $\nu$ cm$^{-1}$: 3350, 1710, 1650, 1595, 970, 750, 700.

NMR (CDCl$_3$) δ: 3.40 (2H, m), 3.68 (3H, s), 3.80 (1H, m), 5.02 (1H, m), 5.20 (1H, m), 5.78 (2H, m), 5.80 (1H, dt, J=15.0 Hz, 2.0 Hz), 6.70 (1H, dt, J=6.0 Hz, 8.5 Hz), 6.90 (2H, m), 7.10 (1H, m), 7.35 (5H, s).

Mass (m/e): 406 (M$^+$).

| Anal. Calcd. for C25H26O5 | Found |
|---|---|
| C = 73.89% | 73.92% |
| H = 6.40% | 6.36% |

| Anal. Calcd. for C24H24O5 | Found |
|---|---|
| C = 76.53% | 76.55% |
| H = 6.12% | 6.09% |

REFERENTIAL EXAMPLE 86

2-phenlylseleno-5,6,7-trinor-4,8-inter-m-phenylene-16,17,18,19,20-pentanor-15-phenyl-PGI$_2$ To a solution of 42 mg of 2-phenlylseleno-5,6,7-trinor-4,8-inter-m-phenylene-16,17,18,19,20-pentanor-15-phenyl-PGI$_2$ methyl ester in 4 ml of methanol was added 0.8 ml of 1N sodium hydroxide, and the resulting solution was stirred at room temperature for 14 hours. The reaction mixture was concentrated under reduced pressure, water was added to the residue, the pH of the mixture cooled in an ice bath was adjusted to 4 with $\frac{1}{4}$N hydrochloric acid and the product was extracted with ethyl acetate 3 times. The combined organic layers were washed with water and saturated brine, dried and thereafter concentrated to give 41 mg of the nearly pure carboxylic acid.

IR (neat) $\nu$ cm$^{-1}$: 3600–2400, 1700, 1595, 1580, 965, 740, 700.

NMR (CDCl$_3$) δ: 3.30 (1H, m), 3.90 (1H, m), 5.00 (1H, m), 5.20 (1H, m), 5.75 (2H, m), 6.65 (1H, t, J=7.0 Hz), 6.85 (2H, m), 7.30 (3H, m), 7.55 (2H, m).

Mass (m/e): 548 (M+).

| Anal. Calcd. for C30H30O5Se | Found |
|---|---|
| C = 65.69% | 65.81% |
| H = 5.47% | 5.38% |

EXAMPLE 94

5,6,7-trinor-4,8-inter-m-phenylene-2,3-dehydro-16,17,18,19,20-pentanor-15-phenyl-PGI$_2$ (97)

To a solution of 41 mg of 2-phenylseleno-5,6,7-trinor-4,8-inter-m-phenylene-16,17,18,19,20-pentanor-15-phenyl-PGI$_2$ in 5 ml of ethyl acetate was added, 0.16 ml of a 35% aqueous solution of hydrogen peroxide, and the resulting solution was stirred at room temperature for 1 hour. One ml of dimethyl sulfide and 100 mg of potassium acetate were added, and the mixture was stirred at room temperature for 10 minutes and thereafter concentrated under reduced pressure. Water was added to the residue, the pH of the mixture cooled in an ice bath was adjusted to 6 with $\frac{1}{4}$N hydrochloric acid. The product was extracted 3 times with ethyl acetate, the organic layer was washed with water and saturated brine, dried and thereafter concentrated to give 34 mg of an oily substance. The oily substance was purified by column chromatography [acidic silica gel; ethyl acetate:cyclohexane (3:1)] to afford 25 mg of the pure unsaturated carboxylic acid.

IR (neat) $\nu$ cm$^{-1}$: 3600–2400, 1700, 1640, 1600, 960, 765, 700.

NMR (CDCl$_3$) δ: 3.40 (3H, m), 3.90 (1H, m), 5.05 (1H, m), 5.20 (1H, m), 5.75 (2H, m), 5.77 (1H, d, J=15.0 Hz) 6.65 (1H, dd, J=8.5 Hz, 6.0 Hz) 6.90 (2H, m), 7.10 (1H, m), 7.35 (5H, m).

Mass (m/e): 392 (M+).

EXAMPLES 95–106

The procedure of Referential Example 85 was followed except the use of 5,6,7-trinor-4,8-inter-m-phenylene-16,17,18,19,20-pentanor-15-cyclohexyl PGI$_2$ methyl ester, 5,6,7-trinor-4,8-inter-m-phenylene-16,17,18,19,20-pentanor-15-cyclopentyl PGI$_2$ methyl ester, 5,6,7-trinor-4,8-inter-m-phenylene-13,14-dehydro-16,17,18,19,20-pentanor-15-phenyl PGI$_2$ methyl ester, 5,6,7-trinor-4,8-inter-m-phenylene-13,14-dehydro-16,17,18,19,20-pentanor-15-cyclopentyl PGI$_2$ methyl ester, 5,6,7-trinor-4,8-inter-m-phenylene-13,14-dehydro-16,17,18,19,20-pentanor-15-cyclohexyl PGI$_2$ methyl ester, 5,6,7-trinor-4,8-inter-m-phenylene-17,18,19,20-tetranor-16-phenyl PGI$_2$, 5,6,7-trinor-4,8-inter-m-phenylene-17-α-methyl PGI$_2$ methyl ester, 5,6,7-trinor-4,8-inter-m-phenylene-17-β-methyl PGI$_2$ methyl ester, 5,6,7-trinor-4,8-inter-m-phenylene-17-α-methyl-ω-homo PGI$_2$ methyl ester, 5,6,7-trinor-4,8-inter-m-phenylene-17-β-methyl-ω-homo PGI$_2$ methyl ester, 5,6,7-trinor-4,8-inter-m-phenylene PGI$_2$ methyl ester, or 5,6,7-trinor-4,8-inter-m-phenylene-ω-homo PGI$_2$ methyl ester, in place of 5,6,7-trinor-4,8-inter-m-phenylene-16,17,18,19,20-pentanor-15-phenyl PGI$_2$ methyl ester and the obtained products were followed by the method of Example 93 to give 5,6,7-trinor-4,8-inter-m-phenylene-2,3-dehydro-16,17,18,19,20-pentanor-15-cyclohexyl PGI$_2$ methyl ester (98), 5,6,7-trinor-4,8-inter-m-phenylene-2,3-dehydro-16,17,18,19,20-pentanor-15-cyclopentyl PGI$_2$ methyl ester (99), 5,6,7-trinor-4,8-inter-m-phenylene-2,3,13,14-tetrahydro-16,17,18,19,20-pentanor-15-phenyl PGI$_2$ methyl ester (100), 5,6,7-trinor-4,8-inter-m-phenylene-2,3,13,14-tetrahydro-16,17,18,19,20-pentanor-15-cyclopentyl PGI$_2$ methyl ester (101), 5,6,7-trinor-4,8-inter-m-phenylene-2,3,13,14-tetrahydro-16,17,18,19,20-pentanor-15-cyclohexyl PGI$_2$ methyl ester (102), 5,6,7-trinor-4,8-inter-m-phenylene-2,3-dehydro-17,18,19,20-tetranor-16-phenyl PGI$_2$ methyl ester (103), 5,6,7-trinor-4,8-inter-m-phenylene-2,3-dehydro-17-α-methyl PGI$_2$ methyl ester (104), 5,6,7-trinor-4,8-inter-m-phenylene-2,3-dehydro-17-β-methyl PGI$_2$ methyl ester (105), 5,6,7-trinor-4,8-inter-m-phenylene-2,3-dehydro-17-α-methyl-ω-homo PGI$_2$ methyl ester (106), 5,6,7-trinor-4,8-inter-m-phenylene-2,3-dehydro-17-β-methyl-ω-homo PGI$_2$ methyl ester (107), 5,6,7-trinor-4,8-inter-m-phenylene-2,3-dehydro PGI$_2$ methyl ester (108), or 5,6,7-trinor-4,8-inter-m-phenylene-2,3-dehydro-ω-homo PGI$_2$ methyl ester (109). In Table 5, the spectral data of these compounds are shown.

TABLE 5

| Example | Compound | Mass spectrum (m/e, M+) | Infrared spectrum cm$^{-1}$ |
|---|---|---|---|
| 95 | 98 | 412 | 3350, 1710, 1650, 1595, 970 |
| 96 | 99 | 398 | 3350, 1710, 1650, 1595, 970 |
| 97 | 100 | 406 | 3350, 1710, 1650, 1595, 970, 750, 700 |
| 98 | 101 | 396 | 1710, 1650, 970 |
| 99 | 102 | 410 | 1710, 1650, 970 |
| 100 | 103 | 422 | 1710, 1650, 1595, 970, 750, 700 |
| 101 | 104 | 414 | 1710, 1650, 1250, 970 |
| 102 | 105 | 414 | 1710, 1650, 1250, 970 |

TABLE 5-continued

| Example | Compound | Mass spectrum (m/e, M+) | Infrared spectrum cm⁻¹ |
|---|---|---|---|
| 103 | 106 | 428 | 1710, 1650, 1450, 1250, 970 |
| 104 | 107 | 428 | 1710, 1650, 1450, 1250, 970 |
| 105 | 108 | 400 | 1710, 1650, 1450, 1250, 970 |
| 106 | 109 | 414 | 1710, 1650, 1450, 1250, 970, 860 |

EXAMPLES 107–118

The procedure of Referential Example 86 was followed except the uses of 2-phenylseleno-5,6,7-trinor-4,8-inter-m-phenylene-16,17,18,19,20-pentanor-15-cyclohexyl PGI₂ methyl ester, 2-phenylseleno-5,6,7-trinor-4,8-inter-m-phenylene-16,17,18,19,20-pentanor-15-cyclopentyl PGI₂ methyl ester, 2-phenylseleno-5,6,7-trinor-4,8-inter-m-phenylene-13,14-dehydro-16,17,18,19,20-pentanor-15-phenyl PGI₂ methyl ester, 2-phenylseleno-5,6,7-trinor-4,8-inter-m-phenylene-13,14-dehydro-16,17,18,19,20-pentanor-15-cyclopentyl PGI₂ methyl ester, 2-phenylseleno-5,6,7-trinor-4,8-inter-m-phenylene-13,14-dehydro-16,17,18,19,20-pentanor-15-cyclohexyl PGI₂ methyl ester, 2-phenyleseleno-5,6,7-trinor-4,8-inter-m-phenylene-17,18,19,20-tetranor-16-phenyl PGI₂ methyl ester, 2-phenylseleno-5,6,7-trinor-4,8-inter-m-phenylene-17-α-methyl PGI₂ methyl ester, 2-phenylseleno-5,6,7-trinor-4,8-inter-m-phenylene-17-β-methyl PGI₂ methyl ester, 2-phenylseleno-5,6,7-trinor-4,8-inter-m-phenylene-17-α-methyl-ω-homo PGI₂ methyl ester, 2-phenylseleno-5,6,7-trinor-4,8-inter-m-phenylene-17-β-methyl-ω-homo PGI₂ methyl ester, 2-phenylseleno-5,6,7-trinor-4,8-inter-m-phenylene PGI₂, or 2-phenylseleno-5,6,7-trinor-4,8-inter-m-phenylene-ω-homo PGI₂ methyl ester, in place of 2-phenylseleno-5,6,7-trinor-4,8-inter-m-phenylene-16,17,18,19,20-pentanor-15-phenyl PGI₂ and the products thus obtained were followed the method of Example 94 to give 5,6,7-trinor-4,8-inter-m-phenylene-2,3-dehydro-16,17,18,19,20-pentanor-15-cyclohexyl PGI₂ (110), 5,6,7-trinor-4,8-inter-m-phenylene-2,3-dehydro-16,17,18,19,20-pentanor-15-cyclopentyl PGI₂ (111), 5,6,7-trinor-4,8-inter-m-phenylene-2,3,13,14-tetrahydro-16,17,18,19,20-pentanor-15-phenyl PGI₂ (112), 5,6,7-trinor-4,8-inter-m-phenylene-2,3,13,14-tetrahydro-16,17,18,19,20-pentanor-15-cyclopentyl PGI₂ (113), 5,6,7-trinor-4,8-inter-m-phenylene-2,3,13,14-tetrahydro-16,17,18,19,20-pentanor-15-cyclohexyl PGI₂ (114), 5,6,7-trinor-4,8-inter-m-phenylene-2,3-dehydro-17,18,19,20-tetronor-16-phenyl PGI₂ (115), 5,6,7-trinor-4,8-inter-m-phenylene-2,3-dehydro-17-α-methyl PGI₂ (116), 5,6,7-trinor-4,8-inter-m-phenylene-2,3-dehydro-17-β-methyl PGI₂ (117), 5,6,7-trinor-4,8-inter-m-phenylene-2,3-dehydro-17-α-methyl-ω-homo PGI₂ (118), 5,6,7-trinor-4,8-inter-m-phenylene-2,3-dehydro-17-β-methyl-ω-homo PGI₂ (119), 5,6,7-trinor-4,8-inter-m-phenylene-2,3-dehydro PGI₂ (120), or 5,6,7-trinor-4,8-inter-m-phenylene-2,3-dehydro-ω-homo PGI₂ (121). In Table 6, the spectral data of these compounds are shown.

TABLE 6

| Example | Compound | Mass spectrum (m/e, M+) | Infrared spectrum cm⁻¹ |
|---|---|---|---|
| 107 | 110 | 398 | 3600–2400, 1700, 1640, 1600, 960 |
| 108 | 111 | 384 | 3600–2400, 1700, 1640, 1600, 960 |
| 109 | 112 | 392 | 3600–2400, 1700, 1640, 1595, 965, 765, 695 |
| 110 | 113 | 382 | 3600–2400, 1700, 1640, 1595, 970 |
| 111 | 114 | 396 | 3600–2400, 1700, 1640, 1595, 970 |
| 112 | 115 | 408 | 3600–2400, 1700, 1640, 1600, 965, 765, 700 |
| 113 | 116 | 400 | 3600–2400, 1700, 1640, 965 |
| 114 | 117 | 400 | 3600–2400, 1700, 1640, 965 |
| 115 | 118 | 414 | 3600–2400, 1700, 1642, 970 |
| 116 | 119 | 414 | 3600–2400, 1700, 1640, 970 |
| 117 | 120 | 386 | 3600–2400, 1700, 1640, 1595, 970 |
| 118 | 121 | 400 | 3600–2400, 1700, 1640, 1595, 970 |

EXAMPLE 119

5,6,7-trinor-4,8-inter-m-phenylene-3,4-didehydro-16,17,18,19,20-pentanor-15-cyclohexyl PGI₂ (122)

To a solution of 20 mg of 5,6,7-trinor-4,8-inter-m-phenylene-2,3-didehydro-16,17,18,19,20-pentanor-15-cyclohexyl PGI₂ methyl ester (98) in 1.5 ml of methanol was added, 0.5 ml of an aqueous solution of 1N sodium hydroxide, and the resulting solution was stirred at room temperature for 3 hours. The reaction solution was concentrated, water was added to the residue, the pH of the mixture cooled in an ice bath was adjusted to 3 with 1N hydrochloric acid and the product was extracted 3 times with ethyl acetate. The combined organic layer was washed with water and saturated brine, dried and thereafter concentrated to give 20 mg of an oily substance. The oily substance was purified by column chromatography (silica gel; 5% methanol-ethyl acetate) to afford 10 mg of a pure product (122).

IR (neat) ν cm⁻¹: 3600–2300, 1715, 975.

NMR (CDCl₃) δ: 3.00–4.00 (5H, m), 5.10 (1H, m), 5.60 (3H, m), 6.50 (2H, s), 6.75 (1H, t, J=7.0 Hz), 6.90 (1H, d J=7.0 Hz), 7.15 (1H, d, J=7.0 Hz).

Mass (m/e): 369 (M+).

EXAMPLES 120–131

The procedure of Example 119 was followed except the uses of (96), (99), (100), (101), (102), (103), (104), (105), (106), (107), (108) or (109) in place of (98) to give 5,6,7-trinor-4,8-inter-m-phenylene-3,4-dehydro-16,17,18,19,20-pentanor-15-phenyl PGI₂ (123), 5,6,7-trinor-4,8-inter-m-phenylene-3,4-dehydro-16,17,18,19,20-pentanor-15-cyclopentyl PGI₂ (124), 5,6,7-trinor-4,8-inter-m-phenylene-3,4,13,14-tetrahydro-16,17,18,19,20-pentanor-15-phenyl PGI₂ (125), 5,6,7-trinor-4,8-inter-m-phenylene-3,4,13,14-tetrahydro-16,17,18,19,20-pentanor-15-cyclopentyl PGI₂ (126), 5,6,7-trinor-4,8-inter-m-phenylene-3,4,13,14-tetrahydro-16,17,18,19,20-pentanor-15-cyclohexyl PGI₂ (127), 5,6,7-trinor-4,8-inter-m-phenylene-3,4-dehydro-17,18,19,20-tetranor-16-phenyl PGI₂ (128), 5,6,7-trinor-4,8-inter-m-phenylene-3,4-dehydro-17-α-methyl PGI₂ (129), 5,6,7-trinor-4,8-inter-m-phenylene-3,4-dehydro-17-β-methyl PGI₂ (130), 5,6,7-trinor-4,8-inter-m-phenylene-3,4-dehydro-17-α-methyl-ω-homo PGI₂ (131), 5,6,7-trinor-4,8-inter-m-phenylene-3,4-dehydro-17-β-methyl-ω-homo PGI₂ (132), 5,6,7-trinor-4,8-inter-m-phenylene-3,4-dehydro PGI₂ (133), or 5,6,7-trinor-4,8-inter-m-pheylene-3,4- dehydro-ω-homo PGI₂ (134). The spectral data of these compounds are shown in Table 7.

TABLE 7

| Example | Compound | Mass spectrum (m/e, M+) | Infrared spectrum cm⁻¹ |
|---|---|---|---|
| 120 | 123 | 392 | 3600–2300, 1715, 975, 750, 695 |
| 121 | 124 | 384 | 3600–2300, 1715, 970 |
| 122 | 125 | 392 | 3600–2300, 1715, 970, 760, 695 |
| 123 | 126 | 382 | 3600–2300, 1715, 970 |
| 124 | 127 | 396 | 3600–2300, 1715, 970 |
| 125 | 128 | 408 | 3600–2300, 1715, 970, 765, 700 |
| 126 | 129 | 400 | 3600–2300, 1715, 970 |
| 127 | 130 | 400 | 3600–2300, 1715, 970 |
| 128 | 131 | 414 | 3600–2300, 1715, 970 |
| 129 | 132 | 414 | 3600–2300, 1712, 970 |
| 130 | 133 | 386 | 3600–2300, 1710, 970 |
| 131 | 134 | 400 | 3600–2300, 1710, 970 |

EXAMPLE 132

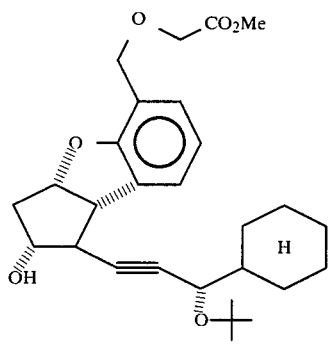

5,6,7-trinor-4,8-inter-m-phenylene-13,14-didehydro-3-oxa-16,17,18,19,20-pentanor-15-cyclohexyl PGI₂ methyl ester 15-t-butyl ether (135)

To a solution of 1.44 g of 3-t-butoxy-3-cyclohexyl-1-propyne in 6 ml of toluene under argon atmosphere was added 4.24 ml of n-butyl lithium (1.58M hexane solution), and the resulting solution was stirred for 15 minutes. A toluene solution (1.98M) of diethyl aluminium chloride (3.2 ml) at 0° C. was added, the temperature was allowed to warm to room temperature, and the resulting solution was stirred for 1 hour. The reaction mixture was again cooled to 0° C., 4 ml of a toluene solution of 168 mg of methyl (1,2,3a,8b-tetrahydro-1,2-syn-epoxycylopenta[b]benzofuran-5-yl methoxy) acetate was added, and the resulting solution was stirred for 1 hour. A saturated aqueous solution of sodium sulfate (0.5 ml) was added, white precipitate was filtered and the filtrate was concentrated to give 2.10 g of an oily substance, which was purified by column chromatography (silica gel; cyclohexane:ethyl acetate 2:1) to afford 25.0 mg of the subject compound (135).

IR (neat) νcm⁻¹: 3650–3000, 1760, 1600.

NMR (CDCl₃) δ: 1.14 (1H, a wide one-double line), 1.24 (9H, s), 1.5–2.1 (11H, m), 2.21 (1H, m), 2.48 (1H, m), 2.88 (1H, dt, J=2.0, 5.0 Hz), 3.75 (3H, s), 3.86 (2H, m), 4.08 (2H, s), 4.29 (1H, m), 4.63 (2H, s), 5.32 (1H, m), 6.88 (1H, dd, J=7.0, 8.0 Hz), 7.22 (2H, m).

Mass: 470 (M+).

EXAMPLE 133

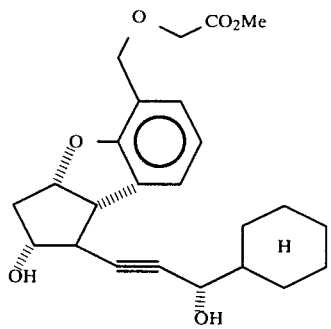

5,6,7-trinor-4,8-inter-m-phenylene-13,14-didehydro-3-oxa-16,17,18,19,20-pentanor-15-cyclohexyl PGI₂ methyl ester (136)

To a solution of 21.2 mg of 3-oxa-5,6,7-trinor-4,8-inter-m-phenylene-13,14-didehydro-15-cyclohexyl-16,17,18,19,20-pentanor PGI₂ methyl ester in 1 ml of methylene chloride at 0° C. under argon atmosphere, 0.2 ml of trifluoroacetic acid was added and the resulting solution was stirred for 1 hour. Removal of the solvent afford 22.5 mg of an oily substance, which was purified by thin-layer chromatography (silica gel; cyclohexane-ethyl acetate; 2:1) to give 1.9 mg of the subject compund (136).

IR (neat) νcm⁻¹: 3650–3000, 1760, 1600.

Mass: 414 (M+).

EXAMPLE 134

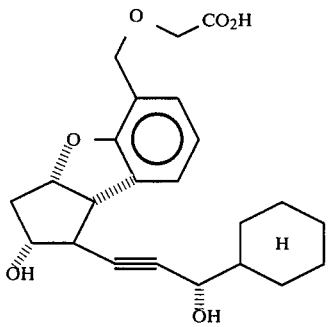

5,6,7-trinor-4,8-inter-m-phenylene-13,14-didehydro-3-oxa-16,17,18,19,20-pentanor-15-cyclohexyl PGI₂ (137)

To a solution of 12.3 mg of 5,6,7-trinor-4,8-inter-m-phenylene-13,14-didehydro-3-oxa-16,17,18,19,20-pentanor-15-cyclohexyl PGI₂ methyl ester in 1 ml of methanol was added 1.0 ml of 0.1N sodium hydroxide, and the resulting solution was stirred at room temperature for 24 hours. After removal of methanol, the reaction mixture was cooled to 0° C., the pH of the mixture was adjusted to 4 with 0.1N hydrochloric acid. The product was extracted with ethyl acetate (10 ml×5) and the organic layer was washed with saturated brine (2 ml) and dried. Removal of the solvent afford 9.5 mg of the subject compound (137) in nearly pure state.

IR (neat) νcm⁻¹: 3650–2200, 1710, 1600.

Mass: 400 (M+).

EXAMPLES 135–142

The procedure of Example 132 is followed except the uses of 3-t-butoxy-3-cyclopentyl-1-propyne, 3-t-butoxy-4-cyclohexyl-1-butyne, 3-t-butoxy-4-cyclopentyl-1-butyne, 3-t-butoxy-4-phenyl-1-butyne, 3-t-butoxy-5-phenyl-1-pentyne, 3-t-butoxy-3-(4-methylcyclohexyl)-1-propyne, 3-t-butoxy-3-(3-methylcyclohexyl)-1-propyne, or 3-t-butoxy-5-methyl-1-nonyne, in place of 3-t-butoxy-3-cyclohexyl-1-propyne and the each resulting product was followed by the methods of Examples 133–134 successively to give 5,6,7-trinor-4,8-inter-m-phenylene-13,14-didehydro-3-oxa-16,17,18,19,20-pentanor-15-cyclopentyl PGI₂ (138), 5,6,7-trinor-4,8-inter-m-phenylene-13,14-didehydro-3-oxa-17,18,19,20-tetranor-16-cyclohexyl PGI₂ (139), 5,6,7-trinor-4,8-inter-m-phenylene-13,14-didehydro-3-oxa-17,18,19,20-tetranor-16-cyclopentyl PGI₂ (140), 5,6,7-trinor-4,8-inter-m-phenylene-13,14-didehydro-3-oxa-17,18,19,20-tetranor-16-phenyl PGI₂ (141), 5,6,7-trinor-4,8-inter-m-phenylene-13,14-didehydro-3-oxa-18,19,20-trinor-17-phenyl PGI₂ (142), 5,6,7-trinor-4,8-inter-m-phenylene-13,14-didehydro-3-oxa-16,17,18,19,20-pentanor-15-(4-methylcyclohexyl) PGI₂ (143), 5,6,7-trinor-4,8-inter-m-phenylene-13,14-didehydro-3-oxa-16,17,18,19,20-pentanor-15-(3-methylcyclohexyl) PGI₂ (144) or 5,6,7-trinor-4,8-inter-m-phenylene-13,14-didehydro-3-oxa-17-methyl-ω-homo PGI₂ (145). The spectral data of these compounds are shown in Table 8.

TABLE 8

| Example | Compound | Mass spectrum (m/e, M⁺) | Infrared spectrum cm⁻¹ |
|---|---|---|---|
| 135 | 138 | 386 | 3650–2200, 1710, 1600 |
| 136 | 139 | 414 | 3650–2200, 1710, 1600, 1190 |
| 137 | 140 | 400 | 3650–2200, 1710, 1600, 1190 |
| 138 | 141 | 408 | 3650–2200, 1710, 1600, 765, 700 |
| 139 | 142 | 422 | 3650–2200, 1715, 1600, 765, 659 |
| 140 | 143 | 414 | 3650–2200, 1715, 1600 |
| 141 | 144 | 414 | 3650–2200, 1710, 1600 |
| 142 | 145 | 416 | 3650–2200, 1715, 1600 |

EXAMPLE 143

5,6,7-trinor-4,8-inter-m-phenylene-13,14-didehydro-16,17,18,19,20-pentanor-15-cyclohexyl-PGI₂ methyl ester (146)

To a solution of 500 mg (1.25 mmol) of 5,6,7-trinor-4,8-inter-m-phenylene-13,14-dehydro-16,17,18,19,20-pentanor-15-cyclohexyl-PGI₂ (9) in 5 ml of methanol was added slowly a large excess of diazomethane ether solution. The resulting mixture was concentrated, the residue was purified by column chromatography (Merck Co.'s Lobar Column B; ethyl acetate) to give 467 mg (90%) of the titled compound.

EXAMPLES 144–152

The procedure of Example 143 was followed except the uses of the compound (10), (11), (12), (13), (14), (15), (16), (17) or (18) in place of (9) to give 5,6,7-trinor-4,8-inter-m-phenylene-13,14-didehydro-16,17,18,19,20-pentanor-15-(4-methylcyclohexyl) PGI₂ methyl ester (147), 5,6,7-trinor-4,8-inter-m-phenylene-13,14-didehydro-16,17,18,19,20-pentanor-15-(3-methylcyclohexyl) PGI₂ methyl ester (148), 5,6,7-trinor-4,8-inter-m-pheylene-13,14-didehydro-16,17,18,19,20-pentanor-15-(2,2-dimethyl-4-methylcyclohexyl) PGI₂ methyl ester (149), 5,6,7-trinor-4,8-inter-m-pheylene-13,14-didehydro-16,17,18,19,20-pentanor-15-(2-methylcyclohexyl) PGI₂ methyl ester (150), 5,6,7-trinor-4,8-inter-m-phenylene-13,14-didehydro-16,17,18,19,20-pentanor-15-cyclopentyl PGI₂ methyl ester (151), 5,6,7-trinor-4,8-inter-m-phenylene-13,14-didehydro-16,17,18,19,20-pentanor-15-(2-methylcyclopentyl) PGI₂ methyl ester (152), 5,6,7-trinor-4,8-inter-m-pheylene-13,14-didehydro-17,18,19,20-tetranor-16-cyclohexyl PGI₂ methyl ester (153), 5,6,7-trinor-4,8-inter-m-phenylene-13,14-didehydro-17,18,19,20-tetranor-16-cyclopentyl PGI₂ methyl ester (154), or 5,6,7-trinor-4,8-inter-m-phenylene-13,14-didehydro-18,19,20-trinor-17-cyclohexyl PGI₂ methyl ester (155). The spectra of the compounds (147)–(155) are shown in Table 9.

TABLE 9

| Example | Compound | Mass spectrum (m/e, M⁺) | Infrared spectrum cm⁻¹ |
|---|---|---|---|
| 144 | 147 | 426 | 3450, 1740, 1595, 1450, 1195, 865, 745 |
| 145 | 148 | 426 | 3450, 1740, 1595, 1450, 1195 |
| 146 | 149 | 454 | 3450, 1740, 1595, 1450 |
| 147 | 150 | 426 | 1740 |
| 148 | 151 | 398 | 1740 |
| 149 | 152 | 412 | 1740 |
| 150 | 153 | 426 | 1740 |
| 151 | 154 | 412 | 1740 |
| 152 | 155 | 440 | 1740 |

EXAMPLES 153–163

The procedure of Example 143 was followed except the uses of the compound (29), (30), (31), (39), (48), (49), (55), (60), (65), (76), or (81) in place of (9) to give 5,6,7-trinor-4,8-inter-m-phenylene-13,14-didehydro-17-methyl PGI₂ methyl ester (156), 5,6,7-trinor-4,8-inter-m-pheylene-13,14-didehydro-17-methyl-ω-homo PGI₂ methyl ester (157), 5,6,7-trinor-4,8-inter-m-phenylene-13,14-didehydro-16,16-dimethyl PGI₂ methyl ester (158), 5,6,7-trinor-4,8-inter-m-phenylene-16,16-dimethyl PGI₂ methyl ester (159), 5,6,7-trinor-4,8-inter-m-phenylene-17-α-methyl PGI₂ methyl ester (160), 5,6,7-trinor-4,8-inter-m-phenylene-17-β-methyl PGI₂ methyl ester (161), 5,6,7-trinor-4,8-inter-m-phenylene-17-α-methyl-20-homo PGI₂ methyl ester (162), 5,6,7-trinor-4,8-inter-m-phenylene-17,18,19,20-tetranor-16-phenoxy PGI₂ methyl ester (163) 5,6,7-trinor-4,8-inter-m-phenylene-17,18,19,20-tetranor-16-(m-chlorophenoxy) PGI₂ (164), 5,6,7-trinor-4,8-inter-m-phenylene-16,16-dimethyl-18,19,20-trinor-17-ethoxy PGI₂ methyl ester (165), or 5,6,7-trinor-4,8-inter-m-phenylene-20-isopropylidene PGI₂ methyl ester (166). The spectra of the compounds (156)–(166) are shown in Table 10.

TABLE 10

| Example | Compound | Mass spectrum (m/e, M⁺) | Infrared spectrum cm⁻¹ |
|---|---|---|---|
| 153 | 156 | 414 | 1730 |
| 154 | 157 | 428 | 1730 |
| 155 | 158 | 442 | 1730 |
| 156 | 159 | 430 | 1735, 970 |
| 157 | 160 | 416 | 1735, 970, 760, 740 |
| 158 | 161 | 416 | 1735, 970, 760, 740 |
| 159 | 162 | 430 | 1730, 970, 760, 740 |
| 160 | 163 | 438 | 1735, 1595, 970, 760, 695 |
| 161 | 164 | 472, 474 | 1735, 965 |
| 162 | 165 | 432 | 1735, 970, 765 |
| 163 | 166 | 442 | 1735, 1595, 970, 765, 745 |

EXAMPLE 164

5,6,7-trinor-4,8-inter-m-phenylene-13,14-didehydro-16,17,18,19,20-pentanor-15-cyclohexyl-PGI$_2$ benzyl ester (167)

To a solution of 35 mg of 5,6,7-trinor-4,8-inter-m-phenylene-13,14-didehydro-16,17,18,19,20-pentanor-15-cyclohexyl-PGI$_2$ in 1 ml of dimethyl formamide 100 μl of triethylamine and 100 μl of benzyl bromide, and the resulting solution was stirred at room temperature for 5 hours. After completion of the reaction, 3 ml of water was added, thereafter, the product was extracted with ether, and the ether layer was dried over Na$_2$SO$_4$ and thereafter concentrated to give a crude product of (167), which was purified by column chromatography (silica gel; developing solvent:ethyl acetate) to afford 30 mg of the pure subject compound (167).

IR (neat) $v$cm$^{-1}$: 3350, 1710, 1650, 965, 760, 695.
Mass (m/e): 488.

EXAMPLE 165

5,6,7-trinor-4,8-inter-m-pheylene-13,14-didehydro-16,17,18,19,20-pentanor-15-cyclohexyl-PGI$_2$ (2-pyridylmethyl) ester (168)

To a solution of 350 mg of 5,6,7-trinor-4,8-inter-m-pheylene-13,14-didehydro-16,17,18,19,20-pentanor-15-cyclohexyl PGI$_2$ (9) in 4 ml of anhydrous tetrahydrofuran, cooled in an ice bath were added 0.16 ml of triethylamine and 0.09 ml of ethyl choroformate, and the resulting solution was stirred at room temperature for 20 minutes. After addition of 0.4 ml of 2-pyridyl methanol, the mixture was stirred for 14 hours at 60° C. under argon atmosphere. Ethyl acetate was added to the cooled mixture and the organic layer was washed with a saturated aqueous solution of sodium hydrogen carbonate and water, thereafter, dried over Na$_2$SO$_4$ and concentrated to give 700 mg of an oily substance. The oily substance was purified by column chromatography [silica gel; ethyl acetate:isopropanol:methanol (97:3:0.5)] to afford 300 mg of the subject compound (169) as a light yellow oil.

IR (neat) $v$cm$^{-1}$: 3350, 1710, 1650, 1590, 965.
Mass (m/e): 489.

EXAMPLES 166-176

The produre of Example 165 is followed except the uses of butanol, ethanol, cyclohexyl methanol, cyclopentyl methanol, 2-methoxy ethanol, methyl glycolate, methyl lactate ester, 2-butyne-1-ol, 1,3-di-(O)-acetyl-glycerin, phenol or p-acetaminophenol in place of 2-pyridyl methanol to give 5,6,7-trinor-4,8-inter-m-pheylene-13,14-didehydro-16,17,18,19,20-pentanor-15-cyclohexyl PGI$_2$ butyl ester (169), 5,6,7-trinor-4,8-inter-m-pheylene-13,14-didehydro-16,17,18,19,20-pentanor-15-cyclohexyl-PGI$_2$ ethyl ester (170), 5,6,7-trinor-4,8-inter-m-pheylene-13,14-didehydro-16,17,18,19,20-pentanor-15-cyclohexyl PGI$_2$ cyclohexylmethyl ester (171), 5,6,7-trinor-4,8-inter-m-pheylene-13,14-didehydro-16,17,18,19,20-pentanor-15-cyclohexyl PGI$_2$ cyclopentylmethyl ester (172), 5,6,7-trinor-4,8-inter-m-pheylene-13,14-didehydro-16,17,18,19,20-pentanor-15-cyclohexyl PGI$_2$ (2-methoxyethyl) ester (173), 5,6,7-trinor-4,8-inter-m-pheylene-13,14-didehydro-16,17,18,19,20-pentanor-15-cyclohexyl PGI$_2$ carbomethoxymethyl ester (174), 5,6,7-trinor-4,8-inter-m-pheylene-13,14-didehydro-16,17,18,19,20-pentanor-15-cyclohexyl PGI$_2$ (1-carbomethyoxyethyl) ester (175), 5,6,7-trinor-4,8-inter-m-phenylene-13,14-didehydro-16,17,18,19,20-pentanor-15-cyclohexyl PGI$_2$ (2-butynyl) ester (176), 5,6,7-trinor-4,8-inter-m-pheylene-13,14-didehydro-16,17,18,19,20-pentanor-15-cyclohexyl PGI$_2$ (1,3-diacetoxy-2-propyl) ester (177), 5,6,7-trinor-4,8-inter-m-pheylene-13,14-didehydro-16,17,18,19,20-pentanor-15-cyclohexyl PGI$_2$ phenyl ester (178), or 5,6,7-trinor-4,8-inter-m-pheylene-13,14-didehydro-16,17,18,19,20-pentanor-15-cyclohexyl PGI$_2$ (p-acetaminophenyl) ester (179). The spectra of the compounds (169)-(179) are shown in Table 11.

TABLE 11

| Example | Compound | Mass spectrum (m/e, M$^+$) | Infrared spectrum cm$^{-1}$ |
|---|---|---|---|
| 166 | 169 | 454 | 1740, 1595 |
| 167 | 170 | 430 | 1740, 1595 |
| 168 | 171 | 494 | 1735 |
| 169 | 172 | 480 | 1740 |
| 170 | 173 | 456 | 1735 |
| 171 | 174 | 470 | 1740 |
| 172 | 175 | 484 | 1740 |
| 173 | 176 | 450 | 1735 |
| 174 | 177 | 556 | 1740 |
| 175 | 178 | 474 | 1745, 1600, 760, 695 |
| 176 | 179 | 531 | 1745 |

EXAMPLE 177

5,6,7-trinor-4,8-inter-m-pheylene-13,14-didehydro-16,17,18,19,20-pentanor-15-cyclohexyl PGI$_2$ carboxamide (180)

To a solution of 11 mg of 5,6,7-trinor-4,8-inter-m-pheylene-13,14-didehydro-16,17,18,19,20-pentanor-15-cyclohexyl PGI$_2$ (9) in 1 ml of anhydrous THF cooled in an ice bath were added 0.3 ml of triethylamine and 0.02 ml of ethyl chloroformate and the resulting solution was stirred at room temperature for 1 hour. This reaction mixture was added slowly dropwise to 5 ml of liquid ammonia in a flask whose temperature had been adjusted to −33° C. and the mixture was stirred at −33° C. for 2 hours. After removal of ammonia, saturated brine was added to the residue, and the the product was extracted twice with ether. The combined ether layers were washed with saturated brine, dried and thereafter concentrated to give 15 mg of an oily substance. The oily substance was purified by column chromatography (silica gel; 20% methanol-ethyl acetate) to afford 7.1 mg of the amide (180).

IR (neat) $v$cm$^{-1}$: 3600-3000, 1660, 1600.
Mass (m/e): 397 (M$^+$).

EXAMPLES 178-197

The procedure of Example 177 was followed except the uses of the compound (10), (11), (12), (13), (14), (15), (16), (17), (18), (29), (30), (31), (39), (48), (49), (55), (60), (65), (76), or (81) in place of (9) to give 5,6,7-trinor-4,8-inter-m-phenylene-13,14-didehydro-16,17,18,19,20-pentanor-15-(4-methylcyclohexyl) PGI$_2$ carboxamide (181), 5,6,7-trinor-4,8-inter-m-phenylene-13,14-didehydro-16,17,18,19,20-pentanor-15-(3-methyl cyclohexyl) PGI$_2$ carboxamide (182), 5,6,7-trinor-4,8-inter-m-pheynlene-13,14-didehydro-16,17,18,19,20-pentanor-15-(2,2-dimethyl-4-methylcyclohexyl) PGI$_2$ carboxamide (183), 5,6,7-trinor-4,8-inter-m-phenylene-13,14-didehydro-16,17,18,19,20-pentanor-15-(2-methylcyclohexyl) PGI$_2$ carboxamide (184), 5,6,7-trinor-4,8-inter-m-phenylene-13,14-didehydro-16,17,18,19,20-pentanor-15-cyclopentyl PGI$_2$ carboxamide (185), 5,6,7-trinor-4,8- inter-m-phenylene-13,14-didehydro-16,17,18,19,20-pentanor-15-(2-methylcyclopentyl) PGI₂ carboxamide (186), 5,6,7-trinor-4,8-inter-m-phenylene-13,14-didehydro-17,18,19,20-tetranor-16-cyclohexyl-PGI₂ carboxamide (187), 5,6,7-trinor-4,8-inter-m-phenylene-13,14-didehydro-17,18,19,20-tetranor-16-cyclopentyl-PGI₂ carboxamide (188), 5,6,7-trinor-4,8-inter-m-phenylene-13,14-didehydro-18,19,20-trinor-17-cyclohexyl-PGI₂ carboxamide (189), 5,6,7-trinor-4,8-inter-m-phenylene-13,14-didehydro-17-methyl PGI₂ carboxamide (190), 5,6,7-trinor-4,8-inter-m-phenylene-13,14-didehydro-17-methyl-ω-homo PGI₂ carboxamide (191), 5,6,7-trinor-4,8-inter-m-phenylene-13,14-didehydro-16,16-dimethyl PGI₂ carboxamide (192), 5,6,7-trinor-4,8-inter-m-phenylene-16,16-dimethyl PGI₂ carboxamide (193), 5,6,7-trinor-4,8-inter-m-phenylene-17-α-methyl PGI₂ carboxamide (194), 5,6,7-trinor-4,8-inter-m-phenylene-17-β-methyl PGI₂ carboxamide (195), 5,6,7-trinor-4,8-inter-m-phenylene-17-α-methly-ω-homo PGI₂ carboxamide (196), 5,6,7-trinor-4,8-inter-m-phenylene-17,18,19,20-tetranor-16-phenoxy PGI₂ carboxamide (197), 5,6,7-trinor-4,8-inter-m-phenylene-17,18,19,20-tetranor-16-(m-chlorophenoxy) PGI₂ carboxamide (198), 5,6,7-trinor-4,8-inter-m-phenylene-16,16-dimethyl-18,19,20-trinor-17-ethoxy PGI₂ carboxamide (199), or 5,6,7-trinor-4,8-inter-m-phenylene-20-isopropylidene PGI₂ carboxamide (200). The spectra of the compounds (181)–(200) are shown in Table 12.

TABLE 12

| Example | Compound | Mass spectrum (m/e, M⁺) | Infrared spectrum cm⁻ |
|---|---|---|---|
| 178 | 181 | 411 | 1660 |
| 179 | 182 | 411 | 1660 |
| 180 | 183 | 439 | 1660 |
| 181 | 184 | 411 | 1660 |
| 182 | 185 | 383 | 1660 |
| 183 | 186 | 397 | 1660 |
| 184 | 187 | 411 | 1660 |
| 185 | 188 | 397 | 1660 |
| 186 | 189 | 425 | 1660 |
| 187 | 190 | 399 | 1660 |
| 188 | 191 | 413 | 1660 |
| 189 | 192 | 427 | 1660 |
| 190 | 193 | 415 | 1660, 970 |
| 191 | 194 | 401 | 1660, 970 |
| 192 | 195 | 401 | 1660, 970 |
| 193 | 196 | 415 | 1660, 970 |
| 194 | 197 | 423 | 1660, 1600, 970, 760, 695 |
| 195 | 198 | 475, 459 | 1660, 1660, 970 |
| 196 | 199 | 417 | 1660 |
| 197 | 200 | 427 | 1660 |

EXAMPLE 198

5,6,7-trinor-4,8-inter-m-phenylene-13,14-didehydro-17,18,19,20-tetranor-16-cyclohexyl PGI₂ [N-(p-toluenesulfonyl)]carboxamide (201)

50 mg of sodium hydride (50% mineral oil dispersion) was washed 3 times with hexane and dried, 1 ml of anhydrous 1,2-dimethoxyethane was added. To the stirred mixture cooled in an ice bath was added, a solution of 260 mg of p-toluene sulfoneamide in 2 ml of 1,2-dimethoxy ethane, and the resulting mixture was stirred at room temperature for 1 hour. To a solution of 80 mg of 5,6,7-trinor-4,8-inter-m-pheylene-13,14-didehydro-17,18,19,20-pentanor-16-cyclohexyl-PGI₂ (16) in 2 ml of anhydrous tetrahydrofuran cooled in an ice bath were added 0.1 ml of triethylamine and 0.06 ml of ethyl chloroformate the resulting solution was stierred at room temperature for 1 hour to give an acid anhydride. The mixture was added dropwise to the stirred ice-cooled above-prepared 1,2-dimethoxyethane suspension of a sodium salt of sulfoneamide. This reaction mixture was stirred at room temperature for 2 hours, water was added under ice cold conditions, the mixture was washed with ether. The pH of the water layer was adjusted to 3–2 under ice cold conditions and the mixture was extracted 3 times with ethyl acetate. The combined ethyl acetae layers were washed with water and saturated brine, dried and thereafter concentrated to give 300 mg of an oily substance. The oily substance was purified by column chromatography (silica gel; after elution with ethyl acetate, eluted with methanol) to afford 79 mg of powder.

IR (CDCl₃) νcm⁻¹: 3600–3000, 1720, 1600, 1450, 1340, 1165, 1085.

EXAMPLE 199

5,6,7-trinor-4,8-inter-m-pheylene-13,14-dihydro-16,16-dimethyl PGI₂ methyl ester (202)

To a solution of 44.2 mg of 5,6,7-trinor-4,8-inter-m-pheylene-16,16-dimethyl PGI₂ methyl ester (159), in 10 ml of ethyl acetate was added 50 mg of a 5% palladium-activated charcoal mixture, and the resulting mixture was hydrogenated at atmospheric pressure. After completion of the reaction, the reaction mixture was filtered and the filtrate was concentrated to give an oily crude product. The product was purified by column chromatography (silica gel; ethyl acetae-cyclohexane 9:1) to afford 14 mg of (202).

IR (cm⁻¹): 1735.

Mass (m/e): 444.

EXAMPLES 200–206

The procedure of Example 199 is followed except the uses of the compound (48), (49), (55), (60), (160), (161), or (162) in place of (159) to give 5,6,7-trinor-4,8-inter-m-phenylene-13,14-didehydro-17-α-methyl PGI₂ (203), 5,6,7-trinor-4,8-inter-m-phenylene-13,14-dihydro-17-β-methyl PGI₂ (204), 5,6,7-trinor-4,8-inter-m-phenylene-13,14-dihydro-17-α-methyl-ω-homo-PGI₂ (205), 5,6,7-trinor-4,8-inter-m-phenylene-13,14-dihydro-17,18,19,20-tetranor-16-phenoxy PGI₂ (206), 5,6,7-trinor-4,8-inter-m-phenylene-13,14-dihydro-17-α-methyl PGI₂ methyl ester (207), 5,6,7-trinor-4,8-inter-m-phenylene-13,14-dihydro-17-β-methyl PGI₂ methyl ester (208), or 5,6,7-trinor-4,8-inter-m-phenylene-13,14-dihydro-17-α-methyl-ω-homo-PGI₂ methyl ester (209). The spectra of the compounds (203)–(209) are shown in Table 13.

TABLE 13

| Example | Compound | Mass spectrum (m/e, M⁺) | Infrared spectrum cm⁻ |
|---|---|---|---|
| 200 | 203 | 404 | 3600–2300, 1710, 1595, 760, 740 |
| 201 | 204 | 404 | 3600–2300, 1710, 1595, 760, 740 |
| 202 | 205 | 418 | 1710 |
| 203 | 206 | 426 | 1710, 760, 695 |
| 204 | 207 | 418 | 1735 |
| 205 | 208 | 418 | 1735 |
| 206 | 209 | 432 | 1735 |

EXAMPLE 207

2-decarboxy-2-hydroxymethyl-5,6,7-trinor-4,8-inter-m-phenylene-17-methyl PGI$_2$ (210)

To a solution of 40 mg of 2-decarboxy-2-hydroxymethyl-5,6,7-trinor-4,8-inter-m-phenylene-11,15-didehydroxy-11,15-diacetoxy-17-α-methyl PGI$_2$ (44) in 1 ml of methanol was added 0.5 ml of an aqueous solution of 1N sodium hyroxide, and the resulting solution was stirred at room temperature overnight. After removing methanol under reduced pressure from the reaction solution, the residue was neutralized with 1N hydrochloric acid and extracted with ethyl acetate (3 ml×4). The ethyl acetate layer was dried and thereafter concentrated to give 21 mg of the subject compound.

IR $\nu$ (cm$^{-1}$): 3500-3300, 1595, 970.
Mass (m/e): 472.

EXAMPLES 208-213

The procedure of Example 207 was followed except the uses of the compound (36), (37), (45), (53), (58) or (79) in place of (44) to give 2-decarboxy-2-hydroxymethyl-5,6,7-trinor-4,8-inter-(5-bromoyl-1,3-phenylene)-16,16-dimethyl PGI$_2$ (211), 2-decarboxy-2-hydroxymethyl-5,6,7-trinor-4,8-inter-m-phenylene-16,16-dimethyl PGI$_2$ (212), 2-decarboxy-2-hydroxymethyl-5,6,7-trinor-4,8-inter-m-phenylene-17-β-methyl PGI$_2$ (213), 2-decarboxy-2-hydroxymethyl-5,6,7-trinor-4,8-inter-m-phenylene-17-α-methyl 20-homo PGI$_2$ (214), 2-decarboxy-2-hydroxymethyl-5,6,7-trinor-4,8-inter-m-phenylene-17,18,19,20-tetranor-16-phenoxy PGI$_2$ (215), or 2-decarboxy-20-hydroxymethyl-5,6,7-trinor-4,8-inter-m-phenylene-20-isopropylidene PGI$_2$ (216). The spectra of these compounds are shown in Table 14.

TABLE 14

| Example | Compound | Mass spectrum (m/e, M$^+$) | Infrared spectrum cm$^-$ |
|---|---|---|---|
| 208 | 211 | 483, 481 | 3600-3300, 970 |
| 209 | 212 | 402 | 3600-3300, 970 |
| 210 | 213 | 472 | 3600-3300, 970 |
| 211 | 214 | 402 | 3600-3300, 970 |
| 212 | 215 | 408 | 3600-3300, 970, 760, 695 |
| 213 | 216 | 414 | 3600-3300, 970 |

EXAMPLE 214

5,6,7-trinor-4,8-inter-m-phenylene-15,17-α-dimethyl PGI$_2$ (217)

To solution of 860 mg (2 mmol) of 5,6,7-trinor-4,8-inter-m-phenylene-17-α-methyl PGI$_2$ methyl ester (160) in 80 ml of methylene chloride was added 28 mg of active manganese dioxide, and the resulting mixture was stirred for 2 hours. Active manganese dioxide was filtered off and the obtained methylene chloride solution was concentrated to give 702 mg of the corresponding 15-oxo compound. To a solution of this 15-oxo compound in 30 ml of tetrahydrofuran were added 5 ml of hexamethyldisilazane and 1 ml of trimethylchlorosilane, and the resulting mixture was allowed to stand at room temperature overnight. The mixture was filtered, the filtrate was concentrated under a reduced pressure, thereafter, 10 ml of xylene was added to the residue and the mixture was concentrated under a reduced pressure. The residue was dissolved in ether, methyl magnesium bromide (1.5M) (1.05 equivalent of the theoretical amount) was added to the solution. After standing the mixture at room temperature for 30 minutes, it was poured into 100 ml of a saturated aqueous solution of ammonium chloride. The ether layer was separated and the water layer was further extracted twice with 20 ml of ether. After the combined ether layer was washed with brine, dried and concentrated, the residue was dissolved in 300 ml of ethanol and 30 ml of water containing a few drops of acetic acid, and the mixture was stirred at room temperature for 2 hours. This mixture was concentrated under reduced pressure to the aqueous residue and the residue was extracted with dichloromethane. The dichloromethane solution was concentrated and the residue was purified by silica gel chromatography (developing solvent; water:saturated ethyl acetate) to give 117 mg of the methyl ester of the subject compound. To this methyl ester solution in 2 ml of ethanol was added 1 ml of an aqueous solution of 1N potassium hydroxide and the resultant mixture was stirred at room temperature for 20 hours. Ethanol was removed under reduced pressure, the residue was cooled to 0° C., and the pH of the residue was adjusted to 3.5-4.0 and the mixture was extracted with ethyl acetate. The ethyl acetate layer was dried and concentrated to give 81 mg of the subject compound (217) (174):

IR $\nu$ (cm$^{-1}$): 3500-2800, 1705, 970.
Mass (m/e): 430.

EXAMPLE 215

The procedure of Example 214 was followed except the use of the compound (162) in place of (160) to give 5,6,7-trinor-4,8-inter-m-phenylene-15,17-α-dimethyl-ω-homo PGI$_2$ (218).

IR $\nu$ (cm$^{-1}$): 3500-2800, 1705, 970.
Mass (m/e): 444.

We claim:

1. A 5,6,7-trinor-4,8-inter-m-phenylene PGI$_2$ derivative represented by the formula $$\text{(I)}$$

wherein
R$_1$ is a group selected from the class consisting of:
(a) a COOR$_2$, wherein R$_2$ denotes
(i) hydrogen or a pharmacologically acceptable cation,
(ii) a straight chain alkyl having 1-12 carbon atoms or a branched alkyl having 3-12 carbon atoms,
(iii)

$$-Z-\underset{(R_3)_{n'}}{\overset{(CH_2)_m}{\diagup\diagdown}},$$

wherein Z denotes valence bond, or straight chain or branched alkylene which may be represented by C$_t$H$_{2t}$, wherein t denotes an integer of 1-5, further, m denotes an integer of 5-12, R$_3$ denotes hydrogen or alkyl having 1–5 carbon atoms, and n' denotes an integer of 1–3, (iv) —(CH$_2$CH$_2$O)$_l$CH$_3$ wherein $l$ is an integer of 1–5, (v) —Z—Ar$_1$, wherein Z is the same as defined above, Ar$_1$ denotes phenyl, α-naphthyl, β-naphthyl, 2-pyridyl, 3-pyridyl, 4-pyridyl, α-furyl, β-furyl, α-thienyl, β-thienyl or substituted phenyl (wherein the substituent is at least one chlorine, bromine, fluorine, trifluoromethyl, alkyl having 1–4 carbon atoms, nitro, methoxy, phenyl, phenoxy,

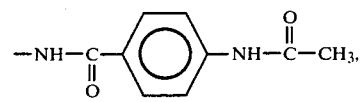

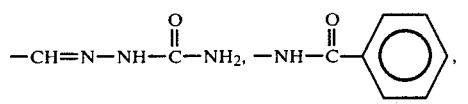

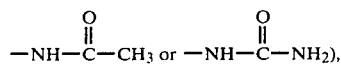

(vi) —C$_l$H$_{2l}$COOR$_3$ (vii) —CH$_2$C$_l$H$_{2l}$N(R$_3$)$_2$ (wherein $l$ and R$_3$ are the same as defined above), (viii)

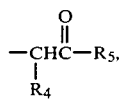

wherein R$_4$ L denotes hydrogen or benzoyl and R$_5$ denotes phenyl, p-bromophenyl, p-biphenyl, p-benzamidophenyl or 2-naphthyl, (ix) —C$_p$H$_{2p}$—B', wherein B' is

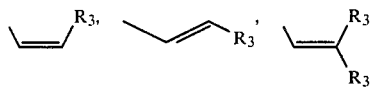

or —C≡C—R$_6$, wherein R$_3$ is the same as defined above, R$_6$ denotes straight chain or branched alkyl having 1–30 carbon atoms, and p is an integer of 1–5, or (x)

wherein R$_7$ denotes alkyl or acyl having 1–30 carbon atoms, (b) —CH$_2$OH, (c)

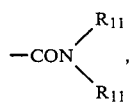

wherein R$_{11}$ denotes hydrogen, alkyl having 1–10 carbon atoms, cycloalkyl having 3–12 carbon atoms, phenyl, substituted phenyl, aralkyl having 7–12 carbon atoms or —SO$_2$R$_{12}$, wherein R$_{12}$ denotes alkyl having 1–10 carbon atoms, cycloalkyl having 3–12 carbon atoms, phenyl, substituted phenyl or aralkyl having 7–12 carbon atoms, the two R$_{11}$ may be the same or different, however, when one denotes —SO$_2$R$_{12}$, the other is not —SO$_2$R$_{12}$, and (d)

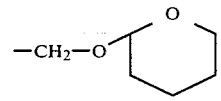

A denotes
(i) —(CH$_2$)$_n$—,
(ii) —CH=CH—CH$_2$—,
(iii) —CH$_2$CH=CH— or
(iv) —CH$_2$—O—CH$_2$—, wherein n is an integer of 1–3

Y denotes hydrogen, alkyl having 1–4 carbon atoms, chlorine, fluorine, bromine, formyl, methoxy or nitro, B denotes to all A and Y (i)

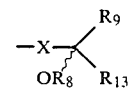

or
(ii)

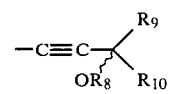

further, when A is (ii) —CH=CH—CH$_2$—, (iii) —CH$_2$CH=CH—, (iv) —CH$_2$O—CH$_2$— or when Y is an alkyl group having 2–4 carbon atoms, chlorine, fluorine, bromine, formyl, methoxy or nitro, B further denotes (iii)

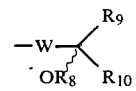

wherein R$_9$ denotes hydrogen or alkyl group having 1–4 carbon atoms, R$_8$ denotes hydrogen, acyl having 1–12 carbon atoms, aroyl having 6–15 carbon atoms, tetrahydropyranyl, tetrahydrofuranyl, 1-ethoxy ethyl or t-butyl, X denotes
(i) —CH$_2$CH$_2$—,
(ii) —CH=CH— (trans) or
(iii) —C≡C—

R$_{10}$ denotes
(i) straight chain alkyl having 4–10 carbon atoms, or
(ii)

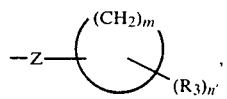

wherein Z, m, $R_3$ and n' are the same as defined above, or
(iii) —Z—$Ar_2$, wherein Z is the same as defined above, and $Ar_2$ denotes phenyl, α-naphthyl, β-naphthyl or at least one chlorine, bromine, fluorine, trifluoromethyl, alkyl having 1-4 carbon atoms, nitro, methoxy, phenyl or phenoxy-substituted phenyl, $R_{13}$ denotes
(i) branched alkyl having 5-10 carbon atoms, or
(ii) —$C_tH_{2t}OR_{14}$, wherein $C_tH_{2t}$ is the same as defined above, and $R_{14}$ denotes straight chain or branched alkyl having 1-5 carbon atoms,

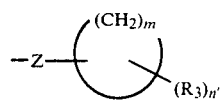

or —Z—$Ar_2$, wherein Z, m, $R_3$, n' and $Ar_2$ are the same as defined above, or
(iii)

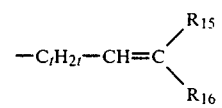

wherein $C_tH_{2t}$ is the same as defined above, $R_{15}$ and $R_{16}$ denote hydrogen, methyl, ethyl, propyl or butyl group, W denotes
(i) —$CH_2CH_2$— or
(ii) —CH=CH— (trans)

and the general formula denotes d form, l form or dl form.

2. A $PGI_2$ derivative of claim 1 wherein $R_2$ is a group selected from the class consisting of hydrogen, pharmacologically acceptable cation and —$CH_3$.

3. A $PGI_2$ derivative of claim 1 wherein A is a group selected from the class consisting of —$(CH_2)_n$— and —$CH_2$—CH=CH—, wherein n is an integer of 1-3.

4. A $PGI_2$ derivative of claim 3 wherein n is 3.

5. A $PGI_2$ derivative of claim 1 wherein A is a group selected from the class consisting of —$(CH_2)_n$— and —$CH_2$—CH=CH—, and B is a group selected from the class consisting of
(i)

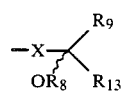

and
(ii)

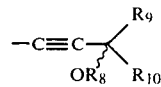

wherein n, $R_8$, $R_9$, $R_{10}$, $R_{13}$ and X are the same as defined in claim 1.

6. A $PGI_2$ derivative of claim 5 wherein X is a group selected from the class consisting of —CH=CH— (trans) and —C≡C—.

7. A $PGI_2$ derivative of claim 5 wherein X is a group selected from the class consisting of —CH=CH— (trans) and —C≡C—, and $R_{13}$ is a group selected from the class consisting of
(i) branched alkyl having 5-10 carbon atoms, and
(ii)

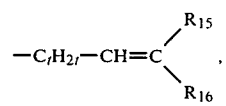

wherein t, $R_{15}$, and $R_{16}$ are the same as defined in claim 1.

8. A $PGI_2$ derivative of claim 5 wherein $R_{10}$ is a group selected from the class consisting of
(i) straight chain alkyl having 4-10 carbon atoms, and
(ii)

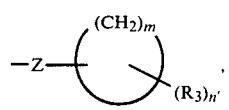

wherein Z, m, $R_3$ and n' are the same as defined in claim 1.

9. A $PGI_2$ derivative of claim 5 wherein n is 3, $R_8$ is hydrogen, and $R_9$ is hydrogen.

10. A $PGI_2$ derivative of claim 7 wherein t is 3 or 4, $R_{15}$ is hydrogen or methyl and $R_{16}$ is methyl or ethyl.

11. A $PGI_2$ derivative of claim 5 wherein A is —$(CH_2)_3$— and B is

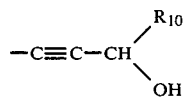

wherein $R_{10}$ is

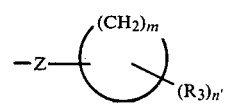

wherein m is 5 or 6, $R_3$ is hydrogen, methyl or ethyl, n' is 1 or 2 and Z is the same as defined in claim 1.

12. A $PGI_2$ derivative of claim 1 wherein
A is a group selected from the class consisting of —$(CH_2)_n$— and —$CH_2$—CH=CH—,
B is

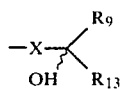

and
Y is hydrogen, wherein
n is an integer of 1–3,
X is —CH=CH— or —C≡C—,
$R_9$ is hydrogen or alkyl group having 1–4 carbon atoms, and $R_{13}$ is a group selected from the class consisting of
(i) branched alkyl having 5–10 carbon atoms, and
(ii)

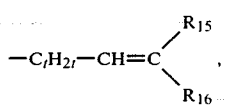

wherein t, $R_{15}$, and $R_{16}$ are the same as defined in claim 1.

13. A $PGI_2$ derivative of claim 12 wherein n is 3, t is 3 or 4, $R_{15}$ is hydrogen or methyl, and $R_{16}$ is methyl or ethyl.

14. A $PGI_2$ derivative of claim 1 wherein
A is a group selected from the class consisting of —$(CH_2)_n$— and —$CH_2$—CH=CH—,
B is

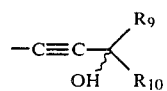

wherein $R_{10}$ is a group selected from the class consisting of
(i) straight chain alkyl having 4–10 carbon atoms, and
(ii)

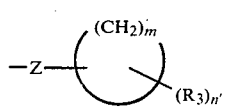

Y is hydrogen, wherein n', $R_9$, Z, m and $R_3$ are the same as in claim 1.

15. A $PGI_2$ derivative of claim 14 wherein n is 3, $R_9$ is hydrogen, m is 5 or 6, $R_3$ is hydrogen, methyl or ethyl and n' is 1 or 2.

16. A $PGI_2$ derivative of claim 1 wherein
A is —$CH_2CH$=CH— and,
B is

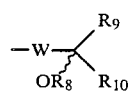

wherein $R_8$, $R_9$, $R_{10}$ and W are the same as defined in claim 1.

17. A $PGI_2$ derivative of claim 16 wherein W is —CH=CH— (trans).

18. A $PGI_2$ derivative of claim 16 wherein W is —CH=CH— (trans) and $R_{10}$ is a group selected from the class consisting of
(i) straight chain alkyl having 4–10 carbon atoms, and
(ii)

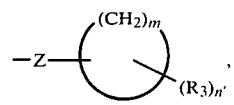

wherein Z, m, $R_3$ and n' are the same as defined in claim 1.

19. A $PGI_2$ derivative of claim 16 wherein W is —CH=CH— (trans), $R_9$ is hydrogen and $R_{10}$ is

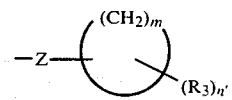

wherein m is 5 or 6, $R_3$ is hydrogen, methyl, ethyl or propyl, n' is 1 or 2 and Z is the same as defined in claim 1.

20. A $PGI_2$ derivative of claim 1 wherein
A is —$CH_2CH$=CH—,
B is

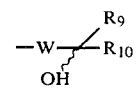

and
Y is hydrogen, wherein
W is —CH=CH— (trans),
$R_{10}$ is a group selected from the class consisting of
(i) straight chain alkyl having 4–10 carbon atoms, and
(ii)

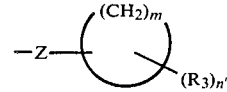

wherein $R_9$, Z, m, $R_3$ and n' are the same as defined in claim 1.

21. A $PGI_2$ derivative of claim 20 wherein m is 5 or 6, $R_3$ is hydrogen, methyl, ethyl or propyl, $R_9$ is hydrogen and n' is 1 or 2.

22. A $PGI_2$ derivative of any one of claims 3,4,5,6,7,8,9,10,11,12,13,14,15,16,17,18,19,20 or 21 wherein $R_1$ is $COOR_2$ wherein $R_2$ is a group selected from the class consisting of hydrogen, pharmacologically acceptable cations and —$CH_3$.

23. 5,6,7-trinor-4,8-inter-m-phenylene-16(S)-methyl $PGI_2$.

24. 5,6,7-trinor-4,8-inter-m-phenylene-16(R)-methyl $PGI_2$.

25. 5,6,7-trinor-4,8-inter-m-phenylene-16-methyl-ω-homo $PGI_2$.

26. 5,6,7-trinor-4,8-inter-m-phenylene-17(S)-methyl-ω-homo $PGI_2$.

27. 5,6,7-trinor-4,8-inter-m-phenylene-13,14-didehydro-ω-homo $PGI_2$.

28. 5,6,7-trinor-4,8-inter-m-phenylene-13,14-didehydro-16,17,18,19,20-pentanor-15-cyclohexyl-$PGI_2$.

29. 5,6,7-trinor-4,8-inter-m-phenylene-2,3-didehydro-17(S)-methyl $PGI_2$.

30. 5,6,7-trinor-4,8-inter-m-phenylene-2,3-didehydro-17(S)-methyl-ω-homo $PGI_2$.

31. 5,6,7-trinor-4,8-inter-m-phenylene-2,3-didehydro-16,17,18,19,20-pentanor-15-cyclopentyl $PGI_2$.

32. 5,6,7-trinor-4,8-inter-m-phenylene-2,3-didehydro-16,17,18,19,20-pentanor-15-cyclohexyl $PGI_2$.

33. A pharmaceutical composition for use as an anti-ulcer agent comprising a pharmaceutically acceptable carrier and a $PGI_2$ derivative of claim 1 in sufficient amount to provide from about 0.01 to about 100 mg of said $PGI_2$ derivative per dose.

34. A pharmaceutical composition for use as an antithrombotic agent comprising a pharmaceutically acceptable carrier and a $PGI_2$ derivative of claim 1 in sufficient amount to provide from about 0.01 to about 50 mg of said $PGI_2$ derivative per dose.

35. A pharmaceutical composition for use as an antihypertensive agent comprising a pharmaceutically acceptable carrier and a $PGI_2$ derivative of claim 1 in sufficient amount to provide from about 0.01 to about 5.0 mg of said $PGI_2$ derivative per dose.

36. A method for the treatment of Buerger's disease comprising intravenously injecting a mixture of a pharmaceutically acceptable carrier and a $PGI_2$ derivative of claim 1, wherein said $PGI_2$ derivative is administered in an amount from about 0.001 to about 100 ng/kg/minute.

* * * * *